US012528787B2

(12) United States Patent
Kostik et al.

(10) Patent No.: US 12,528,787 B2
(45) Date of Patent: Jan. 20, 2026

(54) SOLID STATE FORMS OF A KINASE INHIBITOR

(71) Applicant: Deciphera Pharmaceuticals, LLC, Waltham, MA (US)

(72) Inventors: Elena Kostik, Waltham, MA (US); Michael D. Kaufman, Waltham, MA (US)

(73) Assignee: Deciphera Pharmaceuticals, LLC, Waltham, MA (US)

( * ) Notice: Subject to any disclaimer, the term of this patent is extended or adjusted under 35 U.S.C. 154(b) by 0 days.

(21) Appl. No.: 19/079,010

(22) Filed: Mar. 13, 2025

(65) Prior Publication Data

US 2025/0243182 A1 Jul. 31, 2025

Related U.S. Application Data

(63) Continuation of application No. 18/971,800, filed on Dec. 6, 2024.

(60) Provisional application No. 63/650,144, filed on May 21, 2024, provisional application No. 63/607,617, filed on Dec. 8, 2023.

(51) Int. Cl.
*C07D 401/14* (2006.01)
*A61K 31/506* (2006.01)

(52) U.S. Cl.
CPC .......... *C07D 401/14* (2013.01); *A61K 31/506* (2013.01)

(58) Field of Classification Search
CPC ............................ C07D 401/14; A61K 31/506
See application file for complete search history.

(56) References Cited

U.S. PATENT DOCUMENTS

| | | | |
|---|---|---|---|
| 7,144,911 | B2 | 12/2006 | Flynn et al. |
| 7,202,257 | B2 | 4/2007 | Flynn et al. |
| 7,279,576 | B2 | 10/2007 | Flynn et al. |
| 7,342,037 | B2 | 3/2008 | Flynn et al. |
| 7,531,566 | B2 | 5/2009 | Flynn et al. |
| 7,666,895 | B2 | 2/2010 | Flynn et al. |
| 7,737,283 | B2 | 6/2010 | Flynn et al. |
| 7,790,756 | B2 | 9/2010 | Flynn et al. |
| 7,897,762 | B2 | 3/2011 | Flynn et al. |
| 8,143,293 | B2 | 3/2012 | Flynn et al. |
| 8,163,756 | B2 | 4/2012 | Flynn et al. |
| 8,188,113 | B2 | 5/2012 | Flynn et al. |
| 8,278,331 | B2 | 10/2012 | Flynn et al. |
| 8,461,179 | B1 | 6/2013 | Flynn et al. |
| 8,486,951 | B2 | 7/2013 | Flynn et al. |
| 8,569,319 | B2 | 10/2013 | Flynn et al. |
| 8,586,565 | B2 | 11/2013 | Flynn et al. |
| 8,637,672 | B2 | 1/2014 | Flynn et al. |
| 8,741,911 | B2 | 6/2014 | Allgeier et al. |
| 8,921,565 | B2 | 12/2014 | Flynn et al. |
| 8,940,756 | B2 | 1/2015 | Flynn et al. |
| 9,012,635 | B2 | 4/2015 | Flynn et al. |
| 9,133,183 | B2 | 9/2015 | Flynn et al. |
| 9,181,223 | B2 | 11/2015 | Kaufman et al. |
| 9,187,474 | B2 | 11/2015 | Flynn et al. |
| 9,193,719 | B2 | 11/2015 | Flynn et al. |
| 9,309,224 | B2 | 4/2016 | Flynn et al. |
| 9,334,267 | B2 | 5/2016 | Flynn et al. |
| 9,382,228 | B2 | 7/2016 | Flynn et al. |
| 9,387,202 | B2 | 7/2016 | Flynn et al. |
| 9,457,019 | B2 | 10/2016 | Flynn et al. |
| 11,103,507 | B2 | 8/2021 | Flynn et al. |
| 11,679,110 | B2 | 6/2023 | Flynn et al. |
| 2008/0214544 | A1 | 9/2008 | Bellon et al. |
| 2008/0255155 | A1 | 10/2008 | Raeppel et al. |
| 2010/0120806 | A1 | 5/2010 | Flynn et al. |
| 2010/0166699 | A1 | 7/2010 | Thompson et al. |
| 2011/0053906 | A1 | 3/2011 | Huck et al. |
| 2014/0145025 | A1 | 5/2014 | Fang et al. |
| 2015/0073129 | A1 | 3/2015 | Herting et al. |

(Continued)

FOREIGN PATENT DOCUMENTS

| | | | |
|---|---|---|---|
| CN | 105120864 | A | 12/2015 |
| CN | 105473617 | A | 4/2016 |

(Continued)

OTHER PUBLICATIONS

P. Khadka et al. (Asian Journal of Pharmaceutical Sciences, vol. 9, Issue 6, 2014, pp. 304-316, ISSN 1818-0876, doi.org/10.1016/j.ajps.2014.05.005 (Year: 2014).*

(Continued)

*Primary Examiner* — James H Alstrum-Acevedo
*Assistant Examiner* — Manahil Mirghani Ali Abdalhameed
(74) *Attorney, Agent, or Firm* — Goodwin Procter LLP

(57) ABSTRACT

Described herein, in part, are solid-state forms of the compound represented by Formula (I), pharmaceutical compositions comprising the solid-state forms, processes of making the solid-state forms and methods of using the solid-state forms Formula (I)

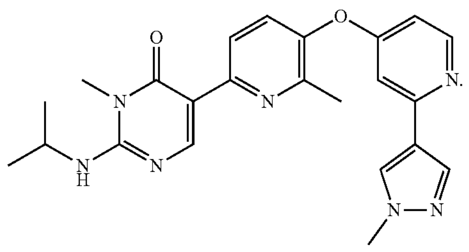

20 Claims, 9 Drawing Sheets

(56) References Cited

U.S. PATENT DOCUMENTS

| | | | |
|---|---|---|---|
| 2019/0091217 A1 | 3/2019 | Flynn et al. |
| 2020/0129489 A1 | 4/2020 | Flynn et al. |
| 2020/0352920 A1 | 11/2020 | Flynn et al. |
| 2020/0354346 A1 | 11/2020 | Flynn et al. |
| 2020/0354352 A1 | 11/2020 | Flynn et al. |
| 2021/0015801 A1 | 1/2021 | Flynn et al. |
| 2023/0414614 A1 | 12/2023 | Flynn et al. |

FOREIGN PATENT DOCUMENTS

| | | | | |
|---|---|---|---|---|
| CN | 113880812 | A | | 1/2022 |
| CN | 116283919 | A | * | 6/2023 |
| EP | 3632907 | A1 | | 4/2020 |
| EP | 3682881 | A1 | | 7/2020 |
| JP | 6364472 | B2 | | 7/2018 |
| RU | 2330024 | C2 | | 7/2008 |
| WO | WO-2003/000660 | A1 | | 1/2003 |
| WO | WO-2008/079291 | A2 | | 7/2008 |
| WO | WO-2010/051373 | A1 | | 5/2010 |
| WO | 2014145015 | A2 | | 9/2014 |
| WO | 2014145028 | A2 | | 9/2014 |
| WO | WO-2014/145025 | A2 | | 9/2014 |
| WO | WO-2020/139828 | A1 | | 7/2020 |
| WO | WO-2022247786 | A1 | | 12/2022 |

OTHER PUBLICATIONS

CN 116283919A Translation, Jun. 23, 2023 (Year: 2023).*
Caira M. R. et al. "Crystalline Polymorphism of Organic Compounds", Design of Organic Solids. Topics in Current Chemistry, vol. 198, p. 163-208 (1998).
Fang Z. et al. Conformational restriction: an effective tactic in 'follow-on'-based drug discovery, Fugure Med Chem. 2014, 6(8): 885-901.
Kumari A. et al. 3D-QSAR analysis of anilinoquinoline inhibitors of colony stimulating factor-1 kinase(cFMS): implementation of field-based molecular alignment, Med Chem Res 22, 5167-5183 (2013).
PCT/US2019/068311 International Search Report and Written Opinion mailed Jul. 2, 2020.
PCT/US2024/058988 International Search Report and Written Opinion dated Mar. 24, 2025.
Silverman R.B. et al. Lead Discovery, The Organic Chemistry of Drug Design and Drug Action, 3rd Ed, Chapter 2, pp. 19-122, Elsevier (2014).
U.S. Appl. No. 11/963,740, filed Dec. 21, 2007, Patented, U.S. Pat. No. 8,163,756.
U.S. Appl. No. 11/870,388, filed Oct. 10, 2007, Patented, U.S. Pat. No. 7,790,756.
U.S. Appl. No. 12/829,561, filed Jul. 2, 2010, Patented, U.S. Pat. No. 8,586,565.
U.S. Appl. No. 11/854,354, filed Sep. 12, 2007, Patented, U.S. Pat. No. 8,188,113.
U.S. Appl. No. 10/746,460, filed Dec. 24, 2003, Patented, U.S. Pat. No. 7,144,911.
U.S. Appl. No. 10/886,329, filed Jul. 6, 2004, Patented, U.S. Pat. No. 7,202,257.
U.S. Appl. No. 11/450,840, filed Jun. 9, 2006, Patented, U.S. Pat. No. 7,342,037.
U.S. Appl. No. 11/336,708, filed Jan. 20, 2006, Patented, U.S. Pat. No. 7,531,566.
U.S. Appl. No. 11/450,850, filed Jun. 9, 2006, Patented, U.S. Pat. No. 7,666,895.
U.S. Appl. No. 10/746,607, filed Dec. 24, 2003, Patented, U.S. Pat. No. 7,279,576.
U.S. Appl. No. 11/854,293, filed Sep. 12, 2007, Patented, U.S. Pat. No. 7,897,762.
U.S. Appl. No. 12/105,408, filed Apr. 18, 2008, Patented, U.S. Pat. No. 8,143,293.
U.S. Appl. No. 13/590,955, filed Aug. 21, 2012, Patented, U.S. Pat. No. 8,486,951.
U.S. Appl. No. 11/450,849, filed Jun. 9, 2006, Patented, U.S. Pat. No. 7,737,283.
U.S. Appl. No. 13/785,575, filed Mar. 5, 2013, Patented, U.S. Pat. No. 8,741,911.
U.S. Appl. No. 12/608,578, filed Oct. 29, 2009, Patented, U.S. Pat. No. 8,278,331.
U.S. Appl. No. 13/098,247, filed Apr. 29, 2011, Patented, U.S. Pat. No. 8,569,319.
U.S. Appl. No. 13/559,170, filed Jul. 26, 2012, Patented, U.S. Pat. No. 8,637,672.
U.S. Appl. No. 14/214,134, filed Mar. 14, 2014, Patented, U.S. Pat. No. 9,133,183.
U.S. Appl. No. 14/383,803, filed Mar. 5, 2013, Patented, U.S. Pat. No. 9,187,474.
U.S. Appl. No. 13/491,394, filed Jun. 7, 2012, Patented, U.S. Pat. No. 8,461,179.
U.S. Appl. No. 13/801,753, filed Mar. 13, 2013, Patented, U.S. Pat. No. 8,940,756.
U.S. Appl. No. 16/387,315, filed Apr. 17, 2019, Pending.
U.S. Appl. No. 14/214,127, filed Mar. 14, 2014, Patented, U.S. Pat. No. 9,012,635.
U.S. Appl. No. 13/683,277, filed Nov. 21, 2012, Patented, U.S. Pat. No. 8,921,565.
U.S. Appl. No. 14/549,125, filed Nov. 20, 2014, Patented, U.S. Pat. No. 9,387,202.
U.S. Appl. No. 14/214,160, filed Mar. 14, 2014, Patented, U.S. Pat. No. 9,193,719.
U.S. Appl. No. 14/214,171, filed Mar. 14, 2014, Patented, U.S. Pat. No. 9,181,223.
U.S. Appl. No. 14/214,185, filed Mar. 14, 2014, Patented, U.S. Pat. No. 9,382,228.
U.S. Appl. No. 14/214,179, filed Mar. 14, 2014, Patented, U.S. Pat. No. 9,309,224.
U.S. Appl. No. 14/383,799, filed Mar. 5, 2013, Patented, U.S. Pat. No. 9,334,267.
U.S. Appl. No. 14/535,900, filed Nov. 7, 2014, Patented, U.S. Pat. No. 9,457,019.
U.S. Appl. No. 16/943,821, filed Jul. 30, 2020, Pending, US 2021-0145805 A1.
U.S. Appl. No. 16/943,871, filed Jul. 30, 2020, Pending, US 2020-0352920 A1.
U.S. Appl. No. 16/725,282, filed Dec. 23, 2019, Patented, U.S. Pat. No. 11,103,507.
U.S. Appl. No. 16/870,384, filed May 8, 2020, Patented, U.S. Pat. No. 11,530,206.
U.S. Appl. No. 16/870,418, filed May 8, 2020, Patented, U.S. Pat. No. 11,518,758.
U.S. Appl. No. 16/902,989, filed Jun. 16, 2020, Patented, U.S. Pat. No. 11,590,134.
U.S. Appl. No. 16/991,644, filed Aug. 12, 2020, Pending, US 2022-0047573 A1.
U.S. Appl. No. 17/028,640, filed Sep. 22, 2020, Pending, U.S. Pat. No. 10,966,966.
U.S. Appl. No. 17/180,234, filed Feb. 19, 2021, Patented, U.S. Pat. No. 11,185,535.
U.S. Appl. No. 17/180,241, filed Feb. 19, 2021, Patented, U.S. Pat. No. 11,395,818.
U.S. Appl. No. 17/504,133, filed Oct. 18, 2021, Patented, U.S. Pat. No. 11,576,103.
U.S. Appl. No. 18/314,348, filed May 9, 2023, Patented, U.S. Pat. No. 11,801,237.
U.S. Appl. No. 17/358,137, filed Jun. 25, 2021, Patented, U.S. Pat. No. 11,679,110.
U.S. Appl. No. 17/583,977, filed Jan. 25, 2022, Patented, U.S. Pat. No. 11,426,390.
U.S. Appl. No. 17/583,985, filed Jan. 25, 2022, Patented, U.S. Pat. No. 11,344,536.
U.S. Appl. No. 17/727,307, filed Apr. 22, 2022, Patented, U.S. Pat. No. 11,534,432.
U.S. Appl. No. 17/735,820, filed May 3, 2022, Patented, U.S. Pat. No. 11,612,591.
U.S. Appl. No. 18/148,766, filed Dec. 30, 2022, Patented, U.S. Pat. No. 11,896,585.

(56) References Cited

OTHER PUBLICATIONS

U.S. Appl. No. 17/845,275, filed Jun. 21, 2022, Pending, US 2022-0370423 A1.
U.S. Appl. No. 17/845,278, filed Jun. 21, 2022, Pending, US 2022-0370424 A1.
U.S. Appl. No. 17/180,218, filed Feb. 19, 2021, Patented, U.S. Pat. No. 11,266,635.
U.S. Appl. No. 17/869,108, filed Jul. 20, 2022, Patented, U.S. Pat. No. 11,969,414.
U.S. Appl. No. 17/583,985, filed Jan. 25, 2022, Patented, U.S. Pat. No. 11,344,546.
U.S. Appl. No. 17/735,678, filed May 3, 2022, Patented, U.S. Pat. No. 11,529,336.
U.S. Appl. No. 17/735,682, filed May 3, 2022, Patented, U.S. Pat. No. 11,576,904.
U.S. Appl. No. 17/938,353, filed Oct. 6, 2022, Patented, U.S. Pat. No. 11,779,572.
U.S. Appl. No. 17/735,862, filed May 3, 2022, Patented, U.S. Pat. No. 11,433,056.
U.S. Appl. No. 18/091,743, filed Dec. 30, 2022, Patented, U.S. Pat. No. 11,813,251.
U.S. Appl. No. 18/140,942, filed Apr. 28, 2023, Pending, US 2023-0414614 A1.
U.S. Appl. No. 17/833,272, filed Jun. 6, 2022, Patented, U.S. Pat. No. 12,071,032.
U.S. Appl. No. 17/832,224, filed Jun. 3, 2022, Pending, US 2023-0047915 A1.
U.S. Appl. No. 18/078,269, filed Dec. 9, 2022, Pending, US 2023-0357179 A1.
U.S. Appl. No. 18/078,271, filed Dec. 9, 2022, Pending, US 2023-0257352 A1.
U.S. Appl. No. 18/073,721, filed Dec. 9, 2022, Pending, US 2024-0116877 A1.
U.S. Appl. No. 18/152,993, filed Jan. 11, 2023, Pending, US 2023-0338376 A1.
U.S. Appl. No. 18/464,519, filed Sep. 11, 2023, Pending, US 2024-0261270 A1.
U.S. Appl. No. 18/463,498, filed Sep. 8, 2023, Pending, US 2024-0197696 A1.
U.S. Appl. No. 18/490,188, filed Oct. 19, 2023, Patented, U.S. Pat. No. 11,911,370.
U.S. Appl. No. 18/490,197, filed Oct. 19, 2023, Patented, U.S. Pat. No. 11,918,564.
U.S. Appl. No. 18/512,447, filed Nov. 17, 2023, Pending.
U.S. Appl. No. 18/518,100, filed Nov. 22, 2023, Patented, U.S. Pat. No. 11,969,415.
U.S. Appl. No. 18/518,110, filed Nov. 22, 2023, Patented, U.S. Pat. No. 12,023,328.
U.S. Appl. No. 18/750,014, filed Jun. 21, 2024, Pending, US 2024-0342144 A1.
U.S. Appl. No. 18/758,007 filed Jun. 28, 2024, Pending, US 2024-0350466 A1.
U.S. Appl. No. 18/795,683, filed Aug. 6, 2024, Pending, U.S. Pat. No. 12,213,967.
U.S. Appl. No. 18/795,711, filed Aug. 6, 2024, Pending, U.S. Pat. No. 12,226,406.
U.S. Appl. No. 18/795,731, filed Aug. 6, 2024, Pending, U.S. Pat. No. 12,213,968.
U.S. Appl. No. 18/815,054, filed Aug. 26, 2024, Pending.
U.S. Appl. No. 18/985,885, filed Dec. 18, 2024, Pending.
U.S. Appl. No. 18/980,378, filed Dec. 13, 2024, Pending.
U.S. Appl. No. 18/971,800, filed Dec. 6, 2024, Pending.
U.S. Appl. No. 18/971,846, filed Dec. 6, 2024, Pending.
U.S. Appl. No. 18/980,426, filed Dec. 13, 2024, Pending.
U.S. Appl. No. 19/001,282, filed Dec. 9, 2024, Pending.
U.S. Appl. No. 19/079,070, filed Mar. 13, 2025, Pending.
U.S. Appl. No. 19/079,727, filed Mar. 14, 2025, Pending.
U.S. Appl. No. 19/079,965, filed Mar. 14, 2025, Pending.
U.S. Appl. No. 19/085,149, filed Mar. 20, 2025, Pending.
"Deciphera Pharmaceuticals Announces Positive, Preliminary, Top-Line Clinical Data for the Ongoing Phase 1 Clincial Study with DCC-3014 and an Update on Future Development Plans," 2019, 1-3.
"History of Changes for Study: NCT03069469 Study of DCC-3014 in Patients with Advanced Malignancies," ClinicalTrials.gov Archive, 2018, 1-5.
Al-Muhsen et al., "The Expression of Stem Cell Factor and c-Kit Receptor in Human Asthmatic Airways," Clinical and Experimental Allergy, 2004, 34: 911-917.
Attoub et al., "The C-Kit Tyrosine Kinase Inhibitor STI571 for Colorectal Cancer Therapy," Cancer Research, 2002, 62: 4879-4883.
Blay, JY et al., "P63: Patient-Reported Outcomes Following Treatment with Vimseltinib for Tenosynovial Giant Cell Tumour in a Phase 2 Expansion Study", Value in Health, Elsevier, Amsterdam, NL, vol. 25, No. 12 (Dec. 1, 2022), XP087229982.
Boisson et al., "c-Kit and c-kit mutations in mastocytosis and other hematological diseases," Journal of Leukocyte Biology, 2000, 67(2):135-148.
Brinkmann et al., "Fingolimod (FTY720): Discovery and Development of an Oral Drug to Treat Multiple Sclerosis," NATURE Reviews | Drug Discovery, 2010, 9: 883-897.
Brunton et al., "Chemotherapy of Neoplastic Diseases," in, Goodman and Gilman's: The Pharmacological Basis of Therapeutics, 2008, 11th ed.: 853-908.
Burns et al., "C-FMS Inhibitors: A Patent Review," Expert Opinion on Therapeutic Patents, 2011, 147-165.
Caldwell, T. M. et al., "Discovery of vimseltinib (DCC-3014), a highly selective CSF1R switch-control kinase inhibitor, in clinical development for the treatment of Tenosynovial Giant Cell Tumor (TGCT)," Biorg. Med. Chem. Lett. 74, (2022) 128928, 7 pages.
Carvajal et al., "KIT as a Therapeutic Target in Metastatic Melanoma," Journal of the American Medical Association, 2011, 305(22): 2327-2334.
Dewar et al., "Inhibition of c-fms by Imatinib: expanding the spectrum of treatment," Cell Cycle, 2005, 4(7):851-853.
Dewar et al., "Macrophage Colony-Stimulating Factor Receptor C-Fms is a Novel Target of Imatinib," Blood, 2005, 105(8): 3127-3132.
Di Lorenzo et al., "Expression of Proto-Oncogene C-Kit in High Risk Prostate Cancer," European Journal of Surgical Oncology, 2004, 30: 987-992.
Dorwald, "Side Reactions in Organic Synthesis," Wiley: VCH Weinhem Preface, 2005, 1-15 & 8: 279-308.
El Agamy et al., "Targeting c-Kit in the Therapy of Mast Cell Disorders: Current Update," European Journal of Pharmacology, 2012, 690: 1-3.
Fine et al., "Neoplasms of the Central Nervous System," Cancer Principles & Practice of Oncology, 2005, 1834-1887.
Fogarty et al., "Development of Protein Kinase Activators: AMPK as a Target in Metabolic Disorders and Cancer," Biochimica et Biophysica Acta, 2010, 1804: 581-591.
Gelderblom, H. et al., "475P: Safety and Efficacy of Vimseltinib in Tenosynovial Giant Cell Tumour (TGCT)): Long-term Phase I Update", Annals of Oncology, vol. 33, (Sep. 1, 2022), p. S757, XP093241096.
Gelderblom, H. et al., "Vimseltinib versus placebo for tenosynovial giant cell tumour (MOTION): a multicentre, randomised, double-blind, placebo-controlled, phase 3 trial", The LANCET, vol. 403, No. 10445, (Jun. 3, 2024), pp. 2709-2719, XP093241015.
Girouard et al., "Neurovascular Coupling in the Normal Brain and in Hypertension, Stroke, and Alzheimer Disease," J. Appl Physiol., 2006, 100: 328-335.
Gupta et al., "IL-3 Inhibits Human Osteoclastogenesis and Bone Resorption through Downregulation of c-Fms and Diverts the Cells to Dendritic Cell Lineage," The Journal of Immunology, 2010, 2261-2272.
Heinrich et al., "Inhibition of c-kit receptor tyrosine kinase activity by STI 571, a selective tyrosine kinase inhibitor," Blood, 2000, 96(3):925-932.

(56) References Cited

OTHER PUBLICATIONS

Henriksen et al., "Assessment of Osteoclast Number and Function: Application in the Development of New and Improved Treatment Modalities for Bone Diseases," Osteoporosis International, 2006, 18: 681-685.
International Search Report and Written Opinion for International Patent Application No. PCT/US2014/029661 mailed Jun. 11, 2014.
International Search Report and Written Opinion for International Patent Application No. PCT/US2014/029664 mailed Jun. 11, 2014.
International Search Report and Written Opinion for International Patent Application No. PCT/US2019/068311 mailed Feb. 7, 2020.
International Search Report and Written Opinion for International Patent Application No. PCT/US2024/053261 mailed Feb. 6, 2025.
Judge et al., "Potassium Channel Blockers in Multiple Sclerosis: Neuronal Kv Channels and Effects of Symptomatic Treatment," Pharmacology & Therapeutics, 2006, 224-259.
Kung et al., "Structure Activity Relationships of Quinoline-Containing c-Met Inhibitors," European Journal of Medicinal Chemistry 43, 2008, 1321-1329.
Kuster et al., "Kinase Inhibitors Methods and Protocols," Methods in Molecular Biology, 2012, 1-46.
Lewitt, "Levodopa for the Treatment of Parkinson's Disease," New England Journal of Medicine, 2008, 359: 2468-2476.
Luo et al., "Principles of Cancer Therapy: Oncogene and Non-oncogene Addiction," Cell, 2009, 36: 823-837.
Minkin, "Bone Acid Phosphatase: Tartrate-Resistant Acid Phosphatase as a Marker of Osteoclast Function," Calcified Tissue International, 1982, 34: 285-290.
Mitchell et al., "Amyotrophic Lateral Sclerosis," The Lancet, 2007, 369: 2031-2041.
National Cancer Institute (http://www.cancer.gov) 2014.
O'Brien et al., "Vascular Cognitive Impairment," The Lancet Neurology, 2003, 2: 89-98.
Ohno et al., "A c-fms tyrosine kinase inhibitor, Ki20227, suppresses osteoclast differentiation and osteolytic bone destruction in a bone metastasis model," Mol Cancer Ther., 2006, 5(11):2634-2643.
Pyonteck et al., "CSF-1R inhibition alters macrophage polarization and blocks glioma progression," Nature Medicine, 2013, 19(10):1264-1274.
Reber et al., "Stem Cell Factor and its Receptor c-Kit as Targets for Inflammatory Diseases," European Journal of Pharmacology, 2006, 533: 327-340.
Roberts et al., "Antiangiogenic and Antitumor Activity of a Selective PDGFR Tyrosine Kinase Inhibitor, CP-673, 451," Cancer Research, 2005, 957-966.
Rubin et al., "KIT activation is a ubiquitous feature of gastrointestinal stromal tumors," Cancer Research, 2001, 61(22):8118-8121.
Shah et al., "Current Approaches in the Treatment of Alzheimer's Disease," Biomedicine & Pharmacotherapy, 2008, 62: 199-207.
Smith, B. D. et al., "Vimseltinib: A Precision CSF1R Therapy for Tenosynovial Giant Cell Tumors and Diseases Promoted by Macrophages", Molecular Cancer Therapeutics, vol. 20, No. 11, (Aug. 25, 2021), pp. 2098-2109, XP093171464.
Tap et al., "Pexidartinib Versus Placebo for Advanced Tenosynovial Giant Cell Tumour (ENLIVEN): a Randomised Phase 3 Trial," Lancet, 2019, 394: 478-487.
Tap et al., "Structure-Guided Blockade of CSF1R Kinase in Tenosynovial Giant-Cell Tumor," New England Journal of Medicine, 2015, 373(5):428-437.
Tap, W. D. et al., "Efficacy, safety, and patient-reported outcomes of vimseltinib in patients with tenosynovial giant cell tumor: Results from the phase 3 MOTION trial", Journal of Clinical Oncology, vol. 42, No. 16_suppl, (Jun. 1, 2024), pp. 11500-11500, XP093241007.
Tap, W. D. et al., "MOTION: A randomized, phase 3, placebo-controlled, double-blind study of vimseltinib (DCC-3014) for the treatment of tenosynovial giant cell tumour", Journal of Clinical Oncology, vol. 40, No. 16_suppl., (Jun. 2, 2022), pp. TPS11590-TPS11590, XP093241022.
Wen et al., "Osteosarcoma Cell-Intrinsic Colony Stimulating Factor-1 Receptor Functions to Promote Tumor Cell Metastasis Through JAG1 Signaling," American Journal of Cancer Research, 2017, 7(4): 801-815.
Yasuda et al., "The Stem Cell Factor/C-Kit Receptor Pathway Enhance Proliferation and Invasion of Pancreatic Cancer Cells," Molecular Cancer, 2006, 5(46): 1-10.
U.S. Appl. No. 19/295,254, filed Aug. 8, 2025, Pending.
PCT/US2024/060067 International Search Report and Written Opinion mailed Apr. 10, 2025, 48 pages.
PCT/US2024/058998 International Search Report and Written Opinion mailed Jun. 2, 2025, 11 pages.
PCT/US2025/027042 International Search Report and Written Opinion mailed Jul. 23, 2025, 12 pages.

* cited by examiner

* = spinning sidebands

SOLID STATE FORMS OF A KINASE INHIBITOR

CROSS-REFERENCE

This application is a continuation of U.S. application Ser. No. 18/971,800 filed on Dec. 6, 2024, which claims priority to U.S. Provisional Application No. 63/607,617 filed Dec. 8, 2023 and U.S. Provisional Application No. 63/650,144 filed May 21, 2024, the contents of each of which are incorporated herein by reference in their entireties.

The present disclosure relates to solid-state forms of the compound represented by Formula (I), their pharmaceutical compositions, processes for their preparation, and methods for their use.

BACKGROUND

Colony-stimulating factor 1 receptor (CSF-1R) and its ligand, colony stimulating factor 1 (CSF-1) together form a lineage dependency for normal macrophage development and differentiation from monocytes. As such, tumor-associated macrophages (TAMs) are dependent on CSF-1R (also known as FMS) kinase activity for proliferation, and maintenance of their differentiated state and immunosuppressive phenotype. The role of TAMs in promoting an invasive and immunosuppressive tumor microenvironment is well established. TAMs mediate tumor growth, angiogenesis, invasiveness, metastasis, and immunosuppression through the secretion of and response to a variety of cytokines or other soluble factors. TAMs are educated by tumors to enable escape from immune surveillance by dampening a cytotoxic T cell immune response, thereby shielding the tumor from T cell eradication. For example, TAMs express PD-L1, a known immunosuppressive checkpoint that induces T cell anergy.

Several inhibitors targeting CSF-1R have advanced into the clinic as direct antitumor therapies and potential immunotherapies. Many of these drugs also inhibit the closely related Type III receptor tyrosine kinases KIT, PDGFRα/β and FLT3, which may limit their utility due to off-target toxicity. Antibodies targeting CSF-1R are much more specific yet result in >10,000-fold increases in plasma levels of CSF-1, the ligand for CSF-1R, due to blockade of CSF-1 clearance, among other drawbacks.

Tenosynovial giant cell tumor (TGCT) is a proliferative and inflammatory disease that includes entities formerly known as pigmented villonodular synovitis (PVNS), and giant cell tumor of the tendon sheath (GCTTS), intraarticular or extraarticular. It is a rare neoplasm of the joint or tendon sheath, with destructive proliferation of synovial like mononuclear cells, admixed with multinucleate giant cells, foam cells, siderophages and inflammatory cells. There are two types of TGCT: the local or nodular form (where the tumor involves the tendons that support the joint, or in one area of the joint) and the diffuse form (where the entire lining of the joint is involved). Treatment is surgical excision of the tumor. However, it is often difficult to perform a marginal excision for the diffuse form of TGCT resulting in a high recurrence rate. It can be characterized by overexpression of CSF-1.

Thus, there is a need for selective small-molecule CSF-1R inhibitors that are useful in the treatment of disorders associated with the proliferation of TAMs including solid tumors of various cancers and treatment of mesenchymal tumors including TGCT and diffuse-type tenosynovial giant cell tumor (DTGCT).

Different solid-state forms, including solvated forms, of an active pharmaceutical ingredient may have different properties. Different solid-state forms and solvates of an active pharmaceutical ingredient may give rise to a variety of other polymorphs or crystalline forms, co-crystals, solvates and other solid-state forms with improved properties. Differences in physical, mechanical, chemical, or physicochemical properties, such as stability, solubility, melting point, hardness, shelf-life, or compressibility, may result in improvement in bioavailability, dissolution profile, process reproducibility, ease of manufacturing, or formulation.

Particle size is also a critical attribute of an active pharmaceutical ingredient (API) and plays a critical role in the development and commercialization of solid dosage forms. Particle size distribution (PSD) has a crucial impact on several aspects of a drug, e.g., absorption rate, dissolution rate, bioavailability, or stability. These factors are crucial parameters for drug efficacy and safety. PSD affects the flowability and ease of handling of the API and excipients, and how the particles move in relation to each other and their container (e.g., capsule, tablet, etc.). Very small particle size is associated with decreased flowability. Reduced flow can cause quality issues such as variations in the weight, homogeneity, or uniformity of the formulation. PSD also influences the storage and packaging properties of the formulation of the API. It plays a crucial role in the manufacturability of the API and the reproducibility of its manufacturing process. In view of all these considerations, there is a need for tightly controlling the PSD in solid-state forms.

SUMMARY

Described herein, in part, are novel solid-state forms of the compound represented by Formula (I):

(I)

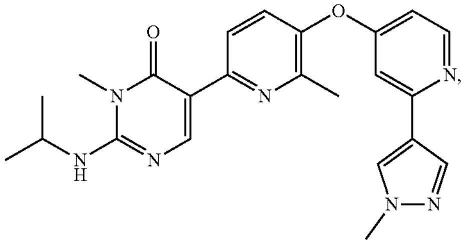

pharmaceutical compositions comprising the solid-state forms, processes of making the solid-state forms, and methods of using the solid-state forms.

Provided herein, in part, are methods of preparing solid-state forms of the compound represented by Formula (I) and the use of these solid-state forms for the preparation of pharmaceutical compositions and/or pharmaceutical formulations of the compound represented by Formula (I).

Provided herein, in part, are methods of treating diseases and conditions including, but not limited to a tenosynovial giant cell tumor (TGCT) including diffuse-type tenosynovial giant cell tumor (DTGCT) and localized tenosynovial giant cell tumor. Provided herein, in part, are methods of treating diseases and conditions including, but not limited to graft versus host disease (GVHD) including chronic graft versus host disease (cGVHD) and acute graft versus host disease (aGVHD). Provided herein, in part, are methods of treating diseases and conditions including, but not limited to a neurodegenerative diseases or conditions including Parkinson's disease (PD), Alzheimer's Disease (AD), frontotemporal dementia (FTD), amyotrophic lateral sclerosis (ALS), mild cognitive impairment, and Huntington's Disease (HD). Provided herein, in part, are methods of treating diseases and conditions including, but not limited to, solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma, wherein solid tumors include, but are not limited to, ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumors. Provided herein, in part, are methods of treating diseases and conditions including, but not limited to tumors known to have expression of colony-stimulating factor 1 receptor (CSF-1R) or its ligands, colony stimulating factor-1 (CSF-1), or interleukin (IL)-34 (IL-34). Provided herein, in part, are methods of treating diseases and conditions including, but not limited to metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis. Provided herein, in part, are methods of treating diseases and conditions using the solid-state forms of the compound represented by Formula (I), and pharmaceutical compositions and/or pharmaceutical formulations thereof.

DETAILED DESCRIPTION

Figure 1:
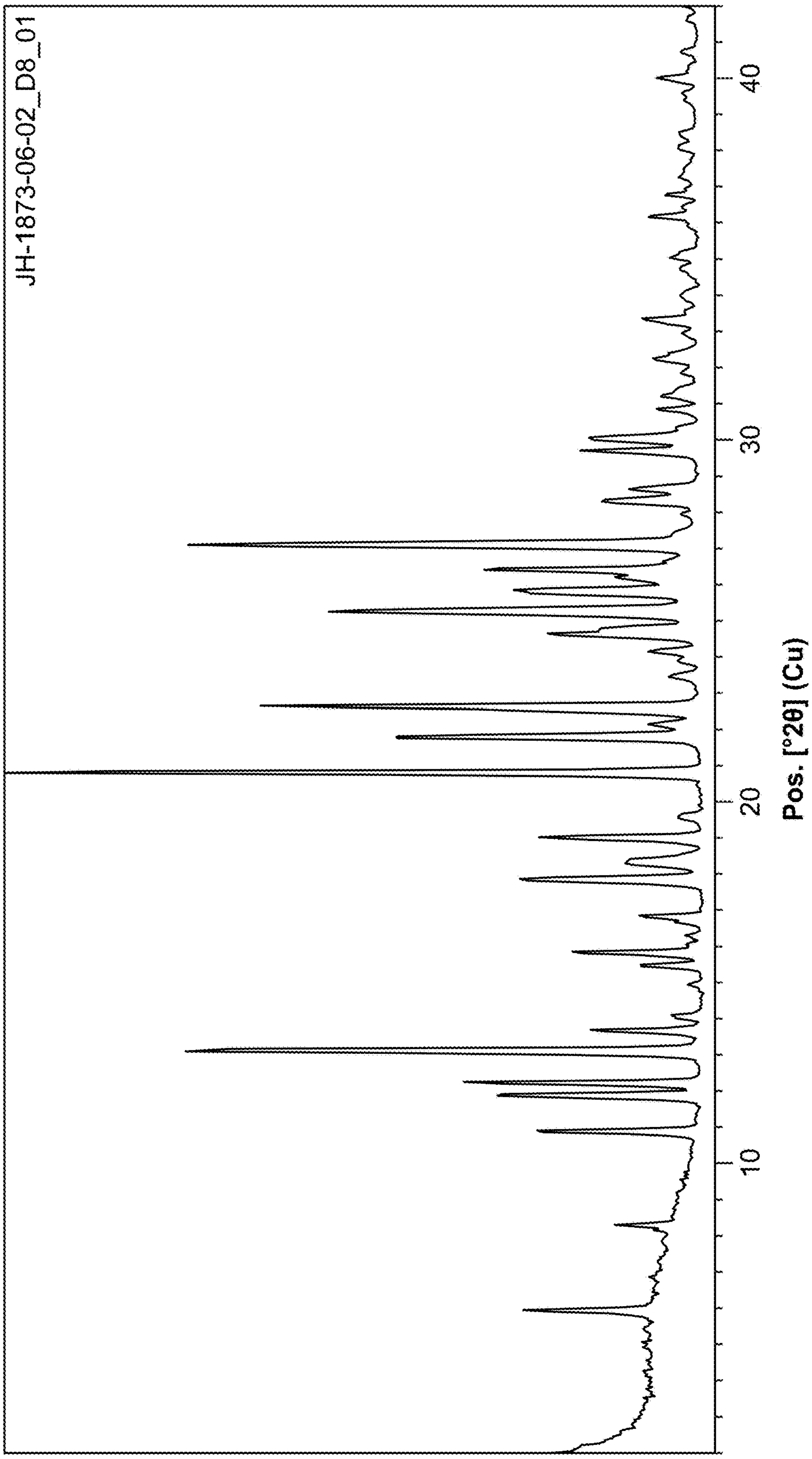
FIG. 1 shows an X-ray powder diffraction ("XRPD") pattern of the crystalline dihydrate form of the compound represented by Formula (I).

The features and other details of the disclosure will now be more particularly described. Certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

DEFINITIONS

The compound represented by Formula (I) as described herein is also referred to as "vimseltinib." The compound represented by Formula (I) as described herein also refers to 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one.

As used herein, the crystalline dihydrate form of the compound represented by Formula (I) is

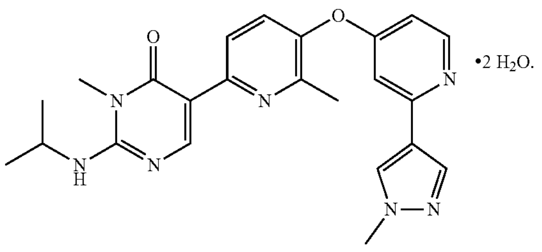 [SMILES: Cc1nc(-c2cnc(NC(C)C)n(C)c2=O)ccc1Oc1ccnc(-c2cnn(C)c2)c1]

The crystalline dihydrate form of the compound represented by Formula (I) is also referred to herein as "vimseltinib dihydrate."

Terms used in the singular will also include the plural. For example, "a" means one or more unless indicated otherwise.

All ranges recited herein include the endpoints, including those that recite a range "between" two values. The terms "substantially" and "about" are to be construed as modifying a term or value such that it is not an absolute. This includes, at very least, the degree of expected experimental variance, experimental error, technique variance, technique error and instrument variance, instrumental error for a given technique used to measure a value.

As used herein, "about" includes and describes the value or parameter per se. For example, "about x" includes and describes "x" per se. In some embodiments, the term "about" when used in association with a measurement, or used to modify a value, a unit, a constant, or a range of values, refers to variations of ±10%. "About" in context of XRPD and DSC means ±0.2° at 2-theta for XRPD peaks, ±3° C. for DSC, respectively.

As used herein, the term "adding" does not limit the order, method or how the materials being added are combined, unless indicated otherwise. For instance, "adding X to Y" may also describe "adding Y to X." Furthermore, "adding X and Y to Z" may also describe the various other combinations such as "adding X to Y and Z," "adding X and Z to Y," "adding Y to X and Z," "adding Y and Z to X," and "adding Z to X and Y."

As used herein, the term "excipient" refers to a substance that may be beneficial to include in a composition with an active agent. The term "excipient" includes inert substances as well as functional excipients that may result in beneficial properties of the composition. Exemplary excipients include but are not limited to polymers, glidants, sugars, lubricants, salts, buffers, fats, fillers, disintegrating agents, binders, surfactants, high surface area substrates, flavorants, carriers, matrix materials, diluents, and so forth.

As used herein, the terms "individual," "patient," or "subject" are used interchangeably and include any animal, including mammals, preferably mice, rats, other rodents, rabbits, dogs, cats, swine, cattle, sheep, horses, or primates, and most preferably humans. The compounds described herein can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like).

As used herein, the terms "pharmaceutically acceptable" or "pharmacologically acceptable" includes molecular entities and compositions that do not produce an adverse, allergic or other untoward reaction when administered to an animal, or a human, as appropriate. For human administration, preparations should meet sterility, pyrogenicity, and general safety and purity standards as required by FDA standards.

As used herein, the term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

As used herein, the term "pharmaceutical composition" as used herein refers to a composition comprising at least one compound as disclosed herein formulated together with one or more pharmaceutically acceptable carriers, excipients or diluents.

As used herein, the term "pharmaceutically acceptable salt(s)" refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts.

As used herein, the term "therapeutically effective amount" means the amount of the subject compound that will elicit the biological or medical response of a tissue, system or animal, (e.g., mammal or human) that is being sought by the researcher, veterinarian, medical doctor or other clinician. A compound described herein, e.g., the compound represented by Formula (I), is administered in therapeutically effective amounts to treat a condition, e.g., TGCT, GVHD, or neurodegenerative diseases. Alternatively, a therapeutically effective amount of a compound is the quantity required to achieve a desired therapeutic and/or prophylactic effect, such as an amount which results in the prevention of or a decrease in the symptoms associated with the condition.

As used herein and unless otherwise indicated, the terms "treat," "treating" and "treatment" refer to the alleviation of a disease or disorder and/or at least one of its attendant symptoms, and includes any effect, e.g., lessening, reducing, modulating, or eliminating, that results in the improvement of the condition, disease, disorder and the like.

As used herein and unless otherwise indicated, the terms "prevent," "preventing" and "prevention" refer to the inhibition of a symptom of a disease or disorder or the disease itself.

As used herein, the term "active agent" means a drug, medicament, pharmaceutical, therapeutic agent, for example, the compound represented by Formula (I), as described herein.

As used herein, the term "oral formulation," refers to a composition or medium used to administer a compound as disclosed herein (e.g., the compound represented by Formula (I)) to a subject in need thereof by oral administration. Typically, an oral formulation is administered via the mouth, however, "oral formulation" as used herein is intended to cover any substance which is administered to a subject and is absorbed across a membrane, e.g., a mucosal membrane, of the gastrointestinal tract, including, e.g., the mouth, esophagus, stomach, small intestine, large intestine, and colon. In one embodiment, the oral formulation is a solid oral formulation. In one embodiment, the oral formulation is a solid oral formulation administered to a subject in need thereof via the mouth.

As used herein, the terms "isolated," "isolating" in reference to solid-state forms of the compound represented by Formula (I) corresponds to a solid-state form of the compound represented by Formula (I) that is physically separated from the reaction mixture or the slurry.

A reaction mixture may be characterized herein as being at or allowed to come to "room temperature" or "ambient temperature," often abbreviated as "RT" or "rt." This means that the temperature of the thing is close to, or the same as, that of the space, e.g., the room or fume hood, in which the thing is located. Typically, room temperature is about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters (mL) of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 mL reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is about 8 to about 24 hours, or about 10-18 hours, typically about 16 hours.

As used herein, the term "reduced pressure" refers to a pressure that is less than atmospheric pressure. For example, a reduced pressure employed, for example in the context of drying conditions, is about 10 mbar to about 50 mbar, preferably 30-50 mbar.

As used herein, and unless indicated otherwise, the terms "wet crystalline form" or "wet form" or "wet cake" refer to a crystalline form or solid that was not dried using any conventional techniques to remove residual solvent. Examples of such conventional techniques can be, but are not limited to, evaporation, vacuum drying, oven drying, drying under nitrogen flow, etc.

As used herein, "TAM" refers to tumor-associated macrophage.

As used herein, "TGCT" refers to tenosynovial giant cell tumor.

As used herein, "DTGCT" refers to diffuse or diffuse-type tenosynovial giant cell tumor.

As used herein, "GCTTS" refers to giant cell tumor of the tendon sheath.

As used herein, "PVNS" refers to pigmented villonodular synovitis.

As used herein, "GVHD" refers to graft versus host disease.

As used herein, "AD" refers to Alzheimer's Disease.

As used herein, "PD" refers to Parkinson's Disease.

As used herein, "HD" refers to Huntington's Disease.

As used herein, "FTD" refers to frontotemporal dementia.

As used herein, "ALS" refers to amyotrophic lateral sclerosis.

In general, a solid-state form, such as a crystal form or amorphous form, may be referred to herein as being characterized by graphical data "as depicted in" or "as substantially depicted in," for example, FIGS. 1-9. This will be understood to describe the solid-state form of the compound represented by Formula (I) characterized with the graphical data having such small variations, as is well known to the skilled person. Such data include, for example, powder X-ray diffractograms and solid-state NMR spectra. As is well-known in the art, the graphical data potentially provides additional technical information to further define the respective solid-state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of the compound represented by Formula (I) referred to herein as being characterized by graphical data "as depicted in" or "as substantially depicted in" a Figure will thus be understood to include any crystal forms of the compound represented by Formula (I) characterized with the graphical data having such small variations, as is well known to the skilled person, in comparison with the Figure.

In addition, where a reference is made to a Figure, it is permissible to, and this document includes and contemplates, the selection of any number of data points illustrated in the figure that uniquely define that crystalline form, within any associated and recited margin of error, for purposes of identification.

As used herein and unless otherwise indicated, the terms "polymorph" and "polymorphic form" refer to solid crystalline forms of a compound or complex. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability).

As used herein, a polymorphic form may be described by reference to patterns, spectra, or other graphical data as "substantially" shown or depicted in a figure, or by one or more data points. It will be appreciated that patterns, spectra, and other graphical data can be shifted in their positions, relative intensities, or other values due to a number of factors known to those of skill in the art. For example, in the crystallographic and powder X-ray diffraction arts, shifts in peak positions or the relative intensities of one or more peaks of a pattern can occur because of, without limitation, the equipment used, the sample preparation protocol, preferred packing and orientations, the radiation source, operator error, method and length of data collection, or the like. However, those of ordinary skill in the art will be able to compare the figures herein with patterns, etc. generated for an unknown form of, in this case, the compound represented by Formula (I), and confirm its identity with the forms disclosed herein. The same holds true for other techniques which may be reported herein.

The occurrence of different polymorphs is possible for some compounds. A single compound may give rise to a variety of solids having distinct physical properties, such as X-ray diffraction patterns, infrared absorption spectra, and NMR spectra. This variation in solid forms may be significant and may result in differences with respect to bioavailability, stability, and other differences for formulated pharmaceutical products. Because polymorphic forms can vary in their physical properties, regulatory authorities require that efforts shall be made to identify all polymorphic forms, e.g., crystalline, amorphous, solvate, hydrate, etc., of new drug substances.

While the existence and possible numbers of polymorphic forms for a given pharmaceutical compound cannot be predicted, different polymorphs can possess different properties such as stability, solubility, melting point, or compressibility. As a result, new forms of a pharmaceutically useful compound may provide an opportunity to improve its characteristics, and ultimately its performance. Further, discovery of additional polymorphic forms, including solvate polymorphs, may help in the identification of the polymorphic content of a batch of an active pharmaceutical ingredient. For example, in some cases, different polymorphs of the same drug can exhibit very different solubility and different dissolution rates.

Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

Polymorphs of a molecule can be obtained by a number of methods known in the art.

Such methods include, but are not limited to, melt recrystallization, melt cooling, solvent recrystallization, desolvation, rapid evaporation, rapid cooling, slow cooling, vapor diffusion and sublimation. Polymorphs can be detected, identified, classified and characterized using well-known techniques such as, but not limited to, differential scanning calorimetry (DSC), thermogravimetry (TGA), X-ray powder diffractometry (XRPD), single crystal X-ray diffractometry, vibrational spectroscopy, solution calorimetry, solid-state nuclear magnetic resonance (NMR), infrared (IR) spectroscopy, Raman spectroscopy, hot stage optical microscopy, scanning electron microscopy (SEM), electron crystallography and quantitative analysis, particle size analysis (PSA), surface area analysis, solubility, and rate of dissolution.

Different solid-state forms can be characterized by scattering techniques, e.g., x-ray powder diffraction (XRPD) pattern, by spectroscopic methods, e.g., infrared absorption fingerprint, Raman absorption fingerprint, nuclear magnetic resonance (e.g., NMR, solid-state NMR) spectroscopy (e.g., $^{1}H$, $^{13}C$, $^{19}F$), and by thermal techniques, e.g., differential scanning calorimetry (DSC) or differential thermal analysis (TGA). Described herein are polymorphs (solid-state forms) of the compound represented by Formula (I). These solid-state forms and their distinct crystal structures and physical properties are characterized by TGA, DSC (measurement of melting point and thermal behavior), XRPD, and NMR such as proton NMR spectrum ($^{1}H$ NMR) and solid-state NMR spectrum (e.g., $^{13}C$ ssNMR).

As used herein to refer to the spectra or data presented in graphical form (e.g., XRPD, IR, Raman and NMR spectra), and unless otherwise indicated, the term "peak" refers to a peak or other special feature that one skilled in the art would recognize as not attributable to background noise.

Generally, a diffraction angle (2θ, "2 theta") in X-ray powder diffractometry may have a variation in the range of ±0.2°. Therefore, the aforementioned diffraction angle values should be understood as including values in the range of about ±0.2°. Accordingly, the solid-state forms described here includes not only crystals whose peak diffraction angles in powder X-ray diffractometry completely coincide with each other, but also crystals whose peak diffraction angles coincide with each other with an error of about ±0.0.2°. Therefore, in the present specification, the phrase "having a diffraction peak at a diffraction angle (2θ±0.2° of 7.9°" means "having a diffraction peak at a diffraction angle (2θ) of 7.7° to 8.1°." Although the intensities of peaks in the x-ray powder diffraction patterns of different batches of a compound may vary slightly, the peak locations are characteristic for a specific polymorphic form. Alternatively, the term "about" means within an acceptable standard error of the mean, when considered by one of ordinary skill in the art. The relative intensities of the XRPD peaks can vary depending on the sample preparation technique, crystal size distribution, various filters used, the sample mounting procedure, and the particular instrument employed. Moreover, instrument variation and other factors can affect the 2-theta values. Therefore, the term "substantially" in the context of XRPD is meant to encompass that peak assignments can vary by plus or minus about 0.2 degree. Moreover, new peaks may be observed, or existing peaks may disappear, depending on the type of the machine or the settings (for example, whether a Ni filter is used or not).

Generally, a DSC thermogram may have a variation in the range of ±3° C. Therefore, the temperature values should be understood as including values in the range of ±3° C.

In general, provided herein are solid-state forms of the compound represented by Formula (I) that are substantially free of any other solid-state forms whether as individual forms or mixtures of other forms, unless indicated otherwise. For example, the dihydrate form of the compound represented by Formula (I) will be substantially free of other forms of compound of formula (I) which may include the crystalline anhydrous form or other solid-state forms or mixtures thereof. As used herein, "substantially free of any solid-state forms" means that the solid-state form of the compound represented by Formula (I) contains about 20% or less, about 10% or less, about 5% or less, about 2% or less, or about 1% or less, of any other solid-state form of the compound represented by Formula (I) as measured, for example, by XRPD. In some embodiments, the solid-state form of the compound represented by Formula (I) contains less than about 20%, less than about 10%, less than about 5%, less than about 4%, less than about 3%, less than about 2%, or less than about 1% of any other solid-state forms of the compound represented by Formula (I) as measured, for example, by XRPD. Thus, a solid-state form of the compound represented by Formula (I) described herein as substantially free of any other solid-state forms would be understood to contain greater than 80% (w/w), greater than 90% (w/w), greater than 95% (w/w), greater than 98% (w/w), or greater than 99% (w/w) of the said solid-state forms of the compound represented by Formula (I). Accordingly, in some embodiments, the described solid-state forms of the compound represented by Formula (I) may contain from 1% to 20% (w/w), from 5% to 20% (w/w), or from 5% to 10% (w/w) of one or more other solid-state forms of the compound represented by Formula (I).

As used herein, "substantially free" means that the solid-state forms of the present disclosure contain 20% (w/w) or less of other polymorphs, or, alternatively, of a specified polymorph of the compound represented by Formula (I). According to some embodiments, the solid-state forms of the present disclosure contain 10% (w/w) or less, 5% (w/w) or less, 2% (w/w), 1% (w/w) or less of other polymorphs, or specified polymorphs of the compound represented by Formula (I). In other embodiments, solid-state forms of the compound represented by Formula (I) of the present disclosure contain from 1% to 20% (w/w), from 5% to 20% (w/w), or from 5% to 10% (w/w) of other solid-state forms, or of a specified polymorph of the compound represented by Formula (I).

As used herein and unless otherwise indicated, the term "substantially pure" when used to describe a polymorph of a compound means a solid form of the compound that comprises that polymorph and is substantially free of other polymorphs of the compound. For example, the dihydrate form of the compound represented by Formula (I) will be substantially pure while substantially free of other forms of compound of formula (I) which may include the crystalline anhydrous form or other solid-state forms or mixtures thereof. A representative substantially pure polymorph comprises greater than about 80% by weight of one polymorphic form of the compound and less than about 20% by weight of other polymorphic forms of the compound. In some embodiments, a representative substantially pure polymorph comprises greater than about 90% by weight of one polymorphic form of the compound and less than about 10% by weight of the other polymorphic forms of the compound. In some embodiments, a representative substantially pure polymorph comprises greater than about 95% by weight of one polymorphic form of the compound and less than about 5% by weight of the other polymorphic forms of the compound In some embodiments, a representative substantially pure polymorph comprises greater than about 97% by weight of one polymorphic form of the compound and less than about 3% by weight of the other polymorphic forms of the compound. In some embodiments, a representative substantially pure polymorph comprises greater than about 98% by weight of one polymorphic form of the compound and less than about 2% by weight of the other polymorphic forms of the compound. In some embodiments, a representative substantially pure polymorph comprises greater than about 99% by weight of one polymorphic form of the compound and less than about 1% by weight of the other polymorphic forms of the compound.

The content of solid-state forms is typically measured by any suitable method appreciated by a skilled person in the art, for example XRPD, solid-state NMR, IR, Raman, or DSC.

Crystalline and partially crystalline solid forms may be prepared by a variety of methods including, but not limited to, for example, crystallization or recrystallization from a suitable solvent mixture; sublimation; growth from a melt; solid-state transformation from another phase; crystallization from a supercritical fluid; antisolvent addition; slurrying at various temperatures (e.g., at room temperature, at 10° C., at 15° C., at 40° C., at 50° C., at 70° C.); solid vapor diffusion; liquid vapor diffusion; evaporation; slow cooling, polymer induced crystallization; milling; spray freezing; spray congealing; lyophilization; and humidity induced crystallization. Techniques for crystallization or recrystallization of crystalline and partially crystalline solid forms of a solvent mixture include, but are not limited to, for example, evaporation of the solvent; decreasing the temperature of the solvent mixture; crystal seeding of a supersaturated solvent mixture of the compound and/or salt thereof; crystal seeding a supersaturated solvent mixture of the compound and/or a salt from thereof; freeze drying the solvent mixture; temperature cycling; and adding anti-solvents (countersolvents) to the solvent mixture. As used herein, the term "anti-solvent" refers to a liquid that, when combined with a solution of the compound represented by Formula (I), reduces solubility of the compound represented by Formula (I) in the solution, causing crystallization or precipitation in some instances spontaneously, and in other instances with additional steps, such as seeding, cooling, scratching and/or concentrating. Crystals of drugs, including polymorphs, methods of preparation, and characterization of drug crystals, are discussed in Solid-State Chemistry of Drugs, S. R. Byrn, R. R. Pfeiffer, and J. G. Stowell, 2nd Edition, SSCI, West Lafayette, Ind. (1999). In a crystallization technique in which solvent is employed, the solvent(s) are typically chosen based on one or more factors including, but not limited to, for example, solubility of the compound; crystallization technique utilized; and vapor pressure of the solvent. Combinations of solvents may be employed. For example, the compound may be solubilized in a first solvent to afford a solution to which antisolvent is then added to decrease the solubility of the compound represented by Formula (I) in the solution and precipitate the formation of crystals. An antisolvent is a solvent in which a compound has low solubility. In one method that can be used in preparing crystals, a compound can be suspended and/or stirred in a suitable solvent to afford a slurry, which may be heated to promote dissolution. A cooled crystallization mixture may be filtered under vacuum and the isolated solid product washed with a suitable solvent, such as, for example, cold recrystallization solvent. After being washed, the product may be dried under a nitrogen purge to afford the desired solid form. After being washed, the product may be dried under vacuum to afford the desired solid form.

The present disclosure encompasses crystalline solid-state forms of the compound represented by Formula (I)

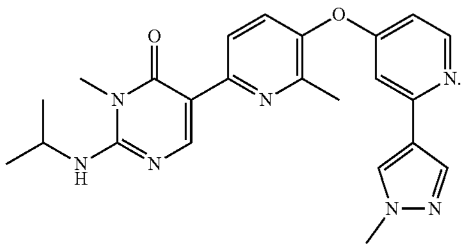 [SMILES: Cc1nc(-c2cnc(NC(C)C)n(C)c2=O)ccc1Oc1ccnc(-c2cnn(C)c2)c1]

Provided herein, in part, are crystalline solid-state forms of the compound represented by Formula (I), described herein as a crystalline dihydrate form and a crystalline anhydrous form, mixtures of these forms, and pharmaceutical compositions comprising these solid-state forms and mixtures thereof. In some embodiments, the crystalline solid-state form of the compound represented by Formula (I) of the disclosure is substantially free of any other forms of the compound represented by Formula (I), or of specified polymorphic forms of the compound represented by Formula (I), respectively.

Provided herein, in part are methods of using crystalline solid-state forms of the compound represented by Formula (I) designated as the crystalline dihydrate form and the crystalline anhydrous form, mixtures of these forms, pharmaceutical compositions comprising these solid-state forms and mixtures thereof. In further embodiments, this disclosure provides methods of making, isolating, and characterizing the crystalline solid-state forms.

Provided herein, in part, is solid-state crystalline 2-(isopropylamino)-3-methyl-5-(6-methyl-5-((2-(1-methyl-1H-pyrazol-4-yl)pyridin-4-yl)oxy)pyridin-2-yl)pyrimidin-4 (3H)-one dihydrate. In some embodiments, provided herein is a solid-state form, which is the crystalline dihydrate form of the compound represented by Formula (I).

Provided herein, in part, is solid-state crystalline anhydrous 2-(isopropylamino)-3-methyl-5-(6-methyl-5-((2-(1-methyl-1H-pyrazol-4-yl)pyridin-4-yl)oxy)pyridin-2-yl)pyrimidin-4 (3H)-one. In some embodiments, provided herein is a solid-state form, which is the crystalline anhydrous form of the compound represented by Formula (I).

Provided herein, in part, are pharmaceutical compositions and single unit dosage forms comprising one or more crystalline solid-state forms of the compound represented by Formula (I).

Provided herein, in part, are methods for the treatment or prevention of a variety of diseases and disorders, which comprise administering to a patient in need of such treatment or prevention a therapeutically effective amount of one or more crystalline solid-state forms of the compound represented by Formula (I).

Crystalline Dihydrate Form

In some embodiments, provided herein is a dihydrate form of the compound represented by Formula (I),

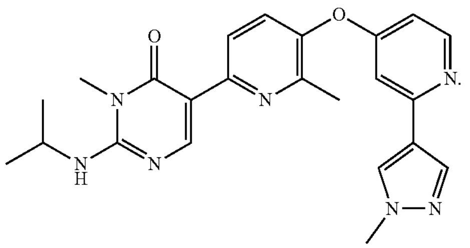 [SMILES: Cc1nc(-c2cnc(NC(C)C)n(C)c2=O)ccc1Oc1ccnc(-c2cnn(C)c2)c1]

(I)

In some embodiments, provided herein is a solid-state form, which is a crystalline dihydrate form of the compound represented by Formula (I).

In some embodiments, provided herein is the crystalline dihydrate form of the compound represented by Formula (I), having an XRPD pattern peaks, in terms of 2-theta, at about 5.9°, about 10.9°, about 11.9°, about 13.7°, about 16.8°, and about 27.1° as measured by CuKα radiation.

In some embodiments, provided herein is the crystalline dihydrate form of the compound represented by Formula (I), having an XRPD pattern comprising peaks, in terms of 2-theta, at about 5.9°, about 10.9°, about 11.9°, about 13.7°, about 16.8°, about 27.1°, about 28.3° and about 28.7° as measured by CuKα radiation.

In some embodiments, provided herein is the crystalline dihydrate form of the compound represented by Formula (I), having an XRPD pattern comprising peaks, in terms of 2-theta, at about 10.9°, about 16.8°, and about 27.1° as measured by CuKα radiation.

In some embodiments, provided herein is the crystalline dihydrate form of the compound represented by Formula (I), having an XRPD pattern comprising a peak, in terms of 2-theta, at about 10.9 as measured by CuKα radiation.

In some embodiments, provided herein is the crystalline dihydrate form of the compound represented by Formula (I) having an XRPD pattern substantially as shown in FIG. 1 or Table 6.

In some embodiments, provided herein is the crystalline dihydrate form of the compound represented by Formula (I), having a differential scanning calorimetry (DSC) thermogram comprising an endothermic event with onset between about 75° C. and about 95° C. In some embodiments, provided herein is the crystalline dihydrate form of the compound represented by Formula (I), having a differential scanning calorimetry (DSC) thermogram comprising an endothermic event with onset at about 95° C. In some embodiments, provided herein is the crystalline dihydrate form of the compound represented by Formula (I), having a differential scanning calorimetry (DSC) thermogram comprising an endothermic peak at about 108° C.

In some embodiments, provided herein is the crystalline dihydrate form of the compound represented by Formula (I), having a differential scanning calorimetry (DSC) thermogram comprising an exothermic event with onset between about 123° C. to about 150° C. In some embodiments, provided herein is the crystalline dihydrate form of the compound represented by Formula (I), having a differential scanning calorimetry (DSC) thermogram comprising an exothermic event with onset at about 141° C. In some embodiments, provided herein is the crystalline dihydrate form of the compound represented by Formula (I), having a differential scanning calorimetry (DSC) thermogram comprising an exothermic peak at about 146° C.

In some embodiments, provided herein is the crystalline dihydrate form of the compound represented by Formula (I), having a differential scanning calorimetry (DSC) thermogram comprising an endothermic event with onset between about 210° C. to about 220° C. In some embodiments, provided herein is the crystalline dihydrate form of the compound represented by Formula (I), having a differential scanning calorimetry (DSC) thermogram comprising an endothermic event with onset at about 214° C. In some embodiments, provided herein is the crystalline dihydrate form of the compound represented by Formula (I), having a differential scanning calorimetry (DSC) thermogram comprising an endothermic peak at about 215° C.

In some embodiments, provided herein is the crystalline dihydrate form of the compound represented by Formula (I), having a differential scanning calorimetry (DSC) thermogram comprising an endothermic event with onset between about 75° C. and about 95° C., an exothermic event with onset between about 123° C. to about 150° C., and an endothermic peak at about 215° C.

In some embodiments, provided herein is the crystalline dihydrate form of the compound represented by Formula (I), having a differential scanning calorimetry (DSC) thermogram comprising an endothermic event at about 108° C., an exothermic event at about 146° C., and an endothermic peak at about 215° C.

Figure 2:
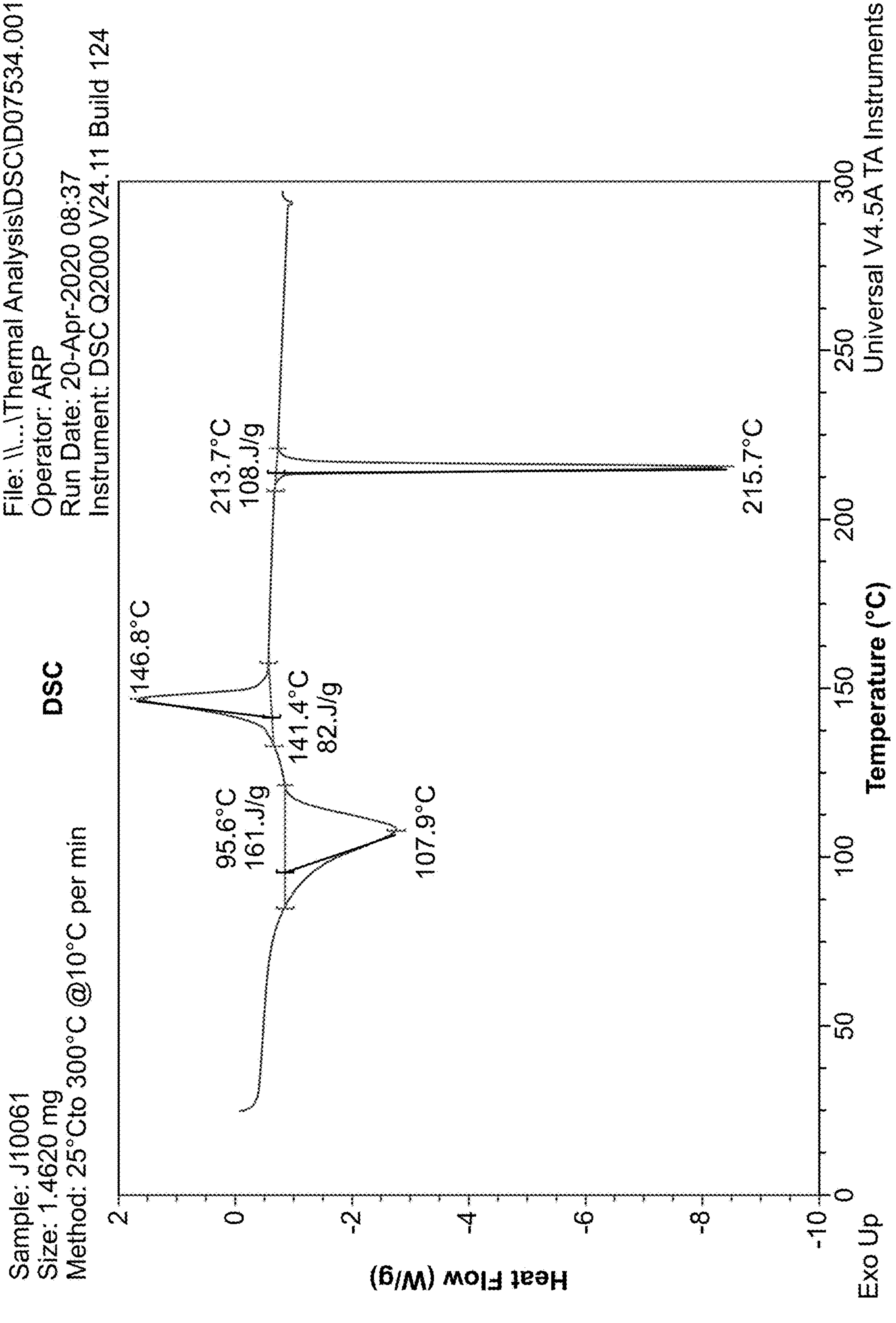
FIG. 2 shows a differential scanning calorimetry ("DSC") thermogram of the crystalline dihydrate form of the compound represented by Formula (I).

In some embodiments, provided herein is the crystalline dihydrate form of the compound represented by Formula (I) having a DSC thermogram substantially as shown in FIG. 2.

In some embodiments, provided herein is the crystalline dihydrate form of the compound represented by Formula (I) having a DSC thermogram comprising a sharp endothermic peak at about 215° C.

Figure 3:
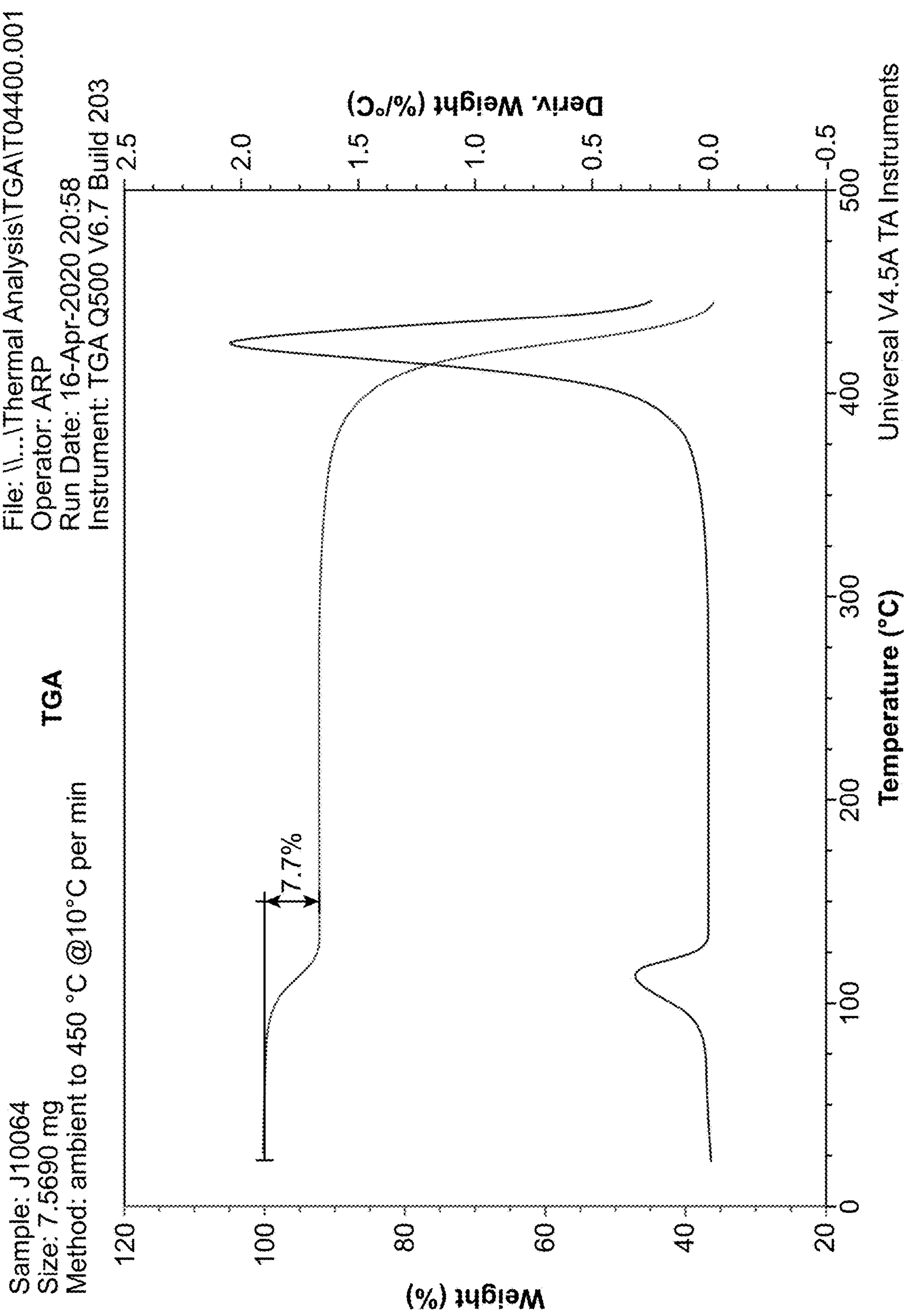
FIG. 3 shows a thermogravimetric analysis ("TGA") thermogram of crystalline dihydrate form of the compound represented by Formula (I) derived from Example 2.

In some embodiments, provided herein is the crystalline dihydrate form of the compound represented by Formula (I) having a TGA thermogram substantially as shown in FIG. 3.

Figure 4:
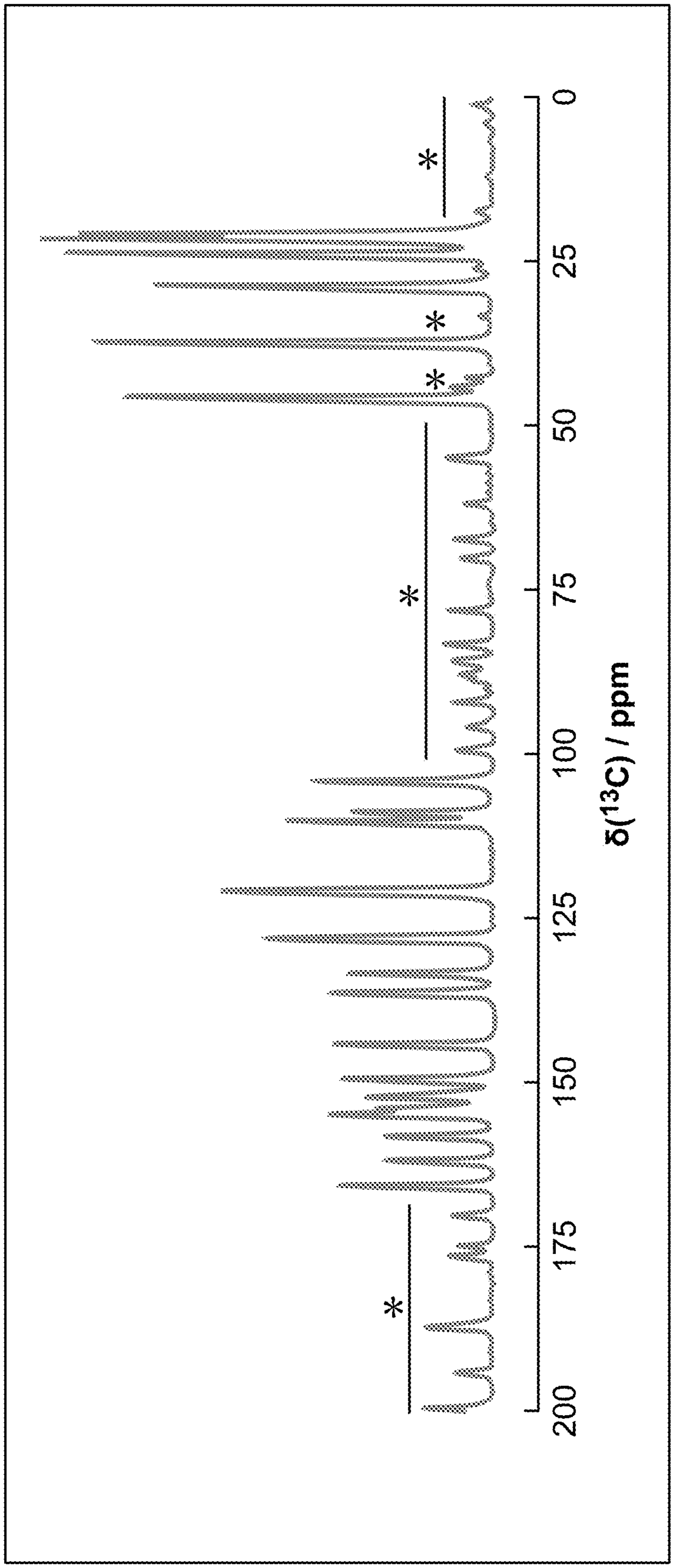
FIG. 4 shows a $^{13}C$ solid-state NMR ("ssNMR") spectrum of the crystalline dihydrate form of the compound represented by Formula (I).

In some embodiments, provided herein is the crystalline dihydrate form of the compound represented by Formula (I) having a ssNMR spectrum substantially as shown in FIG. 4.

In some embodiments, provided herein is the crystalline dihydrate form of the compound represented by Formula (I) having an XRPD pattern substantially as shown in FIG. 1, a DSC thermogram substantially as shown in FIG. 2, a TGA thermogram substantially as shown in FIG. 3, and an ssNMR spectrum substantially as shown in FIG. 4.

In some embodiments, provided herein is the crystalline dihydrate form of the compound represented by Formula (I) which is substantially pure.

In some embodiments, provided herein is the crystalline dihydrate form of the compound represented by Formula (I), which has a chemical purity of greater than 80% by weight.

In some embodiments, provided herein is the crystalline dihydrate form of the compound represented by Formula (I), which has a chemical purity of greater than 90% by weight.

In some embodiments, provided herein is the crystalline dihydrate form of the compound represented by Formula (I), which has a chemical purity of greater than 95% by weight.

In some embodiments, provided herein is the crystalline dihydrate form of the compound represented by Formula (I), which has a chemical purity of greater than 97% by weight.

In some embodiments, provided herein is the crystalline dihydrate form of the compound represented by Formula (I), which has a chemical purity of greater than 98% by weight.

In some embodiments, provided herein is the crystalline dihydrate form of the compound represented by Formula (I), which has a chemical purity of greater than 99% by weight.

For example, in some embodiments, the chemical purity of the crystalline dihydrate form of the compound represented by Formula (I) is at least about 99.9%, about 99.8%, about 99.7%, about 99.6%, about 99.5%, about 99.4%, about 99.3%, about 99.2%, about 99.1%, about 99.0%, about 98%, about 97%, about 96%, or about 95% pure. Chemical purity may be determined using methods known to those skilled in the area (for example, HPLC chromatography with a suitable solvent and column detecting a wavelength of 210 nm). In some embodiments, the substantial purity is determined on a weight percent basis. In some embodiments, the substantial purity is determined on an area under the curve basis.

In some embodiments, provided herein is a crystalline dihydrate form of the compound represented by Formula (I), having not more than about 10 mol %, not more than about 5 mol %, not more than about 3 mol %, or not more than about 1 mol % of other solid-state forms of the compound represented by Formula (I). In some embodiments, the crystalline dihydrate forms of the compound represented by Formula (I), has not more than about 10 mol % of other solid-state forms of the compound represented by Formula (I). In some embodiments, the crystalline dihydrate forms of the compound represented by Formula (I), has not more than about 9 mol % of other solid-state forms of the compound represented by Formula (I). In some embodiments, the crystalline dihydrate forms of the compound represented by Formula (I), has not more than about 8 mol % of other solid-state forms of the compound represented by Formula (I). In some embodiments, the crystalline dihydrate forms of the compound represented by Formula (I), has not more than about 7 mol % of other solid-state forms of the compound represented by Formula (I). In some embodiments, the crystalline dihydrate forms of the compound represented by Formula (I), has not more than about 6 mol % of other solid-state forms of the compound represented by Formula (I). In some embodiments, the crystalline dihydrate forms of the compound represented by Formula (I), has not more than about 5 mol % of other solid-state forms of the compound represented by Formula (I). In some embodiments, the crystalline dihydrate forms of the compound represented by Formula (I), has not more than about 4 mol % of other solid-state forms of the compound represented by Formula (I). In some embodiments, the crystalline dihydrate forms of the compound represented by Formula (I), has not more than about 3 mol % of other solid-state forms of the compound represented by Formula (I). In some embodiments, the crystalline dihydrate forms of the compound represented by Formula (I), has not more than about 2 mol % of other solid-state forms of the compound represented by Formula (I). In some embodiments, the crystalline dihydrate forms of the compound represented by Formula (I), has not more than about 1 mol % of other solid-state forms of the compound represented by Formula (I).

In some embodiments, provided herein is a crystalline dihydrate form of the compound represented by Formula (I), prepared by a process comprising:

(i) providing a mixture of a compound represented by Formula (I) and a solvent;

(ii) charging the mixture with milled seed material of a dihydrate form of the compound represented by Formula (I)

(iii) further charging the mixture of (ii) with a solvent to obtain a charged suspension system;

(iv) cooling the charged suspension system to result in a solid precipitate; and (v) isolating the resulting solid precipitate to obtain the crystalline dihydrate form.

In some embodiments, the solvent in step (i) is selected from the group consisting of water, alcohol, ketone, ether, ester, halogenated alkane, amide, sulfone, acid, nitro compound, methanol, ethanol, n-propanol, iso-propanol, butanol, acetone, methyl ethyl ketone (MEK), methyl isobutyl ketone (MIBK), methyl acetate, ethyl acetate, propyl acetate, diethyl ether, tetrahydrofuran (THF), 2-methyl THF, 2,5-dimethyl THF, 2,2,5,5-tetramethyl THF, acetonitrile, methylene chloride, toluene, 1,1,1-trichloroethane, dimethyl acetamide (DMAC), nitromethane, acetic acid, and dimethyl sulfoxide (DMSO), and a combination thereof. For example, the solvent is water, acetone, DMAC, or DMSO, or a combination thereof.

In some embodiments, the solvent in step (iii) is water.

In some embodiments, in step (iii), the charging is at a temperature above 25° C. For example, the charging is at a temperature of about 50° C., about 55° C., about 60° C., about 65° C., about 70° C., about 75° C., or about 80° C.

In some embodiments, in step (iv), the cooling is to about 15° C., about 20° C., about 25° C., about 30° C., or about 35° C. In some embodiments, in step (iv), the cooling is at about 0.01-10° C./min, such as, at about 0.1° C./min, 0.5° C./min, 1.0° C./min or about 2° C./min.

In some embodiments, the crystalline dihydrate form has a $d_{10}$ particle size of about 1-5 times the $d_{10}$ particle size of the milled seed material. In some embodiments, the crystalline dihydrate form has a $d_{10}$ particle size of about 2 times the $d_{10}$ particle size of the milled seed material. In some embodiments, the crystalline dihydrate form has a $d_{10}$ particle size of about 3 times the $d_{10}$ particle size of the milled seed material. In some embodiments, the crystalline dihydrate form has a $d_{10}$ particle size of about 4 times the $d_{10}$ particle size of the milled seed material. In some embodiments, the crystalline dihydrate form has a $d_{10}$ particle size of about 5 times the $d_{10}$ particle size of the milled seed material.

In some embodiments, the crystalline dihydrate form has a $d_{50}$ particle size of about 1-5 times the $d_{50}$ particle size of the milled seed material. In some embodiments, the crystalline dihydrate form has a $d_{50}$ particle size of about 2 times the $d_{50}$ particle size of the milled seed material. In some embodiments, the crystalline dihydrate form has a $d_{50}$ particle size of about 3 times the $d_{50}$ particle size of the milled seed material. In some embodiments, the crystalline dihydrate form has a $d_{50}$ particle size of about 4 times the $d_{50}$ particle size of the milled seed material. In some embodiments, the crystalline dihydrate form has a $d_{50}$ particle size of about 5 times the $d_{50}$ particle size of the milled seed material.

In some embodiments, the crystalline dihydrate form has a $d_{90}$ particle size of about 1-5 times the doo particle size of the milled seed material. In some embodiments, the crystalline dihydrate form has a $d_{90}$ particle size of about 2 times the $d_{90}$ particle size of the milled seed material. In some embodiments, the crystalline dihydrate form has a $d_{90}$ particle size of about 3 times the doo particle size of the milled seed material. In some embodiments, the crystalline dihydrate form has a $d_{90}$ particle size of about 4 times the $d_{90}$ particle size of the milled seed material. In some embodiments, the crystalline dihydrate form has a $d_{90}$ particle size of about 5 times the $d_{90}$ particle size of the milled seed material.

In some embodiments, the crystalline dihydrate form has a $d_{10}$ particle size distribution of about 2 microns to about 20 microns. In some embodiments, the crystalline dihydrate form has a $d_{10}$ particle size distribution of about 2 microns to about 12 microns. In some embodiments, the crystalline dihydrate form has a $d_{10}$ particle size distribution of about 2 microns to about 10 microns. In some embodiments, the crystalline dihydrate form has a $d_{10}$ particle size distribution of about 4 microns to about 10 microns. In some embodiments, the crystalline dihydrate form has a $d_{10}$ particle size distribution of about 4 microns to about 8 microns. In some embodiments, the crystalline dihydrate form has a $d_{10}$ particle size distribution of about 6 microns to about 8 microns.

In some embodiments, the crystalline dihydrate form has an average $d_{10}$ particle size distribution of about 2 microns. In some embodiments, the crystalline dihydrate form has an average $d_{10}$ particle size distribution of about 4 microns. In some embodiments, the crystalline dihydrate form has an average $d_{10}$ particle size distribution of about 6 microns. In some embodiments, the crystalline dihydrate form has an average $d_{10}$ particle size distribution of about 8 microns. In some embodiments, the crystalline dihydrate form has an average $d_{10}$ particle size distribution of about 10 microns. In some embodiments, the crystalline dihydrate form has an average $d_{10}$ particle size distribution of about 12 microns. In some embodiments, the crystalline dihydrate form has an average $d_{10}$ particle size distribution of about 14 microns. In some embodiments, the crystalline dihydrate form has an average $d_{10}$ particle size distribution of about 16 microns. In some embodiments, the crystalline dihydrate form has an average do particle size distribution of about 18 microns. In some embodiments, the crystalline dihydrate form has an average $d_{10}$ particle size distribution of about 20 microns.

In some embodiments, the crystalline dihydrate form has a $d_{50}$ particle size distribution of about 4 microns to about 40 microns. In some embodiments, the crystalline dihydrate form has a $d_{50}$ particle size distribution of about 4 microns to about 28 microns. In some embodiments, the crystalline dihydrate form has a $d_{50}$ particle size distribution of about 6 microns to about 26 microns. In some embodiments, the crystalline dihydrate form has a $d_{50}$ particle size distribution of about 6 microns to about 24 microns. In some embodiments, the crystalline dihydrate form has a $d_{50}$ particle size distribution of about 8 microns to about 24 microns. In some embodiments, the crystalline dihydrate form has a $d_{50}$ particle size distribution of about 10 microns to about 24 microns. In some embodiments, the crystalline dihydrate form has a $d_{50}$ particle size distribution of about 12 microns to about 24 microns. In some embodiments, the crystalline dihydrate form has a $d_{50}$ particle size distribution of about 14 microns to about 24 microns. In some embodiments, the crystalline dihydrate form has a $d_{50}$ particle size distribution of about 16 microns to about 24 microns. In some embodiments, the crystalline dihydrate form has a $d_{50}$ particle size distribution of about 16 microns to about 22 microns.

In some embodiments, the crystalline dihydrate form has an average $d_{50}$ particle size distribution of about 4 microns. In some embodiments, the crystalline dihydrate form has an average $d_{50}$ particle size distribution of about 6 microns. In some embodiments, the crystalline dihydrate form has an average $d_{50}$ particle size distribution of about 8 microns. In some embodiments, the crystalline dihydrate form has an average $d_{50}$ particle size distribution of about 10 microns. In some embodiments, the crystalline dihydrate form has an average $d_{50}$ particle size distribution of about 12 microns. In some embodiments, the crystalline dihydrate form has an average $d_{50}$ particle size distribution of about 14 microns. In some embodiments, the crystalline dihydrate form has an average $d_{50}$ particle size distribution of about 16 microns. In some embodiments, the crystalline dihydrate form has an average $d_{50}$ particle size distribution of about 18 microns. In some embodiments, the crystalline dihydrate form has an average $d_{50}$ particle size distribution of about 20 microns. In some embodiments, the crystalline dihydrate form has an average $d_{50}$ particle size distribution of about 22 microns. In some embodiments, the crystalline dihydrate form has an average $d_{50}$ particle size distribution of about 24 microns. In some embodiments, the crystalline dihydrate form has an average $d_{50}$ particle size distribution of about 26 microns. In some embodiments, the crystalline dihydrate form has an average $d_{50}$ particle size distribution of about 28 microns. In some embodiments, the crystalline dihydrate form has an average $d_{50}$ particle size distribution of about 30 microns. In some embodiments, the crystalline dihydrate form has an average $d_{50}$ particle size distribution of about 32 microns. In some embodiments, the crystalline dihydrate form has an average $d_{50}$ particle size distribution of about 34 microns. In some embodiments, the crystalline dihydrate form has an average $d_{50}$ particle size distribution of about 36 microns. In some embodiments, the crystalline dihydrate form has an average $d_{50}$ particle size distribution of about 38 microns. In some embodiments, the crystalline dihydrate form has an average $d_{50}$ particle size distribution of about 40 microns.

In some embodiments, the crystalline dihydrate form has a $d_{90}$ particle size distribution of about 10 microns to about 60 microns. In some embodiments, the crystalline dihydrate form has a $d_{90}$ particle size distribution of about 12 microns to about 60 microns. In some embodiments, the crystalline dihydrate form has a $d_{90}$ particle size distribution of about 12 microns to about 44 microns. In some embodiments, the crystalline dihydrate form has a $d_{90}$ particle size distribution of about 14 microns to about 42 microns. In some embodiments, the crystalline dihydrate form has a $d_{90}$ particle size distribution of about 18 microns to about 42 microns. In some embodiments, the crystalline dihydrate form has a $d_{90}$ particle size distribution of about 22 microns to about 42 microns. In some embodiments, the crystalline dihydrate form has a $d_{90}$ particle size distribution of about 26 microns to about 42 microns. In some embodiments, the crystalline dihydrate form has a $d_{90}$ particle size distribution of about 32 microns to about 42 microns. In some embodiments, the crystalline dihydrate form has a $d_{90}$ particle size distribution of about 32 microns to about 40 microns.

In some embodiments, the crystalline dihydrate form has an average $d_{90}$ particle size distribution of about 12 microns. In some embodiments, the crystalline dihydrate form has an average $d_{90}$ particle size distribution of about 14 microns. In some embodiments, the crystalline dihydrate form has an average $d_{90}$ particle size distribution of about 16 microns. In some embodiments, the crystalline dihydrate form has an average $d_{90}$ particle size distribution of about 18 microns. In some embodiments, the crystalline dihydrate form has an average $d_{90}$ particle size distribution of about 20 microns. In some embodiments, the crystalline dihydrate form has an average $d_{90}$ particle size distribution of about 22 microns. In some embodiments, the crystalline dihydrate form has an average $d_{90}$ particle size distribution of about 24 microns. In some embodiments, the crystalline dihydrate form has an average $d_{90}$ particle size distribution of about 26 microns. In some embodiments, the crystalline dihydrate form has an average $d_{90}$ particle size distribution of about 28 microns. In some embodiments, the crystalline dihydrate form has an average $d_{90}$ particle size distribution of about 30 microns. In some embodiments, the crystalline dihydrate form has an average $d_{90}$ particle size distribution of about 32 microns. In some embodiments, the crystalline dihydrate form has an average do particle size distribution of about 34 microns. In some embodiments, the crystalline dihydrate form has an average $d_{90}$ particle size distribution of about 36 microns. In some embodiments, the crystalline dihydrate form has an average $d_{90}$ particle size distribution of about 38 microns. In some embodiments, the crystalline dihydrate form has an average $d_{90}$ particle size distribution of about 40 microns. In some embodiments, the crystalline dihydrate form has an average $d_{90}$ particle size distribution of about 42 microns. In some embodiments, the crystalline dihydrate form has an average $d_{90}$ particle size distribution of about 44 microns. In some embodiments, the crystalline dihydrate form has an average $d_{90}$ particle size distribution of about 46 microns. In some embodiments, the crystalline dihydrate form has an average $d_{90}$ particle size distribution of about 48 microns. In some embodiments, the crystalline dihydrate form has an average $d_{90}$ particle size distribution of about 50 microns. In some embodiments, the crystalline dihydrate form has an average $d_{90}$ particle size distribution of about 52 microns. In some embodiments, the crystalline dihydrate form has an average $d_{90}$ particle size distribution of about 54 microns. In some embodiments, the crystalline dihydrate form has an average do particle size distribution of about 56 microns. In some embodiments, the crystalline dihydrate form has an average $d_{90}$ particle size distribution of about 58 microns. In some embodiments, the crystalline dihydrate form has an average $d_{90}$ particle size distribution of about 60 microns.

In some embodiments, the crystalline dihydrate form has substantially uniform particle size.

In some embodiments, provided herein is a crystalline dihydrate form of the compound represented by Formula (I), having a substantially uniform particle size distribution, prepared by a process comprising:

(i) providing a mixture of a compound represented by Formula (I) and a solvent;

(ii) charging the mixture with milled seed material of a dihydrate form of the compound represented by Formula (I);

(iii) further charging the mixture in (ii) with a solvent to obtain a charged suspension system;

(iv) cooling the charged suspension system to result in a solid precipitate; and (v) isolating the resulting solid precipitate to obtain the crystalline dihydrate form, having a uniform particle sized distribution which is a multiple of the seed material particle size distribution.

In some embodiments, the solvent in step (i) is selected from the group consisting of water, alcohol, ketone, ether, ester, halogenated alkane, amide, sulfone, acid, nitro compound, methanol, ethanol, n-propanol, iso-propanol, butanol, acetone, methyl ethyl ketone (MEK), methyl isobutyl ketone (MIBK), methyl acetate, ethyl acetate, propyl acetate, diethyl ether, tetrahydrofuran (THF), 2-methyl THF, 2,5-dimethyl THF, 2,2,5,5-tetramethyl THF, acetonitrile, methylene chloride, toluene, 1,1,1-trichloroethane, dimethyl acetamide (DMAC), nitromethane, acetic acid, and dimethyl sulfoxide (DMSO), and a combination thereof. For example, the solvent is water, acetone, DMAC, or DMSO, or a combination thereof.

In some embodiments, the solvent in step (iii) is water.

In some embodiments, in step (iii), the charging is at a temperature above 25° C. For example, the charging is at a temperature of about 50° C., about 55° C., about 60° C., about 65° C., about 70° C., about 75° C., or about 80° C.

In some embodiments, in step (iv), the cooling is to about 15° C., about 20° C., about 25° C., about 30° C., or about 35° C. In some embodiments, in step (iv), the cooling is at about 0.01-10° C./min, such as, at about 0.1° C./min, 0.5° C./min, 1.0° C./min or about 2° C./min.

In some embodiments, the crystalline dihydrate form has a $d_{10}$ particle size of about 1-5 times the $d_{10}$ particle size of the milled seed material. In some embodiments, the crystalline dihydrate form has a $d_{10}$ particle size of about 2 times the $d_{10}$ particle size of the milled seed material. In some embodiments, the crystalline dihydrate form has a $d_{10}$ particle size of about 3 times the $d_{10}$ particle size of the milled seed material. In some embodiments, the crystalline dihydrate form has a $d_{10}$ particle size of about 4 times the $d_{10}$ particle size of the milled seed material. In some embodiments, the crystalline dihydrate form has a $d_{10}$ particle size of about 5 times the $d_{10}$ particle size of the milled seed material.

In some embodiments, the crystalline dihydrate form has a $d_{50}$ particle size of about 1-5 times the $d_{50}$ particle size of the milled seed material. In some embodiments, the crystalline dihydrate form has a $d_{50}$ particle size of about 2 times the $d_{50}$ particle size of the milled seed material. In some embodiments, the crystalline dihydrate form has a $d_{50}$ particle size of about 3 times the $d_{50}$ particle size of the milled seed material. In some embodiments, the crystalline dihydrate form has a $d_{50}$ particle size of about 4 times the $d_{50}$ particle size of the milled seed material. In some embodiments, the crystalline dihydrate form has a $d_{50}$ particle size of about 5 times the $d_{50}$ particle size of the milled seed material.

In some embodiments, the crystalline dihydrate form has a $d_{90}$ particle size of about 1-5 times the $d_{90}$ particle size of the milled seed material. In some embodiments, the crystalline dihydrate form has a $d_{90}$ particle size of about 2 times the $d_{90}$ particle size of the milled seed material. In some embodiments, the crystalline dihydrate form has a $d_{90}$ particle size of about 3 times the $d_{90}$ particle size of the milled seed material. In some embodiments, the crystalline dihydrate form has a $d_{90}$ particle size of about 4 times the $d_{90}$ particle size of the milled seed material. In some embodiments, the crystalline dihydrate form has a $d_{90}$ particle size of about 5 times the $d_{90}$ particle size of the milled seed material.

In some embodiments, the crystalline dihydrate form has an average $d_{10}$ particle size distribution of about 2 microns. In some embodiments, the crystalline dihydrate form has an average $d_{10}$ particle size distribution of about 4 microns. In some embodiments, the crystalline dihydrate form has an average $d_{10}$ particle size distribution of about 6 microns. In some embodiments, the crystalline dihydrate form has an average $d_{10}$ particle size distribution of about 8 microns. In some embodiments, the crystalline dihydrate form has an average $d_{10}$ particle size distribution of about 10 microns. In some embodiments, the crystalline dihydrate form has an average $d_{10}$ particle size distribution of about 12 microns. In some embodiments, the crystalline dihydrate form has an average $d_{10}$ particle size distribution of about 14 microns. In some embodiments, the crystalline dihydrate form has an average $d_{10}$ particle size distribution of about 16 microns. In some embodiments, the crystalline dihydrate form has an average $d_{10}$ particle size distribution of about 18 microns. In some embodiments, the crystalline dihydrate form has an average $d_{10}$ particle size distribution of about 20 microns.

In some embodiments, the crystalline dihydrate form has a $d_{50}$ particle size distribution of about 4 microns to about 28 microns. In some embodiments, the crystalline dihydrate form has a $d_{50}$ particle size distribution of about 6 microns to about 26 microns. In some embodiments, the crystalline dihydrate form has a $d_{50}$ particle size distribution of about 6 microns to about 24 microns. In some embodiments, the crystalline dihydrate form has a $d_{50}$ particle size distribution of about 8 microns to about 24 microns. In some embodiments, the crystalline dihydrate form has a $d_{50}$ particle size distribution of about 10 microns to about 24 microns. In some embodiments, the crystalline dihydrate form has a $d_{50}$ particle size distribution of about 12 microns to about 24 microns. In some embodiments, the crystalline dihydrate form has a $d_{50}$ particle size distribution of about 14 microns to about 24 microns. In some embodiments, the crystalline dihydrate form has a $d_{50}$ particle size distribution of about 16 microns to about 24 microns. In some embodiments, the crystalline dihydrate form has a $d_{50}$ particle size distribution of about 16 microns to about 22 microns.

In some embodiments, the crystalline dihydrate form has an average $d_{50}$ particle size distribution of about 4 microns. In some embodiments, the crystalline dihydrate form has an average $d_{50}$ particle size distribution of about 6 microns. In some embodiments, the crystalline dihydrate form has an average $d_{50}$ particle size distribution of about 8 microns. In some embodiments, the crystalline dihydrate form has an average $d_{50}$ particle size distribution of about 10 microns. In some embodiments, the crystalline dihydrate form has an average $d_{50}$ particle size distribution of about 12 microns. In some embodiments, the crystalline dihydrate form has an average $d_{50}$ particle size distribution of about 14 microns. In some embodiments, the crystalline dihydrate form has an average $d_{50}$ particle size distribution of about 16 microns. In some embodiments, the crystalline dihydrate form has an average $d_{50}$ particle size distribution of about 18 microns. In some embodiments, the crystalline dihydrate form has an average $d_{50}$ particle size distribution of about 20 microns. In some embodiments, the crystalline dihydrate form has an average $d_{50}$ particle size distribution of about 22 microns. In some embodiments, the crystalline dihydrate form has an average $d_{50}$ particle size distribution of about 24 microns. In some embodiments, the crystalline dihydrate form has an average $d_{50}$ particle size distribution of about 26 microns. In some embodiments, the crystalline dihydrate form has an average $d_{50}$ particle size distribution of about 28 microns. In some embodiments, the crystalline dihydrate form has an average $d_{50}$ particle size distribution of about 30 microns. In some embodiments, the crystalline dihydrate form has an average $d_{50}$ particle size distribution of about 32 microns. In some embodiments, the crystalline dihydrate form has an average $d_{50}$ particle size distribution of about 34 microns. In some embodiments, the crystalline dihydrate form has an average $d_{50}$ particle size distribution of about 36 microns. In some embodiments, the crystalline dihydrate form has an average $d_{50}$ particle size distribution of about 38 microns. In some embodiments, the crystalline dihydrate form has an average $d_{50}$ particle size distribution of about 40 microns.

In some embodiments, the crystalline dihydrate form has a $d_{90}$ particle size distribution of about 12 microns to about 44 microns. In some embodiments, the crystalline dihydrate form has a $d_{90}$ particle size distribution of about 14 microns to about 42 microns. In some embodiments, the crystalline dihydrate form has a $d_{90}$ particle size distribution of about 18 microns to about 42 microns. In some embodiments, the crystalline dihydrate form has a $d_{90}$ particle size distribution of about 22 microns to about 42 microns. In some embodiments, the crystalline dihydrate form has a $d_{90}$ particle size distribution of about 26 microns to about 42 microns. In some embodiments, the crystalline dihydrate form has a $d_{90}$ particle size distribution of about 32 microns to about 42 microns. In some embodiments, the crystalline dihydrate form has a $d_{90}$ particle size distribution of about 32 microns to about 40 microns.

In some embodiments, the crystalline dihydrate form has an average $d_{90}$ particle size distribution of about 12 microns. In some embodiments, the crystalline dihydrate form has an average $d_{90}$ particle size distribution of about 14 microns. In some embodiments, the crystalline dihydrate form has an average $d_{90}$ particle size distribution of about 16 microns. In some embodiments, the crystalline dihydrate form has an average $d_{90}$ particle size distribution of about 18 microns. In some embodiments, the crystalline dihydrate form has an average $d_{90}$ particle size distribution of about 20 microns. In some embodiments, the crystalline dihydrate form has an average $d_{90}$ particle size distribution of about 22 microns. In some embodiments, the crystalline dihydrate form has an average $d_{90}$ particle size distribution of about 24 microns. In some embodiments, the crystalline dihydrate form has an average $d_{90}$ particle size distribution of about 26 microns. In some embodiments, the crystalline dihydrate form has an average $d_{90}$ particle size distribution of about 28 microns. In some embodiments, the crystalline dihydrate form has an average $d_{90}$ particle size distribution of about 30 microns. In some embodiments, the crystalline dihydrate form has an average $d_{90}$ particle size distribution of about 32 microns. In some embodiments, the crystalline dihydrate form has an average $d_{90}$ particle size distribution of about 34 microns. In some embodiments, the crystalline dihydrate form has an average $d_{90}$ particle size distribution of about 36 microns. In some embodiments, the crystalline dihydrate form has an average $d_{90}$ particle size distribution of about 38 microns. In some embodiments, the crystalline dihydrate form has an average $d_{90}$ particle size distribution of about 40 microns. In some embodiments, the crystalline dihydrate form has an average $d_{90}$ particle size distribution of about 42 microns. In some embodiments, the crystalline dihydrate form has an average $d_{90}$ particle size distribution of about 44 microns. In some embodiments, the crystalline dihydrate form has an average $d_{90}$ particle size distribution of about 46 microns. In some embodiments, the crystalline dihydrate form has an average $d_{90}$ particle size distribution of about 48 microns. In some embodiments, the crystalline dihydrate form has an average $d_{90}$ particle size distribution of about 50 microns. In some embodiments, the crystalline dihydrate form has an average $d_{90}$ particle size distribution of about 52 microns. In some embodiments, the crystalline dihydrate form has an average $d_{90}$ particle size distribution of about 54 microns. In some embodiments, the crystalline dihydrate form has an average $d_{90}$ particle size distribution of about 56 microns. In some embodiments, the crystalline dihydrate form has an average $d_{90}$ particle size distribution of about 58 microns. In some embodiments, the crystalline dihydrate form has an average $d_{90}$ particle size distribution of about 60 microns.

In some embodiments, the crystalline dihydrate form has substantially uniform particle size.

In some embodiments, provided herein is a pharmaceutical composition comprising the crystalline dihydrate form of the compound represented by Formula (I), and a pharmaceutically acceptable excipient.

In some embodiments, provided herein is the crystalline dihydrate form of the compound represented by Formula (I) for use in the preparation of a pharmaceutical composition or pharmaceutical formulation.

In some embodiments, provided herein is a pharmaceutical composition comprising the crystalline dihydrate form of the compound represented by Formula (I), which is present in said composition in an amount of at least about 90% by weight based on the total weight of the compound represented by Formula (I).

In some embodiments, provided herein is a pharmaceutical composition consisting essentially of the crystalline dihydrate form of the compound represented by Formula (I), and a pharmaceutically acceptable excipient.

In some embodiments, provided herein is a pharmaceutical composition consisting essentially of the crystalline dihydrate form of the compound represented by Formula (I) which is present in said composition in an amount of at least about 90% by weight based on the total weight of the compound represented by Formula (I).

In some embodiments, provided herein is a pharmaceutical composition comprising the crystalline dihydrate form of the compound represented by Formula (I), which is in the form of a capsule.

In some embodiments, provided herein is a pharmaceutical composition which is in the form of a capsule containing about 1 mg to about 150 mg of the crystalline dihydrate form of the compound represented by Formula (I).

In some embodiments, provided herein is a pharmaceutical composition which is in the form of a capsule containing about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, or about 3.0 mg of the crystalline dihydrate form of the compound represented by Formula (I).

In some embodiments, provided herein is a pharmaceutical composition which is in the form of a capsule containing about 2.2 mg of the crystalline dihydrate form of the compound represented by Formula (I).

In some embodiments, provided herein is a pharmaceutical composition which is in the form of a capsule containing about 10.0 mg, about 10.1 mg, about 10.2 mg, about 10.3 mg, about 10.4 mg, about 10.5 mg, about 10.6 mg, about 10.7 mg, about 10.8 mg, about 10.9 mg, or about 11.0 mg of the crystalline dihydrate form of the compound represented by Formula (I).

In some embodiments, provided herein is a pharmaceutical composition which is in the form of a capsule containing about 10.8 mg or about 10.9 mg of the crystalline dihydrate form of the compound represented by Formula (I). In some embodiments, the pharmaceutical composition which is in the form of a capsule contains about 10.8 mg of the crystalline dihydrate form of the compound represented by Formula (I). In some embodiments, the pharmaceutical composition which is in the form of a capsule contains about 10.9 mg of the crystalline dihydrate form of the compound represented by Formula (I).

In some embodiments, provided herein is a pharmaceutical composition which is in the form of a capsule containing about 15.0 mg, about 15.1 mg, about 15.2 mg, about 15.3 mg, about 15.4 mg, about 15.5 mg, about 15.6 mg, about 15.7 mg, about 15.8 mg, about 15.9 mg, or about 16.0 mg of the crystalline dihydrate form of the compound represented by Formula (I).

In some embodiments, provided herein is a pharmaceutical composition which is in the form of a capsule containing about 15.2 mg of the crystalline dihydrate form of the compound represented by Formula (I).

In some embodiments, provided herein is a pharmaceutical composition which is in the form of a capsule containing about 21.0 mg, about 21.1 mg, about 21.2 mg, about 21.3 mg, about 21.4 mg, about 21.5 mg, about 21.6 mg, about 21.7 mg, about 21.8 mg, about 21.9 mg, or about 22.0 mg of the crystalline dihydrate form of the compound represented by Formula (I).

In some embodiments, provided herein is a pharmaceutical composition which is in the form of a capsule containing about 21.7 mg of the crystalline dihydrate form of the compound represented by Formula (I).

In some embodiments, provided herein is a pharmaceutical composition which is in the form of a capsule containing about 32.0 mg, about 32.1 mg, about 32.2 mg, about 32.3 mg, about 32.4 mg, about 32.5 mg, about 32.6 mg, about 32.7 mg, about 32.8 mg, about 32.9 mg, or about 33.0 mg of the crystalline dihydrate form of the compound represented by Formula (I).

In some embodiments, provided herein is a pharmaceutical composition which is in the form of a capsule containing about 32.5 mg of the crystalline dihydrate form of the compound represented by Formula (I).

In some embodiments, provided herein is a pharmaceutical composition comprising:

a) crystalline solid form of a compound represented by

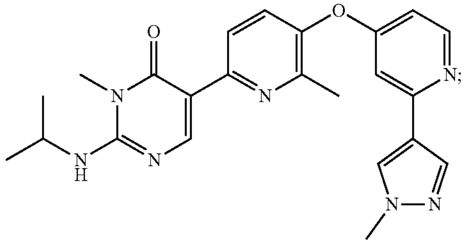 [SMILES: Cc1nc(-c2cnc(NC(C)C)n(C)c2=O)ccc1Oc1ccnc(-c2cnn(C)c2)c1]

and b) a pharmaceutically acceptable excipient, wherein the crystalline solid form is present at least in part as the crystalline dihydrate form disclosed herein, and wherein the crystalline solid form is present in the composition in amount to provide 2 mg of the compound.

In some embodiments, provided herein is a pharmaceutical composition comprising:

a) a crystalline solid form of a compound represented by

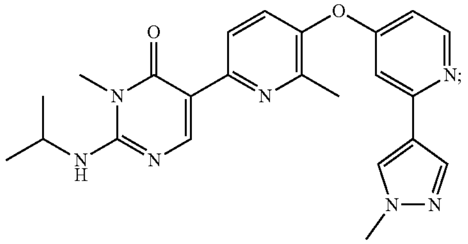 [SMILES: Cc1nc(-c2cnc(NC(C)C)n(C)c2=O)ccc1Oc1ccnc(-c2cnn(C)c2)c1]

and b) a pharmaceutically acceptable excipient, wherein the crystalline solid form is present at least in part as the crystalline dihydrate form disclosed herein, and wherein the crystalline solid form is present in the composition in amount to provide 10 mg of the compound.

In some embodiments, provided herein is a pharmaceutical composition comprising:

a) a crystalline solid form of a compound represented by

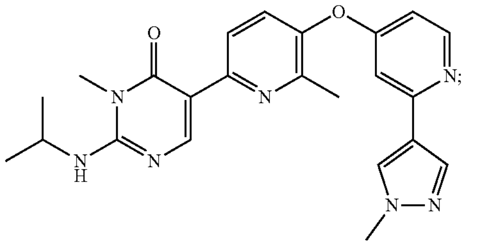 [SMILES: Cc1nc(-c2cnc(NC(C)C)n(C)c2=O)ccc1Oc1ccnc(-c2cnn(C)c2)c1]

and b) a pharmaceutically acceptable excipient, wherein the crystalline solid form is present at least in part as the crystalline dihydrate form disclosed herein, and wherein the crystalline solid form is present in the composition in amount to provide 14 mg of the compound.

In some embodiments, provided herein is a pharmaceutical composition comprising:

a) a crystalline solid form of a compound represented by

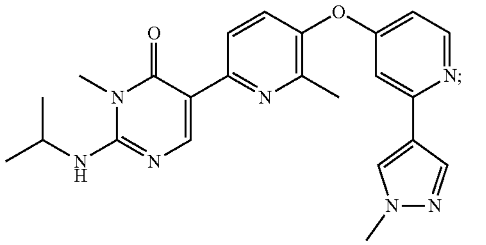 [SMILES: Cc1nc(-c2cnc(NC(C)C)n(C)c2=O)ccc1Oc1ccnc(-c2cnn(C)c2)c1]

and b) a pharmaceutically acceptable excipient, wherein the crystalline solid form is present at least in part as the crystalline dihydrate form disclosed herein, and wherein the crystalline solid form is present in the composition in amount to provide 20 mg of the compound.

In some embodiments, provided herein is a pharmaceutical composition comprising:

a) a crystalline solid form of a compound represented by

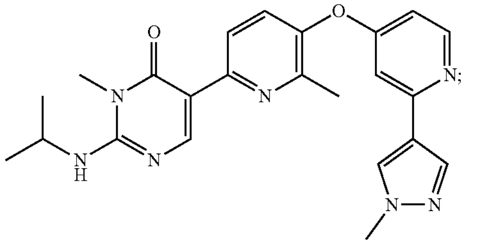 [SMILES: Cc1nc(-c2cnc(NC(C)C)n(C)c2=O)ccc1Oc1ccnc(-c2cnn(C)c2)c1]

and b) a pharmaceutically acceptable excipient, wherein the crystalline solid form is present at least in part as the crystalline dihydrate form disclosed herein, and wherein the crystalline solid form is present in the composition in amount to provide 30 mg of the compound.

In some embodiments, provided herein is a pharmaceutical composition comprising the crystalline dihydrate form of the compound represented by Formula (I), and a pharmaceutically acceptable excipient, wherein the crystalline dihydrate form has a $d_{10}$ particle size distribution of about 2 microns to about 10 microns. In some embodiments, the crystalline dihydrate form has a $d_{10}$ particle size distribution of about 4 microns to about 8 microns. In some embodiments, the crystalline dihydrate form has a $d_{10}$ particle size distribution of about 6 microns to about 8 microns.

In some embodiments, provided herein is a pharmaceutical composition comprising the crystalline dihydrate form of the compound represented by Formula (I), and a pharmaceutically acceptable excipient, wherein the crystalline dihydrate form has a $d_{50}$ particle size distribution of about 6 microns to about 24 microns. In some embodiments, the crystalline dihydrate form has a $d_{50}$ particle size distribution of about 8 microns to about 24 microns. In some embodiments, the crystalline dihydrate form has a $d_{50}$ particle size distribution of about 10 microns to about 24 microns. In some embodiments, the crystalline dihydrate form has a $d_{50}$ particle size distribution of about 12 microns to about 24 microns. In some embodiments, the crystalline dihydrate form has a $d_{50}$ particle size distribution of about 14 microns to about 24 microns. In some embodiments, the crystalline dihydrate form has a $d_{50}$ particle size distribution of about 16 microns to about 24 microns. In some embodiments, the crystalline dihydrate form has a $d_{50}$ particle size distribution of about 16 microns to about 22 microns.

In some embodiments, provided herein is a pharmaceutical composition comprising the crystalline dihydrate form of the compound represented by Formula (I), and a pharmaceutically acceptable excipient, wherein the crystalline dihydrate form has a $d_{90}$ particle size distribution of about 14 microns to about 42 microns. In some embodiments, the crystalline dihydrate form has a $d_{90}$ particle size distribution of about 18 microns to about 42 microns. In some embodiments, the crystalline dihydrate form has a $d_{90}$ particle size distribution of about 22 microns to about 42 microns. In some embodiments, the crystalline dihydrate form has a $d_{90}$ particle size distribution of about 26 microns to about 42 microns. In some embodiments, the crystalline dihydrate form has a $d_{90}$ particle size distribution of about 32 microns to about 42 microns. In some embodiments, the crystalline dihydrate form has a $d_{90}$ particle size distribution of about 32 microns to about 40 microns.

In some embodiments, provided herein is pharmaceutical composition comprising the crystalline dihydrate form of the compound represented by Formula (I), wherein the crystalline dihydrate form has substantially uniform particle size.

In some embodiments, provided herein is pharmaceutical composition comprising the crystalline dihydrate form of the compound represented by Formula (I) which is for use in the treatment of a tenosynovial giant cell tumor (TGCT). In some embodiments, the tenosynovial giant cell tumor is a diffuse-type tenosynovial giant cell tumor. In some embodiments, the tenosynovial giant cell tumor is a localized tenosynovial giant cell tumor.

In some embodiments, provided herein is a pharmaceutical composition comprising the crystalline dihydrate form of the compound represented by Formula (I) which is for use in the treatment of graft versus host disease (GVHD). In some embodiments, the graft versus host disease (GVHD) is chronic graft versus host disease (cGVHD). In some embodiments, the graft versus host disease (GVHD) is acute graft versus host disease (aGVHD).

In some embodiments, provided herein is a pharmaceutical composition comprising the crystalline dihydrate form of the compound represented by Formula (I) which is for use in the treatment of a neurodegenerative disease. In some embodiments, the neurodegenerative disease is selected from the group consisting of Parkinson's disease (PD), Alzheimer's Disease (AD), frontotemporal dementia (FTD), amyotrophic lateral sclerosis (ALS), mild cognitive impairment, and Huntington's Disease (HD).

In some embodiments, provided herein is a pharmaceutical composition comprising the crystalline dihydrate form of the compound represented by Formula (I) which is for use in the treatment of a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma. In some embodiments, the solid tumor is selected from the group consisting of ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumor.

In some embodiments, provided herein is a pharmaceutical composition comprising the crystalline dihydrate form of the compound represented by Formula (I) which is for use in the treatment of tumors known to have expression of colony-stimulating factor 1 receptor (CSF-1R) or its ligands, colony stimulating factor-1 (CSF-1), or interleukin (IL)-34 (IL-34).

In some embodiments, provided herein is a pharmaceutical composition comprising the crystalline dihydrate form of the compound represented by Formula (I) which is for use in the treatment of a disease or condition selected from the group consisting of metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis.

In some embodiments, the crystalline dihydrate form of the compound represented by Formula (I), can be useful in the treatment of diseases and conditions including, but not limited to cancer, autoimmune diseases, and metabolic bone disorders, and other tumors related to the decreased proliferation, the depletion, or the repolarization of tumor-associated macrophages (TAMs) and treatment of associated disorders, for example but not limited to disorders disclosed herein such as tenosynovial giant cell tumor (TGCT), graft-versus-host disease (GVHD), or neurodegenerative diseases. In some embodiments, the treatment of the disease or conditions occurs through the inhibition of CSF-1R kinase.

In some embodiments, the crystalline dihydrate form of the compound represented by Formula (I), can be useful in the inhibition of the proliferation of TAMs, the depletion of TAMs, the repolarization of protumoral M2 TAMs to antitumoral M1 type macrophages, and treatment of related disorders in patients, for example but not limited to disorders disclosed herein such as tenosynovial giant cell tumor (TGCT), graft-versus-host disease (GVHD), or neurodegenerative diseases. In some embodiments, the crystalline dihydrate form of the compound represented by Formula (I), potently inhibit CSF-1R signaling. In some embodiments, the crystalline dihydrate form of the compound represented by Formula (I), block macrophage-mediated tumor cell migration. In some embodiments, crystalline solid-state forms of the compound represented by Formula (I), including the crystalline dihydrate form or the crystalline anhydrous form, block osteoclast differentiation. In some embodiments, the crystalline dihydrate form of the compound represented by Formula (I), block proliferation of a CSF-1R-dependent cell line. In some embodiments, the crystalline dihydrate form of the compound represented by Formula (I), potently inhibit CSF-1R signaling in cellular assays, as well as block macrophage-mediated tumor cell migration, osteoclast differentiation, and proliferation of a CSF-1R-dependent cell line.

In some embodiments, the crystalline dihydrate form of the compound represented by Formula (I), are selective in inhibiting CSF-1R over one or more of the FLT3, KIT, PDGFRα, PDGFRβ and VEGFR2 kinases. In some embodiments, the crystalline dihydrate form of the compound represented by Formula (I), including the crystalline dihydrate form or the crystalline anhydrous form, have greater than 100-fold selectivity in inhibiting CSF-1R over the FLT3, KIT, PDGFRα, PDGFRβ, and VEGFR2 kinases.

In some embodiments, the crystalline dihydrate form of the compound represented by Formula (I), can be useful in the treatment of cancer. In some embodiments, such cancer may include glioblastoma (e.g., recurrent glioblastoma (GBM)), castrate resistant prostate cancer (CRPC), bone metastatic CRPC, cholangiocarcinoma (e.g., unresectable intrahepatic cholangiocarcinoma), ovarian cancer, pancreatic cancer, prostate cancer (e.g., advanced castration-resistant prostate cancer with bone metastasis and high circulating tumor cell counts), lung cancer, breast cancer, kidney cancer, liver cancer, cervical cancer, metastatic cancer (e.g., cancers that are metastatic to bone), papillary thyroid cancer, non-small cell lung cancer (NSCLC), colon cancer, colorectal cancer, gastrointestinal stromal tumor (GIST), solid tumors (e.g., refractory solid tumors, malignant solid tumors, metastatic breast or prostate cancer with bone disease, gastric, ovarian or non-small cell lung cancer that has malignant associated ascites or effusion(s)), advanced solid tumors (e.g., advanced incurable solid tumors in which the target kinases are linked to disease pathophysiology), melanoma, advanced melanoma, mesothelioma, multiple myeloma, follicular lymphoma, leukemia (e.g., refractory leukemia, acute myeloid leukemia (AML), relapsed/refractory acute myeloid leukemia (AML), relapsed acute myeloid leukemia (AML), refractory acute myeloid leukemia (AML), mast cell leukemia associated with CSF-1R), classic Hodgkin's lymphoma (cHL), relapsed or refractory cHL, peripheral T cell lymphoma, neurofibroma, sarcoma (e.g., soft tissue sarcoma, osteosarcoma, advanced sarcoma, high grade sarcoma, leiomyosarcoma, undifferentiated pleomorphic sarcoma, myxofibrosarcoma, dedifferentiated liposarcoma), refractory solid malignancies (e.g., colorectal, breast, pancreatic, prostate, NSCLC), endometrial, urothelial, salivary gland, trophoblastic tumor, gallbladder, renal cell carcinoma, chordoma, and gastric cancer, recurrent platinum-resistant epithelial ovarian, peritoneal, or fallopian tube cancer, squamous cell carcinoma of the head and neck, malignant peripheral nerve sheath tumors, hepatocellular carcinoma, and neoplasms (e.g., advanced malignant neoplasm, unresectable malignant neoplasm).

In some embodiments, the crystalline dihydrate form of the compound represented by Formula (I), can be useful in the treatment of diseases and conditions including idiopathic pulmonary fibrosis (IPF), hyperproliferative diseases, metabolic diseases, myeloproliferative diseases, stroke, SARS- CoV2, hepatic inflammation, rheumatoid arthritis, osteoarthritis, multiple sclerosis, autoimmune nephritis, lupus (e.g., lupus nephritis, systemic lupus erythematosus (SLE), Crohn's disease, asthma, psoriasis, chronic obstructive pulmonary diseases, pulmonary arterial hypertension (PAH), osteoporosis, hypereosinophilic syndromes, neurofibromatosis type 1-associated plexiform neurofibromas and mastocytosis.

In some embodiments, provided herein is a method of treating a tenosynovial giant cell tumor, comprising administering to the patient a therapeutically effective amount of the crystalline dihydrate form of the compound represented by Formula (I), or a therapeutically effective amount of the pharmaceutical composition comprising the crystalline dihydrate form of the compound represented by Formula (I). In some embodiments, the tenosynovial giant cell tumor is a diffuse-type tenosynovial giant cell tumor. In some embodiments, the tenosynovial giant cell tumor is a localized tenosynovial giant cell tumor.

In some embodiments, such tenosynovial giant cell tumor may be localized, e.g., as a single, well-defined nodule. In some embodiments, such tenosynovial giant cell tumor may be diffuse-type tenosynovial giant cell tumor. In some embodiments, such tenosynovial giant cell tumor may be associated with benign tumors. In some embodiments, such tenosynovial giant cell tumor may be associated with multiple nodules which may be aggressive. In some embodiments, the method may include administering about 2 mg to about 150 mg of the crystalline dihydrate form of the Compound of Formula (I) daily to a patient in need thereof. In some embodiments, the method may include administering about 10 mg to about 100 mg of the crystalline dihydrate form of the Compound of Formula (I) daily to a patient in need thereof. In some embodiments, the method may include administering about 10 mg to about 60 mg of the crystalline dihydrate form of the Compound of Formula (I) daily to a patient in need thereof. In some embodiments, the method may include administering about 10 mg to about 35 mg of the crystalline dihydrate form of the Compound of Formula (I) daily to a patient in need thereof. In some embodiments, the method may include administering about 2 mg of the crystalline dihydrate form of the Compound of Formula (I) daily to a patient in need thereof. In some embodiments, the method may include administering about 3 mg of the crystalline dihydrate form of the Compound of Formula (I) daily to a patient in need thereof. In some embodiments, the method may include administering about 4 mg of the crystalline dihydrate form of the Compound of Formula (I) daily to a patient in need thereof. In some embodiments, the method may include administering about 5 mg of the crystalline dihydrate form of the Compound of Formula (I) daily to a patient in need thereof. In some embodiments, the method may include administering about 6 mg of the crystalline dihydrate form of the Compound of Formula (I) daily to a patient in need thereof. In some embodiments, the method may include administering about 7 mg of the crystalline dihydrate form of the Compound of Formula (I) daily to a patient in need thereof. In some embodiments, the method may include administering about 8 mg of the crystalline dihydrate form of the Compound of Formula (I) daily to a patient in need thereof. In some embodiments, the method may include administering about 9 mg of the crystalline dihydrate form of the Compound of Formula (I) daily to a patient in need thereof. In some embodiments, the method may include administering about 10 mg of the crystalline dihydrate form of the Compound of Formula (I) daily to a patient in need thereof. In some embodiments, the method may include administering about 11 mg of the crystalline dihydrate form of the Compound of Formula (I) daily to a patient in need thereof. In some embodiments, the method may include administering about 12 mg of the crystalline dihydrate form of the Compound of Formula (I) daily to a patient in need thereof. In some embodiments, the method may include administering about 13 mg of the crystalline dihydrate form of the Compound of Formula (I) daily to a patient in need thereof. In some embodiments, the method may include administering about 14 mg of the crystalline dihydrate form of the Compound of Formula (I) daily to a patient in need thereof. In some embodiments, the method may include administering about 15 mg of the crystalline dihydrate form of the Compound of Formula (I) daily to a patient in need thereof. In some embodiments, the method may include administering about 16 mg of the crystalline dihydrate form of the Compound of Formula (I) daily to a patient in need thereof. In some embodiments, the method may include administering about 17 mg of the crystalline dihydrate form of the Compound of Formula (I) daily to a patient in need thereof. In some embodiments, the method may include administering about 18 mg of the crystalline dihydrate form of the Compound of Formula (I) daily to a patient in need thereof. In some embodiments, the method may include administering about 19 mg of the crystalline dihydrate form of the Compound of Formula (I) daily to a patient in need thereof. In some embodiments, the method may include administering about 20 mg of the crystalline dihydrate form of the Compound of Formula (I) daily to a patient in need thereof. In some embodiments, the method may include administering about 21 mg of the crystalline dihydrate form of the Compound of Formula (I) daily to a patient in need thereof. In some embodiments, the method may include administering about 22 mg of the crystalline dihydrate form of the Compound of Formula (I) daily to a patient in need thereof. In some embodiments, the method may include administering about 23 mg of the crystalline dihydrate form of the Compound of Formula (I) daily to a patient in need thereof. In some embodiments, the method may include administering about 24 mg of the crystalline dihydrate form of the Compound of Formula (I) daily to a patient in need thereof. In some embodiments, the method may include administering about 25 mg of the crystalline dihydrate form of the Compound of Formula (I) daily to a patient in need thereof. In some embodiments, the method may include administering about 26 mg of the crystalline dihydrate form of the Compound of Formula (I) daily to a patient in need thereof. In some embodiments, the method may include administering about 27 mg of the crystalline dihydrate form of the Compound of Formula (I) daily to a patient in need thereof. In some embodiments, the method may include administering about 28 mg of the crystalline dihydrate form of the Compound of Formula (I) daily to a patient in need thereof. In some embodiments, the method may include administering about 29 mg of the crystalline dihydrate form of the Compound of Formula (I) daily to a patient in need thereof. In some embodiments, the method may include administering about 30 mg of the crystalline dihydrate form of the Compound of Formula (I) daily to a patient in need thereof. In some embodiments, the method may include administering about 31 mg of the crystalline dihydrate form of the Compound of Formula (I) daily to a patient in need thereof. In some embodiments, the method may include administering about 32 mg of the crystalline dihydrate form of the Compound of Formula (I) daily to a patient in need thereof. In some embodiments, the method may include administering about 33 mg of the crystalline dihydrate form of the Compound of Formula (I) daily to a patient in need thereof. In some embodiments, the method may include administering about 34 mg of the crystalline dihydrate form of the Compound of Formula (I) daily to a patient in need thereof. In some embodiments, the method may include administering about 35 mg of the crystalline dihydrate form of the Compound of Formula (I) daily to a patient in need thereof. In some embodiments, the method may include administering about 36 mg of the crystalline dihydrate form of the Compound of Formula (I) daily to a patient in need thereof. In some embodiments, the method may include administering about 37 mg of the crystalline dihydrate form of the Compound of Formula (I) daily to a patient in need thereof. In some embodiments, the method may include administering about 38 mg of the crystalline dihydrate form of the Compound of Formula (I) daily to a patient in need thereof. In some embodiments, the method may include administering about 39 mg of the crystalline dihydrate form of the Compound of Formula (I) daily to a patient in need thereof. In some embodiments, the method may include administering about 40 mg of the crystalline dihydrate form of the Compound of Formula (I) daily to a patient in need thereof. In some embodiments, the method may include administering about 41 mg of the crystalline dihydrate form of the Compound of Formula (I) daily to a patient in need thereof. In some embodiments, the method may include administering about 42 mg of the crystalline dihydrate form of the Compound of Formula (I) daily to a patient in need thereof. In some embodiments, the method may include administering about 43 mg of the crystalline dihydrate form of the Compound of Formula (I) daily to a patient in need thereof. In some embodiments, the method may include administering about 44 mg of the crystalline dihydrate form of the Compound of Formula (I) daily to a patient in need thereof. In some embodiments, the method may include administering about 45 mg of the crystalline dihydrate form of the Compound of Formula (I) daily to a patient in need thereof. In some embodiments, the method may include administering about 46 mg of the crystalline dihydrate form of the Compound of Formula (I) daily to a patient in need thereof. In some embodiments, the method may include administering about 47 mg of the crystalline dihydrate form of the Compound of Formula (I) daily to a patient in need thereof. In some embodiments, the method may include administering about 48 mg of the crystalline dihydrate form of the Compound of Formula (I) daily to a patient in need thereof. In some embodiments, the method may include administering about 49 mg of the crystalline dihydrate form of the Compound of Formula (I) daily to a patient in need thereof. In some embodiments, the method may include administering about 50 mg of the crystalline dihydrate form of the Compound of Formula (I) daily to a patient in need thereof. In some embodiments, the method may include administering about 51 mg of the crystalline dihydrate form of the Compound of Formula (I) daily to a patient in need thereof. In some embodiments, the method may include administering about 52 mg of the crystalline dihydrate form of the Compound of Formula (I) daily to a patient in need thereof. In some embodiments, the method may include administering about 53 mg of the crystalline dihydrate form of the Compound of Formula (I) daily to a patient in need thereof. In some embodiments, the method may include administering about 54 mg of the crystalline dihydrate form of the Compound of Formula (I) daily to a patient in need thereof. In some embodiments, the method may include administering about 55 mg of the crystalline dihydrate form of the Compound of Formula (I) daily to a patient in need thereof. In some embodiments, the method may include administering about 56 mg of the crystalline dihydrate form of the Compound of Formula (I) daily to a patient in need thereof. In some embodiments, the method may include administering about 57 mg of the crystalline dihydrate form of the Compound of Formula (I) daily to a patient in need thereof. In some embodiments, the method may include administering about 58 mg of the crystalline dihydrate form of the Compound of Formula (I) daily to a patient in need thereof. In some embodiments, the method may include administering about 59 mg of the crystalline dihydrate form of the Compound of Formula (I) daily to a patient in need thereof. In some embodiments, the method may include administering about 60 mg of the crystalline dihydrate form of the Compound of Formula (I) daily to a patient in need thereof. In some embodiments, the method may include administering about 65 mg of the crystalline dihydrate form of the Compound of Formula (I) daily to a patient in need thereof. In some embodiments, the method may include administering about 70 mg of the crystalline dihydrate form of the Compound of Formula (I) daily to a patient in need thereof. In some embodiments, the method may include administering about 75 mg of the crystalline dihydrate form of the Compound of Formula (I) daily to a patient in need thereof. In some embodiments, the method may include administering about 80 mg of the crystalline dihydrate form of the Compound of Formula (I) daily to a patient in need thereof. In some embodiments, the method may include administering about 85 mg of the crystalline dihydrate form of the Compound of Formula (I) daily to a patient in need thereof. In some embodiments, the method may include administering about 90 mg of the crystalline dihydrate form of the Compound of Formula (I) daily to a patient in need thereof. In some embodiments, the method may include administering about 95 mg of the crystalline dihydrate form of the Compound of Formula (I) daily to a patient in need thereof. In some embodiments, the method may include administering about 100 mg of the crystalline dihydrate form of the Compound of Formula (I) daily to a patient in need thereof. In some embodiments, the method may include administering about 105 mg of the crystalline dihydrate form of the Compound of Formula (I) daily to a patient in need thereof. In some embodiments, the method may include administering about 110 mg of the crystalline dihydrate form of the Compound of Formula (I) daily to a patient in need thereof. In some embodiments, the method may include administering about 115 mg of the crystalline dihydrate form of the Compound of Formula (I) daily to a patient in need thereof. In some embodiments, the method may include administering about 120 mg of the crystalline dihydrate form of the Compound of Formula (I) daily to a patient in need thereof. In some embodiments, the method may include administering about 125 mg of the crystalline dihydrate form of the Compound of Formula (I) daily to a patient in need thereof. In some embodiments, the method may include administering about 130 mg of the crystalline dihydrate form of the Compound of Formula (I) daily to a patient in need thereof. In some embodiments, the method may include administering about 135 mg of the crystalline dihydrate form of the Compound of Formula (I) daily to a patient in need thereof. In some embodiments, the method may include administering about 140 mg of the crystalline dihydrate form of the Compound of Formula (I) daily to a patient in need thereof. In some embodiments, the method may include administering about 145 mg of the crystalline dihydrate form of the Compound of Formula (I) daily to a patient in need thereof. In some embodiments, the method may include administering about 150 mg of the crystalline dihydrate form of the Compound of Formula (I) daily to a patient in need thereof.

In some embodiments, the method may include administering about 2 mg to about 150 mg of the crystalline dihydrate form of the Compound of Formula (I) once a week to a patient in need thereof. In some embodiments, the method may include administering about 10 mg to about 100 mg of the crystalline dihydrate form of the Compound of Formula (I) once a week to a patient in need thereof. In some embodiments, the method may include administering about 10 mg to about 60 mg of the crystalline dihydrate form of the Compound of Formula (I) once a week to a patient in need thereof. In some embodiments, the method may include administering about 10 mg to about 35 mg of the crystalline dihydrate form of the Compound of Formula (I) once a week to a patient in need thereof. In some embodiments, the method may include administering about 2 mg of the crystalline dihydrate form of the Compound of Formula (I) once a week to a patient in need thereof. In some embodiments, the method may include administering about 3 mg of the crystalline dihydrate form of the Compound of Formula (I) once a week to a patient in need thereof. In some embodiments, the method may include administering about 4 mg of the crystalline dihydrate form of the Compound of Formula (I) once a week to a patient in need thereof. In some embodiments, the method may include administering about 5 mg of the crystalline dihydrate form of the Compound of Formula (I) once a week to a patient in need thereof. In some embodiments, the method may include administering about 6 mg of the crystalline dihydrate form of the Compound of Formula (I) once a week to a patient in need thereof. In some embodiments, the method may include administering about 7 mg of the crystalline dihydrate form of the Compound of Formula (I) once a week to a patient in need thereof. In some embodiments, the method may include administering about 8 mg of the crystalline dihydrate form of the Compound of Formula (I) once a week to a patient in need thereof. In some embodiments, the method may include administering about 9 mg of the crystalline dihydrate form of the Compound of Formula (I) once a week to a patient in need thereof. In some embodiments, the method may include administering about 10 mg of the crystalline dihydrate form of the Compound of Formula (I) once a week to a patient in need thereof. In some embodiments, the method may include administering about 11 mg of the crystalline dihydrate form of the Compound of Formula (I) once a week to a patient in need thereof. In some embodiments, the method may include administering about 12 mg of the crystalline dihydrate form of the Compound of Formula (I) once a week to a patient in need thereof. In some embodiments, the method may include administering about 13 mg of the crystalline dihydrate form of the Compound of Formula (I) once a week to a patient in need thereof. In some embodiments, the method may include administering about 14 mg of the crystalline dihydrate form of the Compound of Formula (I) once a week to a patient in need thereof. In some embodiments, the method may include administering about 15 mg of the crystalline dihydrate form of the Compound of Formula (I) once a week to a patient in need thereof. In some embodiments, the method may include administering about 16 mg of the crystalline dihydrate form of the Compound of Formula (I) once a week to a patient in need thereof. In some embodiments, the method may include administering about 17 mg of the crystalline dihydrate form of the Compound of Formula (I) once a week to a patient in need thereof. In some embodiments, the method may include administering about 18 mg of the crystalline dihydrate form of the Compound of Formula (I) once a week to a patient in need thereof. In some embodiments, the method may include administering about 19 mg of the crystalline dihydrate form of the Compound of Formula (I) once a week to a patient in need thereof. In some embodiments, the method may include administering about 20 mg of the crystalline dihydrate form of the Compound of Formula (I) once a week to a patient in need thereof. In some embodiments, the method may include administering about 21 mg of the crystalline dihydrate form of the Compound of Formula (I) once a week to a patient in need thereof. In some embodiments, the method may include administering about 22 mg of the crystalline dihydrate form of the Compound of Formula (I) once a week to a patient in need thereof. In some embodiments, the method may include administering about 23 mg of the crystalline dihydrate form of the Compound of Formula (I) once a week to a patient in need thereof. In some embodiments, the method may include administering about 24 mg of the crystalline dihydrate form of the Compound of Formula (I) once a week to a patient in need thereof. In some embodiments, the method may include administering about 25 mg of the crystalline dihydrate form of the Compound of Formula (I) once a week to a patient in need thereof. In some embodiments, the method may include administering about 26 mg of the crystalline dihydrate form of the Compound of Formula (I) once a week to a patient in need thereof. In some embodiments, the method may include administering about 27 mg of the crystalline dihydrate form of the Compound of Formula (I) once a week to a patient in need thereof. In some embodiments, the method may include administering about 28 mg of the crystalline dihydrate form of the Compound of Formula (I) once a week to a patient in need thereof. In some embodiments, the method may include administering about 29 mg of the crystalline dihydrate form of the Compound of Formula (I) once a week to a patient in need thereof. In some embodiments, the method may include administering about 30 mg of the crystalline dihydrate form of the Compound of Formula (I) once a week to a patient in need thereof. In some embodiments, the method may include administering about 31 mg of the crystalline dihydrate form of the Compound of Formula (I) once a week to a patient in need thereof. In some embodiments, the method may include administering about 32 mg of the crystalline dihydrate form of the Compound of Formula (I) once a week to a patient in need thereof. In some embodiments, the method may include administering about 33 mg of the crystalline dihydrate form of the Compound of Formula (I) once a week to a patient in need thereof. In some embodiments, the method may include administering about 34 mg of the crystalline dihydrate form of the Compound of Formula (I) once a week to a patient in need thereof. In some embodiments, the method may include administering about 35 mg of the crystalline dihydrate form of the Compound of Formula (I) once a week to a patient in need thereof. In some embodiments, the method may include administering about 36 mg of the crystalline dihydrate form of the Compound of Formula (I) once a week to a patient in need thereof. In some embodiments, the method may include administering about 37 mg of the crystalline dihydrate form of the Compound of Formula (I) once a week to a patient in need thereof. In some embodiments, the method may include administering about 38 mg of the crystalline dihydrate form of the Compound of Formula (I) once a week to a patient in need thereof. In some embodiments, the method may include administering about 39 mg of the crystalline dihydrate form of the Compound of Formula (I) once a week to a patient in need thereof. In some embodiments, the method may include administering about 40 mg of the crystalline dihydrate form of the Compound of Formula (I) once a week to a patient in need thereof. In some embodiments, the method may include administering about 41 mg of the crystalline dihydrate form of the Compound of Formula (I) once a week to a patient in need thereof. In some embodiments, the method may include administering about 42 mg of the crystalline dihydrate form of the Compound of Formula (I) once a week to a patient in need thereof. In some embodiments, the method may include administering about 43 mg of the crystalline dihydrate form of the Compound of Formula (I) once a week to a patient in need thereof. In some embodiments, the method may include administering about 44 mg of the crystalline dihydrate form of the Compound of Formula (I) once a week to a patient in need thereof. In some embodiments, the method may include administering about 45 mg of the crystalline dihydrate form of the Compound of Formula (I) once a week to a patient in need thereof. In some embodiments, the method may include administering about 46 mg of the crystalline dihydrate form of the Compound of Formula (I) once a week to a patient in need thereof. In some embodiments, the method may include administering about 47 mg of the crystalline dihydrate form of the Compound of Formula (I) once a week to a patient in need thereof. In some embodiments, the method may include administering about 48 mg of the crystalline dihydrate form of the Compound of Formula (I) once a week to a patient in need thereof. In some embodiments, the method may include administering about 49 mg of the crystalline dihydrate form of the Compound of Formula (I) once a week to a patient in need thereof. In some embodiments, the method may include administering about 50 mg of the crystalline dihydrate form of the Compound of Formula (I) once a week to a patient in need thereof. In some embodiments, the method may include administering about 51 mg of the crystalline dihydrate form of the Compound of Formula (I) once a week to a patient in need thereof. In some embodiments, the method may include administering about 52 mg of the crystalline dihydrate form of the Compound of Formula (I) once a week to a patient in need thereof. In some embodiments, the method may include administering about 53 mg of the crystalline dihydrate form of the Compound of Formula (I) once a week to a patient in need thereof. In some embodiments, the method may include administering about 54 mg of the crystalline dihydrate form of the Compound of Formula (I) once a week to a patient in need thereof. In some embodiments, the method may include administering about 55 mg of the crystalline dihydrate form of the Compound of Formula (I) once a week to a patient in need thereof. In some embodiments, the method may include administering about 56 mg of the crystalline dihydrate form of the Compound of Formula (I) once a week to a patient in need thereof. In some embodiments, the method may include administering about 57 mg of the crystalline dihydrate form of the Compound of Formula (I) once a week to a patient in need thereof. In some embodiments, the method may include administering about 58 mg of the crystalline dihydrate form of the Compound of Formula (I) once a week to a patient in need thereof. In some embodiments, the method may include administering about 59 mg of the crystalline dihydrate form of the Compound of Formula (I) once a week to a patient in need thereof. In some embodiments, the method may include administering about 60 mg of the crystalline dihydrate form of the Compound of Formula (I) once a week to a patient in need thereof. In some embodiments, the method may include administering about 65 mg of the crystalline dihydrate form of the Compound of Formula (I) once a week to a patient in need thereof. In some embodiments, the method may include administering about 70 mg of the crystalline dihydrate form of the Compound of Formula (I) once a week to a patient in need thereof. In some embodiments, the method may include administering about 75 mg of the crystalline dihydrate form of the Compound of Formula (I) once a week to a patient in need thereof. In some embodiments, the method may include administering about 80 mg of the crystalline dihydrate form of the Compound of Formula (I) once a week to a patient in need thereof. In some embodiments, the method may include administering about 85 mg of the crystalline dihydrate form of the Compound of Formula (I) once a week to a patient in need thereof. In some embodiments, the method may include administering about 90 mg of the crystalline dihydrate form of the Compound of Formula (I) once a week to a patient in need thereof. In some embodiments, the method may include administering about 95 mg of the crystalline dihydrate form of the Compound of Formula (I) once a week to a patient in need thereof. In some embodiments, the method may include administering about 100 mg of the crystalline dihydrate form of the Compound of Formula (I) once a week to a patient in need thereof. In some embodiments, the method may include administering about 105 mg of the crystalline dihydrate form of the Compound of Formula (I) once a week to a patient in need thereof. In some embodiments, the method may include administering about 110 mg of the crystalline dihydrate form of the Compound of Formula (I) once a week to a patient in need thereof. In some embodiments, the method may include administering about 115 mg of the crystalline dihydrate form of the Compound of Formula (I) once a week to a patient in need thereof. In some embodiments, the method may include administering about 120 mg of the crystalline dihydrate form of the Compound of Formula (I) once a week to a patient in need thereof. In some embodiments, the method may include administering about 125 mg of the crystalline dihydrate form of the Compound of Formula (I) once a week to a patient in need thereof. In some embodiments, the method may include administering about 130 mg of the crystalline dihydrate form of the Compound of Formula (I) once a week to a patient in need thereof. In some embodiments, the method may include administering about 135 mg of the crystalline dihydrate form of the Compound of Formula (I) once a week to a patient in need thereof. In some embodiments, the method may include administering about 140 mg of the crystalline dihydrate form of the Compound of Formula (I) once a week to a patient in need thereof. In some embodiments, the method may include administering about 145 mg of the crystalline dihydrate form of the Compound of Formula (I) once a week to a patient in need thereof. In some embodiments, the method may include administering about 150 mg of the crystalline dihydrate form of the Compound of Formula (I) once a week to a patient in need thereof.

In some embodiments, the method may include administering about 2 mg to about 150 mg of the crystalline dihydrate form of the Compound of Formula (I) twice a week to a patient in need thereof. In some embodiments, the method may include administering about 10 mg to about 100 mg of the crystalline dihydrate form of the Compound of Formula (I) twice a week to a patient in need thereof. In some embodiments, the method may include administering about 10 mg to about 60 mg of the crystalline dihydrate form of the Compound of Formula (I) twice a week to a patient in need thereof. In some embodiments, the method may include administering about 10 mg to about 35 mg of the crystalline dihydrate form of the Compound of Formula (I) twice a week to a patient in need thereof. In some embodiments, the method may include administering about 2 mg of the crystalline dihydrate form of the Compound of Formula (I) twice a week to a patient in need thereof. In some embodiments, the method may include administering about 3 mg of the crystalline dihydrate form of the Compound of Formula (I) twice a week to a patient in need thereof. In some embodiments, the method may include administering about 4 mg of the crystalline dihydrate form of the Compound of Formula (I) twice a week to a patient in need thereof. In some embodiments, the method may include administering about 5 mg of the crystalline dihydrate form of the Compound of Formula (I) twice a week to a patient in need thereof. In some embodiments, the method may include administering about 6 mg of the crystalline dihydrate form of the Compound of Formula (I) twice a week to a patient in need thereof. In some embodiments, the method may include administering about 7 mg of the crystalline dihydrate form of the Compound of Formula (I) twice a week to a patient in need thereof. In some embodiments, the method may include administering about 8 mg of the crystalline dihydrate form of the Compound of Formula (I) twice a week to a patient in need thereof. In some embodiments, the method may include administering about 9 mg of the crystalline dihydrate form of the Compound of Formula (I) twice a week to a patient in need thereof. In some embodiments, the method may include administering about 10 mg of the crystalline dihydrate form of the Compound of Formula (I) twice a week to a patient in need thereof. In some embodiments, the method may include administering about 11 mg of the crystalline dihydrate form of the Compound of Formula (I) twice a week to a patient in need thereof. In some embodiments, the method may include administering about 12 mg of the crystalline dihydrate form of the Compound of Formula (I) twice a week to a patient in need thereof. In some embodiments, the method may include administering about 13 mg of the crystalline dihydrate form of the Compound of Formula (I) twice a week to a patient in need thereof. In some embodiments, the method may include administering about 14 mg of the crystalline dihydrate form of the Compound of Formula (I) twice a week to a patient in need thereof. In some embodiments, the method may include administering about 15 mg of the crystalline dihydrate form of the Compound of Formula (I) twice a week to a patient in need thereof. In some embodiments, the method may include administering about 16 mg of the crystalline dihydrate form of the Compound of Formula (I) twice a week to a patient in need thereof. In some embodiments, the method may include administering about 17 mg of the crystalline dihydrate form of the Compound of Formula (I) twice a week to a patient in need thereof. In some embodiments, the method may include administering about 18 mg of the crystalline dihydrate form of the Compound of Formula (I) twice a week to a patient in need thereof. In some embodiments, the method may include administering about 19 mg of the crystalline dihydrate form of the Compound of Formula (I) twice a week to a patient in need thereof. In some embodiments, the method may include administering about 20 mg of the crystalline dihydrate form of the Compound of Formula (I) twice a week to a patient in need thereof. In some embodiments, the method may include administering about 21 mg of the crystalline dihydrate form of the Compound of Formula (I) twice a week to a patient in need thereof. In some embodiments, the method may include administering about 22 mg of the crystalline dihydrate form of the Compound of Formula (I) twice a week to a patient in need thereof. In some embodiments, the method may include administering about 23 mg of the crystalline dihydrate form of the Compound of Formula (I) twice a week to a patient in need thereof. In some embodiments, the method may include administering about 24 mg of the crystalline dihydrate form of the Compound of Formula (I) twice a week to a patient in need thereof. In some embodiments, the method may include administering about 25 mg of the crystalline dihydrate form of the Compound of Formula (I) twice a week to a patient in need thereof. In some embodiments, the method may include administering about 26 mg of the crystalline dihydrate form of the Compound of Formula (I) twice a week to a patient in need thereof. In some embodiments, the method may include administering about 27 mg of the crystalline dihydrate form of the Compound of Formula (I) twice a week to a patient in need thereof. In some embodiments, the method may include administering about 28 mg of the crystalline dihydrate form of the Compound of Formula (I) twice a week to a patient in need thereof. In some embodiments, the method may include administering about 29 mg of the crystalline dihydrate form of the Compound of Formula (I) twice a week to a patient in need thereof. In some embodiments, the method may include administering about 30 mg of the crystalline dihydrate form of the Compound of Formula (I) twice a week to a patient in need thereof. In some embodiments, the method may include administering about 31 mg of the crystalline dihydrate form of the Compound of Formula (I) twice a week to a patient in need thereof. In some embodiments, the method may include administering about 32 mg of the crystalline dihydrate form of the Compound of Formula (I) twice a week to a patient in need thereof. In some embodiments, the method may include administering about 33 mg of the crystalline dihydrate form of the Compound of Formula (I) twice a week to a patient in need thereof. In some embodiments, the method may include administering about 34 mg of the crystalline dihydrate form of the Compound of Formula (I) twice a week to a patient in need thereof. In some embodiments, the method may include administering about 35 mg of the crystalline dihydrate form of the Compound of Formula (I) twice a week to a patient in need thereof. In some embodiments, the method may include administering about 36 mg of the crystalline dihydrate form of the Compound of Formula (I) twice a week to a patient in need thereof. In some embodiments, the method may include administering about 37 mg of the crystalline dihydrate form of the Compound of Formula (I) twice a week to a patient in need thereof. In some embodiments, the method may include administering about 38 mg of the crystalline dihydrate form of the Compound of Formula (I) twice a week to a patient in need thereof. In some embodiments, the method may include administering about 39 mg of the crystalline dihydrate form of the Compound of Formula (I) twice a week to a patient in need thereof. In some embodiments, the method may include administering about 40 mg of the crystalline dihydrate form of the Compound of Formula (I) twice a week to a patient in need thereof. In some embodiments, the method may include administering about 41 mg of the crystalline dihydrate form of the Compound of Formula (I) twice a week to a patient in need thereof. In some embodiments, the method may include administering about 42 mg of the crystalline dihydrate form of the Compound of Formula (I) twice a week to a patient in need thereof. In some embodiments, the method may include administering about 43 mg of the crystalline dihydrate form of the Compound of Formula (I) twice a week to a patient in need thereof. In some embodiments, the method may include administering about 44 mg of the crystalline dihydrate form of the Compound of Formula (I) twice a week to a patient in need thereof. In some embodiments, the method may include administering about 45 mg of the crystalline dihydrate form of the Compound of Formula (I)

twice a week to a patient in need thereof. In some embodiments, the method may include administering about 46 mg of the crystalline dihydrate form of the Compound of Formula (I) twice a week to a patient in need thereof. In some embodiments, the method may include administering about 47 mg of the crystalline dihydrate form of the Compound of Formula (I) twice a week to a patient in need thereof. In some embodiments, the method may include administering about 48 mg of the crystalline dihydrate form of the Compound of Formula (I) twice a week to a patient in need thereof. In some embodiments, the method may include administering about 49 mg of the crystalline dihydrate form of the Compound of Formula (I) twice a week to a patient in need thereof. In some embodiments, the method may include administering about 50 mg of the crystalline dihydrate form of the Compound of Formula (I) twice a week to a patient in need thereof. In some embodiments, the method may include administering about 51 mg of the crystalline dihydrate form of the Compound of Formula (I) twice a week to a patient in need thereof. In some embodiments, the method may include administering about 52 mg of the crystalline dihydrate form of the Compound of Formula (I) twice a week to a patient in need thereof. In some embodiments, the method may include administering about 53 mg of the crystalline dihydrate form of the Compound of Formula (I) twice a week to a patient in need thereof. In some embodiments, the method may include administering about 54 mg of the crystalline dihydrate form of the Compound of Formula (I) twice a week to a patient in need thereof. In some embodiments, the method may include administering about 55 mg of the crystalline dihydrate form of the Compound of Formula (I) twice a week to a patient in need thereof. In some embodiments, the method may include administering about 56 mg of the crystalline dihydrate form of the Compound of Formula (I) twice a week to a patient in need thereof. In some embodiments, the method may include administering about 57 mg of the crystalline dihydrate form of the Compound of Formula (I) twice a week to a patient in need thereof. In some embodiments, the method may include administering about 58 mg of the crystalline dihydrate form of the Compound of Formula (I) twice a week to a patient in need thereof. In some embodiments, the method may include administering about 59 mg of the crystalline dihydrate form of the Compound of Formula (I) twice a week to a patient in need thereof. In some embodiments, the method may include administering about 60 mg of the crystalline dihydrate form of the Compound of Formula (I) twice a week to a patient in need thereof. In some embodiments, the method may include administering about 65 mg of the crystalline dihydrate form of the Compound of Formula (I) twice a week to a patient in need thereof. In some embodiments, the method may include administering about 70 mg of the crystalline dihydrate form of the Compound of Formula (I) twice a week to a patient in need thereof. In some embodiments, the method may include administering about 75 mg of the crystalline dihydrate form of the Compound of Formula (I) twice a week to a patient in need thereof. In some embodiments, the method may include administering about 80 mg of the crystalline dihydrate form of the Compound of Formula (I) twice a week to a patient in need thereof. In some embodiments, the method may include administering about 85 mg of the crystalline dihydrate form of the Compound of Formula (I) twice a week to a patient in need thereof. In some embodiments, the method may include administering about 90 mg of the crystalline dihydrate form of the Compound of Formula (I) twice a week to a patient in need thereof. In some embodiments, the method may include administering about 95 mg of the crystalline dihydrate form of the Compound of Formula (I) twice a week to a patient in need thereof. In some embodiments, the method may include administering about 100 mg of the crystalline dihydrate form of the Compound of Formula (I) twice a week to a patient in need thereof. In some embodiments, the method may include administering about 105 mg of the crystalline dihydrate form of the Compound of Formula (I) twice a week to a patient in need thereof. In some embodiments, the method may include administering about 110 mg of the crystalline dihydrate form of the Compound of Formula (I) twice a week to a patient in need thereof. In some embodiments, the method may include administering about 115 mg of the crystalline dihydrate form of the Compound of Formula (I) twice a week to a patient in need thereof. In some embodiments, the method may include administering about 120 mg of the crystalline dihydrate form of the Compound of Formula (I) twice a week to a patient in need thereof. In some embodiments, the method may include administering about 125 mg of the crystalline dihydrate form of the Compound of Formula (I) twice a week to a patient in need thereof. In some embodiments, the method may include administering about 130 mg of the crystalline dihydrate form of the Compound of Formula (I) twice a week to a patient in need thereof. In some embodiments, the method may include administering about 135 mg of the crystalline dihydrate form of the Compound of Formula (I) twice a week to a patient in need thereof. In some embodiments, the method may include administering about 140 mg of the crystalline dihydrate form of the Compound of Formula (I) twice a week to a patient in need thereof. In some embodiments, the method may include administering about 145 mg of the crystalline dihydrate form of the Compound of Formula (I) twice a week to a patient in need thereof. In some embodiments, the method may include administering about 150 mg of the crystalline dihydrate form of the Compound of Formula (I) twice a week to a patient in need thereof.

In some embodiments, the method may include administering about 2 mg to about 150 mg of the crystalline dihydrate form of the Compound of Formula (I) three times a week to a patient in need thereof. In some embodiments, the method may include administering about 10 mg to about 100 mg of the crystalline dihydrate form of the Compound of Formula (I) three times a week to a patient in need thereof. In some embodiments, the method may include administering about 10 mg to about 60 mg of the crystalline dihydrate form of the Compound of Formula (I) three times a week to a patient in need thereof. In some embodiments, the method may include administering about 10 mg to about 35 mg of the crystalline dihydrate form of the Compound of Formula (I) three times a week to a patient in need thereof. In some embodiments, the method may include administering about 2 mg of the crystalline dihydrate form of the Compound of Formula (I) three times a week to a patient in need thereof. In some embodiments, the method may include administering about 3 mg of the crystalline dihydrate form of the Compound of Formula (I) three times a week to a patient in need thereof. In some embodiments, the method may include administering about 4 mg of the crystalline dihydrate form of the Compound of Formula (I) three times a week to a patient in need thereof. In some embodiments, the method may include administering about 5 mg of the crystalline dihydrate form of the Compound of Formula (I) three times a week to a patient in need thereof. In some embodiments, the method may include administering about 6 mg of the crystalline dihydrate form of the Compound of Formula (I) three times a week to a patient in need thereof. In some embodiments, the method may include administering about 7 mg of the crystalline dihydrate form of the Compound of Formula (I) three times a week to a patient in need thereof. In some embodiments, the method may include administering about 8 mg of the crystalline dihydrate form of the Compound of Formula (I) three times a week to a patient in need thereof. In some embodiments, the method may include administering about 9 mg of the crystalline dihydrate form of the Compound of Formula (I) three times a week to a patient in need thereof. In some embodiments, the method may include administering about 10 mg of the crystalline dihydrate form of the Compound of Formula (I) three times a week to a patient in need thereof. In some embodiments, the method may include administering about 11 mg of the crystalline dihydrate form of the Compound of Formula (I) three times a week to a patient in need thereof. In some embodiments, the method may include administering about 12 mg of the crystalline dihydrate form of the Compound of Formula (I) three times a week to a patient in need thereof. In some embodiments, the method may include administering about 13 mg of the crystalline dihydrate form of the Compound of Formula (I) three times a week to a patient in need thereof. In some embodiments, the method may include administering about 14 mg of the crystalline dihydrate form of the Compound of Formula (I) three times a week to a patient in need thereof. In some embodiments, the method may include administering about 15 mg of the crystalline dihydrate form of the Compound of Formula (I) three times a week to a patient in need thereof. In some embodiments, the method may include administering about 16 mg of the crystalline dihydrate form of the Compound of Formula (I) three times a week to a patient in need thereof. In some embodiments, the method may include administering about 17 mg of the crystalline dihydrate form of the Compound of Formula (I) three times a week to a patient in need thereof. In some embodiments, the method may include administering about 18 mg of the crystalline dihydrate form of the Compound of Formula (I) three times a week to a patient in need thereof. In some embodiments, the method may include administering about 19 mg of the crystalline dihydrate form of the Compound of Formula (I) three times a week to a patient in need thereof. In some embodiments, the method may include administering about 20 mg of the crystalline dihydrate form of the Compound of Formula (I) three times a week to a patient in need thereof. In some embodiments, the method may include administering about 21 mg of the crystalline dihydrate form of the Compound of Formula (I) three times a week to a patient in need thereof. In some embodiments, the method may include administering about 22 mg of the crystalline dihydrate form of the Compound of Formula (I) three times a week to a patient in need thereof. In some embodiments, the method may include administering about 23 mg of the crystalline dihydrate form of the Compound of Formula (I) three times a week to a patient in need thereof. In some embodiments, the method may include administering about 24 mg of the crystalline dihydrate form of the Compound of Formula (I) three times a week to a patient in need thereof. In some embodiments, the method may include administering about 25 mg of the crystalline dihydrate form of the Compound of Formula (I) three times a week to a patient in need thereof. In some embodiments, the method may include administering about 26 mg of the crystalline dihydrate form of the Compound of Formula (I) three times a week to a patient in need thereof. In some embodiments, the method may include administering about 27 mg of the crystalline dihydrate form of the Compound of Formula (I) three times a week to a patient in need thereof. In some embodiments, the method may include administering about 28 mg of the crystalline dihydrate form of the Compound of Formula (I) three times a week to a patient in need thereof. In some embodiments, the method may include administering about 29 mg of the crystalline dihydrate form of the Compound of Formula (I) three times a week to a patient in need thereof. In some embodiments, the method may include administering about 30 mg of the crystalline dihydrate form of the Compound of Formula (I) three times a week to a patient in need thereof. In some embodiments, the method may include administering about 31 mg of the crystalline dihydrate form of the Compound of Formula (I) three times a week to a patient in need thereof. In some embodiments, the method may include administering about 32 mg of the crystalline dihydrate form of the Compound of Formula (I) three times a week to a patient in need thereof. In some embodiments, the method may include administering about 33 mg of the crystalline dihydrate form of the Compound of Formula (I) three times a week to a patient in need thereof. In some embodiments, the method may include administering about 34 mg of the crystalline dihydrate form of the Compound of Formula (I) three times a week to a patient in need thereof. In some embodiments, the method may include administering about 35 mg of the crystalline dihydrate form of the Compound of Formula (I) three times a week to a patient in need thereof. In some embodiments, the method may include administering about 36 mg of the crystalline dihydrate form of the Compound of Formula (I) three times a week to a patient in need thereof. In some embodiments, the method may include administering about 37 mg of the crystalline dihydrate form of the Compound of Formula (I) three times a week to a patient in need thereof. In some embodiments, the method may include administering about 38 mg of the crystalline dihydrate form of the Compound of Formula (I) three times a week to a patient in need thereof. In some embodiments, the method may include administering about 39 mg of the crystalline dihydrate form of the Compound of Formula (I) three times a week to a patient in need thereof. In some embodiments, the method may include administering about 40 mg of the crystalline dihydrate form of the Compound of Formula (I) three times a week to a patient in need thereof. In some embodiments, the method may include administering about 41 mg of the crystalline dihydrate form of the Compound of Formula (I) three times a week to a patient in need thereof. In some embodiments, the method may include administering about 42 mg of the crystalline dihydrate form of the Compound of Formula (I) three times a week to a patient in need thereof. In some embodiments, the method may include administering about 43 mg of the crystalline dihydrate form of the Compound of Formula (I) three times a week to a patient in need thereof. In some embodiments, the method may include administering about 44 mg of the crystalline dihydrate form of the Compound of Formula (I) three times a week to a patient in need thereof. In some embodiments, the method may include administering about 45 mg of the crystalline dihydrate form of the Compound of Formula (I) three times a week to a patient in need thereof. In some embodiments, the method may include administering about 46 mg of the crystalline dihydrate form of the Compound of Formula (I) three times a week to a patient in need thereof. In some embodiments, the method may include administering about 47 mg of the crystalline dihydrate form of the Compound of Formula (I) three times a week to a patient in need thereof. In some embodiments, the method may include administering about 48 mg of the crystalline dihydrate form of the Compound of Formula (I) three times a week to a patient in need thereof. In some embodiments, the method may include administering about 49 mg of the crystalline dihydrate form of the Compound of Formula (I) three times a week to a patient in need thereof. In some embodiments, the method may include administering about 50 mg of the crystalline dihydrate form of the Compound of Formula (I) three times a week to a patient in need thereof. In some embodiments, the method may include administering about 51 mg of the crystalline dihydrate form of the Compound of Formula (I) three times a week to a patient in need thereof. In some embodiments, the method may include administering about 52 mg of the crystalline dihydrate form of the Compound of Formula (I) three times a week to a patient in need thereof. In some embodiments, the method may include administering about 53 mg of the crystalline dihydrate form of the Compound of Formula (I) three times a week to a patient in need thereof. In some embodiments, the method may include administering about 54 mg of the crystalline dihydrate form of the Compound of Formula (I) three times a week to a patient in need thereof. In some embodiments, the method may include administering about 55 mg of the crystalline dihydrate form of the Compound of Formula (I) three times a week to a patient in need thereof. In some embodiments, the method may include administering about 56 mg of the crystalline dihydrate form of the Compound of Formula (I) three times a week to a patient in need thereof. In some embodiments, the method may include administering about 57 mg of the crystalline dihydrate form of the Compound of Formula (I) three times a week to a patient in need thereof. In some embodiments, the method may include administering about 58 mg of the crystalline dihydrate form of the Compound of Formula (I) three times a week to a patient in need thereof. In some embodiments, the method may include administering about 59 mg of the crystalline dihydrate form of the Compound of Formula (I) three times a week to a patient in need thereof. In some embodiments, the method may include administering about 60 mg of the crystalline dihydrate form of the Compound of Formula (I) three times a week to a patient in need thereof. In some embodiments, the method may include administering about 65 mg of the crystalline dihydrate form of the Compound of Formula (I) three times a week to a patient in need thereof. In some embodiments, the method may include administering about 70 mg of the crystalline dihydrate form of the Compound of Formula (I) three times a week to a patient in need thereof. In some embodiments, the method may include administering about 75 mg of the crystalline dihydrate form of the Compound of Formula (I) three times a week to a patient in need thereof. In some embodiments, the method may include administering about 80 mg of the crystalline dihydrate form of the Compound of Formula (I) three times a week to a patient in need thereof. In some embodiments, the method may include administering about 85 mg of the crystalline dihydrate form of the Compound of Formula (I) three times a week to a patient in need thereof. In some embodiments, the method may include administering about 90 mg of the crystalline dihydrate form of the Compound of Formula (I) three times a week to a patient in need thereof. In some embodiments, the method may include administering about 95 mg of the crystalline dihydrate form of the Compound of Formula (I) three times a week to a patient in need thereof. In some embodiments, the method may include administering about 100 mg of the crystalline dihydrate form of the Compound of Formula (I) three times a week to a patient in need thereof. In some embodiments, the method may include administering about 105 mg of the crystalline dihydrate form of the Compound of Formula (I) three times a week to a patient in need thereof. In some embodiments, the method may include administering about 110 mg of the crystalline dihydrate form of the Compound of Formula (I) three times a week to a patient in need thereof. In some embodiments, the method may include administering about 115 mg of the crystalline dihydrate form of the Compound of Formula (I) three times a week to a patient in need thereof. In some embodiments, the method may include administering about 120 mg of the crystalline dihydrate form of the Compound of Formula (I) three times a week to a patient in need thereof. In some embodiments, the method may include administering about 125 mg of the crystalline dihydrate form of the Compound of Formula (I) three times a week to a patient in need thereof. In some embodiments, the method may include administering about 130 mg of the crystalline dihydrate form of the Compound of Formula (I) three times a week to a patient in need thereof. In some embodiments, the method may include administering about 135 mg of the crystalline dihydrate form of the Compound of Formula (I) three times a week to a patient in need thereof. In some embodiments, the method may include administering about 140 mg of the crystalline dihydrate form of the Compound of Formula (I) three times a week to a patient in need thereof. In some embodiments, the method may include administering about 145 mg of the crystalline dihydrate form of the Compound of Formula (I) three times a week to a patient in need thereof. In some embodiments, the method may include administering about 150 mg of the crystalline dihydrate form of the Compound of Formula (I) three times a week to a patient in need thereof.

In some embodiments, such a disclosed method may include, administering a loading dose of the crystalline dihydrate form of the Compound of Formula (I) daily to a patient in need thereof, once a week to a patient in need thereof, twice a week to a patient in need thereof, or three times a week to a patient in need thereof, for a first time period; and administering a maintenance dose of the crystalline dihydrate form to a patient in need thereof daily to a patient in need thereof, once a week to a patient in need thereof, twice a week to a patient in need thereof, or three times a week to a patient in need thereof for a second time period.

In some embodiments, the loading dose is about 2 mg to about 100 mg of the crystalline dihydrate form of the Compound of Formula (I) once a day. In some embodiments, the loading dose is about 5 mg to about 90 mg of the crystalline dihydrate form of the Compound of Formula (I) once a day. In some embodiments, the loading dose is about 10 mg to about 80 mg of the crystalline dihydrate form of the Compound of Formula (I) once a day. In some embodiments, the loading dose is about 10 mg to about 70 mg of the crystalline dihydrate form of the Compound of Formula (I) once a day. In some embodiments, the loading dose is about 10 mg to about 60 mg of the crystalline dihydrate form of the Compound of Formula (I) once a day. In some embodiments, the loading dose is about 10 mg to about 50 mg of the crystalline dihydrate form of the Compound of Formula (I) once a day. In some embodiments, the loading dose is about 10 mg to about 40 mg of the crystalline dihydrate form of the Compound of Formula (I) once a day. In some embodiments, the loading dose is about 10 mg to about 30 mg of the crystalline dihydrate form of the Compound of Formula (I) once a day. In some embodiments, the loading dose is about 10 mg to about 20 mg of the crystalline dihydrate form of the Compound of Formula (I) once a day. In some embodiments, the loading dose is about 2 mg of the crystalline dihydrate form of the Compound of Formula (I) once a day. In some embodiments, the loading dose is about 3 mg of the crystalline dihydrate form of the Compound of Formula (I) once a day. In some embodiments, the loading dose is about 4 mg of the crystalline dihydrate form of the Compound of Formula (I) once a day. In some embodiments, the loading dose is about 5 mg of the crystalline dihydrate form of the Compound of Formula (I) once a day. In some embodiments, the loading dose is about 10 mg of the crystalline dihydrate form of the Compound of Formula (I) once a day. In some embodiments, the loading dose is about 11 mg of the crystalline dihydrate form of the Compound of Formula (I) once a day. In some embodiments, the loading dose is about 12 mg of the crystalline dihydrate form of the Compound of Formula (I) once a day. In some embodiments, the loading dose is about 13 mg of the crystalline dihydrate form of the Compound of Formula (I) once a day. In some embodiments, the loading dose is about 14 mg of the crystalline dihydrate form of the Compound of Formula (I) once a day. In some embodiments, the loading dose is about 15 mg of the crystalline dihydrate form of the Compound of Formula (I) once a day. In some embodiments, the loading dose is about 16 mg of the crystalline dihydrate form of the Compound of Formula (I) once a day. In some embodiments, the loading dose is about 17 mg of the crystalline dihydrate form of the Compound of Formula (I) once a day. In some embodiments, the loading dose is about 18 mg of the crystalline dihydrate form of the Compound of Formula (I) once a day. In some embodiments, the loading dose is about 19 mg of the crystalline dihydrate form of the Compound of Formula (I) once a day. In some embodiments, the loading dose is about 20 mg of the crystalline dihydrate form of the Compound of Formula (I) once a day. In some embodiments, the loading dose is about 22 mg of the crystalline dihydrate form of the Compound of Formula (I) once a day. In some embodiments, the loading dose is about 24 mg of the crystalline dihydrate form of the Compound of Formula (I) once a day. In some embodiments, the loading dose is about 26 mg of the crystalline dihydrate form of the Compound of Formula (I) once a day. In some embodiments, the loading dose is about 28 mg of the crystalline dihydrate form of the Compound of Formula (I) once a day. In some embodiments, the loading dose is about 30 mg of the crystalline dihydrate form of the Compound of Formula (I) once a day. In some embodiments, the loading dose is about 32 mg of the crystalline dihydrate form of the Compound of Formula (I) once a day. In some embodiments, the loading dose is about 34 mg of the crystalline dihydrate form of the Compound of Formula (I) once a day. In some embodiments, the loading dose is about 36 mg of the crystalline dihydrate form of the Compound of Formula (I) once a day. In some embodiments, the loading dose is about 38 mg of the crystalline dihydrate form of the Compound of Formula (I) once a day. In some embodiments, the loading dose is about 40 mg of the crystalline dihydrate form of the Compound of Formula (I) once a day. In some embodiments, the loading dose is about 42 mg of the crystalline dihydrate form of the Compound of Formula (I) once a day. In some embodiments, the loading dose is about 44 mg of the crystalline dihydrate form of the Compound of Formula (I) once a day. In some embodiments, the loading dose is about 46 mg of the crystalline dihydrate form of the Compound of Formula (I) once a day. In some embodiments, the loading dose is about 48 mg of the crystalline dihydrate form of the Compound of Formula (I) once a day. In some embodiments, the loading dose is about 50 mg of the crystalline dihydrate form of the Compound of Formula (I) once a day.

In some embodiments, the loading dose is about 2 mg to about 100 mg of the crystalline dihydrate form of the Compound of Formula (I) once a day for one day. In some embodiments, the loading dose is about 5 mg to about 90 mg of the crystalline dihydrate form of the Compound of Formula (I) once a day for one day. In some embodiments, the loading dose is about 10 mg to about 80 mg of the crystalline dihydrate form of the Compound of Formula (I) once a day for one day. In some embodiments, the loading dose is about 10 mg to about 70 mg of the crystalline dihydrate form of the Compound of Formula (I) once a day for one day. In some embodiments, the loading dose is about 10 mg to about 60 mg of the crystalline dihydrate form of the Compound of Formula (I) once a day for one day. In some embodiments, the loading dose is about 10 mg to about 50 mg of the crystalline dihydrate form of the Compound of Formula (I) once a day for one day. In some embodiments, the loading dose is about 10 mg to about 40 mg of the crystalline dihydrate form of the Compound of Formula (I) once a day for one day. In some embodiments, the loading dose is about 10 mg to about 30 mg of the crystalline dihydrate form of the Compound of Formula (I) once a day for one day. In some embodiments, the loading dose is about 10 mg to about 20 mg of the crystalline dihydrate form of the Compound of Formula (I) once a day for one day. In some embodiments, the loading dose is about 2 mg of the crystalline dihydrate form of the Compound of Formula (I) once a day for one day. In some embodiments, the loading dose is about 3 mg of the crystalline dihydrate form of the Compound of Formula (I) once a day for one day. In some embodiments, the loading dose is about 4 mg of the crystalline dihydrate form of the Compound of Formula (I) once a day for one day. In some embodiments, the loading dose is about 5 mg of the crystalline dihydrate form of the Compound of Formula (I) once a day for one day. In some embodiments, the loading dose is about 10 mg of the crystalline dihydrate form of the Compound of Formula (I) once a day for one day. In some embodiments, the loading dose is about 11 mg of the crystalline dihydrate form of the Compound of Formula (I) once a day for one day. In some embodiments, the loading dose is about 12 mg of the crystalline dihydrate form of the Compound of Formula (I) once a day for one day. In some embodiments, the loading dose is about 13 mg of the crystalline dihydrate form of the Compound of Formula (I) once a day for one day. In some embodiments, the loading dose is about 14 mg of the crystalline dihydrate form of the Compound of Formula (I) once a day for one day. In some embodiments, the loading dose is about 15 mg of the crystalline dihydrate form of the Compound of Formula (I) once a day for one day. In some embodiments, the loading dose is about 16 mg of the crystalline dihydrate form of the Compound of Formula (I) once a day for one day. In some embodiments, the loading dose is about 17 mg of the crystalline dihydrate form of the Compound of Formula (I) once a day for one day. In some embodiments, the loading dose is about 18 mg of the crystalline dihydrate form of the Compound of Formula (I) once a day for one day. In some embodiments, the loading dose is about 19 mg of the crystalline dihydrate form of the Compound of Formula (I) once a day for one day. In some embodiments, the loading dose is about 20 mg of the crystalline dihydrate form of the Compound of Formula (I) once a day for one day. In some embodiments, the loading dose is about 22 mg of the crystalline dihydrate form of the Compound of Formula (I) once a day for one day. In some embodiments, the loading dose is about 24 mg of the crystalline dihydrate form of the Compound of Formula (I) once a day for one day. In some embodiments, the loading dose is about 26 mg of the crystalline dihydrate form of the Compound of Formula (I) once a day for one day. In some embodiments, the loading dose is about 28 mg of the crystalline dihydrate form of the Compound of Formula (I) once a day for one day. In some embodiments, the loading dose is about 30 mg of the crystalline dihydrate form of the Compound of Formula (I) once a day for one day. In some embodiments, the loading dose is about 32 mg of the crystalline dihydrate form of the Compound of Formula (I) once a day for one day. In some embodiments, the loading dose is about 34 mg of the crystalline dihydrate form of the Compound of Formula (I) once a day for one day. In some embodiments, the loading dose is about 36 mg of the crystalline dihydrate form of the Compound of Formula (I) once a day for one day. In some embodiments, the loading dose is about 38 mg of the crystalline dihydrate form of the Compound of Formula (I) once a day for one day. In some embodiments, the loading dose is about 40 mg of the crystalline dihydrate form of the Compound of Formula (I) once a day for one day. In some embodiments, the loading dose is about 42 mg of the crystalline dihydrate form of the Compound of Formula (I) once a day for one day. In some embodiments, the loading dose is about 44 mg of the crystalline dihydrate form of the Compound of Formula (I) once a day for one day. In some embodiments, the loading dose is about 46 mg of the crystalline dihydrate form of the Compound of Formula (I) once a day for one day. In some embodiments, the loading dose is about 48 mg of the crystalline dihydrate form of the Compound of Formula (I) once a day for one day. In some embodiments, the loading dose is about 50 mg of the crystalline dihydrate form of the Compound of Formula (I) once a day for one day.

In some embodiments, the loading dose is about 2 mg to about 100 mg of the crystalline dihydrate form of the Compound of Formula (I) once a day for two days. In some embodiments, the loading dose is about 5 mg to about 90 mg of the crystalline dihydrate form of the Compound of Formula (I) once a day for two days. In some embodiments, the loading dose is about 10 mg to about 80 mg of the crystalline dihydrate form of the Compound of Formula (I) once a day for two days. In some embodiments, the loading dose is about 10 mg to about 70 mg of the crystalline dihydrate form of the Compound of Formula (I) once a day for two days. In some embodiments, the loading dose is about 10 mg to about 60 mg of the crystalline dihydrate form of the Compound of Formula (I) once a day for two days. In some embodiments, the loading dose is about 10 mg to about 50 mg of the crystalline dihydrate form of the Compound of Formula (I) once a day for two days. In some embodiments, the loading dose is about 10 mg to about 40 mg of the crystalline dihydrate form of the Compound of Formula (I) once a day for two days. In some embodiments, the loading dose is about 10 mg to about 30 mg of the crystalline dihydrate form of the Compound of Formula (I) once a day for two days. In some embodiments, the loading dose is about 10 mg to about 20 mg of the crystalline dihydrate form of the Compound of Formula (I) once a day for two days. In some embodiments, the loading dose is about 2 mg of the crystalline dihydrate form of the Compound of Formula (I) once a day for two days. In some embodiments, the loading dose is about 3 mg of the crystalline dihydrate form of the Compound of Formula (I) once a day for two days. In some embodiments, the loading dose is about 4 mg of the crystalline dihydrate form of the Compound of Formula (I) once a day for two days. In some embodiments, the loading dose is about 5 mg of the crystalline dihydrate form of the Compound of Formula (I) once a day for two days. In some embodiments, the loading dose is about 10 mg of the crystalline dihydrate form of the Compound of Formula (I) once a day for two days. In some embodiments, the loading dose is about 11 mg of the crystalline dihydrate form of the Compound of Formula (I) once a day for two days. In some embodiments, the loading dose is about 12 mg of the crystalline dihydrate form of the Compound of Formula (I) once a day for two days. In some embodiments, the loading dose is about 13 mg of the crystalline dihydrate form of the Compound of Formula (I) once a day for two days. In some embodiments, the loading dose is about 14 mg of the crystalline dihydrate form of the Compound of Formula (I) once a day for two days. In some embodiments, the loading dose is about 15 mg of the crystalline dihydrate form of the Compound of Formula (I) once a day for two days. In some embodiments, the loading dose is about 16 mg of the crystalline dihydrate form of the Compound of Formula (I) once a day for two days. In some embodiments, the loading dose is about 17 mg of the crystalline dihydrate form of the Compound of Formula (I) once a day for two days. In some embodiments, the loading dose is about 18 mg of the crystalline dihydrate form of the Compound of Formula (I) once a day for two days. In some embodiments, the loading dose is about 19 mg of the crystalline dihydrate form of the Compound of Formula (I) once a day for two days. In some embodiments, the loading dose is about 20 mg of the crystalline dihydrate form of the Compound of Formula (I) once a day for two days. In some embodiments, the loading dose is about 22 mg of the crystalline dihydrate form of the Compound of Formula (I) once a day for two days. In some embodiments, the loading dose is about 24 mg of the crystalline dihydrate form of the Compound of Formula (I) once a day for two days. In some embodiments, the loading dose is about 26 mg of the crystalline dihydrate form of the Compound of Formula (I) once a day for two days. In some embodiments, the loading dose is about 28 mg of the crystalline dihydrate form of the Compound of Formula (I) once a day for two days. In some embodiments, the loading dose is about 30 mg of the crystalline dihydrate form of the Compound of Formula (I) once a day for two days. In some embodiments, the loading dose is about 32 mg of the crystalline dihydrate form of the Compound of Formula (I) once a day for two days. In some embodiments, the loading dose is about 34 mg of the crystalline dihydrate form of the Compound of Formula (I) once a day for two days. In some embodiments, the loading dose is about 36 mg of the crystalline dihydrate form of the Compound of Formula (I) once a day for two days. In some embodiments, the loading dose is about 38 mg of the crystalline dihydrate form of the Compound of Formula (I) once a day for two days. In some embodiments, the loading dose is about 40 mg of the crystalline dihydrate form of the Compound of Formula (I) once a day for two days. In some embodiments, the loading dose is about 42 mg of the crystalline dihydrate form of the Compound of Formula (I) once a day for two days. In some embodiments, the loading dose is about 44 mg of the crystalline dihydrate form of the Compound of Formula (I) once a day for two days. In some embodiments, the loading dose is about 46 mg of the crystalline dihydrate form of the Compound of Formula (I) once a day for two days. In some embodiments, the loading dose is about 48 mg of the crystalline dihydrate form of the Compound of Formula (I) once a day for two days. In some embodiments, the loading dose is about 50 mg of the crystalline dihydrate form of the Compound of Formula (I) once a day for two days.

In some embodiments, the loading dose is about 2 mg to about 100 mg of the crystalline dihydrate form of the Compound of Formula (I) once a day for three days. In some embodiments, the loading dose is about 5 mg to about 90 mg of the crystalline dihydrate form of the Compound of Formula (I) once a day for three days. In some embodiments, the loading dose is about 10 mg to about 80 mg of the crystalline dihydrate form of the Compound of Formula (I) once a day for three days. In some embodiments, the loading dose is about 10 mg to about 70 mg of the crystalline dihydrate form of the Compound of Formula (I) once a day for three days. In some embodiments, the loading dose is about 10 mg to about 60 mg of the crystalline dihydrate form of the Compound of Formula (I) once a day for three days. In some embodiments, the loading dose is about 10 mg to about 50 mg of the crystalline dihydrate form of the Compound of Formula (I) once a day for three days. In some embodiments, the loading dose is about 10 mg to about 40 mg of the crystalline dihydrate form of the Compound of Formula (I) once a day for three days. In some embodiments, the loading dose is about 10 mg to about 30 mg of the crystalline dihydrate form of the Compound of Formula (I) once a day for three days. In some embodiments, the loading dose is about 10 mg to about 20 mg of the crystalline dihydrate form of the Compound of Formula (I) once a day for three days. In some embodiments, the loading dose is about 2 mg of the crystalline dihydrate form of the Compound of Formula (I) once a day for three days. In some embodiments, the loading dose is about 3 mg of the crystalline dihydrate form of the Compound of Formula (I) once a day for three days. In some embodiments, the loading dose is about 4 mg of the crystalline dihydrate form of the Compound of Formula (I) once a day for three days. In some embodiments, the loading dose is about 5 mg of the crystalline dihydrate form of the Compound of Formula (I) once a day for three days. In some embodiments, the loading dose is about 10 mg of the crystalline dihydrate form of the Compound of Formula (I) once a day for three days. In some embodiments, the loading dose is about 11 mg of the crystalline dihydrate form of the Compound of Formula (I) once a day for three days. In some embodiments, the loading dose is about 12 mg of the crystalline dihydrate form of the Compound of Formula (I) once a day for three days. In some embodiments, the loading dose is about 13 mg of the crystalline dihydrate form of the Compound of Formula (I) once a day for three days. In some embodiments, the loading dose is about 14 mg of the crystalline dihydrate form of the Compound of Formula (I) once a day for three days. In some embodiments, the loading dose is about 15 mg of the crystalline dihydrate form of the Compound of Formula (I) once a day for three days. In some embodiments, the loading dose is about 16 mg of the crystalline dihydrate form of the Compound of Formula (I) once a day for three days. In some embodiments, the loading dose is about 17 mg of the crystalline dihydrate form of the Compound of Formula (I) once a day for three days. In some embodiments, the loading dose is about 18 mg of the crystalline dihydrate form of the Compound of Formula (I) once a day for three days. In some embodiments, the loading dose is about 19 mg of the crystalline dihydrate form of the Compound of Formula (I) once a day for three days. In some embodiments, the loading dose is about 20 mg of the crystalline dihydrate form of the Compound of Formula (I) once a day for three days. In some embodiments, the loading dose is about 22 mg of the crystalline dihydrate form of the Compound of Formula (I) once a day for three days. In some embodiments, the loading dose is about 24 mg of the crystalline dihydrate form of the Compound of Formula (I) once a day for three days. In some embodiments, the loading dose is about 26 mg of the crystalline dihydrate form of the Compound of Formula (I) once a day for three days. In some embodiments, the loading dose is about 28 mg of the crystalline dihydrate form of the Compound of Formula (I) once a day for three days. In some embodiments, the loading dose is about 30 mg of the crystalline dihydrate form of the Compound of Formula (I) once a day for three days. In some embodiments, the loading dose is about 32 mg of the crystalline dihydrate form of the Compound of Formula (I) once a day for three days. In some embodiments, the loading dose is about 34 mg of the crystalline dihydrate form of the Compound of Formula (I) once a day for three days. In some embodiments, the loading dose is about 36 mg of the crystalline dihydrate form of the Compound of Formula (I) once a day for three days. In some embodiments, the loading dose is about 38 mg of the crystalline dihydrate form of the Compound of Formula (I) once a day for three days. In some embodiments, the loading dose is about 40 mg of the crystalline dihydrate form of the Compound of Formula (I) once a day for three days. In some embodiments, the loading dose is about 42 mg of the crystalline dihydrate form of the Compound of Formula (I) once a day for three days. In some embodiments, the loading dose is about 44 mg of the crystalline dihydrate form of the Compound of Formula (I) once a day for three days. In some embodiments, the loading dose is about 46 mg of the crystalline dihydrate form of the Compound of Formula (I) once a day for three days. In some embodiments, the loading dose is about 48 mg of the crystalline dihydrate form of the Compound of Formula (I) once a day for three days. In some embodiments, the loading dose is about 50 mg of the crystalline dihydrate form of the Compound of Formula (I) once a day for three days.

In some embodiments, the loading dose is about 2 mg to about 100 mg of the crystalline dihydrate form of the Compound of Formula (I) once a day for four days. In some embodiments, the loading dose is about 5 mg to about 90 mg of the crystalline dihydrate form of the Compound of Formula (I) once a day for four days. In some embodiments, the loading dose is about 10 mg to about 80 mg of the crystalline dihydrate form of the Compound of Formula (I) once a day for four days. In some embodiments, the loading dose is about 10 mg to about 70 mg of the crystalline dihydrate form of the Compound of Formula (I) once a day for four days. In some embodiments, the loading dose is about 10 mg to about 60 mg of the crystalline dihydrate form of the Compound of Formula (I) once a day for four days. In some embodiments, the loading dose is about 10 mg to about 50 mg of the crystalline dihydrate form of the Compound of Formula (I) once a day for four days. In some embodiments, the loading dose is about 10 mg to about 40 mg of the crystalline dihydrate form of the Compound of Formula (I) once a day for four days. In some embodiments, the loading dose is about 10 mg to about 30 mg of the crystalline dihydrate form of the Compound of Formula (I) once a day for four days. In some embodiments, the loading dose is about 10 mg to about 20 mg of the crystalline dihydrate form of the Compound of Formula (I) once a day for four days. In some embodiments, the loading dose is about 2 mg of the crystalline dihydrate form of the Compound of Formula (I) once a day for four days. In some embodiments, the loading dose is about 3 mg of the crystalline dihydrate form of the Compound of Formula (I) once a day for four days. In some embodiments, the loading dose is about 4 mg of the crystalline dihydrate form of the Compound of Formula (I) once a day for four days. In some embodiments, the loading dose is about 5 mg of the crystalline dihydrate form of the Compound of Formula (I) once a day for four days. In some embodiments, the loading dose is about 10 mg of the crystalline dihydrate form of the Compound of Formula (I) once a day for four days. In some embodiments, the loading dose is about 11 mg of the crystalline dihydrate form of the Compound of Formula (I) once a day for four days. In some embodiments, the loading dose is about 12 mg of the crystalline dihydrate form of the Compound of Formula (I) once a day for four days. In some embodiments, the loading dose is about 13 mg of the crystalline dihydrate form of the Compound of Formula (I) once a day for four days. In some embodiments, the loading dose is about 14 mg of the crystalline dihydrate form of the Compound of Formula (I) once a day for four days. In some embodiments, the loading dose is about 15 mg of the crystalline dihydrate form of the Compound of Formula (I) once a day for four days. In some embodiments, the loading dose is about 16 mg of the crystalline dihydrate form of the Compound of Formula (I) once a day for four days. In some embodiments, the loading dose is about 17 mg of the crystalline dihydrate form of the Compound of Formula (I) once a day for four days. In some embodiments, the loading dose is about 18 mg of the crystalline dihydrate form of the Compound of Formula (I) once a day for four days. In some embodiments, the loading dose is about 19 mg of the crystalline dihydrate form of the Compound of Formula (I) once a day for four days. In some embodiments, the loading dose is about 20 mg of the crystalline dihydrate form of the Compound of Formula (I) once a day for four days. In some embodiments, the loading dose is about 22 mg of the crystalline dihydrate form of the Compound of Formula (I) once a day for four days. In some embodiments, the loading dose is about 24 mg of the crystalline dihydrate form of the Compound of Formula (I) once a day for four days. In some embodiments, the loading dose is about 26 mg of the crystalline dihydrate form of the Compound of Formula (I) once a day for four days. In some embodiments, the loading dose is about 28 mg of the crystalline dihydrate form of the Compound of Formula (I) once a day for four days. In some embodiments, the loading dose is about 30 mg of the crystalline dihydrate form of the Compound of Formula (I) once a day for four days. In some embodiments, the loading dose is about 32 mg of the crystalline dihydrate form of the Compound of Formula (I) once a day for four days. In some embodiments, the loading dose is about 34 mg of the crystalline dihydrate form of the Compound of Formula (I) once a day for four days. In some embodiments, the loading dose is about 36 mg of the crystalline dihydrate form of the Compound of Formula (I) once a day for four days. In some embodiments, the loading dose is about 38 mg of the crystalline dihydrate form of the Compound of Formula (I) once a day for four days. In some embodiments, the loading dose is about 40 mg of the crystalline dihydrate form of the Compound of Formula (I) once a day for four days. In some embodiments, the loading dose is about 42 mg of the crystalline dihydrate form of the Compound of Formula (I) once a day for four days. In some embodiments, the loading dose is about 44 mg of the crystalline dihydrate form of the Compound of Formula (I) once a day for four days. In some embodiments, the loading dose is about 46 mg of the crystalline dihydrate form of the Compound of Formula (I) once a day for four days. In some embodiments, the loading dose is about 48 mg of the crystalline dihydrate form of the Compound of Formula (I) once a day for four days. In some embodiments, the loading dose is about 50 mg of the crystalline dihydrate form of the Compound of Formula (I) once a day for four days.

In some embodiments, the loading dose is about 2 mg to about 100 mg of the crystalline dihydrate form of the Compound of Formula (I) once a day for five days. In some embodiments, the loading dose is about 5 mg to about 90 mg of the crystalline dihydrate form of the Compound of Formula (I) once a day for five days. In some embodiments, the loading dose is about 10 mg to about 80 mg of the crystalline dihydrate form of the Compound of Formula (I) once a day for five days. In some embodiments, the loading dose is about 10 mg to about 70 mg of the crystalline dihydrate form of the Compound of Formula (I) once a day for five days. In some embodiments, the loading dose is about 10 mg to about 60 mg of the crystalline dihydrate form of the Compound of Formula (I) once a day for five days. In some embodiments, the loading dose is about 10 mg to about 50 mg of the crystalline dihydrate form of the Compound of Formula (I) once a day for five days. In some embodiments, the loading dose is about 10 mg to about 40 mg of the crystalline dihydrate form of the Compound of Formula (I) once a day for five days. In some embodiments, the loading dose is about 10 mg to about 30 mg of the crystalline dihydrate form of the Compound of Formula (I) once a day for five days. In some embodiments, the loading dose is about 10 mg to about 20 mg of the crystalline dihydrate form of the Compound of Formula (I) once a day for five days. In some embodiments, the loading dose is about 2 mg of the crystalline dihydrate form of the Compound of Formula (I) once a day for five days. In some embodiments, the loading dose is about 3 mg of the crystalline dihydrate form of the Compound of Formula (I) once a day for five days. In some embodiments, the loading dose is about 4 mg of the crystalline dihydrate form of the Compound of Formula (I) once a day for five days. In some embodiments, the loading dose is about 5 mg of the crystalline dihydrate form of the Compound of Formula (I) once a day for five days. In some embodiments, the loading dose is about 10 mg of the crystalline dihydrate form of the Compound of Formula (I) once a day for five days. In some embodiments, the loading dose is about 11 mg of the crystalline dihydrate form of the Compound of Formula (I) once a day for five days. In some embodiments, the loading dose is about 12 mg of the crystalline dihydrate form of the Compound of Formula (I) once a day for five days. In some embodiments, the loading dose is about 13 mg of the crystalline dihydrate form of the Compound of Formula (I) once a day for five days. In some embodiments, the loading dose is about 14 mg of the crystalline dihydrate form of the Compound of Formula (I) once a day for five days. In some embodiments, the loading dose is about 15 mg of the crystalline dihydrate form of the Compound of Formula (I) once a day for five days. In some embodiments, the loading dose is about 16 mg of the crystalline dihydrate form of the Compound of Formula (I) once a day for five days. In some embodiments, the loading dose is about 17 mg of the crystalline dihydrate form of the Compound of Formula (I) once a day for five days. In some embodiments, the loading dose is about 18 mg of the crystalline dihydrate form of the Compound of Formula (I) once a day for five days. In some embodiments, the loading dose is about 19 mg of the crystalline dihydrate form of the Compound of Formula (I) once a day for five days. In some embodiments, the loading dose is about 20 mg of the crystalline dihydrate form of the Compound of Formula (I) once a day for five days. In some embodiments, the loading dose is about 22 mg of the crystalline dihydrate form of the Compound of Formula (I) once a day for five days. In some embodiments, the loading dose is about 24 mg of the crystalline dihydrate form of the Compound of Formula (I) once a day for five days. In some embodiments, the loading dose is about 26 mg of the crystalline dihydrate form of the Compound of Formula (I) once a day for five days. In some embodiments, the loading dose is about 28 mg of the crystalline dihydrate form of the Compound of Formula (I) once a day for five days. In some embodiments, the loading dose is about 30 mg of the crystalline dihydrate form of the Compound of Formula (I) once a day for five days. In some embodiments, the loading dose is about 32 mg of the crystalline dihydrate form of the Compound of Formula (I) once a day for five days. In some embodiments, the loading dose is about 34 mg of the crystalline dihydrate form of the Compound of Formula (I) once a day for five days. In some embodiments, the loading dose is about 36 mg of the crystalline dihydrate form of the Compound of Formula (I) once a day for five days. In some embodiments, the loading dose is about 38 mg of the crystalline dihydrate form of the Compound of Formula (I) once a day for five days. In some embodiments, the loading dose is about 40 mg of the crystalline dihydrate form of the Compound of Formula (I) once a day for five days. In some embodiments, the loading dose is about 42 mg of the crystalline dihydrate form of the Compound of Formula (I) once a day for five days. In some embodiments, the loading dose is about 44 mg of the crystalline dihydrate form of the Compound of Formula (I) once a day for five days. In some embodiments, the loading dose is about 46 mg of the crystalline dihydrate form of the Compound of Formula (I) once a day for five days. In some embodiments, the loading dose is about 48 mg of the crystalline dihydrate form of the Compound of Formula (I) once a day for five days. In some embodiments, the loading dose is about 50 mg of the crystalline dihydrate form of the Compound of Formula (I) once a day for five days.

In some embodiments, the loading dose is about 2 mg to about 100 mg of the crystalline dihydrate form of the Compound of Formula (I) once a day for six days. In some embodiments, the loading dose is about 5 mg to about 90 mg of the crystalline dihydrate form of the Compound of Formula (I) once a day for six days. In some embodiments, the loading dose is about 10 mg to about 80 mg of the crystalline dihydrate form of the Compound of Formula (I) once a day for six days. In some embodiments, the loading dose is about 10 mg to about 70 mg of the crystalline dihydrate form of the Compound of Formula (I) once a day for six days. In some embodiments, the loading dose is about 10 mg to about 60 mg of the crystalline dihydrate form of the Compound of Formula (I) once a day for six days. In some embodiments, the loading dose is about 10 mg to about 50 mg of the crystalline dihydrate form of the Compound of Formula (I) once a day for six days. In some embodiments, the loading dose is about 10 mg to about 40 mg of the crystalline dihydrate form of the Compound of Formula (I) once a day for six days. In some embodiments, the loading dose is about 10 mg to about 30 mg of the crystalline dihydrate form of the Compound of Formula (I) once a day for six days. In some embodiments, the loading dose is about 10 mg to about 20 mg of the crystalline dihydrate form of the Compound of Formula (I) once a day for six days. In some embodiments, the loading dose is about 2 mg of the crystalline dihydrate form of the Compound of Formula (I) once a day for six days. In some embodiments, the loading dose is about 3 mg of the crystalline dihydrate form of the Compound of Formula (I) once a day for six days. In some embodiments, the loading dose is about 4 mg of the crystalline dihydrate form of the Compound of Formula (I) once a day for six days. In some embodiments, the loading dose is about 5 mg of the crystalline dihydrate form of the Compound of Formula (I) once a day for six days. In some embodiments, the loading dose is about 10 mg of the crystalline dihydrate form of the Compound of Formula (I) once a day for six days. In some embodiments, the loading dose is about 11 mg of the crystalline dihydrate form of the Compound of Formula (I) once a day for six days. In some embodiments, the loading dose is about 12 mg of the crystalline dihydrate form of the Compound of Formula (I) once a day for six days. In some embodiments, the loading dose is about 13 mg of the crystalline dihydrate form of the Compound of Formula (I) once a day for six days. In some embodiments, the loading dose is about 14 mg of the crystalline dihydrate form of the Compound of Formula (I) once a day for six days. In some embodiments, the loading dose is about 15 mg of the crystalline dihydrate form of the Compound of Formula (I) once a day for six days. In some embodiments, the loading dose is about 16 mg of the crystalline dihydrate form of the Compound of Formula (I) once a day for six days. In some embodiments, the loading dose is about 17 mg of the crystalline dihydrate form of the Compound of Formula (I) once a day for six days. In some embodiments, the loading dose is about 18 mg of the crystalline dihydrate form of the Compound of Formula (I) once a day for six days. In some embodiments, the loading dose is about 19 mg of the crystalline dihydrate form of the Compound of Formula (I) once a day for six days. In some embodiments, the loading dose is about 20 mg of the crystalline dihydrate form of the Compound of Formula (I) once a day for six days. In some embodiments, the loading dose is about 22 mg of the crystalline dihydrate form of the Compound of Formula (I) once a day for six days. In some embodiments, the loading dose is about 24 mg of the crystalline dihydrate form of the Compound of Formula (I) once a day for six days. In some embodiments, the loading dose is about 26 mg of the crystalline dihydrate form of the Compound of Formula (I) once a day for six days. In some embodiments, the loading dose is about 28 mg of the crystalline dihydrate form of the Compound of Formula (I) once a day for six days. In some embodiments, the loading dose is about 30 mg of the crystalline dihydrate form of the Compound of Formula (I) once a day for six days. In some embodiments, the loading dose is about 32 mg of the crystalline dihydrate form of the Compound of Formula (I) once a day for six days. In some embodiments, the loading dose is about 34 mg of the crystalline dihydrate form of the Compound of Formula (I) once a day for six days. In some embodiments, the loading dose is about 36 mg of the crystalline dihydrate form of the Compound of Formula (I) once a day for six days. In some embodiments, the loading dose is about 38 mg of the crystalline dihydrate form of the Compound of Formula (I) once a day for six days. In some embodiments, the loading dose is about 40 mg of the crystalline dihydrate form of the Compound of Formula (I) once a day for six days. In some embodiments, the loading dose is about 42 mg of the crystalline dihydrate form of the Compound of Formula (I) once a day for six days. In some embodiments, the loading dose is about 44 mg of the crystalline dihydrate form of the Compound of Formula (I) once a day for six days. In some embodiments, the loading dose is about 46 mg of the crystalline dihydrate form of the Compound of Formula (I) once a day for six days. In some embodiments, the loading dose is about 48 mg of the crystalline dihydrate form of the Compound of Formula (I) once a day for six days. In some embodiments, the loading dose is about 50 mg of the crystalline dihydrate form of the Compound of Formula (I) once a day for six days.

In some embodiments, the loading dose is about 2 mg to about 100 mg of the crystalline dihydrate form of the Compound of Formula (I) once a day for seven days. In some embodiments, the loading dose is about 5 mg to about 90 mg of the crystalline dihydrate form of the Compound of Formula (I) once a day for seven days. In some embodiments, the loading dose is about 10 mg to about 80 mg of the crystalline dihydrate form of the Compound of Formula (I) once a day for seven days. In some embodiments, the loading dose is about 10 mg to about 70 mg of the crystalline dihydrate form of the Compound of Formula (I) once a day for seven days. In some embodiments, the loading dose is about 10 mg to about 60 mg of the crystalline dihydrate form of the Compound of Formula (I) once a day for seven days. In some embodiments, the loading dose is about 10 mg to about 50 mg of the crystalline dihydrate form of the Compound of Formula (I) once a day for seven days. In some embodiments, the loading dose is about 10 mg to about 40 mg of the crystalline dihydrate form of the Compound of Formula (I) once a day for seven days. In some embodiments, the loading dose is about 10 mg to about 30 mg of the crystalline dihydrate form of the Compound of Formula (I) once a day for seven days. In some embodiments, the loading dose is about 10 mg to about 20 mg of the crystalline dihydrate form of the Compound of Formula (I) once a day for seven days. In some embodiments, the loading dose is about 2 mg of the crystalline dihydrate form of the Compound of Formula (I) once a day for seven days. In some embodiments, the loading dose is about 3 mg of the crystalline dihydrate form of the Compound of Formula (I) once a day for seven days. In some embodiments, the loading dose is about 4 mg of the crystalline dihydrate form of the Compound of Formula (I) once a day for seven days. In some embodiments, the loading dose is about 5 mg of the crystalline dihydrate form of the Compound of Formula (I) once a day for seven days. In some embodiments, the loading dose is about 10 mg of the crystalline dihydrate form of the Compound of Formula (I) once a day for seven days. In some embodiments, the loading dose is about 11 mg of the crystalline dihydrate form of the Compound of Formula (I) once a day for seven days. In some embodiments, the loading dose is about 12 mg of the crystalline dihydrate form of the Compound of Formula (I) once a day for seven days. In some embodiments, the loading dose is about 13 mg of the crystalline dihydrate form of the Compound of Formula (I) once a day for seven days. In some embodiments, the loading dose is about 14 mg of the crystalline dihydrate form of the Compound of Formula (I) once a day for seven days. In some embodiments, the loading dose is about 15 mg of the crystalline dihydrate form of the Compound of Formula (I) once a day for seven days. In some embodiments, the loading dose is about 16 mg of the crystalline dihydrate form of the Compound of Formula (I) once a day for seven days. In some embodiments, the loading dose is about 17 mg of the crystalline dihydrate form of the Compound of Formula (I) once a day for seven days. In some embodiments, the loading dose is about 18 mg of the crystalline dihydrate form of the Compound of Formula (I) once a day for seven days. In some embodiments, the loading dose is about 19 mg of the crystalline dihydrate form of the Compound of Formula (I) once a day for seven days. In some embodiments, the loading dose is about 20 mg of the crystalline dihydrate form of the Compound of Formula (I) once a day for seven days. In some embodiments, the loading dose is about 22 mg of the crystalline dihydrate form of the Compound of Formula (I) once a day for seven days. In some embodiments, the loading dose is about 24 mg of the crystalline dihydrate form of the Compound of Formula (I) once a day for seven days. In some embodiments, the loading dose is about 26 mg of the crystalline dihydrate form of the Compound of Formula (I) once a day for seven days. In some embodiments, the loading dose is about 28 mg of the crystalline dihydrate form of the Compound of Formula (I) once a day for seven days. In some embodiments, the loading dose is about 30 mg of the crystalline dihydrate form of the Compound of Formula (I) once a day for seven days. In some embodiments, the loading dose is about 32 mg of the crystalline dihydrate form of the Compound of Formula (I) once a day for seven days. In some embodiments, the loading dose is about 34 mg of the crystalline dihydrate form of the Compound of Formula (I) once a day for seven days. In some embodiments, the loading dose is about 36 mg of the crystalline dihydrate form of the Compound of Formula (I) once a day for seven days. In some embodiments, the loading dose is about 38 mg of the crystalline dihydrate form of the Compound of Formula (I) once a day for seven days. In some embodiments, the loading dose is about 40 mg of the crystalline dihydrate form of the Compound of Formula (I) once a day for seven days. In some embodiments, the loading dose is about 42 mg of the crystalline dihydrate form of the Compound of Formula (I) once a day for seven days. In some embodiments, the loading dose is about 44 mg of the crystalline dihydrate form of the Compound of Formula (I) once a day for seven days. In some embodiments, the loading dose is about 46 mg of the crystalline dihydrate form of the Compound of Formula (I) once a day for seven days. In some embodiments, the loading dose is about 48 mg of the crystalline dihydrate form of the Compound of Formula (I) once a day for seven days. In some embodiments, the loading dose is about 50 mg of the crystalline dihydrate form of the Compound of Formula (I) once a day for seven days.

In some embodiments, the loading dose is about 2 mg to about 100 mg of the crystalline dihydrate form of the Compound of Formula (I) once a day for eight days. In some embodiments, the loading dose is about 5 mg to about 90 mg of the crystalline dihydrate form of the Compound of Formula (I) once a day for eight days. In some embodiments, the loading dose is about 10 mg to about 80 mg of the crystalline dihydrate form of the Compound of Formula (I) once a day for eight days. In some embodiments, the loading dose is about 10 mg to about 70 mg of the crystalline dihydrate form of the Compound of Formula (I) once a day for eight days. In some embodiments, the loading dose is about 10 mg to about 60 mg of the crystalline dihydrate form of the Compound of Formula (I) once a day for eight days. In some embodiments, the loading dose is about 10 mg to about 50 mg of the crystalline dihydrate form of the Compound of Formula (I) once a day for eight days. In some embodiments, the loading dose is about 10 mg to about 40 mg of the crystalline dihydrate form of the Compound of Formula (I) once a day for eight days. In some embodiments, the loading dose is about 10 mg to about 30 mg of the crystalline dihydrate form of the Compound of Formula (I) once a day for eight days. In some embodiments, the loading dose is about 10 mg to about 20 mg of the crystalline dihydrate form of the Compound of Formula (I) once a day for eight days. In some embodiments, the loading dose is about 2 mg of the crystalline dihydrate form of the Compound of Formula (I) once a day for eight days. In some embodiments, the loading dose is about 3 mg of the crystalline dihydrate form of the Compound of Formula (I) once a day for eight days. In some embodiments, the loading dose is about 4 mg of the crystalline dihydrate form of the Compound of Formula (I) once a day for eight days. In some embodiments, the loading dose is about 5 mg of the crystalline dihydrate form of the Compound of Formula (I) once a day for eight days. In some embodiments, the loading dose is about 10 mg of the crystalline dihydrate form of the Compound of Formula (I) once a day for eight days. In some embodiments, the loading dose is about 11 mg of the crystalline dihydrate form of the Compound of Formula (I) once a day for eight days. In some embodiments, the loading dose is about 12 mg of the crystalline dihydrate form of the Compound of Formula (I) once a day for eight days. In some embodiments, the loading dose is about 13 mg of the crystalline dihydrate form of the Compound of Formula (I) once a day for eight days. In some embodiments, the loading dose is about 14 mg of the crystalline dihydrate form of the Compound of Formula (I) once a day for eight days. In some embodiments, the loading dose is about 15 mg of the crystalline dihydrate form of the Compound of Formula (I) once a day for eight days. In some embodiments, the loading dose is about 16 mg of the crystalline dihydrate form of the Compound of Formula (I) once a day for eight days. In some embodiments, the loading dose is about 17 mg of the crystalline dihydrate form of the Compound of Formula (I) once a day for eight days. In some embodiments, the loading dose is about 18 mg of the crystalline dihydrate form of the Compound of Formula (I) once a day for eight days. In some embodiments, the loading dose is about 19 mg of the crystalline dihydrate form of the Compound of Formula (I) once a day for eight days. In some embodiments, the loading dose is about 20 mg of the crystalline dihydrate form of the Compound of Formula (I) once a day for eight days. In some embodiments, the loading dose is about 22 mg of the crystalline dihydrate form of the Compound of Formula (I) once a day for eight days. In some embodiments, the loading dose is about 24 mg of the crystalline dihydrate form of the Compound of Formula (I) once a day for eight days. In some embodiments, the loading dose is about 26 mg of the crystalline dihydrate form of the Compound of Formula (I) once a day for eight days. In some embodiments, the loading dose is about 28 mg of the crystalline dihydrate form of the Compound of Formula (I) once a day for eight days. In some embodiments, the loading dose is about 30 mg of the crystalline dihydrate form of the Compound of Formula (I) once a day for eight days. In some embodiments, the loading dose is about 32 mg of the crystalline dihydrate form of the Compound of Formula (I) once a day for eight days. In some embodiments, the loading dose is about 34 mg of the crystalline dihydrate form of the Compound of Formula (I) once a day for eight days. In some embodiments, the loading dose is about 36 mg of the crystalline dihydrate form of the Compound of Formula (I) once a day for eight days. In some embodiments, the loading dose is about 38 mg of the crystalline dihydrate form of the Compound of Formula (I) once a day for eight days. In some embodiments, the loading dose is about 40 mg of the crystalline dihydrate form of the Compound of Formula (I) once a day for eight days. In some embodiments, the loading dose is about 42 mg of the crystalline dihydrate form of the Compound of Formula (I) once a day for eight days. In some embodiments, the loading dose is about 44 mg of the crystalline dihydrate form of the Compound of Formula (I) once a day for eight days. In some embodiments, the loading dose is about 46 mg of the crystalline dihydrate form of the Compound of Formula (I) once a day for eight days. In some embodiments, the loading dose is about 48 mg of the crystalline dihydrate form of the Compound of Formula (I) once a day for eight days. In some embodiments, the loading dose is about 50 mg of the crystalline dihydrate form of the Compound of Formula (I) once a day for eight days.

In some embodiments, the loading dose is about 2 mg to about 100 mg of the crystalline dihydrate form of the Compound of Formula (I) once a day for nine days. In some embodiments, the loading dose is about 5 mg to about 90 mg of the crystalline dihydrate form of the Compound of Formula (I) once a day for nine days. In some embodiments, the loading dose is about 10 mg to about 80 mg of the crystalline dihydrate form of the Compound of Formula (I) once a day for nine days. In some embodiments, the loading dose is about 10 mg to about 70 mg of the crystalline dihydrate form of the Compound of Formula (I) once a day for nine days. In some embodiments, the loading dose is about 10 mg to about 60 mg of the crystalline dihydrate form of the Compound of Formula (I) once a day for nine days. In some embodiments, the loading dose is about 10 mg to about 50 mg of the crystalline dihydrate form of the Compound of Formula (I) once a day for nine days. In some embodiments, the loading dose is about 10 mg to about 40 mg of the crystalline dihydrate form of the Compound of Formula (I) once a day for nine days. In some embodiments, the loading dose is about 10 mg to about 30 mg of the crystalline dihydrate form of the Compound of Formula (I) once a day for nine days. In some embodiments, the loading dose is about 10 mg to about 20 mg of the crystalline dihydrate form of the Compound of Formula (I) once a day for nine days. In some embodiments, the loading dose is about 2 mg of the crystalline dihydrate form of the Compound of Formula (I) once a day for nine days. In some embodiments, the loading dose is about 3 mg of the crystalline dihydrate form of the Compound of Formula (I) once a day for nine days. In some embodiments, the loading dose is about 4 mg of the crystalline dihydrate form of the Compound of Formula (I) once a day for nine days. In some embodiments, the loading dose is about 5 mg of the crystalline dihydrate form of the Compound of Formula (I) once a day for nine days. In some embodiments, the loading dose is about 10 mg of the crystalline dihydrate form of the Compound of Formula (I) once a day for nine days. In some embodiments, the loading dose is about 11 mg of the crystalline dihydrate form of the Compound of Formula (I) once a day for nine days. In some embodiments, the loading dose is about 12 mg of the crystalline dihydrate form of the Compound of Formula (I) once a day for nine days. In some embodiments, the loading dose is about 13 mg of the crystalline dihydrate form of the Compound of Formula (I) once a day for nine days. In some embodiments, the loading dose is about 14 mg of the crystalline dihydrate form of the Compound of Formula (I) once a day for nine days. In some embodiments, the loading dose is about 15 mg of the crystalline dihydrate form of the Compound of Formula (I) once a day for nine days. In some embodiments, the loading dose is about 16 mg of the crystalline dihydrate form of the Compound of Formula (I) once a day for nine days. In some embodiments, the loading dose is about 17 mg of the crystalline dihydrate form of the Compound of Formula (I) once a day for nine days. In some embodiments, the loading dose is about 18 mg of the crystalline dihydrate form of the Compound of Formula (I) once a day for nine days. In some embodiments, the loading dose is about 19 mg of the crystalline dihydrate form of the Compound of Formula (I) once a day for nine days. In some embodiments, the loading dose is about 20 mg of the crystalline dihydrate form of the Compound of Formula (I) once a day for nine days. In some embodiments, the loading dose is about 22 mg of the crystalline dihydrate form of the Compound of Formula (I) once a day for nine days. In some embodiments, the loading dose is about 24 mg of the crystalline dihydrate form of the Compound of Formula (I) once a day for nine days. In some embodiments, the loading dose is about 26 mg of the crystalline dihydrate form of the Compound of Formula (I) once a day for nine days. In some embodiments, the loading dose is about 28 mg of the crystalline dihydrate form of the Compound of Formula (I) once a day for nine days. In some embodiments, the loading dose is about 30 mg of the crystalline dihydrate form of the Compound of Formula (I) once a day for nine days. In some embodiments, the loading dose is about 32 mg of the crystalline dihydrate form of the Compound of Formula (I) once a day for nine days. In some embodiments, the loading dose is about 34 mg of the crystalline dihydrate form of the Compound of Formula (I) once a day for nine days. In some embodiments, the loading dose is about 36 mg of the crystalline dihydrate form of the Compound of Formula (I) once a day for nine days. In some embodiments, the loading dose is about 38 mg of the crystalline dihydrate form of the Compound of Formula (I) once a day for nine days. In some embodiments, the loading dose is about 40 mg of the crystalline dihydrate form of the Compound of Formula (I) once a day for nine days. In some embodiments, the loading dose is about 42 mg of the crystalline dihydrate form of the Compound of Formula (I) once a day for nine days. In some embodiments, the loading dose is about 44 mg of the crystalline dihydrate form of the Compound of Formula (I) once a day for nine days. In some embodiments, the loading dose is about 46 mg of the crystalline dihydrate form of the Compound of Formula (I) once a day for nine days. In some embodiments, the loading dose is about 48 mg of the crystalline dihydrate form of the Compound of Formula (I) once a day for nine days. In some embodiments, the loading dose is about 50 mg of the crystalline dihydrate form of the Compound of Formula (I) once a day for nine days.

In some embodiments, the loading dose is about 2 mg to about 100 mg of the crystalline dihydrate form of the Compound of Formula (I) once a day for ten days. In some embodiments, the loading dose is about 5 mg to about 90 mg of the crystalline dihydrate form of the Compound of Formula (I) once a day for ten days. In some embodiments, the loading dose is about 10 mg to about 80 mg of the crystalline dihydrate form of the Compound of Formula (I) once a day for ten days. In some embodiments, the loading dose is about 10 mg to about 70 mg of the crystalline dihydrate form of the Compound of Formula (I) once a day for ten days. In some embodiments, the loading dose is about 10 mg to about 60 mg of the crystalline dihydrate form of the Compound of Formula (I) once a day for ten days. In some embodiments, the loading dose is about 10 mg to about 50 mg of the crystalline dihydrate form of the Compound of Formula (I) once a day for ten days. In some embodiments, the loading dose is about 10 mg to about 40 mg of the crystalline dihydrate form of the Compound of Formula (I) once a day for ten days. In some embodiments, the loading dose is about 10 mg to about 30 mg of the crystalline dihydrate form of the Compound of Formula (I) once a day for ten days. In some embodiments, the loading dose is about 10 mg to about 20 mg of the crystalline dihydrate form of the Compound of Formula (I) once a day for ten days. In some embodiments, the loading dose is about 2 mg of the crystalline dihydrate form of the Compound of Formula (I) once a day for ten days. In some embodiments, the loading dose is about 3 mg of the crystalline dihydrate form of the Compound of Formula (I) once a day for ten days. In some embodiments, the loading dose is about 4 mg of the crystalline dihydrate form of the Compound of Formula (I) once a day for ten days. In some embodiments, the loading dose is about 5 mg of the crystalline dihydrate form of the Compound of Formula (I) once a day for ten days. In some embodiments, the loading dose is about 10 mg of the crystalline dihydrate form of the Compound of Formula (I) once a day for ten days. In some embodiments, the loading dose is about 11 mg of the crystalline dihydrate form of the Compound of Formula (I) once a day for ten days. In some embodiments, the loading dose is about 12 mg of the crystalline dihydrate form of the Compound of Formula (I) once a day for ten days. In some embodiments, the loading dose is about 13 mg of the crystalline dihydrate form of the Compound of Formula (I) once a day for ten days. In some embodiments, the loading dose is about 14 mg of the crystalline dihydrate form of the Compound of Formula (I) once a day for ten days. In some embodiments, the loading dose is about 15 mg of the crystalline dihydrate form of the Compound of Formula (I) once a day for ten days. In some embodiments, the loading dose is about 16 mg of the crystalline dihydrate form of the Compound of Formula (I) once a day for ten days. In some embodiments, the loading dose is about 17 mg of the crystalline dihydrate form of the Compound of Formula (I) once a day for ten days. In some embodiments, the loading dose is about 18 mg of the crystalline dihydrate form of the Compound of Formula (I) once a day for ten days. In some embodiments, the loading dose is about 19 mg of the crystalline dihydrate form of the Compound of Formula (I) once a day for ten days. In some embodiments, the loading dose is about 20 mg of the crystalline dihydrate form of the Compound of Formula (I) once a day for ten days. In some embodiments, the loading dose is about 22 mg of the crystalline dihydrate form of the Compound of Formula (I) once a day for ten days. In some embodiments, the loading dose is about 24 mg of the crystalline dihydrate form of the Compound of Formula (I) once a day for ten days. In some embodiments, the loading dose is about 26 mg of the crystalline dihydrate form of the Compound of Formula (I) once a day for ten days. In some embodiments, the loading dose is about 28 mg of the crystalline dihydrate form of the Compound of Formula (I) once a day for ten days. In some embodiments, the loading dose is about 30 mg of the crystalline dihydrate form of the Compound of Formula (I) once a day for ten days. In some embodiments, the loading dose is about 32 mg of the crystalline dihydrate form of the Compound of Formula (I) once a day for ten days. In some embodiments, the loading dose is about 34 mg of the crystalline dihydrate form of the Compound of Formula (I) once a day for ten days. In some embodiments, the loading dose is about 36 mg of the crystalline dihydrate form of the Compound of Formula (I) once a day for ten days. In some embodiments, the loading dose is about 38 mg of the crystalline dihydrate form of the Compound of Formula (I) once a day for ten days. In some embodiments, the loading dose is about 40 mg of the crystalline dihydrate form of the Compound of Formula (I) once a day for ten days. In some embodiments, the loading dose is about 42 mg of the crystalline dihydrate form of the Compound of Formula (I) once a day for ten days. In some embodiments, the loading dose is about 44 mg of the crystalline dihydrate form of the Compound of Formula (I) once a day for ten days. In some embodiments, the loading dose is about 46 mg of the crystalline dihydrate form of the Compound of Formula (I) once a day for ten days. In some embodiments, the loading dose is about 48 mg of the crystalline dihydrate form of the Compound of Formula (I) once a day for ten days. In some embodiments, the loading dose is about 50 mg of the crystalline dihydrate form of the Compound of Formula (I) once a day for ten days.

In some embodiments, the loading dose is about 2 mg to about 100 mg of the crystalline dihydrate form of the Compound of Formula (I) once a week. In some embodiments, the loading dose is about 5 mg to about 90 mg of the crystalline dihydrate form of the Compound of Formula (I) once a week. In some embodiments, the loading dose is about 10 mg to about 80 mg of the crystalline dihydrate form of the Compound of Formula (I) once a week. In some embodiments, the loading dose is about 10 mg to about 70 mg of the crystalline dihydrate form of the Compound of Formula (I) once a week. In some embodiments, the loading dose is about 10 mg to about 60 mg of the crystalline dihydrate form of the Compound of Formula (I) once a week. In some embodiments, the loading dose is about 10 mg to about 50 mg of the crystalline dihydrate form of the Compound of Formula (I) once a week. In some embodiments, the loading dose is about 10 mg to about 40 mg of the crystalline dihydrate form of the Compound of Formula (I) once a week. In some embodiments, the loading dose is about 10 mg to about 30 mg of the crystalline dihydrate form of the Compound of Formula (I) once a week. In some embodiments, the loading dose is about 10 mg to about 20 mg of the crystalline dihydrate form of the Compound of Formula (I) once a week. In some embodiments, the loading dose is about 2 mg of the crystalline dihydrate form of the Compound of Formula (I) once a week. In some embodiments, the loading dose is about 3 mg of the crystalline dihydrate form of the Compound of Formula (I) once a week. In some embodiments, the loading dose is about 4 mg of the crystalline dihydrate form of the Compound of Formula (I) once a week. In some embodiments, the loading dose is about 5 mg of the crystalline dihydrate form of the Compound of Formula (I) once a week. In some embodiments, the loading dose is about 10 mg of the crystalline dihydrate form of the Compound of Formula (I) once a week. In some embodiments, the loading dose is about 11 mg of the crystalline dihydrate form of the Compound of Formula (I) once a week. In some embodiments, the loading dose is about 12 mg of the crystalline dihydrate form of the Compound of Formula (I) once a week. In some embodiments, the loading dose is about 13 mg of the crystalline dihydrate form of the Compound of Formula (I) once a week. In some embodiments, the loading dose is about 14 mg of the crystalline dihydrate form of the Compound of Formula (I) once a week. In some embodiments, the loading dose is about 15 mg of the crystalline dihydrate form of the Compound of Formula (I) once a week. In some embodiments, the loading dose is about 16 mg of the crystalline dihydrate form of the Compound of Formula (I) once a week. In some embodiments, the loading dose is about 17 mg of the crystalline dihydrate form of the Compound of Formula (I) once a week. In some embodiments, the loading dose is about 18 mg of the crystalline dihydrate form of the Compound of Formula (I) once a week. In some embodiments, the loading dose is about 19 mg of the crystalline dihydrate form of the Compound of Formula (I) once a week. In some embodiments, the loading dose is about 20 mg of the crystalline dihydrate form of the Compound of Formula (I) once a week. In some embodiments, the loading dose is about 22 mg of the crystalline dihydrate form of the Compound of Formula (I) once a week. In some embodiments, the loading dose is about 24 mg of the crystalline dihydrate form of the Compound of Formula (I) once a week. In some embodiments, the loading dose is about 26 mg of the crystalline dihydrate form of the Compound of Formula (I) once a week. In some embodiments, the loading dose is about 28 mg of the crystalline dihydrate form of the Compound of Formula (I) once a week. In some embodiments, the loading dose is about 30 mg of the crystalline dihydrate form of the Compound of Formula (I) once a week. In some embodiments, the loading dose is about 32 mg of the crystalline dihydrate form of the Compound of Formula (I) once a week. In some embodiments, the loading dose is about 34 mg of the crystalline dihydrate form of the Compound of Formula (I) once a week. In some embodiments, the loading dose is about 36 mg of the crystalline dihydrate form of the Compound of Formula (I) once a week. In some embodiments, the loading dose is about 38 mg of the crystalline dihydrate form of the Compound of Formula (I) once a week. In some embodiments, the loading dose is about 40 mg of the crystalline dihydrate form of the Compound of Formula (I) once a week. In some embodiments, the loading dose is about 42 mg of the crystalline dihydrate form of the Compound of Formula (I) once a week. In some embodiments, the loading dose is about 44 mg of the crystalline dihydrate form of the Compound of Formula (I) once a week. In some embodiments, the loading dose is about 46 mg of the crystalline dihydrate form of the Compound of Formula (I) once a week. In some embodiments, the loading dose is about 48 mg of the crystalline dihydrate form of the Compound of Formula (I) once a week. In some embodiments, the loading dose is about 50 mg of the crystalline dihydrate form of the Compound of Formula (I) once a week.

In some embodiments, the loading dose is about 2 mg to about 100 mg of the crystalline dihydrate form of the Compound of Formula (I) twice a week. In some embodiments, the loading dose is about 5 mg to about 90 mg of the crystalline dihydrate form of the Compound of Formula (I) twice a week. In some embodiments, the loading dose is about 10 mg to about 80 mg of the crystalline dihydrate form of the Compound of Formula (I) twice a week. In some embodiments, the loading dose is about 10 mg to about 70 mg of the crystalline dihydrate form of the Compound of Formula (I) twice a week. In some embodiments, the loading dose is about 10 mg to about 60 mg of the crystalline dihydrate form of the Compound of Formula (I) twice a week. In some embodiments, the loading dose is about 10 mg to about 50 mg of the crystalline dihydrate form of the Compound of Formula (I) twice a week. In some embodiments, the loading dose is about 10 mg to about 40 mg of the crystalline dihydrate form of the Compound of Formula (I) twice a week. In some embodiments, the loading dose is about 10 mg to about 30 mg of the crystalline dihydrate form of the Compound of Formula (I) twice a week. In some embodiments, the loading dose is about 10 mg to about 20 mg of the crystalline dihydrate form of the Compound of Formula (I) twice a week. In some embodiments, the loading dose is about 2 mg of the crystalline dihydrate form of the Compound of Formula (I) twice a week. In some embodiments, the loading dose is about 3 mg of the crystalline dihydrate form of the Compound of Formula (I) twice a week. In some embodiments, the loading dose is about 4 mg of the crystalline dihydrate form of the Compound of Formula (I) twice a week. In some embodiments, the loading dose is about 5 mg of the crystalline dihydrate form of the Compound of Formula (I) twice a week. In some embodiments, the loading dose is about 10 mg of the crystalline dihydrate form of the Compound of Formula (I) twice a week. In some embodiments, the loading dose is about 11 mg of the crystalline dihydrate form of the Compound of Formula (I) twice a week. In some embodiments, the loading dose is about 12 mg of the crystalline dihydrate form of the Compound of Formula (I) twice a week. In some embodiments, the loading dose is about 13 mg of the crystalline dihydrate form of the Compound of Formula (I) twice a week. In some embodiments, the loading dose is about 14 mg of the crystalline dihydrate form of the Compound of Formula (I) twice a week. In some embodiments, the loading dose is about 15 mg of the crystalline dihydrate form of the Compound of Formula (I) twice a week. In some embodiments, the loading dose is about 16 mg of the crystalline dihydrate form of the Compound of Formula (I) twice a week. In some embodiments, the loading dose is about 17 mg of the crystalline dihydrate form of the Compound of Formula (I) twice a week. In some embodiments, the loading dose is about 18 mg of the crystalline dihydrate form of the Compound of Formula (I) twice a week. In some embodiments, the loading dose is about 19 mg of the crystalline dihydrate form of the Compound of Formula (I) twice a week. In some embodiments, the loading dose is about 20 mg of the crystalline dihydrate form of the Compound of Formula (I) twice a week. In some embodiments, the loading dose is about 22 mg of the crystalline dihydrate form of the Compound of Formula (I) twice a week. In some embodiments, the loading dose is about 24 mg of the crystalline dihydrate form of the Compound of Formula (I) twice a week. In some embodiments, the loading dose is about 26 mg of the crystalline dihydrate form of the Compound of Formula (I) twice a week. In some embodiments, the loading dose is about 28 mg of the crystalline dihydrate form of the Compound of Formula (I) twice a week. In some embodiments, the loading dose is about 30 mg of the crystalline dihydrate form of the Compound of Formula (I) twice a week. In some embodiments, the loading dose is about 32 mg of the crystalline dihydrate form of the Compound of Formula (I) twice a week. In some embodiments, the loading dose is about 34 mg of the crystalline dihydrate form of the Compound of Formula (I) twice a week. In some embodiments, the loading dose is about 36 mg of the crystalline dihydrate form of the Compound of Formula (I) twice a week. In some embodiments, the loading dose is about 38 mg of the crystalline dihydrate form of the Compound of Formula (I) twice a week. In some embodiments, the loading dose is about 40 mg of the crystalline dihydrate form of the Compound of Formula (I) twice a week. In some embodiments, the loading dose is about 42 mg of the crystalline dihydrate form of the Compound of Formula (I) twice a week. In some embodiments, the loading dose is about 44 mg of the crystalline dihydrate form of the Compound of Formula (I) twice a week. In some embodiments, the loading dose is about 46 mg of the crystalline dihydrate form of the Compound of Formula (I) twice a week. In some embodiments, the loading dose is about 48 mg of the crystalline dihydrate form of the Compound of Formula (I) twice a week. In some embodiments, the loading dose is about 50 mg of the crystalline dihydrate form of the Compound of Formula (I) twice a week.

In some embodiments, the loading dose is about 2 mg to about 100 mg of the crystalline dihydrate form of the Compound of Formula (I) three times a week. In some embodiments, the loading dose is about 5 mg to about 90 mg of the crystalline dihydrate form of the Compound of Formula (I) three times a week. In some embodiments, the loading dose is about 10 mg to about 80 mg of the crystalline dihydrate form of the Compound of Formula (I) three times a week. In some embodiments, the loading dose is about 10 mg to about 70 mg of the crystalline dihydrate form of the Compound of Formula (I) three times a week. In some embodiments, the loading dose is about 10 mg to about 60 mg of the crystalline dihydrate form of the Compound of Formula (I) three times a week. In some embodiments, the loading dose is about 10 mg to about 50 mg of the crystalline dihydrate form of the Compound of Formula (I) three times a week. In some embodiments, the loading dose is about 10 mg to about 40 mg of the crystalline dihydrate form of the Compound of Formula (I) three times a week. In some embodiments, the loading dose is about 10 mg to about 30 mg of the crystalline dihydrate form of the Compound of Formula (I) three times a week. In some embodiments, the loading dose is about 10 mg to about 20 mg of the crystalline dihydrate form of the Compound of Formula (I) three times a week. In some embodiments, the loading dose is about 2 mg of the crystalline dihydrate form of the Compound of Formula (I) three times a week. In some embodiments, the loading dose is about 3 mg of the crystalline dihydrate form of the Compound of Formula (I) three times a week. In some embodiments, the loading dose is about 4 mg of the crystalline dihydrate form of the Compound of Formula (I) three times a week. In some embodiments, the loading dose is about 5 mg of the crystalline dihydrate form of the Compound of Formula (I) three times a week. In some embodiments, the loading dose is about 10 mg of the crystalline dihydrate form of the Compound of Formula (I) three times a week. In some embodiments, the loading dose is about 11 mg of the crystalline dihydrate form of the Compound of Formula (I) three times a week. In some embodiments, the loading dose is about 12 mg of the crystalline dihydrate form of the Compound of Formula (I) three times a week. In some embodiments, the loading dose is about 13 mg of the crystalline dihydrate form of the Compound of Formula (I) three times a week. In some embodiments, the loading dose is about 14 mg of the crystalline dihydrate form of the Compound of Formula (I) three times a week. In some embodiments, the loading dose is about 15 mg of the crystalline dihydrate form of the Compound of Formula (I) three times a week. In some embodiments, the loading dose is about 16 mg of the crystalline dihydrate form of the Compound of Formula (I) three times a week. In some embodiments, the loading dose is about 17 mg of the crystalline dihydrate form of the Compound of Formula (I) three times a week. In some embodiments, the loading dose is about 18 mg of the crystalline dihydrate form of the Compound of Formula (I) three times a week. In some embodiments, the loading dose is about 19 mg of the crystalline dihydrate form of the Compound of Formula (I) three times a week. In some embodiments, the loading dose is about 20 mg of the crystalline dihydrate form of the Compound of Formula (I) three times a week. In some embodiments, the loading dose is about 22 mg of the crystalline dihydrate form of the Compound of Formula (I) three times a week. In some embodiments, the loading dose is about 24 mg of the crystalline dihydrate form of the Compound of Formula (I) three times a week. In some embodiments, the loading dose is about 26 mg of the crystalline dihydrate form of the Compound of Formula (I) three times a week. In some embodiments, the loading dose is about 28 mg of the crystalline dihydrate form of the Compound of Formula (I) three times a week. In some embodiments, the loading dose is about 30 mg of the crystalline dihydrate form of the Compound of Formula (I) three times a week. In some embodiments, the loading dose is about 32 mg of the crystalline dihydrate form of the Compound of Formula (I) three times a week. In some embodiments, the loading dose is about 34 mg of the crystalline dihydrate form of the Compound of Formula (I) three times a week. In some embodiments, the loading dose is about 36 mg of the crystalline dihydrate form of the Compound of Formula (I) three times a week. In some embodiments, the loading dose is about 38 mg of the crystalline dihydrate form of the Compound of Formula (I) three times a week. In some embodiments, the loading dose is about 40 mg of the crystalline dihydrate form of the Compound of Formula (I) three times a week. In some embodiments, the loading dose is about 42 mg of the crystalline dihydrate form of the Compound of Formula (I) three times a week. In some embodiments, the loading dose is about 44 mg of the crystalline dihydrate form of the Compound of Formula (I) three times a week. In some embodiments, the loading dose is about 46 mg of the crystalline dihydrate form of the Compound of Formula (I) three times a week. In some embodiments, the loading dose is about 48 mg of the crystalline dihydrate form of the Compound of Formula (I) three times a week. In some embodiments, the loading dose is about 50 mg of the crystalline dihydrate form of the Compound of Formula (I) three times a week.

In some embodiments, administering a maintenance dose may include administering about 2 mg to about 150 mg of the crystalline dihydrate form of the compound of Formula (I) daily to a patient in need thereof. In some embodiments, the maintenance dose is about 2 mg to about 100 mg of the crystalline dihydrate form of the Compound of Formula (I) daily. In some embodiments, the maintenance dose is about 5 mg to about 90 mg of the crystalline dihydrate form of the Compound of Formula (I) daily. In some embodiments, the maintenance dose is about 10 mg to about 80 mg of the crystalline dihydrate form of the Compound of Formula (I) daily. In some embodiments, the maintenance dose is about 10 mg to about 70 mg of the crystalline dihydrate form of the Compound of Formula (I) daily. In some embodiments, the maintenance dose is about 10 mg to about 60 mg of the crystalline dihydrate form of the Compound of Formula (I) daily. In some embodiments, the maintenance dose is about 10 mg to about 50 mg of the crystalline dihydrate form of the Compound of Formula (I) daily. In some embodiments, the maintenance dose is about 10 mg to about 40 mg of the crystalline dihydrate form of the Compound of Formula (I) daily. In some embodiments, the maintenance dose is about 10 mg to about 30 mg of the crystalline dihydrate form of the Compound of Formula (I) daily. In some embodiments, the maintenance dose is about 10 mg to about 20 mg of the crystalline dihydrate form of the Compound of Formula (I) daily. In some embodiments, the maintenance dose is about 2 mg of the crystalline dihydrate form of the Compound of Formula (I) daily. In some embodiments, the maintenance dose is about 3 mg of the crystalline dihydrate form of the Compound of Formula (I) daily. In some embodiments, the maintenance dose is about 4 mg of the crystalline dihydrate form of the Compound of Formula (I) daily. In some embodiments, the maintenance dose is about 5 mg of the crystalline dihydrate form of the Compound of Formula (I) daily. In some embodiments, the maintenance dose is about 6 mg of the crystalline dihydrate form of the Compound of Formula (I) daily. In some embodiments, the maintenance dose is about 7 mg of the crystalline dihydrate form of the Compound of Formula (I) daily. In some embodiments, the maintenance dose is about 8 mg of the crystalline dihydrate form of the Compound of Formula (I) daily. In some embodiments, the maintenance dose is about 9 mg of the crystalline dihydrate form of the Compound of Formula (I) daily. In some embodiments, the maintenance dose is about 10 mg of the crystalline dihydrate form of the Compound of Formula (I) daily. In some embodiments, the maintenance dose is about 11 mg of the crystalline dihydrate form of the Compound of Formula (I) daily. In some embodiments, the maintenance dose is about 12 mg of the crystalline dihydrate form of the Compound of Formula (I) daily. In some embodiments, the maintenance dose is about 13 mg of the crystalline dihydrate form of the Compound of Formula (I) daily. In some embodiments, the maintenance dose is about 14 mg of the crystalline dihydrate form of the Compound of Formula (I) daily. In some embodiments, the maintenance dose is about 15 mg of the crystalline dihydrate form of the Compound of Formula (I) daily. In some embodiments, the maintenance dose is about 16 mg of the crystalline dihydrate form of the Compound of Formula (I) daily. In some embodiments, the maintenance dose is about 17 mg of the crystalline dihydrate form of the Compound of Formula (I) daily. In some embodiments, the maintenance dose is about 18 mg of the crystalline dihydrate form of the Compound of Formula (I) daily. In some embodiments, the maintenance dose is about 19 mg of the crystalline dihydrate form of the Compound of Formula (I) daily. In some embodiments, the maintenance dose is about 20 mg of the crystalline dihydrate form of the Compound of Formula (I) daily. In some embodiments, the maintenance dose is about 22 mg of the crystalline dihydrate form of the Compound of Formula (I) daily. In some embodiments, the maintenance dose is about 24 mg of the crystalline dihydrate form of the Compound of Formula (I) daily. In some embodiments, the maintenance dose is about 26 mg of the crystalline dihydrate form of the Compound of Formula (I) daily. In some embodiments, the maintenance dose is about 28 mg of the crystalline dihydrate form of the Compound of Formula (I) daily. In some embodiments, the maintenance dose is about 30 mg of the crystalline dihydrate form of the Compound of Formula (I) daily. In some embodiments, the maintenance dose is about 32 mg of the crystalline dihydrate form of the Compound of Formula (I) daily. In some embodiments, the maintenance dose is about 34 mg of the crystalline dihydrate form of the Compound of Formula (I) daily. In some embodiments, the maintenance dose is about 36 mg of the crystalline dihydrate form of the Compound of Formula (I) daily. In some embodiments, the maintenance dose is about 38 mg of the crystalline dihydrate form of the Compound of Formula (I) daily. In some embodiments, the maintenance dose is about 40 mg of the crystalline dihydrate form of the Compound of Formula (I) daily. In some embodiments, the maintenance dose is about 42 mg of the crystalline dihydrate form of the Compound of Formula (I) daily. In some embodiments, the maintenance dose is about 44 mg of the crystalline dihydrate form of the Compound of Formula (I) daily. In some embodiments, the maintenance dose is about 46 mg of the crystalline dihydrate form of the Compound of Formula (I) daily. In some embodiments, the maintenance dose is about 48 mg of the crystalline dihydrate form of the Compound of Formula (I) daily. In some embodiments, the maintenance dose is about 50 mg of the crystalline dihydrate form of the Compound of Formula (I) daily.

In some embodiments, administering a maintenance dose may include administering about 2 mg to about 150 mg of the crystalline dihydrate form of the compound of Formula (I) once a week to a patient in need thereof. In some embodiments, the maintenance dose is about 2 mg to about 100 mg of the crystalline dihydrate form of the Compound of Formula (I) once a week. In some embodiments, the maintenance dose is about 5 mg to about 90 mg of the crystalline dihydrate form of the Compound of Formula (I) once a week. In some embodiments, the maintenance dose is about 10 mg to about 80 mg of the crystalline dihydrate form of the Compound of Formula (I) once a week. In some embodiments, the maintenance dose is about 10 mg to about 70 mg of the crystalline dihydrate form of the Compound of Formula (I) once a week. In some embodiments, the maintenance dose is about 10 mg to about 60 mg of the crystalline dihydrate form of the Compound of Formula (I) once a week. In some embodiments, the maintenance dose is about 10 mg to about 50 mg of the crystalline dihydrate form of the Compound of Formula (I) once a week. In some embodiments, the maintenance dose is about 10 mg to about 40 mg of the crystalline dihydrate form of the Compound of Formula (I) once a week. In some embodiments, the maintenance dose is about 10 mg to about 30 mg of the crystalline dihydrate form of the Compound of Formula (I) once a week. In some embodiments, the maintenance dose is about 10 mg to about 20 mg of the crystalline dihydrate form of the Compound of Formula (I) once a week. In some embodiments, the maintenance dose is about 2 mg of the crystalline dihydrate form of the Compound of Formula (I) once a week. In some embodiments, the maintenance dose is about 3 mg of the crystalline dihydrate form of the Compound of Formula (I) once a week. In some embodiments, the maintenance dose is about 4 mg of the crystalline dihydrate form of the Compound of Formula (I) once a week. In some embodiments, the maintenance dose is about 5 mg of the crystalline dihydrate form of the Compound of Formula (I) once a week. In some embodiments, the maintenance dose is about 6 mg of the crystalline dihydrate form of the Compound of Formula (I) once a week. In some embodiments, the maintenance dose is about 7 mg of the crystalline dihydrate form of the Compound of Formula (I) once a week. In some embodiments, the maintenance dose is about 8 mg of the crystalline dihydrate form of the Compound of Formula (I) once a week. In some embodiments, the maintenance dose is about 9 mg of the crystalline dihydrate form of the Compound of Formula (I) once a week. In some embodiments, the maintenance dose is about 10 mg of the crystalline dihydrate form of the Compound of Formula (I) once a week. In some embodiments, the maintenance dose is about 11 mg of the crystalline dihydrate form of the Compound of Formula (I) once a week. In some embodiments, the maintenance dose is about 12 mg of the crystalline dihydrate form of the Compound of Formula (I) once a week. In some embodiments, the maintenance dose is about 13 mg of the crystalline dihydrate form of the Compound of Formula (I) once a week. In some embodiments, the maintenance dose is about 14 mg of the crystalline dihydrate form of the Compound of Formula (I) once a week. In some embodiments, the maintenance dose is about 15 mg of the crystalline dihydrate form of the Compound of Formula (I) once a week. In some embodiments, the maintenance dose is about 16 mg of the crystalline dihydrate form of the Compound of Formula (I) once a week. In some embodiments, the maintenance dose is about 17 mg of the crystalline dihydrate form of the Compound of Formula (I) once a week. In some embodiments, the maintenance dose is about 18 mg of the crystalline dihydrate form of the Compound of Formula (I) once a week. In some embodiments, the maintenance dose is about 19 mg of the crystalline dihydrate form of the Compound of Formula (I) once a week. In some embodiments, the maintenance dose is about 20 mg of the crystalline dihydrate form of the Compound of Formula (I) once a week. In some embodiments, the maintenance dose is about 22 mg of the crystalline dihydrate form of the Compound of Formula (I) once a week. In some embodiments, the maintenance dose is about 24 mg of the crystalline dihydrate form of the Compound of Formula (I) once a week. In some embodiments, the maintenance dose is about 26 mg of the crystalline dihydrate form of the Compound of Formula (I) once a week. In some embodiments, the maintenance dose is about 28 mg of the crystalline dihydrate form of the Compound of Formula (I) once a week. In some embodiments, the maintenance dose is about 30 mg of the crystalline dihydrate form of the Compound of Formula (I) once a week. In some embodiments, the maintenance dose is about 32 mg of the crystalline dihydrate form of the Compound of Formula (I) once a week. In some embodiments, the maintenance dose is about 34 mg of the crystalline dihydrate form of the Compound of Formula (I) once a week. In some embodiments, the maintenance dose is about 36 mg of the crystalline dihydrate form of the Compound of Formula (I) once a week. In some embodiments, the maintenance dose is about 38 mg of the crystalline dihydrate form of the Compound of Formula (I) once a week. In some embodiments, the maintenance dose is about 40 mg of the crystalline dihydrate form of the Compound of Formula (I) once a week. In some embodiments, the maintenance dose is about 42 mg of the crystalline dihydrate form of the Compound of Formula (I) once a week. In some embodiments, the maintenance dose is about 44 mg of the crystalline dihydrate form of the Compound of Formula (I) once a week. In some embodiments, the maintenance dose is about 46 mg of the crystalline dihydrate form of the Compound of Formula (I) once a week. In some embodiments, the maintenance dose is about 48 mg of the crystalline dihydrate form of the Compound of Formula (I) once a week. In some embodiments, the maintenance dose is about 50 mg of the crystalline dihydrate form of the Compound of Formula (I) once a week.

In some embodiments, administering a maintenance dose may include administering about 2 mg to about 150 mg of the crystalline dihydrate form of the compound of Formula (I) twice a week to a patient in need thereof. In some embodiments, the maintenance dose is about 2 mg to about 100 mg of the crystalline dihydrate form of the Compound of Formula (I) twice a week. In some embodiments, the maintenance dose is about 5 mg to about 90 mg of the crystalline dihydrate form of the Compound of Formula (I) twice a week. In some embodiments, the maintenance dose is about 10 mg to about 80 mg of the crystalline dihydrate form of the Compound of Formula (I) twice a week. In some embodiments, the maintenance dose is about 10 mg to about 70 mg of the crystalline dihydrate form of the Compound of Formula (I) twice a week. In some embodiments, the maintenance dose is about 10 mg to about 60 mg of the crystalline dihydrate form of the Compound of Formula (I) twice a week. In some embodiments, the maintenance dose is about 10 mg to about 50 mg of the crystalline dihydrate form of the Compound of Formula (I) twice a week. In some embodiments, the maintenance dose is about 10 mg to about 40 mg of the crystalline dihydrate form of the Compound of Formula (I) twice a week. In some embodiments, the maintenance dose is about 10 mg to about 30 mg of the crystalline dihydrate form of the Compound of Formula (I) twice a week. In some embodiments, the maintenance dose is about 10 mg to about 20 mg of the crystalline dihydrate form of the Compound of Formula (I) twice a week. In some embodiments, the maintenance dose is about 2 mg of the crystalline dihydrate form of the Compound of Formula (I) twice a week. In some embodiments, the maintenance dose is about 3 mg of the crystalline dihydrate form of the Compound of Formula (I) twice a week. In some embodiments, the maintenance dose is about 4 mg of the crystalline dihydrate form of the Compound of Formula (I) twice a week. In some embodiments, the maintenance dose is about 5 mg of the crystalline dihydrate form of the Compound of Formula (I) twice a week. In some embodiments, the maintenance dose is about 6 mg of the crystalline dihydrate form of the Compound of Formula (I) twice a week. In some embodiments, the maintenance dose is about 7 mg of the crystalline dihydrate form of the Compound of Formula (I) twice a week. In some embodiments, the maintenance dose is about 8 mg of the crystalline dihydrate form of the Compound of Formula (I) twice a week. In some embodiments, the maintenance dose is about 9 mg of the crystalline dihydrate form of the Compound of Formula (I) twice a week. In some embodiments, the maintenance dose is about 10 mg of the crystalline dihydrate form of the Compound of Formula (I) twice a week. In some embodiments, the maintenance dose is about 11 mg of the crystalline dihydrate form of the Compound of Formula (I) twice a week. In some embodiments, the maintenance dose is about 12 mg of the crystalline dihydrate form of the Compound of Formula (I) twice a week. In some embodiments, the maintenance dose is about 13 mg of the crystalline dihydrate form of the Compound of Formula (I) twice a week. In some embodiments, the maintenance dose is about 14 mg of the crystalline dihydrate form of the Compound of Formula (I) twice a week. In some embodiments, the maintenance dose is about 15 mg of the crystalline dihydrate form of the Compound of Formula (I) twice a week. In some embodiments, the maintenance dose is about 16 mg of the crystalline dihydrate form of the Compound of Formula (I) twice a week. In some embodiments, the maintenance dose is about 17 mg of the crystalline dihydrate form of the Compound of Formula (I) twice a week. In some embodiments, the maintenance dose is about 18 mg of the crystalline dihydrate form of the Compound of Formula (I) twice a week. In some embodiments, the maintenance dose is about 19 mg of the crystalline dihydrate form of the Compound of Formula (I) twice a week. In some embodiments, the maintenance dose is about 20 mg of the crystalline dihydrate form of the Compound of Formula (I) twice a week. In some embodiments, the maintenance dose is about 22 mg of the crystalline dihydrate form of the Compound of Formula (I) twice a week. In some embodiments, the maintenance dose is about 24 mg of the crystalline dihydrate form of the Compound of Formula (I) twice a week. In some embodiments, the maintenance dose is about 26 mg of the crystalline dihydrate form of the Compound of Formula (I) twice a week. In some embodiments, the maintenance dose is about 28 mg of the crystalline dihydrate form of the Compound of Formula (I) twice a week. In some embodiments, the maintenance dose is about 30 mg of the crystalline dihydrate form of the Compound of Formula (I) twice a week. In some embodiments, the maintenance dose is about 32 mg of the crystalline dihydrate form of the Compound of Formula (I) twice a week. In some embodiments, the maintenance dose is about 34 mg of the crystalline dihydrate form of the Compound of Formula (I) twice a week. In some embodiments, the maintenance dose is about 36 mg of the crystalline dihydrate form of the Compound of Formula (I) twice a week. In some embodiments, the maintenance dose is about 38 mg of the crystalline dihydrate form of the Compound of Formula (I) twice a week. In some embodiments, the maintenance dose is about 40 mg of the crystalline dihydrate form of the Compound of Formula (I) twice a week. In some embodiments, the maintenance dose is about 42 mg of the crystalline dihydrate form of the Compound of Formula (I) twice a week. In some embodiments, the maintenance dose is about 44 mg of the crystalline dihydrate form of the Compound of Formula (I) twice a week. In some embodiments, the maintenance dose is about 46 mg of the crystalline dihydrate form of the Compound of Formula (I) twice a week. In some embodiments, the maintenance dose is about 48 mg of the crystalline dihydrate form of the Compound of Formula (I) twice a week. In some embodiments, the maintenance dose is about 50 mg of the crystalline dihydrate form of the Compound of Formula (I) twice a week.

In some embodiments, administering a maintenance dose may include administering about 2 mg to about 150 mg of the crystalline dihydrate form of the compound of Formula (I) three times a week to a patient in need thereof. In some embodiments, the maintenance dose is about 2 mg to about 100 mg of the crystalline dihydrate form of the Compound of Formula (I) three times a week. In some embodiments, the maintenance dose is about 5 mg to about 90 mg of the crystalline dihydrate form of the Compound of Formula (I) three times a week. In some embodiments, the maintenance dose is about 10 mg to about 80 mg of the crystalline dihydrate form of the Compound of Formula (I) three times a week. In some embodiments, the maintenance dose is about 10 mg to about 70 mg of the crystalline dihydrate form of the Compound of Formula (I) three times a week. In some embodiments, the maintenance dose is about 10 mg to about 60 mg of the crystalline dihydrate form of the Compound of Formula (I) three times a week. In some embodiments, the maintenance dose is about 10 mg to about 50 mg of the crystalline dihydrate form of the Compound of Formula (I) three times a week. In some embodiments, the maintenance dose is about 10 mg to about 40 mg of the crystalline dihydrate form of the Compound of Formula (I) three times a week. In some embodiments, the maintenance dose is about 10 mg to about 30 mg of the crystalline dihydrate form of the Compound of Formula (I) three times a week. In some embodiments, the maintenance dose is about 10 mg to about 20 mg of the crystalline dihydrate form of the Compound of Formula (I) three times a week. In some embodiments, the maintenance dose is about 2 mg of the crystalline dihydrate form of the Compound of Formula (I) three times a week. In some embodiments, the maintenance dose is about 3 mg of the crystalline dihydrate form of the Compound of Formula (I) three times a week. In some embodiments, the maintenance dose is about 4 mg of the crystalline dihydrate form of the Compound of Formula (I) three times a week. In some embodiments, the maintenance dose is about 5 mg of the crystalline dihydrate form of the Compound of Formula (I) three times a week. In some embodiments, the maintenance dose is about 6 mg of the crystalline dihydrate form of the Compound of Formula (I) three times a week. In some embodiments, the maintenance dose is about 7 mg of the crystalline dihydrate form of the Compound of Formula (I) three times a week. In some embodiments, the maintenance dose is about 8 mg of the crystalline dihydrate form of the Compound of Formula (I) three times a week. In some embodiments, the maintenance dose is about 9 mg of the crystalline dihydrate form of the Compound of Formula (I) three times a week. In some embodiments, the maintenance dose is about 10 mg of the crystalline dihydrate form of the Compound of Formula (I) three times a week. In some embodiments, the maintenance dose is about 11 mg of the crystalline dihydrate form of the Compound of Formula (I)

three times a week. In some embodiments, the maintenance dose is about 12 mg of the crystalline dihydrate form of the Compound of Formula (I) three times a week. In some embodiments, the maintenance dose is about 13 mg of the crystalline dihydrate form of the Compound of Formula (I) three times a week. In some embodiments, the maintenance dose is about 14 mg of the crystalline dihydrate form of the Compound of Formula (I) three times a week. In some embodiments, the maintenance dose is about 15 mg of the crystalline dihydrate form of the Compound of Formula (I) three times a week. In some embodiments, the maintenance dose is about 16 mg of the crystalline dihydrate form of the Compound of Formula (I) three times a week. In some embodiments, the maintenance dose is about 17 mg of the crystalline dihydrate form of the Compound of Formula (I) three times a week. In some embodiments, the maintenance dose is about 18 mg of the crystalline dihydrate form of the Compound of Formula (I) three times a week. In some embodiments, the maintenance dose is about 19 mg of the crystalline dihydrate form of the Compound of Formula (I) three times a week. In some embodiments, the maintenance dose is about 20 mg of the crystalline dihydrate form of the Compound of Formula (I) three times a week. In some embodiments, the maintenance dose is about 22 mg of the crystalline dihydrate form of the Compound of Formula (I) three times a week. In some embodiments, the maintenance dose is about 24 mg of the crystalline dihydrate form of the Compound of Formula (I) three times a week. In some embodiments, the maintenance dose is about 26 mg of the crystalline dihydrate form of the Compound of Formula (I) three times a week. In some embodiments, the maintenance dose is about 28 mg of the crystalline dihydrate form of the Compound of Formula (I) three times a week. In some embodiments, the maintenance dose is about 30 mg of the crystalline dihydrate form of the Compound of Formula (I) three times a week. In some embodiments, the maintenance dose is about 32 mg of the crystalline dihydrate form of the Compound of Formula (I) three times a week. In some embodiments, the maintenance dose is about 34 mg of the crystalline dihydrate form of the Compound of Formula (I) three times a week. In some embodiments, the maintenance dose is about 36 mg of the crystalline dihydrate form of the Compound of Formula (I) three times a week. In some embodiments, the maintenance dose is about 38 mg of the crystalline dihydrate form of the Compound of Formula (I) three times a week. In some embodiments, the maintenance dose is about 40 mg of the crystalline dihydrate form of the Compound of Formula (I) three times a week. In some embodiments, the maintenance dose is about 42 mg of the crystalline dihydrate form of the Compound of Formula (I) three times a week. In some embodiments, the maintenance dose is about 44 mg of the crystalline dihydrate form of the Compound of Formula (I) three times a week. In some embodiments, the maintenance dose is about 46 mg of the crystalline dihydrate form of the Compound of Formula (I) three times a week. In some embodiments, the maintenance dose is about 48 mg of the crystalline dihydrate form of the Compound of Formula (I) three times a week. In some embodiments, the maintenance dose is about 50 mg of the crystalline dihydrate form of the Compound of Formula (I) three times a week.

In some embodiments, such a disclosed method may include, administering a loading dose of 30 mg daily for 5 days, followed by a maintenance dose of 30 mg twice a week, of the crystalline dihydrate form of the Compound of Formula (I) to a patient in need thereof.

In some embodiments, such a disclosed method may include, administering a loading dose of 30 mg daily for 3 days, followed by a maintenance dose of 10 mg daily, of the crystalline dihydrate form of the Compound of Formula (I) to a patient in need thereof.

In some embodiments, such a disclosed method may include, administering a loading dose of 20 mg daily for 3 days, followed by a maintenance dose of 6 mg daily, of the crystalline dihydrate form of the Compound of Formula (I) to a patient in need thereof.

In some embodiments, such a disclosed method may include, administering a dose of 30 mg twice a week, of the crystalline dihydrate form of the Compound of Formula (I) to a patient in need thereof.

In some embodiments, administration of the crystalline dihydrate form of the compound of Formula (I), may be effected by any appropriate route including, but not limited to, oral routes, intravenous routes, intramuscular routes, subcutaneous, intratumoral injection, intraarticular injection, and direct absorption through mucous membrane tissues. In some embodiments, administration of the crystalline dihydrate form of the compound of Formula (I), may be effected by oral routes. In some embodiments, administration of the crystalline dihydrate form of the compound of Formula (I), may be effected by intraarticular injection. In some embodiments, administration of the crystalline dihydrate form of the compound of Formula (I), may be effected by intratumoral injection.

In some embodiments, the most suitable administration in any given case will depend on the nature and severity of the condition being treated. The dosages can be conveniently presented in unit dosage form and prepared by any of the methods well-known in the pharmaceutical arts.

In some embodiments, provided herein is a method of treating graft versus host disease (GVHD), comprising administering to the patient a therapeutically effective amount of the crystalline dihydrate form of the compound represented by Formula (I), or a therapeutically effective amount of the pharmaceutical composition comprising the crystalline dihydrate form of the compound represented by Formula (I). In some embodiments, the graft versus host disease (GVHD) is chronic graft versus host disease (cGVHD). In some embodiments, the graft versus host disease (GVHD) is acute graft versus host disease (aGVHD).

In some embodiments, provided herein is a method of treating a neurodegenerative disease, comprising administering to the patient a therapeutically effective amount of the crystalline dihydrate form of the compound represented by Formula (I), or a therapeutically effective amount of the pharmaceutical composition comprising the crystalline dihydrate form of the compound represented by Formula (I). In some embodiments, the neurodegenerative disease is selected from the group consisting of Parkinson's disease (PD), Alzheimer's Disease (AD), frontotemporal dementia (FTD), amyotrophic lateral sclerosis (ALS), mild cognitive impairment, and Huntington's Disease (HD).

In some embodiments, provided herein is a method of treating a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma, comprising administering to the patient a therapeutically effective amount of the crystalline dihydrate form of the compound represented by Formula (I), or a therapeutically effective amount of the pharmaceutical composition comprising the crystalline dihydrate form of the compound represented by Formula (I). In some embodiments, the solid tumor is selected from the group consisting of ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumor.

In some embodiments, provided herein is a method of treating tumors known to have expression of colony-stimulating factor 1 receptor (CSF-1R) or its ligands, colony stimulating factor-1 (CSF-1), or interleukin (IL)-34 (IL-34), comprising administering to the patient a therapeutically effective amount of the crystalline dihydrate form of the compound represented by Formula (I), or a therapeutically effective amount of the pharmaceutical composition comprising the crystalline dihydrate form of the compound represented by Formula (I).

In some embodiments, provided herein is a method of treating a disease or condition selected from the group consisting of metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis, comprising administering to the patient a therapeutically effective amount of the crystalline dihydrate form of the compound represented by Formula (I), or a therapeutically effective amount of the pharmaceutical composition comprising the crystalline dihydrate form of the compound represented by Formula (I).

The disclosure contemplates administration of the crystalline dihydrate form of the compound represented by Formula (I), to a patient in need thereof prior (neo-adjuvant) or after (adjuvant) surgery (e.g., surgical treatment of TGCT). In some embodiments, the crystalline dihydrate form of the compound represented by Formula (I), is administered as an adjuvant. In some embodiments, the crystalline dihydrate form of the compound represented by Formula (I), is administered as a neo-adjuvant. In some embodiments, the crystalline dihydrate form of the compound represented by Formula (I), is administered as a neo-adjuvant and an adjuvant. In some embodiments, the crystalline dihydrate form of the compound represented by Formula (I), is administered to a patient in need thereof as a neo-adjuvant for a period of 1 month to 6 months, followed by administration of the crystalline dihydrate form of the compound represented by Formula (I), as an adjuvant for a period from 1 day to 100 years. In some embodiments, administration of the crystalline dihydrate form of the compound represented by Formula (I), is administered to a patient in need thereof as a neo-adjuvant for a period of 1 month to 6 months, followed by administration of the crystalline dihydrate form of the compound represented by Formula (I), as an adjuvant for a period from 1 day to 5 years. In some embodiments, administration of the crystalline dihydrate form of the compound represented by Formula (I), is administered to a patient in need thereof as a neo-adjuvant for a period of 3 months to 6 months, followed by administration of the crystalline dihydrate form of the compound represented by Formula (I), as an adjuvant for a period from 1 day to 5 years. In some embodiments, no administration of the crystalline dihydrate form of the compound represented by Formula (I), occurs prior to surgery. In some embodiments, the crystalline dihydrate form of the compound represented by Formula (I), is administered as an adjuvant for a period from 1 day to 100 years. In some embodiments, the crystalline dihydrate form of the compound represented by Formula (I), is administered as an adjuvant for a period from 1 day to 5 years.

In some embodiments, provided herein is a method of treating a disease or condition of any other aspects of the disclosure, further comprising administering to the patient a therapeutically effective amount of one or more additional therapeutic agents. In some embodiments, the disease or condition is graft versus host disease (GVHD). In some embodiments, the disease or condition is chronic graft versus host disease (cGVHD). In some embodiments, the disease or condition is acute graft versus host disease (aGVHD). In some embodiments, the one or more additional therapeutic agents is selected from the group consisting of methoxsalen, abatacept, everolimus, alemtuzumab, antithymocyte globulin, autologous serum eye drops, azathioprine, belumosudil, bortezomib, mycophenolate mofetil, cyclophosphamide, cyclosporine, extracorporeal photopheresis, etanercept, imatinib mesylate, ibrutinib, interleukin-2, infliximab, ruxolitinib, methotrexate, muromab-CD3, pentostatin, denileukin diftitox, prednisone, prednisolone, tacrolimus, psoralen with ultraviolet A light, sirolimus, rituximab, methylprednisolone, budesonide, thalidomide, halofuginone, and hydroxychloroquine. In some embodiments, the one or more additional therapeutic agents is belumosudil.

In some embodiments, provided herein is a method of treating a disease or condition of any other aspects of the disclosure, further comprising administering to the patient a therapeutically effective amount of one or more additional therapeutic agents. In some embodiments, the disease or condition is a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma. In some embodiments, the one or more additional therapeutic agents is an immunomodulatory therapeutic. In some embodiments, the one or more additional therapeutic agents is a chemotherapeutic agent. In some embodiments, the one or more additional therapeutic agents is an immunomodulatory therapeutic and a chemotherapeutic agent.

The crystalline dihydrate form of the compound represented by Formula (I), can be administered in combination with one or more additional therapeutic agents to treat a disorder described herein, such as cancer. For example, provided in the present disclosure is a pharmaceutical composition comprising the crystalline dihydrate form of the compound represented by Formula (I), one or more additional therapeutic agents, and a pharmaceutically acceptable excipient. In some embodiments, the crystalline dihydrate form of the compound represented by Formula (I), and one additional therapeutic agent is administered. In some embodiments, the crystalline dihydrate form of the compound represented by Formula (I), and two additional therapeutic agents are administered. In some embodiments, the crystalline dihydrate form of the compound represented by Formula (I), and three additional therapeutic agents are administered. Combination therapy can be achieved by administering two or more therapeutic agents, each of which is formulated and administered separately. For example, the crystalline dihydrate form of the compound represented by Formula (I), and an additional therapeutic agent can be formulated and administered separately. Combination therapy can also be achieved by administering two or more therapeutic agents in a single formulation, for example a pharmaceutical composition comprising the crystalline dihydrate form of the compound represented by Formula (I), as one therapeutic agent and one or more additional therapeutic agents. For example, crystalline dihydrate form of the compound represented by Formula (I), and an additional therapeutic agent can be administered in a single formulation. Other combinations are also encompassed by combination therapy. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases, even longer intervals are possible. While in many cases it is desirable that the two or more agents used in a combination therapy be present in within the patient's body at the same time, this need not be so.

"Combination therapy" (or "co-therapy") includes the administration of the crystalline dihydrate form of the compound represented by Formula (I), and at least a second agent, e.g., an anti-PD1 or anti-PD-L1 therapeutic, an anti-PD1 or anti-PD-L1 antibody, an immune-check point inhibitor, or a chemotherapeutic agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination can be carried out over a defined time period (usually minutes, hours, days or weeks depending upon the combination selected) or until disease progression. Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single tablet or capsule having a fixed ratio of each therapeutic agent or in multiple, single unit doses for each of the therapeutic agents. Sequential or substantially simultaneous administration of each therapeutic agent can be effected by any appropriate route including, but not limited to, oral routes, intravenous routes, intramuscular routes, subcutaneous, intratumoral injection, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally, or all therapeutic agents may be administered by intravenous injection. The sequence in which the therapeutic agents are administered is not narrowly critical.

Combination therapy also can embrace the administration of the therapeutic agents as described above in further combination with other biologically active ingredients and non-drug therapies, including, but not limited to radiation therapy. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination may be administered to a patient simultaneously, sequentially or in combination. It will be appreciated that when using a composition or method the components may be in the same pharmaceutically acceptable excipient and therefore administered simultaneously. They may be in separate pharmaceutical excipients such as conventional oral dosage forms which are taken simultaneously. The term "combination" further refers to the case where the compounds are provided in separate dosage forms and are administered sequentially.

Although not wishing to be bound by theory, it is thought that the administration of the crystalline dihydrate form of the compound represented by Formula (I), in accordance with the methods described herein, in combination with one or more anti-PD1 or anti-PD-L1 therapeutics may provide additive effects in significantly inhibiting primary tumor growth and modulating the immune system into an antitumoral state, which can be beneficial in the treatment of disorders associated with the proliferation, survival, or biological action of macrophages, including the treatment of TGCT. Examples of anti-PD1 or anti-PD-L1 therapeutics that may be administered in combination with CSF-1R inhibitors described herein include, but are not limited to, nivolumab, pidilizumab, cemiplimab, tislelizumab, AMP-224, AMP-514, and pembrolizumab.

The crystalline dihydrate form of the compound represented by Formula (I), can be used in combination with other immunomodulatory agents including but not limited to anti-PD-L1 therapeutics including atezolizumab, durvalumab, BMS-936559, and avelumab, anti-TIM3 therapeutics including TSR-022 and MBG453, anti-LAG3 therapeutics including relatlimab, LAG525, and TSR-033, CD40 agonist therapeutics including SGN-40, CP-870,893 and RO7009789, anti-CD47 therapeutics including Hu5F9-G4, anti-CD20 therapeutics, anti-CD38 therapeutics, or other immunomodulatory therapeutics including thalidomide, lenalidomide, pomalidomide, mezigdomide, prednisone, and dexamethasone.

Sarcomas comprise a diverse group of malignancies including more than fifty subtypes of bone and soft tissue origin. In some embodiments, a method of treating a cancer comprises administering to a patient with locally advanced and metastatic high-grade sarcoma the crystalline dihydrate form of the compound represented by Formula (I), in combination with avelumab. In some embodiments, a method of treating a cancer comprises administering to a patient with locally advanced sarcoma the crystalline dihydrate form of the compound represented by Formula (I), in combination with avelumab. In some embodiments, a method of treating a cancer comprises administering to a patient with metastatic high-grade sarcoma the crystalline dihydrate form of the compound represented by Formula (I), in combination with avelumab. In some embodiments, a method of treating a cancer comprises administering to a patient with advanced metastatic sarcoma the crystalline dihydrate form of the compound represented by Formula (I), in combination with avelumab. In some embodiments, a method of treating a cancer comprises administering to a patient with undifferentiated pleomorphic sarcoma (UPS) the crystalline dihydrate form of the compound represented by Formula (I), in combination with avelumab. In some embodiments, a method of treating a cancer comprises administering to a patient with myxofibrosarcoma (MFS) the crystalline dihydrate form of the compound represented by Formula (I), in combination with avelumab. In some embodiments, a method of treating a cancer comprises administering to a patient with leiomyosarcoma (LMS) the crystalline dihydrate form of the compound represented by Formula (I), in combination with avelumab. In some embodiments, a method of treating a cancer comprises administering to a patient with dedifferentiated liposarcoma (DDLPS) the crystalline dihydrate form of the compound represented by Formula (I), in combination with avelumab.

The crystalline dihydrate form of the compound represented by Formula (I), can also be used in combination with one or more chemotherapeutic agents including but not limited to anti-tubulin agents (e.g., paclitaxel, paclitaxel protein-bound particles for injectable suspension, eribulin, abraxane, docetaxel, ixabepilone, vincristine or vinorelbine), LHRH antagonists including but not limited to leuprolide, goserelin, triptorelin, or histrelin, anti-androgen agents including but not limited to abiraterone, flutamide, bicalutamide, nilutamide, cyproterone acetate, enzalutamide, and apalutamide, anti-estrogen agents including but not limited to tamoxifen, fulvestrant, anastrozole, letrozole, and exemestane, DNA-alkylating agents (including cisplatin, carboplatin, oxaliplatin, cyclophosphamide, ifosfamide, and temozolomide), DNA intercalating agents (including doxorubicin, pegylated liposomal doxorubicin, daunorubicin, idarubicin, and epirubicin), 5-fluorouracil, capecitabine, cytarabine, decitabine, 5-aza cytidine, gemcitabine methotrexate, bortezomib, and carfilzomib.

The crystalline dihydrate form of the compound represented by Formula (I), can also be used in combination with targeted therapeutics including kinase inhibitors erlotinib, gefitinib, lapatanib, everolimus, temsirolimus, abemaciclib, LEE011, palbociclib, ribociclib, crizotinib, cabozantinib, sunitinib, pazopanib, sorafenib, regorafenib, axitinib, dasatinib, imatinib, nilotinib, vemurafenib, dabrafenib, trametinib, cobimetinib, binimetinib, idelalisib, quizartinib, avapritinib, BLU-667, BLU-263, Loxo 292, larotrectinib, and quizartinib, anti-estrogen agents including but not limited to tamoxifen, fulvestrant, anastrozole, letrozole, and exemestane, anti-androgen agents including but not limited to abiraterone acetate, enzalutamide, nilutamide, bicalutamide, flutamide, cyproterone acetate, steroid agents including but not limited to prednisone and dexamethasone, PARP inhibitors including but not limited to neraparib, olaparib, and rucaparib, topoisomerase I inhibitors including but not limited to irinotecan, camptothecin, and topotecan, topoisomerase II inhibitors including but not limited to etoposide, etoposide phosphate, and mitoxantrone, Histone Deacetylase (HDAC) inhibitors including but not limited to vorinostat, romidepsin, panobinostat, valproic acid, and belinostat, DNA methylation inhibitors including but not limited to DZNeP and 5-aza-2'-deoxycytidine, proteasome inhibitors including but not limited to bortezomib and carfilzomib, thalidomide, lenalidomide, pomalidomide, biological agents including but not limited to trastuzumab, ado-trastuzumab, pertuzumab, cetuximab, panitumumab, ipilimumab, tremelimumab, vaccines including but not limited to sipuleucel-T, and radiotherapy.

The crystalline dihydrate form of the compound represented by Formula (I), can also be used in combination with anti-angiogenic agents including AMG386, bevacizumab and aflibercept, and antibody-drug-conjugates (ADCs) including but not limited to gemtuzumab ozogamicin, brentuximab vedotin, trastuzumab emtansine, inotuzumab ozogamicin, polatuzumab vedotin, enfortumab vedotin, trastuzumab deruxtecan, sacituzumab govitecan, belantamab mafodotin, moxetumomab pasudotox, loncastuximab tesirine, wherein the payload contained in the ADCs includes but is not limited to a derivative of camptothecin, a pyrrolobenzodiazepine dimer (PBD), an indolinobenzodiazepine dimer (IGN), DM1, DM4, MMAE, or MMAF.

In some embodiments, the additional therapeutic agent is selected from a luteinizing hormone-releasing hormone (LHRH) analog, including goserelin and leuprolide.

In some embodiments, the additional therapeutic agent is selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, AZD2171, batabulin, of atumtunab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, $IPdR_1$ KRX-0402, lucanthone, LY 317615, neuradiab, vitespan, RTA 744, SDX 102, talampanel, atrasentan, XR 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib, PD0325901, AZD-6244, capecitabine, L-Glutamic acid, N-[4-[2-(2-amino-4,7-dihydro-4-oxo-1H-pyrrolo[2,3-d]pyrimidin-5-yl)-ethyl] benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258), 3-[5-(methylsulfonylpiperadinemethyl)-indolyl]-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutanide, nilutamide, megestrol acetate, CP-724714, TAK-165, HKI-272, erlotinib, lapatanib, canertinib, ABX-EGF antibody, erbitux, EKB-569, PKI-166, GW-572016, Ionafarnib, BMS-214662, tipifarnib, amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa, ipilumumab, vemurafenib, and mixtures thereof.

In some embodiments of any other aspects of the disclosure, the therapeutically effective amount of the crystalline dihydrate form of the compound represented by Formula (I), or the therapeutically effective amount of the pharmaceutical composition comprising the crystalline dihydrate form of the compound represented by Formula (I), is administered orally.

In some embodiments, provided herein is a method of treating a tenosynovial giant cell tumor, comprising orally administering to the patient a therapeutically effective amount of the crystalline dihydrate form of the compound represented by Formula (I), or a therapeutically effective amount of the pharmaceutical composition comprising the crystalline dihydrate form of the compound represented by Formula (I). In some embodiments, the tenosynovial giant cell tumor is a diffuse-type tenosynovial giant cell tumor. In some embodiments, the tenosynovial giant cell tumor is a localized tenosynovial giant cell tumor.

In some embodiments, provided herein is a method of treating graft versus host disease (GVHD), comprising orally administering to the patient a therapeutically effective amount of the crystalline dihydrate form of the compound represented by Formula (I), or a therapeutically effective amount of the pharmaceutical composition comprising the crystalline dihydrate form of the compound represented by Formula (I). In some embodiments, the graft versus host disease (GVHD) is chronic graft versus host disease (cGVHD). In some embodiments, the graft versus host disease (GVHD) is acute graft versus host disease (aGVHD).

In some embodiments, provided herein is a method of treating a neurodegenerative disease, comprising orally administering to the patient a therapeutically effective amount of the crystalline dihydrate form of the compound represented by Formula (I), or a therapeutically effective amount of the pharmaceutical composition comprising the crystalline dihydrate form of the compound represented by Formula (I). In some embodiments, the neurodegenerative disease is selected from the group consisting of Parkinson's disease (PD), Alzheimer's Disease (AD), frontotemporal dementia (FTD), amyotrophic lateral sclerosis (ALS), mild cognitive impairment, and Huntington's Disease (HD).

In some embodiments, provided herein is a method of treating a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma, comprising orally administering to the patient a therapeutically effective amount of the crystalline dihydrate form of the compound represented by Formula (I), or a therapeutically effective amount of the pharmaceutical composition comprising the crystalline dihydrate form of the compound represented by Formula (I). In some embodiments, the solid tumor is selected from the group consisting of ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumor.

In some embodiments, provided herein is a method of treating tumors known to have expression of colony-stimulating factor 1 receptor (CSF-1R) or its ligands, colony stimulating factor-1 (CSF-1), or interleukin (IL)-34 (IL-34), comprising orally administering to the patient a therapeutically effective amount of the crystalline dihydrate form of the compound represented by Formula (I), or a therapeutically effective amount of the pharmaceutical composition comprising the crystalline dihydrate form of the compound represented by Formula (I).

In some embodiments, provided herein is a method of treating a disease or condition selected from the group consisting of metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis, comprising orally administering to the patient a therapeutically effective amount of the crystalline dihydrate form of the compound represented by Formula (I), or a therapeutically effective amount of the pharmaceutical composition comprising the crystalline dihydrate form of the compound represented by Formula (I).

In some embodiments, provided herein is a method of treating a disease or condition of any other aspects of the disclosure, further comprising administering to the patient a therapeutically effective amount of one or more additional therapeutic agents. In some embodiments, the disease or condition is graft versus host disease (GVHD). In some embodiments, the disease or condition is chronic graft versus host disease (cGVHD). In some embodiments, the disease or condition is acute graft versus host disease (aGVHD). In some embodiments, the one or more additional therapeutic agents is selected from the group consisting of methoxsalen, abatacept, everolimus, alemtuzumab, antithymocyte globulin, autologous serum eye drops, azathioprine, belumosudil, bortezomib, mycophenolate mofetil, cyclophosphamide, cyclosporine, extracorporeal photopheresis, etanercept, imatinib mesylate, ibrutinib, interleukin-2, infliximab, ruxolitinib, methotrexate, muromab-CD3, pentostatin, denileukin diftitox, prednisone, prednisolone, tacrolimus, psoralen with ultraviolet A light, sirolimus, rituximab, methylprednisolone, budesonide, thalidomide, halofuginone, and hydroxychloroquine. In some embodiments, the one or more additional therapeutic agents is belumosudil.

In some embodiments, provided herein is a method of treating a disease or condition of any other aspects of the disclosure, further comprising administering to the patient a therapeutically effective amount of one or more additional therapeutic agents. In some embodiments, the disease or condition is a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma. In some embodiments, the one or more additional therapeutic agents is an immunomodulatory therapeutic. In some embodiments, the one or more additional therapeutic agents is a chemotherapeutic agent. In some embodiments, the one or more additional therapeutic agents is an immunomodulatory therapeutic and a chemotherapeutic agent.

In some embodiments, provided herein is a use of the crystalline dihydrate form of the compound represented by Formula (I), in the manufacture of a medicament for the treatment of a tenosynovial giant cell tumor. In some embodiments, the tenosynovial giant cell tumor is a diffuse-type tenosynovial giant cell tumor. In some embodiments, the tenosynovial giant cell tumor is a localized tenosynovial giant cell tumor.

In some embodiments, provided herein is a use of the crystalline dihydrate form of the compound represented by Formula (I), in the manufacture of a medicament for the treatment of graft versus host disease (GVHD). In some embodiments, the graft versus host disease (GVHD) is chronic graft versus host disease (cGVHD). In some embodiments, the graft versus host disease (GVHD) is acute graft versus host disease (aGVHD).

In some embodiments, provided herein is a use of the crystalline dihydrate form of the compound represented by Formula (I), in the manufacture of a medicament for the treatment of a neurodegenerative disease. In some embodiments, the neurodegenerative disease is selected from the group consisting of Parkinson's disease (PD), Alzheimer's Disease (AD), frontotemporal dementia (FTD), amyotrophic lateral sclerosis (ALS), mild cognitive impairment, and Huntington's Disease (HD).

In some embodiments, provided herein is a use of the crystalline dihydrate form of the compound represented by Formula (I), in the manufacture of a medicament for the treatment of a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma. In some embodiments, the solid tumor is selected from the group consisting of ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumor.

In some embodiments, provided herein is a use of the crystalline dihydrate form of the compound represented by Formula (I), in the manufacture of a medicament for the treatment of tumors known to have expression of colony-stimulating factor 1 receptor (CSF-1R) or its ligands, colony stimulating factor-1 (CSF-1), or interleukin (IL)-34 (IL-34.

In some embodiments, provided herein is a use of the crystalline dihydrate form of the compound represented by Formula (I), in the manufacture of a medicament for the treatment of a disease or condition selected from the group consisting of metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis.

In some aspects of the disclosure, in the use of the crystalline dihydrate form of the compound represented by Formula (I), in the manufacture of a medicament for the treatment of a disease or condition, the amount of the crystalline dihydrate form is about 1 mg to about 150 mg. In some embodiments, the amount of the crystalline dihydrate form is about 2 mg to about 35 mg. In some embodiments, the amount of the crystalline dihydrate form is about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, or about 3.0 mg. In some embodiments, the amount of the crystalline dihydrate form is about 2.2 mg. In some embodiments, the amount of the crystalline dihydrate form is about 10.0 mg, about 10.1 mg, about 10.2 mg, about 10.3 mg, about 10.4 mg, about 10.5 mg, about 10.6 mg, about 10.7 mg, about 10.8 mg, about 10.9 mg, or about 11.0 mg. In some embodiments, the amount of the crystalline dihydrate form is about 10.8 mg. In some embodiments, the amount of the crystalline dihydrate form is about 15.0 mg, about 15.1 mg, about 15.2 mg, about 15.3 mg, about 15.4 mg, about 15.5 mg, about 15.6 mg, about 15.7 mg, about 15.8 mg, about 15.9 mg, or about 16.0 mg. In some embodiments, the amount of the crystalline dihydrate form is about 15.2 mg. In some embodiments, the amount of the crystalline dihydrate form is about 21.1 mg, about 21.2 mg, about 21.3 mg, about 21.4 mg, about 21.5 mg, about 21.6 mg, about 21.7 mg, about 21.8 mg, about 21.9 mg, or about 22.0 mg. In some embodiments, the amount of the crystalline dihydrate form is about 21.7 mg. In some embodiments, the amount of the solid-state crystalline dihydrate form is about 32.0 mg, about 32.1 mg, about 32.2 mg, about 32.3 mg, about 32.4 mg, about 32.5 mg, about 32.6 mg, about 32.7 mg, about 32.8 mg, about 32.9 mg, or about 33.0 mg. In some embodiments, the amount of the crystalline dihydrate form is about 32.5 mg.

Crystalline Anhydrous Form

In some embodiments, provided herein is an anhydrous form of the compound represented by Formula (I),

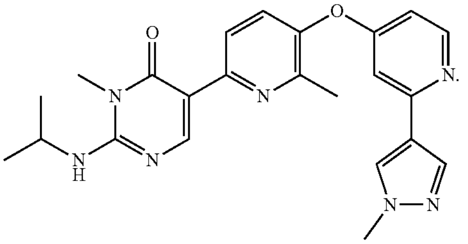 [SMILES: Cc1nc(-c2cnc(NC(C)C)n(C)c2=O)ccc1Oc1ccnc(-c2cnn(C)c2)c1]
(I)

In some embodiments, provided herein is a crystalline solid-state form, which is a crystalline anhydrous form of the compound represented by Formula (I).

In some embodiments, provided herein is the crystalline anhydrous form of the compound represented by Formula (I), having an XRPD pattern comprising two or more of the characteristic peaks, in terms of 2-theta, at about 11.4°, about 14.7°, about 17.1°, about 20.1°, about 21.3°, and about 29.1° as measured by CuKα radiation.

In some embodiments, provided herein is the crystalline anhydrous form of the compound represented by Formula (I), having an XRPD pattern comprising two or more of the characteristic peaks, in terms of 2-theta, at about 10.2°, about 10.5°, about 11.4°, about 14.7°, about 17.1°, about 20.1°, about 21.3°, and about 29.1° as measured by CuKα radiation.

In some embodiments, provided herein is the crystalline anhydrous form of the compound represented by Formula (I), having an XRPD pattern comprising two or more of the characteristic peaks, in terms of 2-theta, at about 11.4°, about 14.7°, about 17.1°, and about 21.3° as measured by CuKα radiation.

In some embodiments, provided herein is the crystalline anhydrous form of the compound represented by Formula (I), having an XRPD pattern comprising a peak, in terms of 2-theta, at about 11.4° as measured by CuKα radiation.

Figure 5:
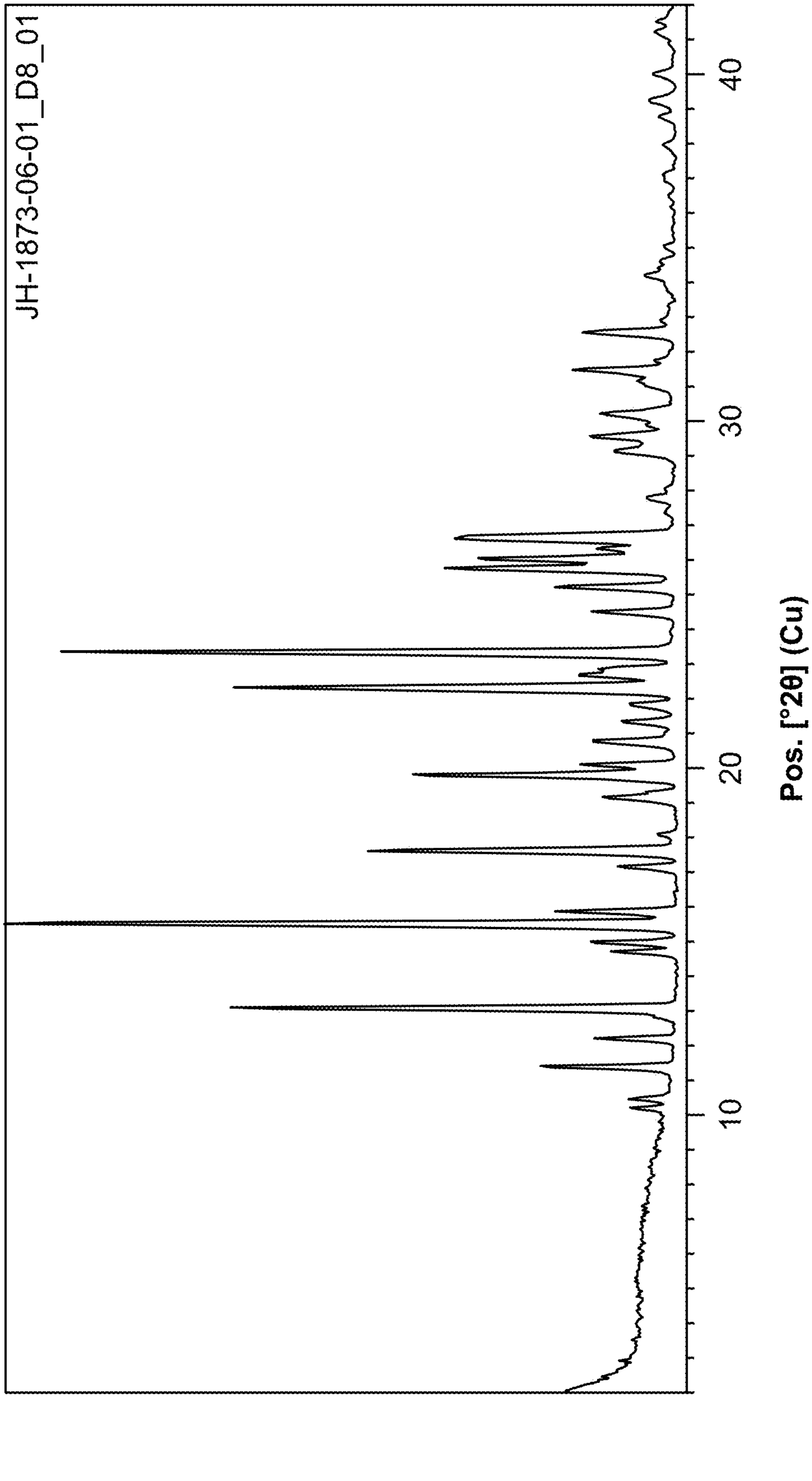
FIG. 5 shows an XRPD pattern of the crystalline anhydrous form of the compound represented by Formula (I).

In some embodiments, provided herein is the crystalline anhydrous form of the compound represented by Formula (I), having an XRPD pattern substantially as shown in FIG. 5 or Table 7.

In some embodiments, provided herein is the crystalline anhydrous form of the compound represented by Formula (I), having a DSC thermogram comprising an endothermic peak with onset between about 210° C. to about 220° C.

In some embodiments, provided herein is the crystalline anhydrous form of the compound represented by Formula (I), having a DSC thermogram comprising an endothermic peak with onset at about 215° C.

In some embodiments, provided herein is the crystalline anhydrous form of the compound represented by Formula (I), having a DSC thermogram comprising an endothermic peak at about 216° C.

Figure 6:
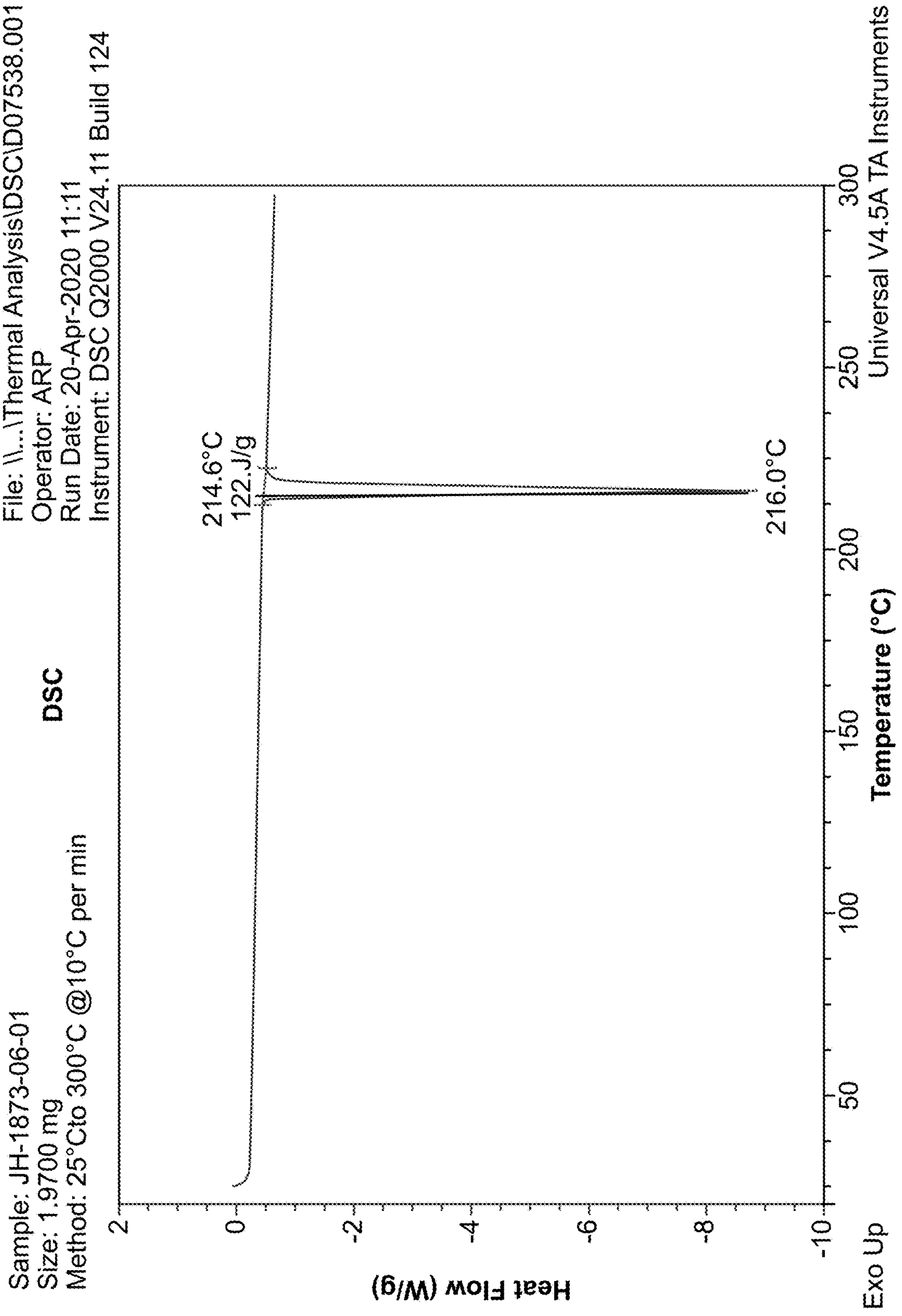
FIG. 6 shows a DSC thermogram of the crystalline anhydrous form of the compound represented by Formula (I).

In some embodiments, provided herein is the crystalline anhydrous form of the compound represented by Formula (I), having a DSC thermogram substantially as shown in FIG. 6.

Figure 7:
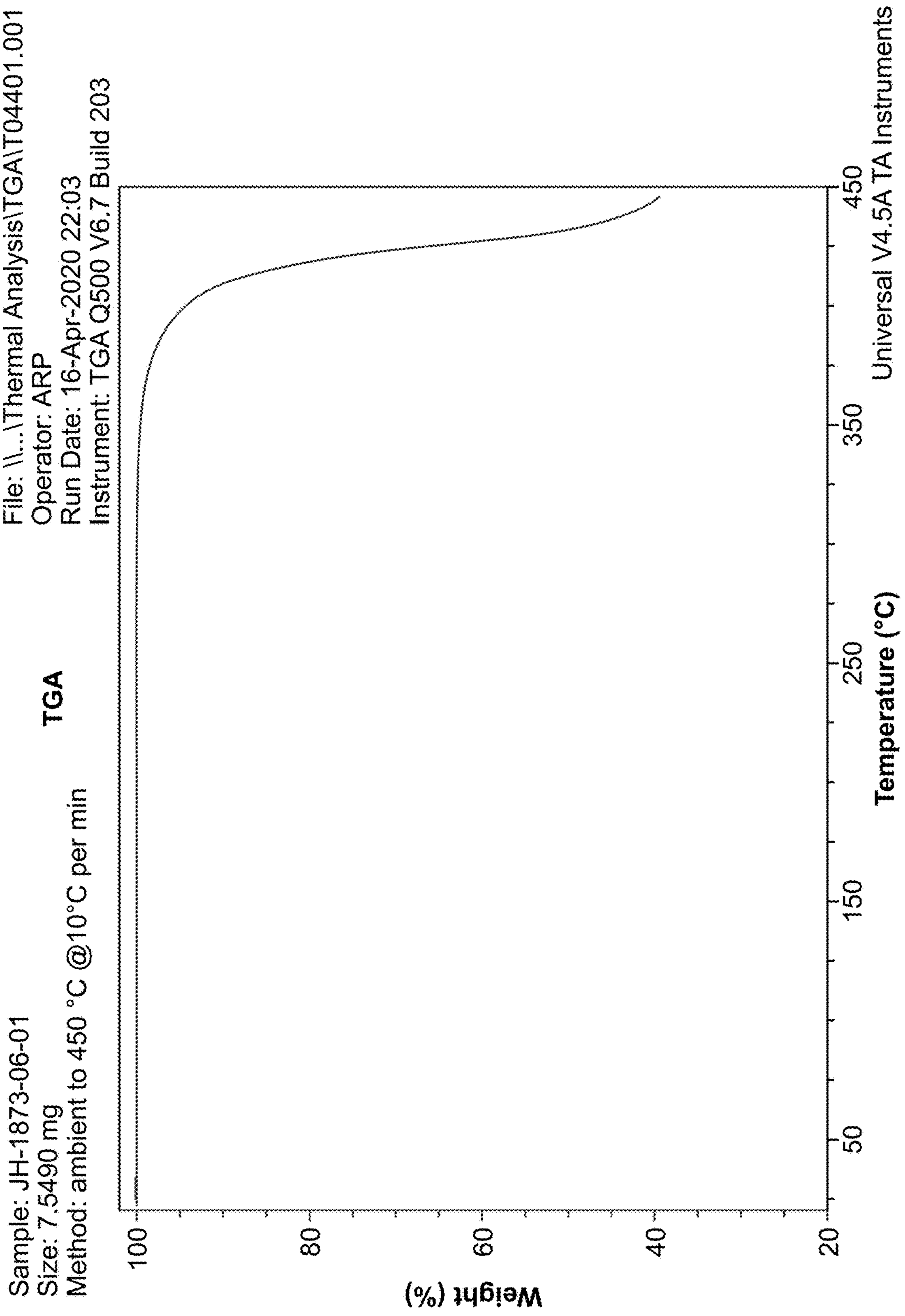
FIG. 7 shows a TGA thermogram of the crystalline anhydrous form of the compound represented by Formula (I).

In some embodiments, provided herein is the crystalline anhydrous form of the compound represented by Formula (I), having a TGA thermogram substantially as shown in FIG. 7.

Figure 8:
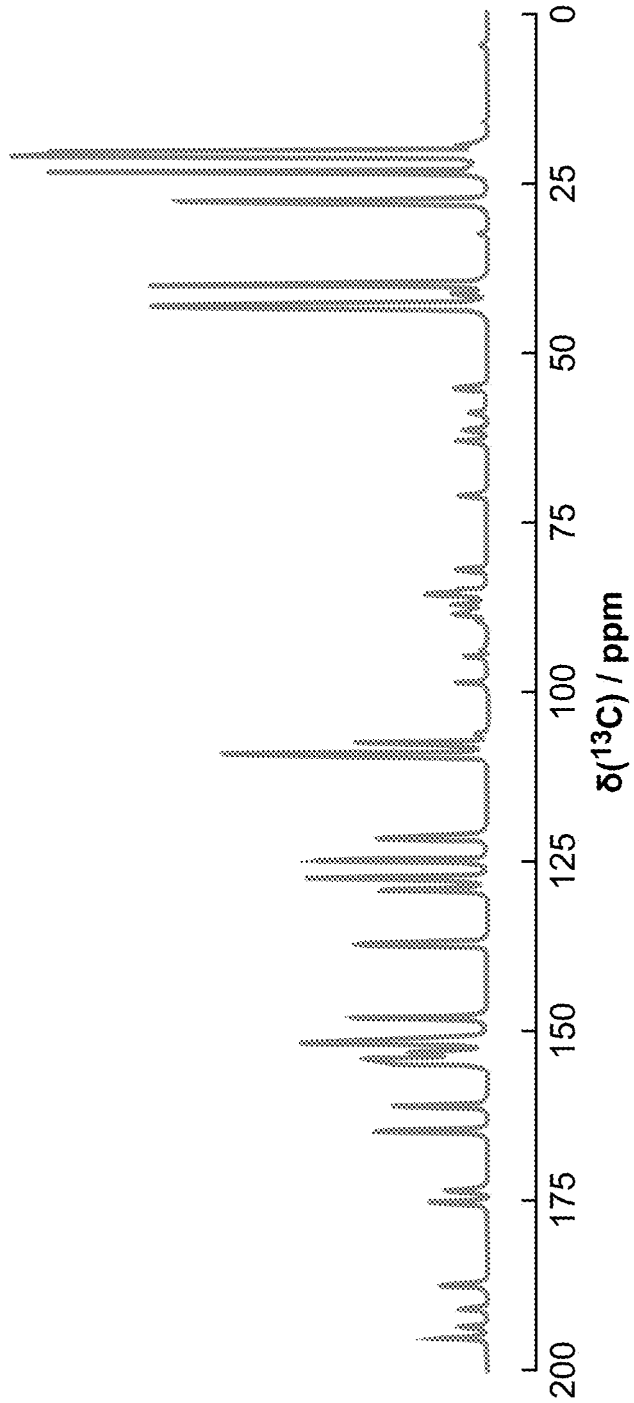
FIG. 8 shows a $^{13}C$ ssNMR spectrum of the crystalline anhydrous form of the compound represented by Formula (I).

In some embodiments, provided herein is the crystalline anhydrous form of the compound represented by Formula (I), having a ssNMR spectrum substantially as shown in FIG. 8.

In some embodiments, provided herein is the crystalline anhydrous form of the compound represented by Formula (I), having an XRPD pattern substantially as shown in FIG. 5, a DSC thermogram substantially as shown in FIG. 6, a TGA thermogram substantially as shown in FIG. 7, and a ssNMR spectrum substantially as shown in FIG. 8.

In some embodiments, provided herein is the crystalline anhydrous form of the compound represented by Formula (I), which is substantially pure.

In some embodiments, provided herein is the crystalline anhydrous form of the compound represented by Formula (I), which has a chemical purity of greater than 90% by weight.

In some embodiments, provided herein is the crystalline anhydrous form of the compound represented by Formula (I), which has a chemical purity of greater than 95% by weight.

In some embodiments, provided herein is the crystalline anhydrous form of the compound represented by Formula (I), which has a chemical purity of greater than 97% by weight.

In some embodiments, provided herein is the crystalline anhydrous form of the compound represented by Formula (I), which has a chemical purity of greater than 98% by weight.

In some embodiments, provided herein is the crystalline anhydrous form of the compound represented by Formula (I), which has a chemical purity of greater than 99% by weight.

For example, in some embodiments, the chemical purity of the crystalline anhydrous form of the compound represented by Formula (I) is at least about 99.9%, about 99.8%, about 99.7%, about 99.6%, about 99.5%, about 99.4%, about 99.3%, about 99.2%, about 99.1%, about 99.0%, about 98%, about 97%, about 96%, or about 95% pure. Chemical purity may be determined using methods known to those skilled in the area (for example, HPLC chromatography with a suitable solvent and column detecting a wavelength of 210 nm). In some embodiments, the substantial purity is determined on a weight percent basis. In some embodiments, the substantial purity is determined on an area under the curve basis.

In some embodiments, provided herein is a pharmaceutical composition comprising the crystalline anhydrous form of the compound represented by Formula (I), and a pharmaceutically acceptable excipient.

In some embodiments, provided herein is the crystalline anhydrous form of the compound represented by Formula (I), for use in the preparation of a pharmaceutical composition or pharmaceutical formulation.

In some embodiments, provided herein is a pharmaceutical composition comprising the crystalline anhydrous form of the compound represented by Formula (I), which is present in said composition in an amount of at least about 90% by weight based on the total weight of the compound represented by Formula (I).

In some embodiments, provided herein is a pharmaceutical composition consisting essentially of the crystalline anhydrous form of the compound represented by Formula (I), and a pharmaceutically acceptable excipient.

In some embodiments, provided herein is a pharmaceutical composition consisting essentially of the crystalline anhydrous form of the compound represented by Formula (I) which is present in said composition in an amount of at least about 90% by weight based on the total weight of the compound represented by Formula (I).

In some embodiments, provided herein is a pharmaceutical composition comprising the crystalline anhydrous form of the compound represented by Formula (I), which is in the form of a capsule.

In some embodiments, provided herein is a pharmaceutical composition which is in the form of a capsule containing about 1 mg to about 150 mg of the crystalline anhydrous form of the compound represented by Formula (I).

In some embodiments, provided herein is a pharmaceutical composition which is in the form of a capsule containing about 2 mg to about 35 mg of the crystalline anhydrous form of the compound represented by Formula (I).

In some embodiments, provided herein is a pharmaceutical composition which is in the form of a capsule containing about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, or about 3.0 mg of the crystalline anhydrous form of the compound represented by Formula (I).

In some embodiments, provided herein is a pharmaceutical composition which is in the form of a capsule containing about 2.0 mg of the crystalline anhydrous form of the compound represented by Formula (I).

In some embodiments, provided herein is a pharmaceutical composition which is in the form of a capsule containing about 10.0 mg, about 10.1 mg, about 10.2 mg, about 10.3 mg, about 10.4 mg, about 10.5 mg, about 10.6 mg, about 10.7 mg, about 10.8 mg, about 10.9 mg, or about 11.0 mg of the crystalline anhydrous form of the compound represented by Formula (I).

In some embodiments, provided herein is a pharmaceutical composition which is in the form of a capsule containing about 10.0 mg of the crystalline anhydrous form of the compound represented by Formula (I).

In some embodiments, provided herein is a pharmaceutical composition which is in the form of a capsule containing about 14.0 mg, about 14.1 mg, about 14.2 mg, about 14.3 mg, about 14.4 mg, about 14.5 mg, about 14.6 mg, about 14.7 mg, 14.8 mg, about 14.9 mg, or about 15.0 mg of the crystalline anhydrous form of the compound represented by Formula (I).

In some embodiments, provided herein is a pharmaceutical composition which is in the form of a capsule containing about 14.0 mg of the crystalline anhydrous form of the compound represented by Formula (I).

In some embodiments, provided herein is a pharmaceutical composition which is in the form of a capsule containing about 20.0 mg, about 20.1 mg, about 20.2 mg, about 20.3 mg, about 20.4 mg, about 20.5 mg, about 20.6 mg, about 20.7 mg, about 20.8 mg, about 20.9 mg, or about 21.0 mg of the crystalline anhydrous form of the compound represented by Formula (I).

In some embodiments, provided herein is a pharmaceutical composition which is in the form of a capsule containing about 20.0 mg of the crystalline anhydrous form of the compound represented by Formula (I).

In some embodiments, provided herein is a pharmaceutical composition which is in the form of a capsule containing about 30.0 mg, about 30.1 mg, about 30.2 mg, about 30.3 mg, about 30.4 mg, about 30.5 mg, about 30.6 mg, about 30.7 mg, about 30.8 mg, about 30.9 mg, or about 31.0 mg of the crystalline anhydrous form of the compound represented by Formula (I).

In some embodiments, provided herein is a pharmaceutical composition which is in the form of a capsule containing about 30.0 mg of the crystalline anhydrous form of the compound represented by Formula (I).

In some embodiments, provided herein is a pharmaceutical composition comprising:

a) a crystalline solid form of a compound represented by

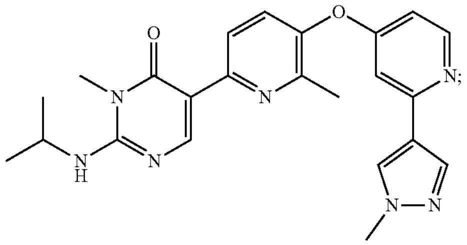 [SMILES: Cc1nc(-c2cnc(NC(C)C)n(C)c2=O)ccc1Oc1ccnc(-c2cnn(C)c2)c1]

and b) a pharmaceutically acceptable excipient, wherein the crystalline solid form is present at least in part as the crystalline anhydrous form of disclosed herein, and wherein the crystalline solid form is present in the composition in amount to provide 2 mg of the compound.

In some embodiments, provided herein is a pharmaceutical composition comprising:

a) a crystalline solid form of a compound represented by

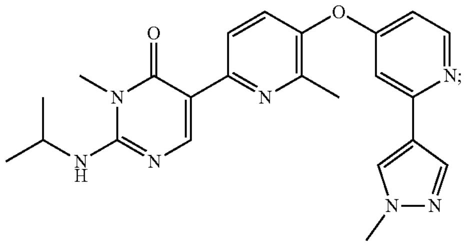 [SMILES: Cc1nc(-c2cnc(NC(C)C)n(C)c2=O)ccc1Oc1ccnc(-c2cnn(C)c2)c1]

and b) a pharmaceutically acceptable excipient, wherein the crystalline solid form is present at least in part as the crystalline anhydrous form of disclosed herein, and wherein the crystalline solid form is present in the composition in amount to provide 10 mg of the compound.

In some embodiments, provided herein is a pharmaceutical composition comprising:

a) a crystalline solid form of a compound represented by

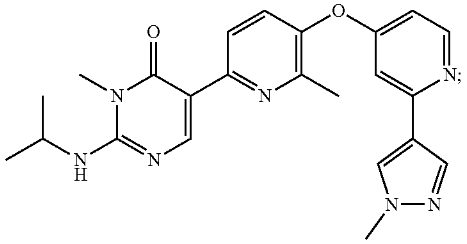

and b) a pharmaceutically acceptable excipient, wherein the crystalline solid form is present at least in part as the crystalline anhydrous form of disclosed herein, and wherein the crystalline solid form is present in the composition in amount to provide 14 mg of the compound.

In some embodiments, provided herein is a pharmaceutical composition comprising:

a) a crystalline solid form of a compound represented by

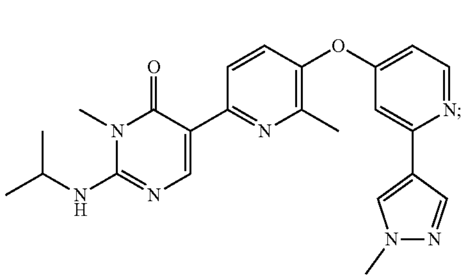

and b) a pharmaceutically acceptable excipient, wherein the crystalline solid form is present at least in part as the crystalline anhydrous form of disclosed herein, and wherein the crystalline solid form is present in the composition in amount to provide 20 mg of the compound.

In some embodiments, provided herein is a pharmaceutical composition comprising:

a) a crystalline solid form of a compound represented by

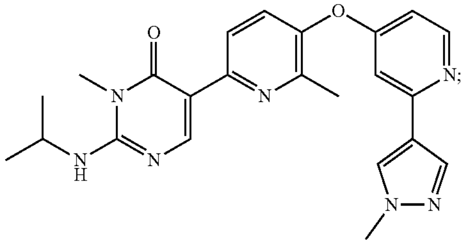

and b) a pharmaceutically acceptable excipient, wherein the crystalline solid form is present at least in part as the crystalline anhydrous form of disclosed herein, and wherein the crystalline solid form is present in the composition in amount to provide 30 mg of the compound.

In some embodiments, provided herein is a crystalline dihydrate form of the compound represented by Formula (I):

Formula (I)

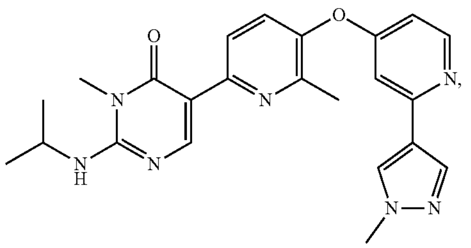

and a means for controlling the particle size distribution $d_{90}$, $d_{50}$, and $d_{10}$ values of the crystalline dihydrate form of the compound represented by Formula (I).

In some embodiments, provided herein is a crystalline dihydrate form of the compound represented by Formula (I):

Formula (I)

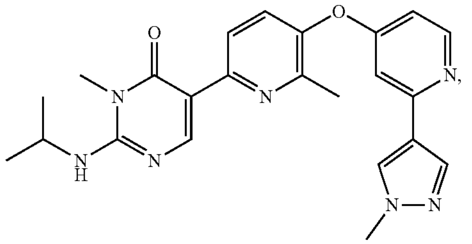 [SMILES: Cc1nc(-c2cnc(NC(C)C)n(C)c2=O)ccc1Oc1ccnc(-c2cnn(C)c2)c1]

and a means for controlling the particle size distribution $d_{90}$ value of the crystalline dihydrate form of the compound represented by Formula (I).

In some embodiments, provided herein is a crystalline dihydrate form of the compound represented by Formula (I):

Formula (I)

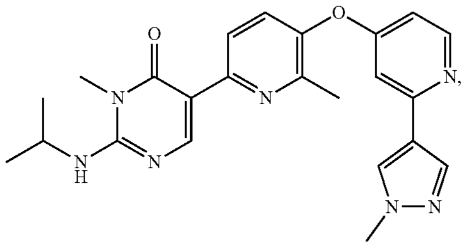

and a means for controlling the particle size distribution $d_{50}$ value of the crystalline dihydrate form of the compound represented by Formula (I).

In some embodiments, provided herein is a crystalline dihydrate form of the compound represented by Formula (I):

Formula (I)

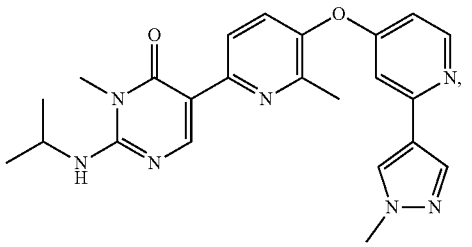

and a means for controlling the particle size distribution $d_{10}$ value of the crystalline dihydrate form of the compound represented by Formula (I).

In some embodiments, provided herein is a crystalline dihydrate form of the compound represented by Formula (I):

Formula (I)

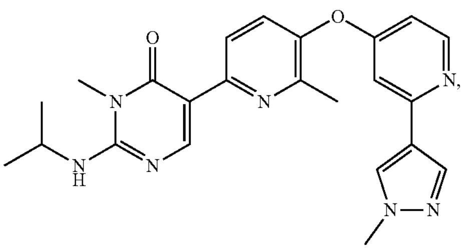

and a means for controlling the particle size distribution $d_{90}$ value of the crystalline dihydrate form of the compound represented by Formula (I), wherein the $d_{90}$ value is about three times that of the doo value of a seed material.

In some embodiments, provided herein is a crystalline dihydrate form of the compound represented by Formula (I):

Formula (I)

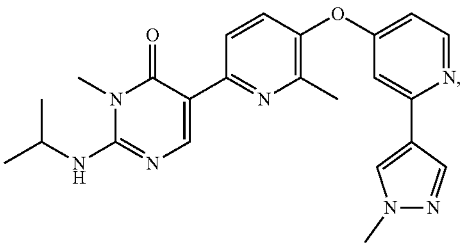

and a means for controlling the particle size distribution $d_{50}$ value of the crystalline dihydrate form of the compound represented by Formula (I), wherein the $d_{50}$ value is about three times that of the $d_{50}$ value of a seed material.

In some embodiments, provided herein is a composition comprising particles having a crystalline dihydrate form of the compound represented by Formula (I):

Formula (I)

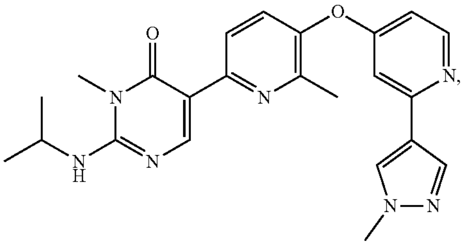

and a means for controlling the particle size distribution $d_{90}$, $d_{50}$, and $d_{10}$ values of the particles.

In some embodiments, provided herein is a composition comprising particles having a crystalline dihydrate form of the compound represented by Formula (I):

Formula (I)

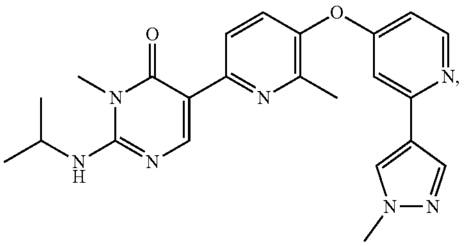

and a means for controlling the particle size distribution $d_{90}$ value of the particles.

In some embodiments, provided herein is a composition comprising particles having a crystalline dihydrate form of the compound represented by Formula (I):

Formula (I)

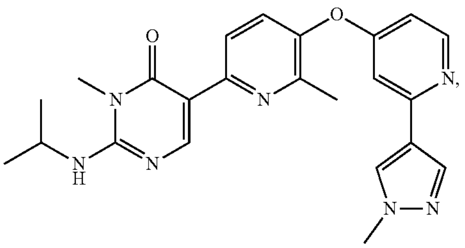

and a means for controlling the particle size distribution $d_{50}$ value of the particles.

In some embodiments, provided herein is a composition comprising particles having a crystalline dihydrate form of the compound represented by Formula (I):

Formula (I)

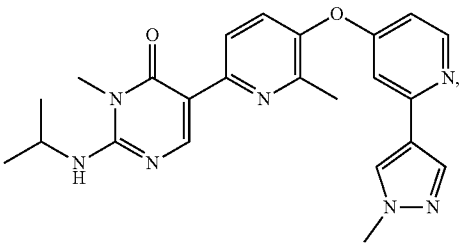

and a means for controlling the particle size distribution $d_{10}$ value of the particles.

In some embodiments, provided herein is a composition comprising particles having a crystalline dihydrate form of the compound represented by Formula (I):

Formula (I)

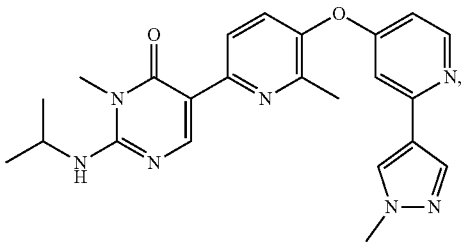

and a means for controlling the particle size distribution $d_{90}$ value of the particles, wherein the $d_{90}$ value is about three times that of the doo value of a seed material.

In some embodiments, provided herein is a composition comprising particles having a crystalline dihydrate form of the compound represented by Formula (I):

Formula (I)

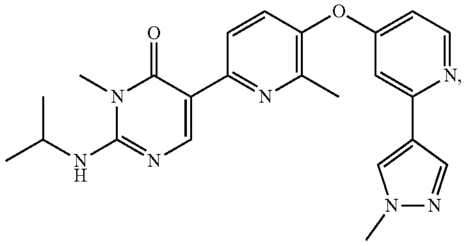

and a means for controlling the particle size distribution $d_{50}$ value of the particles, wherein the $d_{50}$ value is about three times that of the $d_{50}$ value of a seed material.

In some embodiments, provided herein is a pharmaceutical composition comprising particles having a crystalline dihydrate form of the compound represented by Formula (I):

Formula (I)

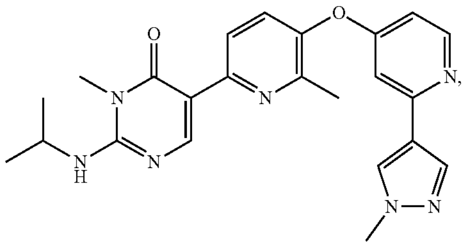

a means for controlling the particle size distribution $d_{90}$, $d_{50}$, and $d_{10}$ values of the particles; and a pharmaceutically acceptable excipient.

In some embodiments, provided herein is a pharmaceutical composition comprising particles having a crystalline dihydrate form of the compound represented by Formula (I):

Formula (I)

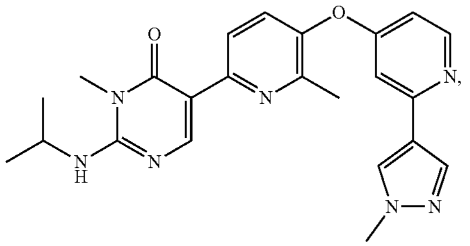

a means for controlling the particle size distribution $d_{90}$ value of the particles; and a pharmaceutically acceptable excipient.

In some embodiments, provided herein is a pharmaceutical composition comprising particles having a crystalline dihydrate form of the compound represented by Formula (I):

Formula (I)

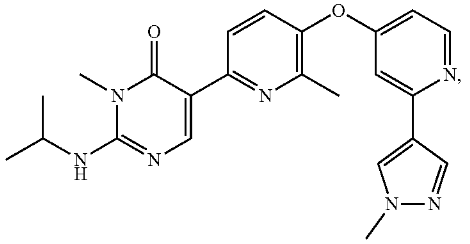

a means for controlling the particle size distribution $d_{50}$ value of the particles; and a pharmaceutically acceptable excipient.

In some embodiments, provided herein is a pharmaceutical composition comprising particles having a crystalline dihydrate form of the compound represented by Formula (I):

Formula (I)

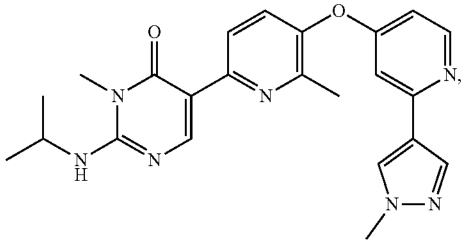

a means for controlling the particle size distribution $d_{10}$ value of the particles; and a pharmaceutically acceptable excipient.

In some embodiments, provided herein is a pharmaceutical composition comprising particles having a crystalline dihydrate form of the compound represented by Formula (I):

Formula (I)

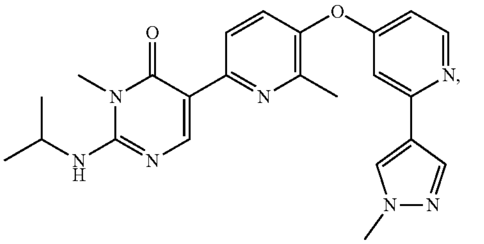

a means for controlling the particle size distribution $d_{90}$ value of the particles, wherein the do value is about three times that of the $d_{90}$ value of a seed material; and a pharmaceutically acceptable excipient.

In some embodiments, provided herein is a pharmaceutical composition comprising particles having a crystalline dihydrate form of the compound represented by Formula (I):

Formula (I)

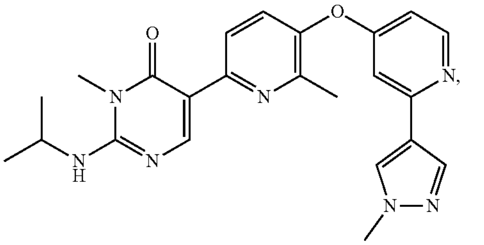

and a means for controlling the particle size distribution $d_{50}$ value of the particles, wherein the $d_{50}$ value is about three times that of the $d_{50}$ value of a seed material; and a pharmaceutically acceptable excipient.

In some embodiments, the crystalline dihydrate form of the compound represented by Formula (I), the composition comprising the crystalline dihydrate form of the compound represented by Formula (I), or the pharmaceutical composition comprising the crystalline dihydrate form of the compound represented by Formula (I), wherein the seed material is milled seed material.

In some embodiments, the crystalline dihydrate form of the compound represented by Formula (I), the composition comprising the crystalline dihydrate form of the compound represented by Formula (I), or the pharmaceutical composition comprising the crystalline dihydrate form of the compound represented by Formula (I), wherein the milled seed material is obtained by jet milling.

In some embodiments, provided herein is pharmaceutical composition comprising the crystalline anhydrous form of the compound represented by Formula (I) which is for use in the treatment of a tenosynovial giant cell tumor. In some embodiments, the tenosynovial giant cell tumor is a diffuse-type tenosynovial giant cell tumor. In some embodiments, the tenosynovial giant cell tumor is a localized tenosynovial giant cell tumor.

In some embodiments, provided herein is a pharmaceutical composition comprising the crystalline anhydrous form of the compound represented by Formula (I) which is for use in the treatment of graft versus host disease (GVHD). In some embodiments, the graft versus host disease (GVHD) is chronic graft versus host disease (cGVHD). In some embodiments, the graft versus host disease (GVHD) is acute graft versus host disease (aGVHD).

In some embodiments, provided herein is a pharmaceutical composition comprising the crystalline anhydrous form of the compound represented by Formula (I) which is for use in the treatment of a neurodegenerative disease. In some embodiments, the neurodegenerative disease is selected from the group consisting of Parkinson's disease (PD), Alzheimer's Disease (AD), frontotemporal dementia (FTD), amyotrophic lateral sclerosis (ALS), mild cognitive impairment, and Huntington's Disease (HD).

In some embodiments, provided herein is a pharmaceutical composition comprising the crystalline anhydrous form of the compound represented by Formula (I) which is for use in the treatment of a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma. In some embodiments, the solid tumor is selected from the group consisting of ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumor.

In some embodiments, provided herein is a pharmaceutical composition comprising the crystalline anhydrous form of the compound represented by Formula (I) which is for use in the treatment of tumors known to have expression of colony-stimulating factor 1 receptor (CSF-1R) or its ligands, colony stimulating factor-1 (CSF-1), or interleukin (IL)-34 (IL-34).

In some embodiments, provided herein is a pharmaceutical composition comprising the crystalline anhydrous form of the compound represented by Formula (I) which is for use in the treatment of a disease or condition selected from the group consisting of metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis.

In some embodiments, the crystalline anhydrous form of the compound represented by Formula (I), can be useful in the treatment of diseases and conditions including, but not limited to cancer, autoimmune diseases, and metabolic bone disorders, and other tumors related to the decreased proliferation, the depletion, or the repolarization of tumor-associated macrophages (TAMs) and treatment of associated disorders, for example but not limited to disorders disclosed herein such as tenosynovial giant cell tumor (TGCT), graft-versus-host disease (GVHD), or neurodegenerative diseases. In some embodiments, the treatment of the disease or conditions occurs through the inhibition of CSF-1R kinase.

In some embodiments, the crystalline anhydrous form of the compound represented by Formula (I), can be useful in the inhibition of the proliferation of TAMs, the depletion of TAMs, the repolarization of protumoral M2 TAMs to anti-tumoral M1 type macrophages, and treatment of related disorders in patients, for example but not limited to disorders disclosed herein such as tenosynovial giant cell tumor (TGCT), graft-versus-host disease (GVHD), or neurodegenerative diseases. In some embodiments, the crystalline anhydrous form of the compound represented by Formula (I), potently inhibit CSF-1R signaling. In some embodiments, the crystalline anhydrous form of the compound represented by Formula (I), block macrophage-mediated tumor cell migration. In some embodiments, the crystalline anhydrous form of the compound represented by Formula (I), block osteoclast differentiation. In some embodiments, the crystalline anhydrous form of the compound represented by Formula (I), block proliferation of a CSF-1R-dependent cell line. In some embodiments, the crystalline anhydrous form of the compound represented by Formula (I), potently inhibit CSF-1R signaling in cellular assays, as well as block macrophage-mediated tumor cell migration, osteoclast differentiation, and proliferation of a CSF-1R-dependent cell line.

In some embodiments, the crystalline anhydrous form of the compound represented by Formula (I), are selective in inhibiting CSF-1R over one or more of the FLT3, KIT, PDGFRα, PDGFRβ and VEGFR2 kinases. In some embodiments, the crystalline anhydrous form of the compound represented by Formula (I), have greater than 100-fold selectivity in inhibiting CSF-1R over the FLT3, KIT, PDGFRα, PDGFRβ, and VEGFR2 kinases.

In some embodiments, the crystalline anhydrous form of the compound represented by Formula (I), can be useful in the treatment of cancer. In some embodiments, such cancer may include glioblastoma (e.g., recurrent glioblastoma (GBM)), castrate resistant prostate cancer (CRPC), bone metastatic CRPC, cholangiocarcinoma (e.g., unresectable intrahepatic cholangiocarcinoma), ovarian cancer, pancreatic cancer, prostate cancer (e.g., advanced castration-resistant prostate cancer with bone metastasis and high circulating tumor cell counts), lung cancer, breast cancer, kidney cancer, liver cancer, cervical cancer, metastatic cancer (e.g., cancers that are metastatic to bone), papillary thyroid cancer, non-small cell lung cancer (NSCLC), colon cancer, colorectal cancer, gastrointestinal stromal tumor (GIST), solid tumors (e.g., refractory solid tumors, malignant solid tumors, metastatic breast or prostate cancer with bone disease, gastric, ovarian or non-small cell lung cancer that has malignant associated ascites or effusion(s)), advanced solid tumors (e.g., advanced incurable solid tumors in which the target kinases are linked to disease pathophysiology), melanoma, advanced melanoma, mesothelioma, multiple myeloma, follicular lymphoma, leukemia (e.g., refractory leukemia, acute myeloid leukemia (AML), relapsed/refractory acute myeloid leukemia (AML), relapsed acute myeloid leukemia (AML), refractory acute myeloid leukemia (AML), mast cell leukemia associated with CSF-1R), classic Hodgkin's lymphoma (cHL), relapsed or refractory cHL, peripheral T cell lymphoma, neurofibroma, sarcoma (e.g., soft tissue sarcoma, osteosarcoma, advanced sarcoma, high grade sarcoma, leiomyosarcoma, undifferentiated pleomorphic sarcoma, myxofibrosarcoma, dedifferentiated liposarcoma), refractory solid malignancies (e.g., colorectal, breast, pancreatic, prostate, NSCLC), endometrial, urothelial, salivary gland, trophoblastic tumor, gallbladder, renal cell carcinoma, chordoma, and gastric cancer, recurrent platinum-resistant epithelial ovarian, peritoneal, or fallopian tube cancer, squamous cell carcinoma of the head and neck, malignant peripheral nerve sheath tumors, hepatocellular carcinoma, and neoplasms (e.g., advanced malignant neoplasm, unresectable malignant neoplasm).

In some embodiments, the crystalline anhydrous form of the compound represented by Formula (I), can be useful in the treatment of diseases and conditions including idiopathic pulmonary fibrosis (IPF), hyperproliferative diseases, metabolic diseases, myeloproliferative diseases, stroke, SARS-CoV2, hepatic inflammation, rheumatoid arthritis, osteoarthritis, multiple sclerosis, autoimmune nephritis, lupus (e.g., lupus nephritis, systemic lupus erythematosus (SLE), Crohn's disease, asthma, psoriasis, chronic obstructive pulmonary diseases, pulmonary arterial hypertension (PAH), osteoporosis, hypereosinophilic syndromes, neurofibromatosis type 1-associated plexiform neurofibromas and mastocytosis.

In some embodiments, provided herein is a method of treating a tenosynovial giant cell tumor, comprising administering to the patient a therapeutically effective amount of the crystalline anhydrous form of the compound represented by Formula (I), or a therapeutically effective amount of the pharmaceutical composition comprising the crystalline anhydrous form of the compound represented by Formula (I). In some embodiments, the tenosynovial giant cell tumor is a diffuse-type tenosynovial giant cell tumor. In some embodiments, the tenosynovial giant cell tumor is a localized tenosynovial giant cell tumor.

In some embodiments, such tenosynovial giant cell tumor may be localized, e.g., as a single, well-defined nodule. In some embodiments, such tenosynovial giant cell tumor may be diffuse-type tenosynovial giant cell tumor. In some embodiments, such tenosynovial giant cell tumor may be associated with benign tumors. In some embodiments, such tenosynovial giant cell tumor may be associated with multiple nodules which may be aggressive. In some embodiments, the method may include administering about 2 mg to about 150 mg of the crystalline anhydrous form of the Compound of Formula (I) daily to a patient in need thereof. In some embodiments, the method may include administering about 10 mg to about 100 mg of the crystalline anhydrous form of the Compound of Formula (I) daily to a patient in need thereof. In some embodiments, the method may include administering about 10 mg to about 60 mg of the crystalline anhydrous form of the Compound of Formula (I) daily to a patient in need thereof. In some embodiments, the method may include administering about 10 mg to about 35 mg of the crystalline anhydrous form of the Compound of Formula (I) daily to a patient in need thereof. In some embodiments, the method may include administering about 2 mg of the crystalline anhydrous form of the Compound of Formula (I) daily to a patient in need thereof. In some embodiments, the method may include administering about 3 mg of the crystalline anhydrous form of the Compound of Formula (I) daily to a patient in need thereof. In some embodiments, the method may include administering about 4 mg of the crystalline anhydrous form of the Compound of Formula (I) daily to a patient in need thereof. In some embodiments, the method may include administering about 5 mg of the crystalline anhydrous form of the Compound of Formula (I) daily to a patient in need thereof. In some embodiments, the method may include administering about 6 mg of the crystalline anhydrous form of the Compound of Formula (I) daily to a patient in need thereof. In some embodiments, the method may include administering about 7 mg of the crystalline anhydrous form of the Compound of Formula (I) daily to a patient in need thereof. In some embodiments, the method may include administering about 8 mg of the crystalline anhydrous form of the Compound of Formula (I) daily to a patient in need thereof. In some embodiments, the method may include administering about 9 mg of the crystalline anhydrous form of the Compound of Formula (I) daily to a patient in need thereof. In some embodiments, the method may include administering about 10 mg of the crystalline anhydrous form of the Compound of Formula (I) daily to a patient in need thereof. In some embodiments, the method may include administering about 11 mg of the crystalline anhydrous form of the Compound of Formula (I) daily to a patient in need thereof. In some embodiments, the method may include administering about 12 mg of the crystalline anhydrous form of the Compound of Formula (I) daily to a patient in need thereof. In some embodiments, the method may include administering about 13 mg of the crystalline anhydrous form of the Compound of Formula (I) daily to a patient in need thereof. In some embodiments, the method may include administering about 14 mg of the crystalline anhydrous form of the Compound of Formula (I) daily to a patient in need thereof. In some embodiments, the method may include administering about 15 mg of the crystalline anhydrous form of the Compound of Formula (I) daily to a patient in need thereof. In some embodiments, the method may include administering about 16 mg of the crystalline anhydrous form of the Compound of Formula (I) daily to a patient in need thereof. In some embodiments, the method may include administering about 17 mg of the crystalline anhydrous form of the Compound of Formula (I) daily to a patient in need thereof. In some embodiments, the method may include administering about 18 mg of the crystalline anhydrous form of the Compound of Formula (I) daily to a patient in need thereof. In some embodiments, the method may include administering about 19 mg of the crystalline anhydrous form of the Compound of Formula (I) daily to a patient in need thereof. In some embodiments, the method may include administering about 20 mg of the crystalline anhydrous form of the Compound of Formula (I) daily to a patient in need thereof. In some embodiments, the method may include administering about 21 mg of the crystalline anhydrous form of the Compound of Formula (I) daily to a patient in need thereof. In some embodiments, the method may include administering about 22 mg of the crystalline anhydrous form of the Compound of Formula (I) daily to a patient in need thereof. In some embodiments, the method may include administering about 23 mg of the crystalline anhydrous form of the Compound of Formula (I) daily to a patient in need thereof. In some embodiments, the method may include administering about 24 mg of the crystalline anhydrous form of the Compound of Formula (I) daily to a patient in need thereof. In some embodiments, the method may include administering about 25 mg of the crystalline anhydrous form of the Compound of Formula (I) daily to a patient in need thereof. In some embodiments, the method may include administering about 26 mg of the crystalline anhydrous form of the Compound of Formula (I) daily to a patient in need thereof. In some embodiments, the method may include administering about 27 mg of the crystalline anhydrous form of the Compound of Formula (I) daily to a patient in need thereof. In some embodiments, the method may include administering about 28 mg of the crystalline anhydrous form of the Compound of Formula (I) daily to a patient in need thereof. In some embodiments, the method may include administering about 29 mg of the crystalline anhydrous form of the Compound of Formula (I) daily to a patient in need thereof. In some embodiments, the method may include administering about 30 mg of the crystalline anhydrous form of the Compound of Formula (I) daily to a patient in need thereof. In some embodiments, the method may include administering about 31 mg of the crystalline anhydrous form of the Compound of Formula (I) daily to a patient in need thereof. In some embodiments, the method may include administering about 32 mg of the crystalline anhydrous form of the Compound of Formula (I) daily to a patient in need thereof. In some embodiments, the method may include administering about 33 mg of the crystalline anhydrous form of the Compound of Formula (I) daily to a patient in need thereof. In some embodiments, the method may include administering about 34 mg of the crystalline anhydrous form of the Compound of Formula (I) daily to a patient in need thereof. In some embodiments, the method may include administering about 35 mg of the crystalline anhydrous form of the Compound of Formula (I) daily to a patient in need thereof. In some embodiments, the method may include administering about 36 mg of the crystalline anhydrous form of the Compound of Formula (I) daily to a patient in need thereof. In some embodiments, the method may include administering about 37 mg of the crystalline anhydrous form of the Compound of Formula (I) daily to a patient in need thereof. In some embodiments, the method may include administering about 38 mg of the crystalline anhydrous form of the Compound of Formula (I) daily to a patient in need thereof. In some embodiments, the method may include administering about 39 mg of the crystalline anhydrous form of the Compound of Formula (I) daily to a patient in need thereof. In some embodiments, the method may include administering about 40 mg of the crystalline anhydrous form of the Compound of Formula (I) daily to a patient in need thereof. In some embodiments, the method may include administering about 41 mg of the crystalline anhydrous form of the Compound of Formula (I) daily to a patient in need thereof. In some embodiments, the method may include administering about 42 mg of the crystalline anhydrous form of the Compound of Formula (I) daily to a patient in need thereof. In some embodiments, the method may include administering about 43 mg of the crystalline anhydrous form of the Compound of Formula (I) daily to a patient in need thereof. In some embodiments, the method may include administering about 44 mg of the crystalline anhydrous form of the Compound of Formula (I) daily to a patient in need thereof. In some embodiments, the method may include administering about 45 mg of the crystalline anhydrous form of the Compound of Formula (I) daily to a patient in need thereof. In some embodiments, the method may include administering about 46 mg of the crystalline anhydrous form of the Compound of Formula (I) daily to a patient in need thereof. In some embodiments, the method may include administering about 47 mg of the crystalline anhydrous form of the Compound of Formula (I) daily to a patient in need thereof. In some embodiments, the method may include administering about 48 mg of the crystalline anhydrous form of the Compound of Formula (I) daily to a patient in need thereof. In some embodiments, the method may include administering about 49 mg of the crystalline anhydrous form of the Compound of Formula (I) daily to a patient in need thereof. In some embodiments, the method may include administering about 50 mg of the crystalline anhydrous form of the Compound of Formula (I) daily to a patient in need thereof. In some embodiments, the method may include administering about 51 mg of the crystalline anhydrous form of the Compound of Formula (I) daily to a patient in need thereof. In some embodiments, the method may include administering about 52 mg of the crystalline anhydrous form of the Compound of Formula (I) daily to a patient in need thereof. In some embodiments, the method may include administering about 53 mg of the crystalline anhydrous form of the Compound of Formula (I) daily to a patient in need thereof. In some embodiments, the method may include administering about 54 mg of the crystalline anhydrous form of the Compound of Formula (I) daily to a patient in need thereof. In some embodiments, the method may include administering about 55 mg of the crystalline anhydrous form of the Compound of Formula (I) daily to a patient in need thereof. In some embodiments, the method may include administering about 56 mg of the crystalline anhydrous form of the Compound of Formula (I) daily to a patient in need thereof. In some embodiments, the method may include administering about 57 mg of the crystalline anhydrous form of the Compound of Formula (I) daily to a patient in need thereof. In some embodiments, the method may include administering about 58 mg of the crystalline anhydrous form of the Compound of Formula (I) daily to a patient in need thereof. In some embodiments, the method may include administering about 59 mg of the crystalline anhydrous form of the Compound of Formula (I) daily to a patient in need thereof. In some embodiments, the method may include administering about 60 mg of the crystalline anhydrous form of the Compound of Formula (I) daily to a patient in need thereof. In some embodiments, the method may include administering about 65 mg of the crystalline anhydrous form of the Compound of Formula (I) daily to a patient in need thereof. In some embodiments, the method may include administering about 70 mg of the crystalline anhydrous form of the Compound of Formula (I) daily to a patient in need thereof. In some embodiments, the method may include administering about 75 mg of the crystalline anhydrous form of the Compound of Formula (I) daily to a patient in need thereof. In some embodiments, the method may include administering about 80 mg of the crystalline anhydrous form of the Compound of Formula (I) daily to a patient in need thereof. In some embodiments, the method may include administering about 85 mg of the crystalline anhydrous form of the Compound of Formula (I) daily to a patient in need thereof. In some embodiments, the method may include administering about 90 mg of the crystalline anhydrous form of the Compound of Formula (I) daily to a patient in need thereof. In some embodiments, the method may include administering about 95 mg of the crystalline anhydrous form of the Compound of Formula (I) daily to a patient in need thereof. In some embodiments, the method may include administering about 100 mg of the crystalline anhydrous form of the Compound of Formula (I) daily to a patient in need thereof. In some embodiments, the method may include administering about 105 mg of the crystalline anhydrous form of the Compound of Formula (I) daily to a patient in need thereof. In some embodiments, the method may include administering about 110 mg of the crystalline anhydrous form of the Compound of Formula (I) daily to a patient in need thereof. In some embodiments, the method may include administering about 115 mg of the crystalline anhydrous form of the Compound of Formula (I) daily to a patient in need thereof. In some embodiments, the method may include administering about 120 mg of the crystalline anhydrous form of the Compound of Formula (I) daily to a patient in need thereof. In some embodiments, the method may include administering about 125 mg of the crystalline anhydrous form of the Compound of Formula (I) daily to a patient in need thereof. In some embodiments, the method may include administering about 130 mg of the crystalline anhydrous form of the Compound of Formula (I) daily to a patient in need thereof. In some embodiments, the method may include administering about 135 mg of the crystalline anhydrous form of the Compound of Formula (I) daily to a patient in need thereof. In some embodiments, the method may include administering about 140 mg of the crystalline anhydrous form of the Compound of Formula (I) daily to a patient in need thereof. In some embodiments, the method may include administering about 145 mg of the crystalline anhydrous form of the Compound of Formula (I) daily to a patient in need thereof. In some embodiments, the method may include administering about 150 mg of the crystalline anhydrous form of the Compound of Formula (I) daily to a patient in need thereof.

In some embodiments, the method may include administering about 2 mg to about 150 mg of the crystalline anhydrous form of the Compound of Formula (I) once a week to a patient in need thereof. In some embodiments, the method may include administering about 10 mg to about 100 mg of the crystalline anhydrous form of the Compound of Formula (I) once a week to a patient in need thereof. In some embodiments, the method may include administering about 10 mg to about 60 mg of the crystalline anhydrous form of the Compound of Formula (I) once a week to a patient in need thereof. In some embodiments, the method may include administering about 10 mg to about 35 mg of the crystalline anhydrous form of the Compound of Formula (I) once a week to a patient in need thereof. In some embodiments, the method may include administering about 2 mg of the crystalline anhydrous form of the Compound of Formula (I) once a week to a patient in need thereof. In some embodiments, the method may include administering about 3 mg of the crystalline anhydrous form of the Compound of Formula (I) once a week to a patient in need thereof. In some embodiments, the method may include administering about 4 mg of the crystalline anhydrous form of the Compound of Formula (I) once a week to a patient in need thereof. In some embodiments, the method may include administering about 5 mg of the crystalline anhydrous form of the Compound of Formula (I) once a week to a patient in need thereof. In some embodiments, the method may include administering about 6 mg of the crystalline anhydrous form of the Compound of Formula (I) once a week to a patient in need thereof. In some embodiments, the method may include administering about 7 mg of the crystalline anhydrous form of the Compound of Formula (I) once a week to a patient in need thereof. In some embodiments, the method may include administering about 8 mg of the crystalline anhydrous form of the Compound of Formula (I) once a week to a patient in need thereof. In some embodiments, the method may include administering about 9 mg of the crystalline anhydrous form of the Compound of Formula (I) once a week to a patient in need thereof. In some embodiments, the method may include administering about 10 mg of the crystalline anhydrous form of the Compound of Formula (I) once a week to a patient in need thereof. In some embodiments, the method may include administering about 11 mg of the crystalline anhydrous form of the Compound of Formula (I) once a week to a patient in need thereof. In some embodiments, the method may include administering about 12 mg of the crystalline anhydrous form of the Compound of Formula (I) once a week to a patient in need thereof. In some embodiments, the method may include administering about 13 mg of the crystalline anhydrous form of the Compound of Formula (I) once a week to a patient in need thereof. In some embodiments, the method may include administering about 14 mg of the crystalline anhydrous form of the Compound of Formula (I) once a week to a patient in need thereof. In some embodiments, the method may include administering about 15 mg of the crystalline anhydrous form of the Compound of Formula (I) once a week to a patient in need thereof. In some embodiments, the method may include administering about 16 mg of the crystalline anhydrous form of the Compound of Formula (I) once a week to a patient in need thereof. In some embodiments, the method may include administering about 17 mg of the crystalline anhydrous form of the Compound of Formula (I) once a week to a patient in need thereof. In some embodiments, the method may include administering about 18 mg of the crystalline anhydrous form of the Compound of Formula (I) once a week to a patient in need thereof. In some embodiments, the method may include administering about 19 mg of the crystalline anhydrous form of the Compound of Formula (I) once a week to a patient in need thereof. In some embodiments, the method may include administering about 20 mg of the crystalline anhydrous form of the Compound of Formula (I) once a week to a patient in need thereof. In some embodiments, the method may include administering about 21 mg of the crystalline anhydrous form of the Compound of Formula (I) once a week to a patient in need thereof. In some embodiments, the method may include administering about 22 mg of the crystalline anhydrous form of the Compound of Formula (I) once a week to a patient in need thereof. In some embodiments, the method may include administering about 23 mg of the crystalline anhydrous form of the Compound of Formula (I) once a week to a patient in need thereof. In some embodiments, the method may include administering about 24 mg of the crystalline anhydrous form of the Compound of Formula (I) once a week to a patient in need thereof. In some embodiments, the method may include administering about 25 mg of the crystalline anhydrous form of the Compound of Formula (I) once a week to a patient in need thereof. In some embodiments, the method may include administering about 26 mg of the crystalline anhydrous form of the Compound of Formula (I) once a week to a patient in need thereof. In some embodiments, the method may include administering about 27 mg of the crystalline anhydrous form of the Compound of Formula (I) once a week to a patient in need thereof. In some embodiments, the method may include administering about 28 mg of the crystalline anhydrous form of the Compound of Formula (I) once a week to a patient in need thereof. In some embodiments, the method may include administering about 29 mg of the crystalline anhydrous form of the Compound of Formula (I) once a week to a patient in need thereof. In some embodiments, the method may include administering about 30 mg of the crystalline anhydrous form of the Compound of Formula (I) once a week to a patient in need thereof. In some embodiments, the method may include administering about 31 mg of the crystalline anhydrous form of the Compound of Formula (I) once a week to a patient in need thereof. In some embodiments, the method may include administering about 32 mg of the crystalline anhydrous form of the Compound of Formula (I) once a week to a patient in need thereof. In some embodiments, the method may include administering about 33 mg of the crystalline anhydrous form of the Compound of Formula (I) once a week to a patient in need thereof. In some embodiments, the method may include administering about 34 mg of the crystalline anhydrous form of the Compound of Formula (I) once a week to a patient in need thereof. In some embodiments, the method may include administering about 35 mg of the crystalline anhydrous form of the Compound of Formula (I) once a week to a patient in need thereof. In some embodiments, the method may include administering about 36 mg of the crystalline anhydrous form of the Compound of Formula (I) once a week to a patient in need thereof. In some embodiments, the method may include administering about 37 mg of the crystalline anhydrous form of the Compound of Formula (I) once a week to a patient in need thereof. In some embodiments, the method may include administering about 38 mg of the crystalline anhydrous form of the Compound of Formula (I) once a week to a patient in need thereof. In some embodiments, the method may include administering about 39 mg of the crystalline anhydrous form of the Compound of Formula (I) once a week to a patient in need thereof. In some embodiments, the method may include administering about 40 mg of the crystalline anhydrous form of the Compound of Formula (I) once a week to a patient in need thereof. In some embodiments, the method may include administering about 41 mg of the crystalline anhydrous form of the Compound of Formula (I) once a week to a patient in need thereof. In some embodiments, the method may include administering about 42 mg of the crystalline anhydrous form of the Compound of Formula (I) once a week to a patient in need thereof. In some embodiments, the method may include administering about 43 mg of the crystalline anhydrous form of the Compound of Formula (I) once a week to a patient in need thereof. In some embodiments, the method may include administering about 44 mg of the crystalline anhydrous form of the Compound of Formula (I) once a week to a patient in need thereof. In some embodiments, the method may include administering about 45 mg of the crystalline anhydrous form of the Compound of Formula (I) once a week to a patient in need thereof. In some embodiments, the method may include administering about 46 mg of the crystalline anhydrous form of the Compound of Formula (I) once a week to a patient in need thereof. In some embodiments, the method may include administering about 47 mg of the crystalline anhydrous form of the Compound of Formula (I) once a week to a patient in need thereof. In some embodiments, the method may include administering about 48 mg of the crystalline anhydrous form of the Compound of Formula (I) once a week to a patient in need thereof. In some embodiments, the method may include administering about 49 mg of the crystalline anhydrous form of the Compound of Formula (I) once a week to a patient in need thereof. In some embodiments, the method may include administering about 50 mg of the crystalline anhydrous form of the Compound of Formula (I) once a week to a patient in need thereof. In some embodiments, the method may include administering about 51 mg of the crystalline anhydrous form of the Compound of Formula (I) once a week to a patient in need thereof. In some embodiments, the method may include administering about 52 mg of the crystalline anhydrous form of the Compound of Formula (I) once a week to a patient in need thereof. In some embodiments, the method may include administering about 53 mg of the crystalline anhydrous form of the Compound of Formula (I) once a week to a patient in need thereof. In some embodiments, the method may include administering about 54 mg of the crystalline anhydrous form of the Compound of Formula (I) once a week to a patient in need thereof. In some embodiments, the method may include administering about 55 mg of the crystalline anhydrous form of the Compound of Formula (I) once a week to a patient in need thereof. In some embodiments, the method may include administering about 56 mg of the crystalline anhydrous form of the Compound of Formula (I) once a week to a patient in need thereof. In some embodiments, the method may include administering about 57 mg of the crystalline anhydrous form of the Compound of Formula (I) once a week to a patient in need thereof. In some embodiments, the method may include administering about 58 mg of the crystalline anhydrous form of the Compound of Formula (I) once a week to a patient in need thereof. In some embodiments, the method may include administering about 59 mg of the crystalline anhydrous form of the Compound of Formula (I) once a week to a patient in need thereof. In some embodiments, the method may include administering about 60 mg of the crystalline anhydrous form of the Compound of Formula (I) once a week to a patient in need thereof. In some embodiments, the method may include administering about 65 mg of the crystalline anhydrous form of the Compound of Formula (I) once a week to a patient in need thereof. In some embodiments, the method may include administering about 70 mg of the crystalline anhydrous form of the Compound of Formula (I) once a week to a patient in need thereof. In some embodiments, the method may include administering about 75 mg of the crystalline anhydrous form of the Compound of Formula (I) once a week to a patient in need thereof. In some embodiments, the method may include administering about 80 mg of the crystalline anhydrous form of the Compound of Formula (I) once a week to a patient in need thereof. In some embodiments, the method may include administering about 85 mg of the crystalline anhydrous form of the Compound of Formula (I) once a week to a patient in need thereof. In some embodiments, the method may include administering about 90 mg of the crystalline anhydrous form of the Compound of Formula (I) once a week to a patient in need thereof. In some embodiments, the method may include administering about 95 mg of the crystalline anhydrous form of the Compound of Formula (I) once a week to a patient in need thereof. In some embodiments, the method may include administering about 100 mg of the crystalline anhydrous form of the Compound of Formula (I) once a week to a patient in need thereof. In some embodiments, the method may include administering about 105 mg of the crystalline anhydrous form of the Compound of Formula (I) once a week to a patient in need thereof. In some embodiments, the method may include administering about 110 mg of the crystalline anhydrous form of the Compound of Formula (I) once a week to a patient in need thereof. In some embodiments, the method may include administering about 115 mg of the crystalline anhydrous form of the Compound of Formula (I) once a week to a patient in need thereof. In some embodiments, the method may include administering about 120 mg of the crystalline anhydrous form of the Compound of Formula (I) once a week to a patient in need thereof. In some embodiments, the method may include administering about 125 mg of the crystalline anhydrous form of the Compound of Formula (I) once a week to a patient in need thereof. In some embodiments, the method may include administering about 130 mg of the crystalline anhydrous form of the Compound of Formula (I) once a week to a patient in need thereof. In some embodiments, the method may include administering about 135 mg of the crystalline anhydrous form of the Compound of Formula (I) once a week to a patient in need thereof. In some embodiments, the method may include administering about 140 mg of the crystalline anhydrous form of the Compound of Formula (I) once a week to a patient in need thereof. In some embodiments, the method may include administering about 145 mg of the crystalline anhydrous form of the Compound of Formula (I) once a week to a patient in need thereof. In some embodiments, the method may include administering about 150 mg of the crystalline anhydrous form of the Compound of Formula (I) once a week to a patient in need thereof.

In some embodiments, the method may include administering about 2 mg to about 150 mg of the crystalline anhydrous form of the Compound of Formula (I) twice a week to a patient in need thereof. In some embodiments, the method may include administering about 10 mg to about 100 mg of the crystalline anhydrous form of the Compound of Formula (I) twice a week to a patient in need thereof. In some embodiments, the method may include administering about 10 mg to about 60 mg of the crystalline anhydrous form of the Compound of Formula (I) twice a week to a patient in need thereof. In some embodiments, the method may include administering about 10 mg to about 35 mg of the crystalline anhydrous form of the Compound of Formula (I) twice a week to a patient in need thereof. In some embodiments, the method may include administering about 2 mg of the crystalline anhydrous form of the Compound of Formula (I) twice a week to a patient in need thereof. In some embodiments, the method may include administering about 3 mg of the crystalline anhydrous form of the Compound of Formula (I) twice a week to a patient in need thereof. In some embodiments, the method may include administering about 4 mg of the crystalline anhydrous form of the Compound of Formula (I) twice a week to a patient in need thereof. In some embodiments, the method may include administering about 5 mg of the crystalline anhydrous form of the Compound of Formula (I) twice a week to a patient in need thereof. In some embodiments, the method may include administering about 6 mg of the crystalline anhydrous form of the Compound of Formula (I) twice a week to a patient in need thereof. In some embodiments, the method may include administering about 7 mg of the crystalline anhydrous form of the Compound of Formula (I) twice a week to a patient in need thereof. In some embodiments, the method may include administering about 8 mg of the crystalline anhydrous form of the Compound of Formula (I) twice a week to a patient in need thereof. In some embodiments, the method may include administering about 9 mg of the crystalline anhydrous form of the Compound of Formula (I) twice a week to a patient in need thereof. In some embodiments, the method may include administering about 10 mg of the crystalline anhydrous form of the Compound of Formula (I) twice a week to a patient in need thereof. In some embodiments, the method may include administering about 11 mg of the crystalline anhydrous form of the Compound of Formula (I) twice a week to a patient in need thereof. In some embodiments, the method may include administering about 12 mg of the crystalline anhydrous form of the Compound of Formula (I) twice a week to a patient in need thereof. In some embodiments, the method may include administering about 13 mg of the crystalline anhydrous form of the Compound of Formula (I) twice a week to a patient in need thereof. In some embodiments, the method may include administering about 14 mg of the crystalline anhydrous form of the Compound of Formula (I) twice a week to a patient in need thereof. In some embodiments, the method may include administering about 15 mg of the crystalline anhydrous form of the Compound of Formula (I) twice a week to a patient in need thereof. In some embodiments, the method may include administering about 16 mg of the crystalline anhydrous form of the Compound of Formula (I) twice a week to a patient in need thereof. In some embodiments, the method may include administering about 17 mg of the crystalline anhydrous form of the Compound of Formula (I) twice a week to a patient in need thereof. In some embodiments, the method may include administering about 18 mg of the crystalline anhydrous form of the Compound of Formula (I) twice a week to a patient in need thereof. In some embodiments, the method may include administering about 19 mg of the crystalline anhydrous form of the Compound of Formula (I) twice a week to a patient in need thereof. In some embodiments, the method may include administering about 20 mg of the crystalline anhydrous form of the Compound of Formula (I) twice a week to a patient in need thereof. In some embodiments, the method may include administering about 21 mg of the crystalline anhydrous form of the Compound of Formula (I) twice a week to a patient in need thereof. In some embodiments, the method may include administering about 22 mg of the crystalline anhydrous form of the Compound of Formula (I) twice a week to a patient in need thereof. In some embodiments, the method may include administering about 23 mg of the crystalline anhydrous form of the Compound of Formula (I) twice a week to a patient in need thereof. In some embodiments, the method may include administering about 24 mg of the crystalline anhydrous form of the Compound of Formula (I) twice a week to a patient in need thereof. In some embodiments, the method may include administering about 25 mg of the crystalline anhydrous form of the Compound of Formula (I) twice a week to a patient in need thereof. In some embodiments, the method may include administering about 26 mg of the crystalline anhydrous form of the Compound of Formula (I) twice a week to a patient in need thereof. In some embodiments, the method may include administering about 27 mg of the crystalline anhydrous form of the Compound of Formula (I) twice a week to a patient in need thereof. In some embodiments, the method may include administering about 28 mg of the crystalline anhydrous form of the Compound of Formula (I) twice a week to a patient in need thereof. In some embodiments, the method may include administering about 29 mg of the crystalline anhydrous form of the Compound of Formula (I) twice a week to a patient in need thereof. In some embodiments, the method may include administering about 30 mg of the crystalline anhydrous form of the Compound of Formula (I) twice a week to a patient in need thereof. In some embodiments, the method may include administering about 31 mg of the crystalline anhydrous form of the Compound of Formula (I) twice a week to a patient in need thereof. In some embodiments, the method may include administering about 32 mg of the crystalline anhydrous form of the Compound of Formula (I) twice a week to a patient in need thereof. In some embodiments, the method may include administering about 33 mg of the crystalline anhydrous form of the Compound of Formula (I) twice a week to a patient in need thereof. In some embodiments, the method may include administering about 34 mg of the crystalline anhydrous form of the Compound of Formula (I) twice a week to a patient in need thereof. In some embodiments, the method may include administering about 35 mg of the crystalline anhydrous form of the Compound of Formula (I) twice a week to a patient in need thereof. In some embodiments, the method may include administering about 36 mg of the crystalline anhydrous form of the Compound of Formula (I) twice a week to a patient in need thereof. In some embodiments, the method may include administering about 37 mg of the crystalline anhydrous form of the Compound of Formula (I) twice a week to a patient in need thereof. In some embodiments, the method may include administering about 38 mg of the crystalline anhydrous form of the Compound of Formula (I) twice a week to a patient in need thereof. In some embodiments, the method may include administering about 39 mg of the crystalline anhydrous form of the Compound of Formula (I) twice a week to a patient in need thereof. In some embodiments, the method may include administering about 40 mg of the crystalline anhydrous form of the Compound of Formula (I) twice a week to a patient in need thereof. In some embodiments, the method may include administering about 41 mg of the crystalline anhydrous form of the Compound of Formula (I) twice a week to a patient in need thereof. In some embodiments, the method may include administering about 42 mg of the crystalline anhydrous form of the Compound of Formula (I) twice a week to a patient in need thereof. In some embodiments, the method may include administering about 43 mg of the crystalline anhydrous form of the Compound of Formula (I) twice a week to a patient in need thereof. In some embodiments, the method may include administering about 44 mg of the crystalline anhydrous form of the Compound of Formula (I) twice a week to a patient in need thereof. In some embodiments, the method may include administering about 45 mg of the crystalline anhydrous form of the Compound of Formula (I) twice a week to a patient in need thereof. In some embodiments, the method may include administering about 46 mg of the crystalline anhydrous form of the Compound of Formula (I) twice a week to a patient in need thereof. In some embodiments, the method may include administering about 47 mg of the crystalline anhydrous form of the Compound of Formula (I) twice a week to a patient in need thereof. In some embodiments, the method may include administering about 48 mg of the crystalline anhydrous form of the Compound of Formula (I) twice a week to a patient in need thereof. In some embodiments, the method may include administering about 49 mg of the crystalline anhydrous form of the Compound of Formula (I) twice a week to a patient in need thereof. In some embodiments, the method may include administering about 50 mg of the crystalline anhydrous form of the Compound of Formula (I) twice a week to a patient in need thereof. In some embodiments, the method may include administering about 51 mg of the crystalline anhydrous form of the Compound of Formula (I) twice a week to a patient in need thereof. In some embodiments, the method may include administering about 52 mg of the crystalline anhydrous form of the Compound of Formula (I) twice a week to a patient in need thereof. In some embodiments, the method may include administering about 53 mg of the crystalline anhydrous form of the Compound of Formula (I) twice a week to a patient in need thereof. In some embodiments, the method may include administering about 54 mg of the crystalline anhydrous form of the Compound of Formula (I) twice a week to a patient in need thereof. In some embodiments, the method may include administering about 55 mg of the crystalline anhydrous form of the Compound of Formula (I) twice a week to a patient in need thereof. In some embodiments, the method may include administering about 56 mg of the crystalline anhydrous form of the Compound of Formula (I) twice a week to a patient in need thereof. In some embodiments, the method may include administering about 57 mg of the crystalline anhydrous form of the Compound of Formula (I) twice a week to a patient in need thereof. In some embodiments, the method may include administering about 58 mg of the crystalline anhydrous form of the Compound of Formula (I) twice a week to a patient in need thereof. In some embodiments, the method may include administering about 59 mg of the crystalline anhydrous form of the Compound of Formula (I) twice a week to a patient in need thereof. In some embodiments, the method may include administering about 60 mg of the crystalline anhydrous form of the Compound of Formula (I) twice a week to a patient in need thereof. In some embodiments, the method may include administering about 65 mg of the crystalline anhydrous form of the Compound of Formula (I) twice a week to a patient in need thereof. In some embodiments, the method may include administering about 70 mg of the crystalline anhydrous form of the Compound of Formula (I) twice a week to a patient in need thereof. In some embodiments, the method may include administering about 75 mg of the crystalline anhydrous form of the Compound of Formula (I) twice a week to a patient in need thereof. In some embodiments, the method may include administering about 80 mg of the crystalline anhydrous form of the Compound of Formula (I) twice a week to a patient in need thereof. In some embodiments, the method may include administering about 85 mg of the crystalline anhydrous form of the Compound of Formula (I) twice a week to a patient in need thereof. In some embodiments, the method may include administering about 90 mg of the crystalline anhydrous form of the Compound of Formula (I) twice a week to a patient in need thereof. In some embodiments, the method may include administering about 95 mg of the crystalline anhydrous form of the Compound of Formula (I) twice a week to a patient in need thereof. In some embodiments, the method may include administering about 100 mg of the crystalline anhydrous form of the Compound of Formula (I) twice a week to a patient in need thereof. In some embodiments, the method may include administering about 105 mg of the crystalline anhydrous form of the Compound of Formula (I) twice a week to a patient in need thereof. In some embodiments, the method may include administering about 110 mg of the crystalline anhydrous form of the Compound of Formula (I) twice a week to a patient in need thereof. In some embodiments, the method may include administering about 115 mg of the crystalline anhydrous form of the Compound of Formula (I) twice a week to a patient in need thereof. In some embodiments, the method may include administering about 120 mg of the crystalline anhydrous form of the Compound of Formula (I) twice a week to a patient in need thereof. In some embodiments, the method may include administering about 125 mg of the crystalline anhydrous form of the Compound of Formula (I) twice a week to a patient in need thereof. In some embodiments, the method may include administering about 130 mg of the crystalline anhydrous form of the Compound of Formula (I) twice a week to a patient in need thereof. In some embodiments, the method may include administering about 135 mg of the crystalline anhydrous form of the Compound of Formula (I) twice a week to a patient in need thereof. In some embodiments, the method may include administering about 140 mg of the crystalline anhydrous form of the Compound of Formula (I) twice a week to a patient in need thereof. In some embodiments, the method may include administering about 145 mg of the crystalline anhydrous form of the Compound of Formula (I) twice a week to a patient in need thereof. In some embodiments, the method may include administering about 150 mg of the crystalline anhydrous form of the Compound of Formula (I) twice a week to a patient in need thereof.

In some embodiments, the method may include administering about 2 mg to about 150 mg of the crystalline anhydrous form of the Compound of Formula (I) three times a week to a patient in need thereof. In some embodiments, the method may include administering about 10 mg to about 100 mg of the crystalline anhydrous form of the Compound of Formula (I) three times a week to a patient in need thereof. In some embodiments, the method may include administering about 10 mg to about 60 mg of the crystalline anhydrous form of the Compound of Formula (I) three times a week to a patient in need thereof. In some embodiments, the method may include administering about 10 mg to about 35 mg of the crystalline anhydrous form of the Compound of Formula (I) three times a week to a patient in need thereof. In some embodiments, the method may include administering about 2 mg of the crystalline anhydrous form of the Compound of Formula (I) three times a week to a patient in need thereof. In some embodiments, the method may include administering about 3 mg of the crystalline anhydrous form of the Compound of Formula (I) three times a week to a patient in need thereof. In some embodiments, the method may include administering about 4 mg of the crystalline anhydrous form of the Compound of Formula (I) three times a week to a patient in need thereof. In some embodiments, the method may include administering about 5 mg of the crystalline anhydrous form of the Compound of Formula (I) three times a week to a patient in need thereof. In some embodiments, the method may include administering about 6 mg of the crystalline anhydrous form of the Compound of Formula (I) three times a week to a patient in need thereof. In some embodiments, the method may include administering about 7 mg of the crystalline anhydrous form of the Compound of Formula (I) three times a week to a patient in need thereof. In some embodiments, the method may include administering about 8 mg of the crystalline anhydrous form of the Compound of Formula (I) three times a week to a patient in need thereof. In some embodiments, the method may include administering about 9 mg of the crystalline anhydrous form of the Compound of Formula (I) three times a week to a patient in need thereof. In some embodiments, the method may include administering about 10 mg of the crystalline anhydrous form of the Compound of Formula (I) three times a week to a patient in need thereof. In some embodiments, the method may include administering about 11 mg of the crystalline anhydrous form of the Compound of Formula (I) three times a week to a patient in need thereof. In some embodiments, the method may include administering about 12 mg of the crystalline anhydrous form of the Compound of Formula (I) three times a week to a patient in need thereof. In some embodiments, the method may include administering about 13 mg of the crystalline anhydrous form of the Compound of Formula (I) three times a week to a patient in need thereof. In some embodiments, the method may include administering about 14 mg of the crystalline anhydrous form of the Compound of Formula (I) three times a week to a patient in need thereof. In some embodiments, the method may include administering about 15 mg of the crystalline anhydrous form of the Compound of Formula (I) three times a week to a patient in need thereof. In some embodiments, the method may include administering about 16 mg of the crystalline anhydrous form of the Compound of Formula (I) three times a week to a patient in need thereof. In some embodiments, the method may include administering about 17 mg of the crystalline anhydrous form of the Compound of Formula (I) three times a week to a patient in need thereof. In some embodiments, the method may include administering about 18 mg of the crystalline anhydrous form of the Compound of Formula (I) three times a week to a patient in need thereof. In some embodiments, the method may include administering about 19 mg of the crystalline anhydrous form of the Compound of Formula (I) three times a week to a patient in need thereof. In some embodiments, the method may include administering about 20 mg of the crystalline anhydrous form of the Compound of Formula (I) three times a week to a patient in need thereof. In some embodiments, the method may include administering about 21 mg of the crystalline anhydrous form of the Compound of Formula (I) three times a week to a patient in need thereof. In some embodiments, the method may include administering about 22 mg of the crystalline anhydrous form of the Compound of Formula (I) three times a week to a patient in need thereof. In some embodiments, the method may include administering about 23 mg of the crystalline anhydrous form of the Compound of Formula (I) three times a week to a patient in need thereof. In some embodiments, the method may include administering about 24 mg of the crystalline anhydrous form of the Compound of Formula (I) three times a week to a patient in need thereof. In some embodiments, the method may include administering about 25 mg of the crystalline anhydrous form of the Compound of Formula (I) three times a week to a patient in need thereof. In some embodiments, the method may include administering about 26 mg of the crystalline anhydrous form of the Compound of Formula (I) three times a week to a patient in need thereof. In some embodiments, the method may include administering about 27 mg of the crystalline anhydrous form of the Compound of Formula (I) three times a week to a patient in need thereof. In some embodiments, the method may include administering about 28 mg of the crystalline anhydrous form of the Compound of Formula (I) three times a week to a patient in need thereof. In some embodiments, the method may include administering about 29 mg of the crystalline anhydrous form of the Compound of Formula (I) three times a week to a patient in need thereof. In some embodiments, the method may include administering about 30 mg of the crystalline anhydrous form of the Compound of Formula (I) three times a week to a patient in need thereof. In some embodiments, the method may include administering about 31 mg of the crystalline anhydrous form of the Compound of Formula (I) three times a week to a patient in need thereof. In some embodiments, the method may include administering about 32 mg of the crystalline anhydrous form of the Compound of Formula (I) three times a week to a patient in need thereof. In some embodiments, the method may include administering about 33 mg of the crystalline anhydrous form of the Compound of Formula (I) three times a week to a patient in need thereof. In some embodiments, the method may include administering about 34 mg of the crystalline anhydrous form of the Compound of Formula (I) three times a week to a patient in need thereof. In some embodiments, the method may include administering about 35 mg of the crystalline anhydrous form of the Compound of Formula (I) three times a week to a patient in need thereof. In some embodiments, the method may include administering about 36 mg of the crystalline anhydrous form of the Compound of Formula (I) three times a week to a patient in need thereof. In some embodiments, the method may include administering about 37 mg of the crystalline anhydrous form of the Compound of Formula (I) three times a week to a patient in need thereof. In some embodiments, the method may include administering about 38 mg of the crystalline anhydrous form of the Compound of Formula (I) three times a week to a patient in need thereof. In some embodiments, the method may include administering about 39 mg of the crystalline anhydrous form of the Compound of Formula (I) three times a week to a patient in need thereof. In some embodiments, the method may include administering about 40 mg of the crystalline anhydrous form of the Compound of Formula (I) three times a week to a patient in need thereof. In some embodiments, the method may include administering about 41 mg of the crystalline anhydrous form of the Compound of Formula (I) three times a week to a patient in need thereof. In some embodiments, the method may include administering about 42 mg of the crystalline anhydrous form of the Compound of Formula (I) three times a week to a patient in need thereof. In some embodiments, the method may include administering about 43 mg of the crystalline anhydrous form of the Compound of Formula (I) three times a week to a patient in need thereof. In some embodiments, the method may include administering about 44 mg of the crystalline anhydrous form of the Compound of Formula (I) three times a week to a patient in need thereof. In some embodiments, the method may include administering about 45 mg of the crystalline anhydrous form of the Compound of Formula (I) three times a week to a patient in need thereof. In some embodiments, the method may include administering about 46 mg of the crystalline anhydrous form of the Compound of Formula (I) three times a week to a patient in need thereof. In some embodiments, the method may include administering about 47 mg of the crystalline anhydrous form of the Compound of Formula (I) three times a week to a patient in need thereof. In some embodiments, the method may include administering about 48 mg of the crystalline anhydrous form of the Compound of Formula (I) three times a week to a patient in need thereof. In some embodiments, the method may include administering about 49 mg of the crystalline anhydrous form of the Compound of Formula (I) three times a week to a patient in need thereof. In some embodiments, the method may include administering about 50 mg of the crystalline anhydrous form of the Compound of Formula (I) three times a week to a patient in need thereof. In some embodiments, the method may include administering about 51 mg of the crystalline anhydrous form of the Compound of Formula (I) three times a week to a patient in need thereof. In some embodiments, the method may include administering about 52 mg of the crystalline anhydrous form of the Compound of Formula (I) three times a week to a patient in need thereof. In some embodiments, the method may include administering about 53 mg of the crystalline anhydrous form of the Compound of Formula (I) three times a week to a patient in need thereof. In some embodiments, the method may include administering about 54 mg of the crystalline anhydrous form of the Compound of Formula (I) three times a week to a patient in need thereof. In some embodiments, the method may include administering about 55 mg of the crystalline anhydrous form of the Compound of Formula (I) three times a week to a patient in need thereof. In some embodiments, the method may include administering about 56 mg of the crystalline anhydrous form of the Compound of Formula (I) three times a week to a patient in need thereof. In some embodiments, the method may include administering about 57 mg of the crystalline anhydrous form of the Compound of Formula (I) three times a week to a patient in need thereof. In some embodiments, the method may include administering about 58 mg of the crystalline anhydrous form of the Compound of Formula (I) three times a week to a patient in need thereof. In some embodiments, the method may include administering about 59 mg of the crystalline anhydrous form of the Compound of Formula (I) three times a week to a patient in need thereof. In some embodiments, the method may include administering about 60 mg of the crystalline anhydrous form of the Compound of Formula (I) three times a week to a patient in need thereof. In some embodiments, the method may include administering about 65 mg of the crystalline anhydrous form of the Compound of Formula (I) three times a week to a patient in need thereof. In some embodiments, the method may include administering about 70 mg of the crystalline anhydrous form of the Compound of Formula (I) three times a week to a patient in need thereof. In some embodiments, the method may include administering about 75 mg of the crystalline anhydrous form of the Compound of Formula (I) three times a week to a patient in need thereof. In some embodiments, the method may include administering about 80 mg of the crystalline anhydrous form of the Compound of Formula (I) three times a week to a patient in need thereof. In some embodiments, the method may include administering about 85 mg of the crystalline anhydrous form of the Compound of Formula (I) three times a week to a patient in need thereof. In some embodiments, the method may include administering about 90 mg of the crystalline anhydrous form of the Compound of Formula (I) three times a week to a patient in need thereof. In some embodiments, the method may include administering about 95 mg of the crystalline anhydrous form of the Compound of Formula (I) three times a week to a patient in need thereof. In some embodiments, the method may include administering about 100 mg of the crystalline anhydrous form of the Compound of Formula (I) three times a week to a patient in need thereof. In some embodiments, the method may include administering about 105 mg of the crystalline anhydrous form of the Compound of Formula (I) three times a week to a patient in need thereof. In some embodiments, the method may include administering about 110 mg of the crystalline anhydrous form of the Compound of Formula (I) three times a week to a patient in need thereof. In some embodiments, the method may include administering about 115 mg of the crystalline anhydrous form of the Compound of Formula (I) three times a week to a patient in need thereof. In some embodiments, the method may include administering about 120 mg of the crystalline anhydrous form of the Compound of Formula (I) three times a week to a patient in need thereof. In some embodiments, the method may include administering about 125 mg of the crystalline anhydrous form of the Compound of Formula (I) three times a week to a patient in need thereof. In some embodiments, the method may include administering about 130 mg of the crystalline anhydrous form of the Compound of Formula (I) three times a week to a patient in need thereof. In some embodiments, the method may include administering about 135 mg of the crystalline anhydrous form of the Compound of Formula (I) three times a week to a patient in need thereof. In some embodiments, the method may include administering about 140 mg of the crystalline anhydrous form of the Compound of Formula (I) three times a week to a patient in need thereof. In some embodiments, the method may include administering about 145 mg of the crystalline anhydrous form of the Compound of Formula (I) three times a week to a patient in need thereof. In some embodiments, the method may include administering about 150 mg of the crystalline anhydrous form of the Compound of Formula (I) three times a week to a patient in need thereof.

In some embodiments, such a disclosed method may include, administering a loading dose of the crystalline anhydrous form of the Compound of Formula (I) daily to a patient in need thereof, once a week to a patient in need thereof, twice a week to a patient in need thereof, or three times a week to a patient in need thereof, for a first time period; and administering a maintenance dose of the crystalline anhydrous form to a patient in need thereof daily to a patient in need thereof, once a week to a patient in need thereof, twice a week to a patient in need thereof, or three times a week to a patient in need thereof for a second time period.

In some embodiments, the loading dose is about 2 mg to about 100 mg of the crystalline anhydrous form of the Compound of Formula (I) once a day. In some embodiments, the loading dose is about 5 mg to about 90 mg of the crystalline anhydrous form of the Compound of Formula (I) once a day. In some embodiments, the loading dose is about 10 mg to about 80 mg of the crystalline anhydrous form of the Compound of Formula (I) once a day. In some embodiments, the loading dose is about 10 mg to about 70 mg of the crystalline anhydrous form of the Compound of Formula (I) once a day. In some embodiments, the loading dose is about 10 mg to about 60 mg of the crystalline anhydrous form of the Compound of Formula (I) once a day. In some embodiments, the loading dose is about 10 mg to about 50 mg of the crystalline anhydrous form of the Compound of Formula (I) once a day. In some embodiments, the loading dose is about 10 mg to about 40 mg of the crystalline anhydrous form of the Compound of Formula (I) once a day. In some embodiments, the loading dose is about 10 mg to about 30 mg of the crystalline anhydrous form of the Compound of Formula (I) once a day. In some embodiments, the loading dose is about 10 mg to about 20 mg of the crystalline anhydrous form of the Compound of Formula (I) once a day. In some embodiments, the loading dose is about 2 mg of the crystalline anhydrous form of the Compound of Formula (I) once a day. In some embodiments, the loading dose is about 3 mg of the crystalline anhydrous form of the Compound of Formula (I) once a day. In some embodiments, the loading dose is about 4 mg of the crystalline anhydrous form of the Compound of Formula (I) once a day. In some embodiments, the loading dose is about 5 mg of the crystalline anhydrous form of the Compound of Formula (I) once a day. In some embodiments, the loading dose is about 10 mg of the crystalline anhydrous form of the Compound of Formula (I) once a day. In some embodiments, the loading dose is about 11 mg of the crystalline anhydrous form of the Compound of Formula (I) once a day. In some embodiments, the loading dose is about 12 mg of the crystalline anhydrous form of the Compound of Formula (I) once a day. In some embodiments, the loading dose is about 13 mg of the crystalline anhydrous form of the Compound of Formula (I) once a day. In some embodiments, the loading dose is about 14 mg of the crystalline anhydrous form of the Compound of Formula (I) once a day. In some embodiments, the loading dose is about 15 mg of the crystalline anhydrous form of the Compound of Formula (I) once a day. In some embodiments, the loading dose is about 16 mg of the crystalline anhydrous form of the Compound of Formula (I) once a day. In some embodiments, the loading dose is about 17 mg of the crystalline anhydrous form of the Compound of Formula (I) once a day. In some embodiments, the loading dose is about 18 mg of the crystalline anhydrous form of the Compound of Formula (I) once a day. In some embodiments, the loading dose is about 19 mg of the crystalline anhydrous form of the Compound of Formula (I) once a day. In some embodiments, the loading dose is about 20 mg of the crystalline anhydrous form of the Compound of Formula (I) once a day. In some embodiments, the loading dose is about 22 mg of the crystalline anhydrous form of the Compound of Formula (I) once a day. In some embodiments, the loading dose is about 24 mg of the crystalline anhydrous form of the Compound of Formula (I) once a day. In some embodiments, the loading dose is about 26 mg of the crystalline anhydrous form of the Compound of Formula (I) once a day. In some embodiments, the loading dose is about 28 mg of the crystalline anhydrous form of the Compound of Formula (I) once a day. In some embodiments, the loading dose is about 30 mg of the crystalline anhydrous form of the Compound of Formula (I) once a day. In some embodiments, the loading dose is about 32 mg of the crystalline anhydrous form of the Compound of Formula (I) once a day. In some embodiments, the loading dose is about 34 mg of the crystalline anhydrous form of the Compound of Formula (I) once a day. In some embodiments, the loading dose is about 36 mg of the crystalline anhydrous form of the Compound of Formula (I) once a day. In some embodiments, the loading dose is about 38 mg of the crystalline anhydrous form of the Compound of Formula (I) once a day. In some embodiments, the loading dose is about 40 mg of the crystalline anhydrous form of the Compound of Formula (I) once a day. In some embodiments, the loading dose is about 42 mg of the crystalline anhydrous form of the Compound of Formula (I) once a day. In some embodiments, the loading dose is about 44 mg of the crystalline anhydrous form of the Compound of Formula (I) once a day. In some embodiments, the loading dose is about 46 mg of the crystalline anhydrous form of the Compound of Formula (I) once a day. In some embodiments, the loading dose is about 48 mg of the crystalline anhydrous form of the Compound of Formula (I) once a day. In some embodiments, the loading dose is about 50 mg of the crystalline anhydrous form of the Compound of Formula (I) once a day.

In some embodiments, the loading dose is about 2 mg to about 100 mg of the crystalline anhydrous form of the Compound of Formula (I) once a day for one day. In some embodiments, the loading dose is about 5 mg to about 90 mg of the crystalline anhydrous form of the Compound of Formula (I) once a day for one day. In some embodiments, the loading dose is about 10 mg to about 80 mg of the crystalline anhydrous form of the Compound of Formula (I) once a day for one day. In some embodiments, the loading dose is about 10 mg to about 70 mg of the crystalline anhydrous form of the Compound of Formula (I) once a day for one day. In some embodiments, the loading dose is about 10 mg to about 60 mg of the crystalline anhydrous form of the Compound of Formula (I) once a day for one day. In some embodiments, the loading dose is about 10 mg to about 50 mg of the crystalline anhydrous form of the Compound of Formula (I) once a day for one day. In some embodiments, the loading dose is about 10 mg to about 40 mg of the crystalline anhydrous form of the Compound of Formula (I) once a day for one day. In some embodiments, the loading dose is about 10 mg to about 30 mg of the crystalline anhydrous form of the Compound of Formula (I) once a day for one day. In some embodiments, the loading dose is about 10 mg to about 20 mg of the crystalline anhydrous form of the Compound of Formula (I) once a day for one day. In some embodiments, the loading dose is about 2 mg of the crystalline anhydrous form of the Compound of Formula (I) once a day for one day. In some embodiments, the loading dose is about 3 mg of the crystalline anhydrous form of the Compound of Formula (I) once a day for one day. In some embodiments, the loading dose is about 4 mg of the crystalline anhydrous form of the Compound of Formula (I) once a day for one day. In some embodiments, the loading dose is about 5 mg of the crystalline anhydrous form of the Compound of Formula (I) once a day for one day. In some embodiments, the loading dose is about 10 mg of the crystalline anhydrous form of the Compound of Formula (I) once a day for one day. In some embodiments, the loading dose is about 11 mg of the crystalline anhydrous form of the Compound of Formula (I) once a day for one day. In some embodiments, the loading dose is about 12 mg of the crystalline anhydrous form of the Compound of Formula (I) once a day for one day. In some embodiments, the loading dose is about 13 mg of the crystalline anhydrous form of the Compound of Formula (I) once a day for one day. In some embodiments, the loading dose is about 14 mg of the crystalline anhydrous form of the Compound of Formula (I) once a day for one day. In some embodiments, the loading dose is about 15 mg of the crystalline anhydrous form of the Compound of Formula (I) once a day for one day. In some embodiments, the loading dose is about 16 mg of the crystalline anhydrous form of the Compound of Formula (I) once a day for one day. In some embodiments, the loading dose is about 17 mg of the crystalline anhydrous form of the Compound of Formula (I) once a day for one day. In some embodiments, the loading dose is about 18 mg of the crystalline anhydrous form of the Compound of Formula (I) once a day for one day. In some embodiments, the loading dose is about 19 mg of the crystalline anhydrous form of the Compound of Formula (I) once a day for one day. In some embodiments, the loading dose is about 20 mg of the crystalline anhydrous form of the Compound of Formula (I) once a day for one day. In some embodiments, the loading dose is about 22 mg of the crystalline anhydrous form of the Compound of Formula (I) once a day for one day. In some embodiments, the loading dose is about 24 mg of the crystalline anhydrous form of the Compound of Formula (I) once a day for one day. In some embodiments, the loading dose is about 26 mg of the crystalline anhydrous form of the Compound of Formula (I) once a day for one day. In some embodiments, the loading dose is about 28 mg of the crystalline anhydrous form of the Compound of Formula (I) once a day for one day. In some embodiments, the loading dose is about 30 mg of the crystalline anhydrous form of the Compound of Formula (I) once a day for one day. In some embodiments, the loading dose is about 32 mg of the crystalline anhydrous form of the Compound of Formula (I) once a day for one day. In some embodiments, the loading dose is about 34 mg of the crystalline anhydrous form of the Compound of Formula (I) once a day for one day. In some embodiments, the loading dose is about 36 mg of the crystalline anhydrous form of the Compound of Formula (I) once a day for one day. In some embodiments, the loading dose is about 38 mg of the crystalline anhydrous form of the Compound of Formula (I) once a day for one day. In some embodiments, the loading dose is about 40 mg of the crystalline anhydrous form of the Compound of Formula (I) once a day for one day. In some embodiments, the loading dose is about 42 mg of the crystalline anhydrous form of the Compound of Formula (I) once a day for one day. In some embodiments, the loading dose is about 44 mg of the crystalline anhydrous form of the Compound of Formula (I) once a day for one day. In some embodiments, the loading dose is about 46 mg of the crystalline anhydrous form of the Compound of Formula (I) once a day for one day. In some embodiments, the loading dose is about 48 mg of the crystalline anhydrous form of the Compound of Formula (I) once a day for one day. In some embodiments, the loading dose is about 50 mg of the crystalline anhydrous form of the Compound of Formula (I) once a day for one day.

In some embodiments, the loading dose is about 2 mg to about 100 mg of the crystalline anhydrous form of the Compound of Formula (I) once a day for two days. In some embodiments, the loading dose is about 5 mg to about 90 mg of the crystalline anhydrous form of the Compound of Formula (I) once a day for two days. In some embodiments, the loading dose is about 10 mg to about 80 mg of the crystalline anhydrous form of the Compound of Formula (I) once a day for two days. In some embodiments, the loading dose is about 10 mg to about 70 mg of the crystalline anhydrous form of the Compound of Formula (I) once a day for two days. In some embodiments, the loading dose is about 10 mg to about 60 mg of the crystalline anhydrous form of the Compound of Formula (I) once a day for two days. In some embodiments, the loading dose is about 10 mg to about 50 mg of the crystalline anhydrous form of the Compound of Formula (I) once a day for two days. In some embodiments, the loading dose is about 10 mg to about 40 mg of the crystalline anhydrous form of the Compound of Formula (I) once a day for two days. In some embodiments, the loading dose is about 10 mg to about 30 mg of the crystalline anhydrous form of the Compound of Formula (I) once a day for two days. In some embodiments, the loading dose is about 10 mg to about 20 mg of the crystalline anhydrous form of the Compound of Formula (I) once a day for two days. In some embodiments, the loading dose is about 2 mg of the crystalline anhydrous form of the Compound of Formula (I) once a day for two days. In some embodiments, the loading dose is about 3 mg of the crystalline anhydrous form of the Compound of Formula (I) once a day for two days. In some embodiments, the loading dose is about 4 mg of the crystalline anhydrous form of the Compound of Formula (I) once a day for two days. In some embodiments, the loading dose is about 5 mg of the crystalline anhydrous form of the Compound of Formula (I) once a day for two days. In some embodiments, the loading dose is about 10 mg of the crystalline anhydrous form of the Compound of Formula (I) once a day for two days. In some embodiments, the loading dose is about 11 mg of the crystalline anhydrous form of the Compound of Formula (I) once a day for two days. In some embodiments, the loading dose is about 12 mg of the crystalline anhydrous form of the Compound of Formula (I) once a day for two days. In some embodiments, the loading dose is about 13 mg of the crystalline anhydrous form of the Compound of Formula (I) once a day for two days. In some embodiments, the loading dose is about 14 mg of the crystalline anhydrous form of the Compound of Formula (I) once a day for two days. In some embodiments, the loading dose is about 15 mg of the crystalline anhydrous form of the Compound of Formula (I) once a day for two days. In some embodiments, the loading dose is about 16 mg of the crystalline anhydrous form of the Compound of Formula (I) once a day for two days. In some embodiments, the loading dose is about 17 mg of the crystalline anhydrous form of the Compound of Formula (I) once a day for two days. In some embodiments, the loading dose is about 18 mg of the crystalline anhydrous form of the Compound of Formula (I) once a day for two days. In some embodiments, the loading dose is about 19 mg of the crystalline anhydrous form of the Compound of Formula (I) once a day for two days. In some embodiments, the loading dose is about 20 mg of the crystalline anhydrous form of the Compound of Formula (I) once a day for two days. In some embodiments, the loading dose is about 22 mg of the crystalline anhydrous form of the Compound of Formula (I) once a day for two days. In some embodiments, the loading dose is about 24 mg of the crystalline anhydrous form of the Compound of Formula (I) once a day for two days. In some embodiments, the loading dose is about 26 mg of the crystalline anhydrous form of the Compound of Formula (I) once a day for two days. In some embodiments, the loading dose is about 28 mg of the crystalline anhydrous form of the Compound of Formula (I) once a day for two days. In some embodiments, the loading dose is about 30 mg of the crystalline anhydrous form of the Compound of Formula (I) once a day for two days. In some embodiments, the loading dose is about 32 mg of the crystalline anhydrous form of the Compound of Formula (I) once a day for two days. In some embodiments, the loading dose is about 34 mg of the crystalline anhydrous form of the Compound of Formula (I) once a day for two days. In some embodiments, the loading dose is about 36 mg of the crystalline anhydrous form of the Compound of Formula (I) once a day for two days. In some embodiments, the loading dose is about 38 mg of the crystalline anhydrous form of the Compound of Formula (I) once a day for two days. In some embodiments, the loading dose is about 40 mg of the crystalline anhydrous form of the Compound of Formula (I) once a day for two days. In some embodiments, the loading dose is about 42 mg of the crystalline anhydrous form of the Compound of Formula (I) once a day for two days. In some embodiments, the loading dose is about 44 mg of the crystalline anhydrous form of the Compound of Formula (I) once a day for two days. In some embodiments, the loading dose is about 46 mg of the crystalline anhydrous form of the Compound of Formula (I) once a day for two days. In some embodiments, the loading dose is about 48 mg of the crystalline anhydrous form of the Compound of Formula (I) once a day for two days. In some embodiments, the loading dose is about 50 mg of the crystalline anhydrous form of the Compound of Formula (I) once a day for two days.

In some embodiments, the loading dose is about 2 mg to about 100 mg of the crystalline anhydrous form of the Compound of Formula (I) once a day for three days. In some embodiments, the loading dose is about 5 mg to about 90 mg of the crystalline anhydrous form of the Compound of Formula (I) once a day for three days. In some embodiments, the loading dose is about 10 mg to about 80 mg of the crystalline anhydrous form of the Compound of Formula (I) once a day for three days. In some embodiments, the loading dose is about 10 mg to about 70 mg of the crystalline anhydrous form of the Compound of Formula (I) once a day for three days. In some embodiments, the loading dose is about 10 mg to about 60 mg of the crystalline anhydrous form of the Compound of Formula (I) once a day for three days. In some embodiments, the loading dose is about 10 mg to about 50 mg of the crystalline anhydrous form of the Compound of Formula (I) once a day for three days. In some embodiments, the loading dose is about 10 mg to about 40 mg of the crystalline anhydrous form of the Compound of Formula (I) once a day for three days. In some embodiments, the loading dose is about 10 mg to about 30 mg of the crystalline anhydrous form of the Compound of Formula (I) once a day for three days. In some embodiments, the loading dose is about 10 mg to about 20 mg of the crystalline anhydrous form of the Compound of Formula (I) once a day for three days. In some embodiments, the loading dose is about 2 mg of the crystalline anhydrous form of the Compound of Formula (I) once a day for three days. In some embodiments, the loading dose is about 3 mg of the crystalline anhydrous form of the Compound of Formula (I) once a day for three days. In some embodiments, the loading dose is about 4 mg of the crystalline anhydrous form of the Compound of Formula (I) once a day for three days. In some embodiments, the loading dose is about 5 mg of the crystalline anhydrous form of the Compound of Formula (I) once a day for three days. In some embodiments, the loading dose is about 10 mg of the crystalline anhydrous form of the Compound of Formula (I) once a day for three days. In some embodiments, the loading dose is about 11 mg of the crystalline anhydrous form of the Compound of Formula (I) once a day for three days. In some embodiments, the loading dose is about 12 mg of the crystalline anhydrous form of the Compound of Formula (I) once a day for three days. In some embodiments, the loading dose is about 13 mg of the crystalline anhydrous form of the Compound of Formula (I) once a day for three days. In some embodiments, the loading dose is about 14 mg of the crystalline anhydrous form of the Compound of Formula (I) once a day for three days. In some embodiments, the loading dose is about 15 mg of the crystalline anhydrous form of the Compound of Formula (I) once a day for three days. In some embodiments, the loading dose is about 16 mg of the crystalline anhydrous form of the Compound of Formula (I) once a day for three days. In some embodiments, the loading dose is about 17 mg of the crystalline anhydrous form of the Compound of Formula (I) once a day for three days. In some embodiments, the loading dose is about 18 mg of the crystalline anhydrous form of the Compound of Formula (I) once a day for three days. In some embodiments, the loading dose is about 19 mg of the crystalline anhydrous form of the Compound of Formula (I) once a day for three days. In some embodiments, the loading dose is about 20 mg of the crystalline anhydrous form of the Compound of Formula (I) once a day for three days. In some embodiments, the loading dose is about 22 mg of the crystalline anhydrous form of the Compound of Formula (I) once a day for three days. In some embodiments, the loading dose is about 24 mg of the crystalline anhydrous form of the Compound of Formula (I) once a day for three days. In some embodiments, the loading dose is about 26 mg of the crystalline anhydrous form of the Compound of Formula (I) once a day for three days. In some embodiments, the loading dose is about 28 mg of the crystalline anhydrous form of the Compound of Formula (I) once a day for three days. In some embodiments, the loading dose is about 30 mg of the crystalline anhydrous form of the Compound of Formula (I) once a day for three days. In some embodiments, the loading dose is about 32 mg of the crystalline anhydrous form of the Compound of Formula (I) once a day for three days. In some embodiments, the loading dose is about 34 mg of the crystalline anhydrous form of the Compound of Formula (I) once a day for three days. In some embodiments, the loading dose is about 36 mg of the crystalline anhydrous form of the Compound of Formula (I) once a day for three days. In some embodiments, the loading dose is about 38 mg of the crystalline anhydrous form of the Compound of Formula (I) once a day for three days. In some embodiments, the loading dose is about 40 mg of the crystalline anhydrous form of the Compound of Formula (I) once a day for three days. In some embodiments, the loading dose is about 42 mg of the crystalline anhydrous form of the Compound of Formula (I) once a day for three days. In some embodiments, the loading dose is about 44 mg of the crystalline anhydrous form of the Compound of Formula (I) once a day for three days. In some embodiments, the loading dose is about 46 mg of the crystalline anhydrous form of the Compound of Formula (I) once a day for three days. In some embodiments, the loading dose is about 48 mg of the crystalline anhydrous form of the Compound of Formula (I) once a day for three days. In some embodiments, the loading dose is about 50 mg of the crystalline anhydrous form of the Compound of Formula (I) once a day for three days.

In some embodiments, the loading dose is about 2 mg to about 100 mg of the crystalline anhydrous form of the Compound of Formula (I) once a day for four days. In some embodiments, the loading dose is about 5 mg to about 90 mg of the crystalline anhydrous form of the Compound of Formula (I) once a day for four days. In some embodiments, the loading dose is about 10 mg to about 80 mg of the crystalline anhydrous form of the Compound of Formula (I) once a day for four days. In some embodiments, the loading dose is about 10 mg to about 70 mg of the crystalline anhydrous form of the Compound of Formula (I) once a day for four days. In some embodiments, the loading dose is about 10 mg to about 60 mg of the crystalline anhydrous form of the Compound of Formula (I) once a day for four days. In some embodiments, the loading dose is about 10 mg to about 50 mg of the crystalline anhydrous form of the Compound of Formula (I) once a day for four days. In some embodiments, the loading dose is about 10 mg to about 40 mg of the crystalline anhydrous form of the Compound of Formula (I) once a day for four days. In some embodiments, the loading dose is about 10 mg to about 30 mg of the crystalline anhydrous form of the Compound of Formula (I) once a day for four days. In some embodiments, the loading dose is about 10 mg to about 20 mg of the crystalline anhydrous form of the Compound of Formula (I) once a day for four days. In some embodiments, the loading dose is about 2 mg of the crystalline anhydrous form of the Compound of Formula (I) once a day for four days. In some embodiments, the loading dose is about 3 mg of the crystalline anhydrous form of the Compound of Formula (I) once a day for four days. In some embodiments, the loading dose is about 4 mg of the crystalline anhydrous form of the Compound of Formula (I) once a day for four days. In some embodiments, the loading dose is about 5 mg of the crystalline anhydrous form of the Compound of Formula (I) once a day for four days. In some embodiments, the loading dose is about 10 mg of the crystalline anhydrous form of the Compound of Formula (I) once a day for four days. In some embodiments, the loading dose is about 11 mg of the crystalline anhydrous form of the Compound of Formula (I) once a day for four days. In some embodiments, the loading dose is about 12 mg of the crystalline anhydrous form of the Compound of Formula (I) once a day for four days. In some embodiments, the loading dose is about 13 mg of the crystalline anhydrous form of the Compound of Formula (I) once a day for four days. In some embodiments, the loading dose is about 14 mg of the crystalline anhydrous form of the Compound of Formula (I) once a day for four days. In some embodiments, the loading dose is about 15 mg of the crystalline anhydrous form of the Compound of Formula (I) once a day for four days. In some embodiments, the loading dose is about 16 mg of the crystalline anhydrous form of the Compound of Formula (I) once a day for four days. In some embodiments, the loading dose is about 17 mg of the crystalline anhydrous form of the Compound of Formula (I) once a day for four days. In some embodiments, the loading dose is about 18 mg of the crystalline anhydrous form of the Compound of Formula (I) once a day for four days. In some embodiments, the loading dose is about 19 mg of the crystalline anhydrous form of the Compound of Formula (I) once a day for four days. In some embodiments, the loading dose is about 20 mg of the crystalline anhydrous form of the Compound of Formula (I) once a day for four days. In some embodiments, the loading dose is about 22 mg of the crystalline anhydrous form of the Compound of Formula (I) once a day for four days. In some embodiments, the loading dose is about 24 mg of the crystalline anhydrous form of the Compound of Formula (I) once a day for four days. In some embodiments, the loading dose is about 26 mg of the crystalline anhydrous form of the Compound of Formula (I) once a day for four days. In some embodiments, the loading dose is about 28 mg of the crystalline anhydrous form of the Compound of Formula (I) once a day for four days. In some embodiments, the loading dose is about 30 mg of the crystalline anhydrous form of the Compound of Formula (I) once a day for four days. In some embodiments, the loading dose is about 32 mg of the crystalline anhydrous form of the Compound of Formula (I) once a day for four days. In some embodiments, the loading dose is about 34 mg of the crystalline anhydrous form of the Compound of Formula (I) once a day for four days. In some embodiments, the loading dose is about 36 mg of the crystalline anhydrous form of the Compound of Formula (I) once a day for four days. In some embodiments, the loading dose is about 38 mg of the crystalline anhydrous form of the Compound of Formula (I) once a day for four days. In some embodiments, the loading dose is about 40 mg of the crystalline anhydrous form of the Compound of Formula (I) once a day for four days. In some embodiments, the loading dose is about 42 mg of the crystalline anhydrous form of the Compound of Formula (I) once a day for four days. In some embodiments, the loading dose is about 44 mg of the crystalline anhydrous form of the Compound of Formula (I) once a day for four days. In some embodiments, the loading dose is about 46 mg of the crystalline anhydrous form of the Compound of Formula (I) once a day for four days. In some embodiments, the loading dose is about 48 mg of the crystalline anhydrous form of the Compound of Formula (I) once a day for four days. In some embodiments, the loading dose is about 50 mg of the crystalline anhydrous form of the Compound of Formula (I) once a day for four days.

In some embodiments, the loading dose is about 2 mg to about 100 mg of the crystalline anhydrous form of the Compound of Formula (I) once a day for five days. In some embodiments, the loading dose is about 5 mg to about 90 mg of the crystalline anhydrous form of the Compound of Formula (I) once a day for five days. In some embodiments, the loading dose is about 10 mg to about 80 mg of the crystalline anhydrous form of the Compound of Formula (I) once a day for five days. In some embodiments, the loading dose is about 10 mg to about 70 mg of the crystalline anhydrous form of the Compound of Formula (I) once a day for five days. In some embodiments, the loading dose is about 10 mg to about 60 mg of the crystalline anhydrous form of the Compound of Formula (I) once a day for five days. In some embodiments, the loading dose is about 10 mg to about 50 mg of the crystalline anhydrous form of the Compound of Formula (I) once a day for five days. In some embodiments, the loading dose is about 10 mg to about 40 mg of the crystalline anhydrous form of the Compound of Formula (I) once a day for five days. In some embodiments, the loading dose is about 10 mg to about 30 mg of the crystalline anhydrous form of the Compound of Formula (I) once a day for five days. In some embodiments, the loading dose is about 10 mg to about 20 mg of the crystalline anhydrous form of the Compound of Formula (I) once a day for five days. In some embodiments, the loading dose is about 2 mg of the crystalline anhydrous form of the Compound of Formula (I) once a day for five days. In some embodiments, the loading dose is about 3 mg of the crystalline anhydrous form of the Compound of Formula (I) once a day for five days. In some embodiments, the loading dose is about 4 mg of the crystalline anhydrous form of the Compound of Formula (I) once a day for five days. In some embodiments, the loading dose is about 5 mg of the crystalline anhydrous form of the Compound of Formula (I) once a day for five days. In some embodiments, the loading dose is about 10 mg of the crystalline anhydrous form of the Compound of Formula (I) once a day for five days. In some embodiments, the loading dose is about 11 mg of the crystalline anhydrous form of the Compound of Formula (I) once a day for five days. In some embodiments, the loading dose is about 12 mg of the crystalline anhydrous form of the Compound of Formula (I) once a day for five days. In some embodiments, the loading dose is about 13 mg of the crystalline anhydrous form of the Compound of Formula (I) once a day for five days. In some embodiments, the loading dose is about 14 mg of the crystalline anhydrous form of the Compound of Formula (I) once a day for five days. In some embodiments, the loading dose is about 15 mg of the crystalline anhydrous form of the Compound of Formula (I) once a day for five days. In some embodiments, the loading dose is about 16 mg of the crystalline anhydrous form of the Compound of Formula (I) once a day for five days. In some embodiments, the loading dose is about 17 mg of the crystalline anhydrous form of the Compound of Formula (I) once a day for five days. In some embodiments, the loading dose is about 18 mg of the crystalline anhydrous form of the Compound of Formula (I) once a day for five days. In some embodiments, the loading dose is about 19 mg of the crystalline anhydrous form of the Compound of Formula (I) once a day for five days. In some embodiments, the loading dose is about 20 mg of the crystalline anhydrous form of the Compound of Formula (I) once a day for five days. In some embodiments, the loading dose is about 22 mg of the crystalline anhydrous form of the Compound of Formula (I) once a day for five days. In some embodiments, the loading dose is about 24 mg of the crystalline anhydrous form of the Compound of Formula (I) once a day for five days. In some embodiments, the loading dose is about 26 mg of the crystalline anhydrous form of the Compound of Formula (I) once a day for five days. In some embodiments, the loading dose is about 28 mg of the crystalline anhydrous form of the Compound of Formula (I) once a day for five days. In some embodiments, the loading dose is about 30 mg of the crystalline anhydrous form of the Compound of Formula (I) once a day for five days. In some embodiments, the loading dose is about 32 mg of the crystalline anhydrous form of the Compound of Formula (I) once a day for five days. In some embodiments, the loading dose is about 34 mg of the crystalline anhydrous form of the Compound of Formula (I) once a day for five days. In some embodiments, the loading dose is about 36 mg of the crystalline anhydrous form of the Compound of Formula (I) once a day for five days. In some embodiments, the loading dose is about 38 mg of the crystalline anhydrous form of the Compound of Formula (I) once a day for five days. In some embodiments, the loading dose is about 40 mg of the crystalline anhydrous form of the Compound of Formula (I) once a day for five days. In some embodiments, the loading dose is about 42 mg of the crystalline anhydrous form of the Compound of Formula (I) once a day for five days. In some embodiments, the loading dose is about 44 mg of the crystalline anhydrous form of the Compound of Formula (I) once a day for five days. In some embodiments, the loading dose is about 46 mg of the crystalline anhydrous form of the Compound of Formula (I) once a day for five days. In some embodiments, the loading dose is about 48 mg of the crystalline anhydrous form of the Compound of Formula (I) once a day for five days. In some embodiments, the loading dose is about 50 mg of the crystalline anhydrous form of the Compound of Formula (I) once a day for five days.

In some embodiments, the loading dose is about 2 mg to about 100 mg of the crystalline anhydrous form of the Compound of Formula (I) once a day for six days. In some embodiments, the loading dose is about 5 mg to about 90 mg of the crystalline anhydrous form of the Compound of Formula (I) once a day for six days. In some embodiments, the loading dose is about 10 mg to about 80 mg of the crystalline anhydrous form of the Compound of Formula (I) once a day for six days. In some embodiments, the loading dose is about 10 mg to about 70 mg of the crystalline anhydrous form of the Compound of Formula (I) once a day for six days. In some embodiments, the loading dose is about 10 mg to about 60 mg of the crystalline anhydrous form of the Compound of Formula (I) once a day for six days. In some embodiments, the loading dose is about 10 mg to about 50 mg of the crystalline anhydrous form of the Compound of Formula (I) once a day for six days. In some embodiments, the loading dose is about 10 mg to about 40 mg of the crystalline anhydrous form of the Compound of Formula (I) once a day for six days. In some embodiments, the loading dose is about 10 mg to about 30 mg of the crystalline anhydrous form of the Compound of Formula (I) once a day for six days. In some embodiments, the loading dose is about 10 mg to about 20 mg of the crystalline anhydrous form of the Compound of Formula (I) once a day for six days. In some embodiments, the loading dose is about 2 mg of the crystalline anhydrous form of the Compound of Formula (I) once a day for six days. In some embodiments, the loading dose is about 3 mg of the crystalline anhydrous form of the Compound of Formula (I) once a day for six days. In some embodiments, the loading dose is about 4 mg of the crystalline anhydrous form of the Compound of Formula (I) once a day for six days. In some embodiments, the loading dose is about 5 mg of the crystalline anhydrous form of the Compound of Formula (I) once a day for six days. In some embodiments, the loading dose is about 10 mg of the crystalline anhydrous form of the Compound of Formula (I) once a day for six days. In some embodiments, the loading dose is about 11 mg of the crystalline anhydrous form of the Compound of Formula (I) once a day for six days. In some embodiments, the loading dose is about 12 mg of the crystalline anhydrous form of the Compound of Formula (I) once a day for six days. In some embodiments, the loading dose is about 13 mg of the crystalline anhydrous form of the Compound of Formula (I) once a day for six days. In some embodiments, the loading dose is about 14 mg of the crystalline anhydrous form of the Compound of Formula (I) once a day for six days. In some embodiments, the loading dose is about 15 mg of the crystalline anhydrous form of the Compound of Formula (I) once a day for six days. In some embodiments, the loading dose is about 16 mg of the crystalline anhydrous form of the Compound of Formula (I) once a day for six days. In some embodiments, the loading dose is about 17 mg of the crystalline anhydrous form of the Compound of Formula (I) once a day for six days. In some embodiments, the loading dose is about 18 mg of the crystalline anhydrous form of the Compound of Formula (I) once a day for six days. In some embodiments, the loading dose is about 19 mg of the crystalline anhydrous form of the Compound of Formula (I) once a day for six days. In some embodiments, the loading dose is about 20 mg of the crystalline anhydrous form of the Compound of Formula (I) once a day for six days. In some embodiments, the loading dose is about 22 mg of the crystalline anhydrous form of the Compound of Formula (I) once a day for six days. In some embodiments, the loading dose is about 24 mg of the crystalline anhydrous form of the Compound of Formula (I) once a day for six days. In some embodiments, the loading dose is about 26 mg of the crystalline anhydrous form of the Compound of Formula (I) once a day for six days. In some embodiments, the loading dose is about 28 mg of the crystalline anhydrous form of the Compound of Formula (I) once a day for six days. In some embodiments, the loading dose is about 30 mg of the crystalline anhydrous form of the Compound of Formula (I) once a day for six days. In some embodiments, the loading dose is about 32 mg of the crystalline anhydrous form of the Compound of Formula (I) once a day for six days. In some embodiments, the loading dose is about 34 mg of the crystalline anhydrous form of the Compound of Formula (I) once a day for six days. In some embodiments, the loading dose is about 36 mg of the crystalline anhydrous form of the Compound of Formula (I) once a day for six days. In some embodiments, the loading dose is about 38 mg of the crystalline anhydrous form of the Compound of Formula (I) once a day for six days. In some embodiments, the loading dose is about 40 mg of the crystalline anhydrous form of the Compound of Formula (I) once a day for six days. In some embodiments, the loading dose is about 42 mg of the crystalline anhydrous form of the Compound of Formula (I) once a day for six days. In some embodiments, the loading dose is about 44 mg of the crystalline anhydrous form of the Compound of Formula (I) once a day for six days. In some embodiments, the loading dose is about 46 mg of the crystalline anhydrous form of the Compound of Formula (I) once a day for six days. In some embodiments, the loading dose is about 48 mg of the crystalline anhydrous form of the Compound of Formula (I) once a day for six days. In some embodiments, the loading dose is about 50 mg of the crystalline anhydrous form of the Compound of Formula (I) once a day for six days.

In some embodiments, the loading dose is about 2 mg to about 100 mg of the crystalline anhydrous form of the Compound of Formula (I) once a day for seven days. In some embodiments, the loading dose is about 5 mg to about 90 mg of the crystalline anhydrous form of the Compound of Formula (I) once a day for seven days. In some embodiments, the loading dose is about 10 mg to about 80 mg of the crystalline anhydrous form of the Compound of Formula (I) once a day for seven days. In some embodiments, the loading dose is about 10 mg to about 70 mg of the crystalline anhydrous form of the Compound of Formula (I) once a day for seven days. In some embodiments, the loading dose is about 10 mg to about 60 mg of the crystalline anhydrous form of the Compound of Formula (I) once a day for seven days. In some embodiments, the loading dose is about 10 mg to about 50 mg of the crystalline anhydrous form of the Compound of Formula (I) once a day for seven days. In some embodiments, the loading dose is about 10 mg to about 40 mg of the crystalline anhydrous form of the Compound of Formula (I) once a day for seven days. In some embodiments, the loading dose is about 10 mg to about 30 mg of the crystalline anhydrous form of the Compound of Formula (I) once a day for seven days. In some embodiments, the loading dose is about 10 mg to about 20 mg of the crystalline anhydrous form of the Compound of Formula (I) once a day for seven days. In some embodiments, the loading dose is about 2 mg of the crystalline anhydrous form of the Compound of Formula (I) once a day for seven days. In some embodiments, the loading dose is about 3 mg of the crystalline anhydrous form of the Compound of Formula (I) once a day for seven days. In some embodiments, the loading dose is about 4 mg of the crystalline anhydrous form of the Compound of Formula (I) once a day for seven days. In some embodiments, the loading dose is about 5 mg of the crystalline anhydrous form of the Compound of Formula (I) once a day for seven days. In some embodiments, the loading dose is about 10 mg of the crystalline anhydrous form of the Compound of Formula (I) once a day for seven days. In some embodiments, the loading dose is about 11 mg of the crystalline anhydrous form of the Compound of Formula (I) once a day for seven days. In some embodiments, the loading dose is about 12 mg of the crystalline anhydrous form of the Compound of Formula (I) once a day for seven days. In some embodiments, the loading dose is about 13 mg of the crystalline anhydrous form of the Compound of Formula (I) once a day for seven days. In some embodiments, the loading dose is about 14 mg of the crystalline anhydrous form of the Compound of Formula (I) once a day for seven days. In some embodiments, the loading dose is about 15 mg of the crystalline anhydrous form of the Compound of Formula (I) once a day for seven days. In some embodiments, the loading dose is about 16 mg of the crystalline anhydrous form of the Compound of Formula (I) once a day for seven days. In some embodiments, the loading dose is about 17 mg of the crystalline anhydrous form of the Compound of Formula (I) once a day for seven days. In some embodiments, the loading dose is about 18 mg of the crystalline anhydrous form of the Compound of Formula (I) once a day for seven days. In some embodiments, the loading dose is about 19 mg of the crystalline anhydrous form of the Compound of Formula (I) once a day for seven days. In some embodiments, the loading dose is about 20 mg of the crystalline anhydrous form of the Compound of Formula (I) once a day for seven days. In some embodiments, the loading dose is about 22 mg of the crystalline anhydrous form of the Compound of Formula (I) once a day for seven days. In some embodiments, the loading dose is about 24 mg of the crystalline anhydrous form of the Compound of Formula (I) once a day for seven days. In some embodiments, the loading dose is about 26 mg of the crystalline anhydrous form of the Compound of Formula (I) once a day for seven days. In some embodiments, the loading dose is about 28 mg of the crystalline anhydrous form of the Compound of Formula (I) once a day for seven days. In some embodiments, the loading dose is about 30 mg of the crystalline anhydrous form of the Compound of Formula (I) once a day for seven days. In some embodiments, the loading dose is about 32 mg of the crystalline anhydrous form of the Compound of Formula (I) once a day for seven days. In some embodiments, the loading dose is about 34 mg of the crystalline anhydrous form of the Compound of Formula (I) once a day for seven days. In some embodiments, the loading dose is about 36 mg of the crystalline anhydrous form of the Compound of Formula (I) once a day for seven days. In some embodiments, the loading dose is about 38 mg of the crystalline anhydrous form of the Compound of Formula (I) once a day for seven days. In some embodiments, the loading dose is about 40 mg of the crystalline anhydrous form of the Compound of Formula (I) once a day for seven days. In some embodiments, the loading dose is about 42 mg of the crystalline anhydrous form of the Compound of Formula (I) once a day for seven days. In some embodiments, the loading dose is about 44 mg of the crystalline anhydrous form of the Compound of Formula (I) once a day for seven days. In some embodiments, the loading dose is about 46 mg of the crystalline anhydrous form of the Compound of Formula (I) once a day for seven days. In some embodiments, the loading dose is about 48 mg of the crystalline anhydrous form of the Compound of Formula (I) once a day for seven days. In some embodiments, the loading dose is about 50 mg of the crystalline anhydrous form of the Compound of Formula (I) once a day for seven days.

In some embodiments, the loading dose is about 2 mg to about 100 mg of the crystalline anhydrous form of the Compound of Formula (I) once a day for eight days. In some embodiments, the loading dose is about 5 mg to about 90 mg of the crystalline anhydrous form of the Compound of Formula (I) once a day for eight days. In some embodiments, the loading dose is about 10 mg to about 80 mg of the crystalline anhydrous form of the Compound of Formula (I) once a day for eight days. In some embodiments, the loading dose is about 10 mg to about 70 mg of the crystalline anhydrous form of the Compound of Formula (I) once a day for eight days. In some embodiments, the loading dose is about 10 mg to about 60 mg of the crystalline anhydrous form of the Compound of Formula (I) once a day for eight days. In some embodiments, the loading dose is about 10 mg to about 50 mg of the crystalline anhydrous form of the Compound of Formula (I) once a day for eight days. In some embodiments, the loading dose is about 10 mg to about 40 mg of the crystalline anhydrous form of the Compound of Formula (I) once a day for eight days. In some embodiments, the loading dose is about 10 mg to about 30 mg of the crystalline anhydrous form of the Compound of Formula (I) once a day for eight days. In some embodiments, the loading dose is about 10 mg to about 20 mg of the crystalline anhydrous form of the Compound of Formula (I) once a day for eight days. In some embodiments, the loading dose is about 2 mg of the crystalline anhydrous form of the Compound of Formula (I) once a day for eight days. In some embodiments, the loading dose is about 3 mg of the crystalline anhydrous form of the Compound of Formula (I) once a day for eight days. In some embodiments, the loading dose is about 4 mg of the crystalline anhydrous form of the Compound of Formula (I) once a day for eight days. In some embodiments, the loading dose is about 5 mg of the crystalline anhydrous form of the Compound of Formula (I) once a day for eight days. In some embodiments, the loading dose is about 10 mg of the crystalline anhydrous form of the Compound of Formula (I) once a day for eight days. In some embodiments, the loading dose is about 11 mg of the crystalline anhydrous form of the Compound of Formula (I) once a day for eight days. In some embodiments, the loading dose is about 12 mg of the crystalline anhydrous form of the Compound of Formula (I) once a day for eight days. In some embodiments, the loading dose is about 13 mg of the crystalline anhydrous form of the Compound of Formula (I) once a day for eight days. In some embodiments, the loading dose is about 14 mg of the crystalline anhydrous form of the Compound of Formula (I) once a day for eight days. In some embodiments, the loading dose is about 15 mg of the crystalline anhydrous form of the Compound of Formula (I) once a day for eight days. In some embodiments, the loading dose is about 16 mg of the crystalline anhydrous form of the Compound of Formula (I) once a day for eight days. In some embodiments, the loading dose is about 17 mg of the crystalline anhydrous form of the Compound of Formula (I) once a day for eight days. In some embodiments, the loading dose is about 18 mg of the crystalline anhydrous form of the Compound of Formula (I) once a day for eight days. In some embodiments, the loading dose is about 19 mg of the crystalline anhydrous form of the Compound of Formula (I) once a day for eight days. In some embodiments, the loading dose is about 20 mg of the crystalline anhydrous form of the Compound of Formula (I) once a day for eight days. In some embodiments, the loading dose is about 22 mg of the crystalline anhydrous form of the Compound of Formula (I) once a day for eight days. In some embodiments, the loading dose is about 24 mg of the crystalline anhydrous form of the Compound of Formula (I) once a day for eight days. In some embodiments, the loading dose is about 26 mg of the crystalline anhydrous form of the Compound of Formula (I) once a day for eight days. In some embodiments, the loading dose is about 28 mg of the crystalline anhydrous form of the Compound of Formula (I) once a day for eight days. In some embodiments, the loading dose is about 30 mg of the crystalline anhydrous form of the Compound of Formula (I) once a day for eight days. In some embodiments, the loading dose is about 32 mg of the crystalline anhydrous form of the Compound of Formula (I) once a day for eight days. In some embodiments, the loading dose is about 34 mg of the crystalline anhydrous form of the Compound of Formula (I)

once a day for eight days. In some embodiments, the loading dose is about 36 mg of the crystalline anhydrous form of the Compound of Formula (I) once a day for eight days. In some embodiments, the loading dose is about 38 mg of the crystalline anhydrous form of the Compound of Formula (I) once a day for eight days. In some embodiments, the loading dose is about 40 mg of the crystalline anhydrous form of the Compound of Formula (I) once a day for eight days. In some embodiments, the loading dose is about 42 mg of the crystalline anhydrous form of the Compound of Formula (I) once a day for eight days. In some embodiments, the loading dose is about 44 mg of the crystalline anhydrous form of the Compound of Formula (I) once a day for eight days. In some embodiments, the loading dose is about 46 mg of the crystalline anhydrous form of the Compound of Formula (I) once a day for eight days. In some embodiments, the loading dose is about 48 mg of the crystalline anhydrous form of the Compound of Formula (I) once a day for eight days. In some embodiments, the loading dose is about 50 mg of the crystalline anhydrous form of the Compound of Formula (I) once a day for eight days.

In some embodiments, the loading dose is about 2 mg to about 100 mg of the crystalline anhydrous form of the Compound of Formula (I) once a day for nine days. In some embodiments, the loading dose is about 5 mg to about 90 mg of the crystalline anhydrous form of the Compound of Formula (I) once a day for nine days. In some embodiments, the loading dose is about 10 mg to about 80 mg of the crystalline anhydrous form of the Compound of Formula (I) once a day for nine days. In some embodiments, the loading dose is about 10 mg to about 70 mg of the crystalline anhydrous form of the Compound of Formula (I) once a day for nine days. In some embodiments, the loading dose is about 10 mg to about 60 mg of the crystalline anhydrous form of the Compound of Formula (I) once a day for nine days. In some embodiments, the loading dose is about 10 mg to about 50 mg of the crystalline anhydrous form of the Compound of Formula (I) once a day for nine days. In some embodiments, the loading dose is about 10 mg to about 40 mg of the crystalline anhydrous form of the Compound of Formula (I) once a day for nine days. In some embodiments, the loading dose is about 10 mg to about 30 mg of the crystalline anhydrous form of the Compound of Formula (I) once a day for nine days. In some embodiments, the loading dose is about 10 mg to about 20 mg of the crystalline anhydrous form of the Compound of Formula (I) once a day for nine days. In some embodiments, the loading dose is about 2 mg of the crystalline anhydrous form of the Compound of Formula (I) once a day for nine days. In some embodiments, the loading dose is about 3 mg of the crystalline anhydrous form of the Compound of Formula (I) once a day for nine days. In some embodiments, the loading dose is about 4 mg of the crystalline anhydrous form of the Compound of Formula (I) once a day for nine days. In some embodiments, the loading dose is about 5 mg of the crystalline anhydrous form of the Compound of Formula (I) once a day for nine days. In some embodiments, the loading dose is about 10 mg of the crystalline anhydrous form of the Compound of Formula (I) once a day for nine days. In some embodiments, the loading dose is about 11 mg of the crystalline anhydrous form of the Compound of Formula (I) once a day for nine days. In some embodiments, the loading dose is about 12 mg of the crystalline anhydrous form of the Compound of Formula (I) once a day for nine days. In some embodiments, the loading dose is about 13 mg of the crystalline anhydrous form of the Compound of Formula (I) once a day for nine days. In some embodiments, the loading dose is about 14 mg of the crystalline anhydrous form of the Compound of Formula (I) once a day for nine days. In some embodiments, the loading dose is about 15 mg of the crystalline anhydrous form of the Compound of Formula (I) once a day for nine days. In some embodiments, the loading dose is about 16 mg of the crystalline anhydrous form of the Compound of Formula (I) once a day for nine days. In some embodiments, the loading dose is about 17 mg of the crystalline anhydrous form of the Compound of Formula (I) once a day for nine days. In some embodiments, the loading dose is about 18 mg of the crystalline anhydrous form of the Compound of Formula (I) once a day for nine days. In some embodiments, the loading dose is about 19 mg of the crystalline anhydrous form of the Compound of Formula (I) once a day for nine days. In some embodiments, the loading dose is about 20 mg of the crystalline anhydrous form of the Compound of Formula (I) once a day for nine days. In some embodiments, the loading dose is about 22 mg of the crystalline anhydrous form of the Compound of Formula (I) once a day for nine days. In some embodiments, the loading dose is about 24 mg of the crystalline anhydrous form of the Compound of Formula (I) once a day for nine days. In some embodiments, the loading dose is about 26 mg of the crystalline anhydrous form of the Compound of Formula (I) once a day for nine days. In some embodiments, the loading dose is about 28 mg of the crystalline anhydrous form of the Compound of Formula (I) once a day for nine days. In some embodiments, the loading dose is about 30 mg of the crystalline anhydrous form of the Compound of Formula (I) once a day for nine days. In some embodiments, the loading dose is about 32 mg of the crystalline anhydrous form of the Compound of Formula (I) once a day for nine days. In some embodiments, the loading dose is about 34 mg of the crystalline anhydrous form of the Compound of Formula (I) once a day for nine days. In some embodiments, the loading dose is about 36 mg of the crystalline anhydrous form of the Compound of Formula (I) once a day for nine days. In some embodiments, the loading dose is about 38 mg of the crystalline anhydrous form of the Compound of Formula (I) once a day for nine days. In some embodiments, the loading dose is about 40 mg of the crystalline anhydrous form of the Compound of Formula (I) once a day for nine days. In some embodiments, the loading dose is about 42 mg of the crystalline anhydrous form of the Compound of Formula (I) once a day for nine days. In some embodiments, the loading dose is about 44 mg of the crystalline anhydrous form of the Compound of Formula (I) once a day for nine days. In some embodiments, the loading dose is about 46 mg of the crystalline anhydrous form of the Compound of Formula (I) once a day for nine days. In some embodiments, the loading dose is about 48 mg of the crystalline anhydrous form of the Compound of Formula (I) once a day for nine days. In some embodiments, the loading dose is about 50 mg of the crystalline anhydrous form of the Compound of Formula (I) once a day for nine days.

In some embodiments, the loading dose is about 2 mg to about 100 mg of the crystalline anhydrous form of the Compound of Formula (I) once a day for ten days. In some embodiments, the loading dose is about 5 mg to about 90 mg of the crystalline anhydrous form of the Compound of Formula (I) once a day for ten days. In some embodiments, the loading dose is about 10 mg to about 80 mg of the crystalline anhydrous form of the Compound of Formula (I) once a day for ten days. In some embodiments, the loading dose is about 10 mg to about 70 mg of the crystalline anhydrous form of the Compound of Formula (I) once a day for ten days. In some embodiments, the loading dose is about 10 mg to about 60 mg of the crystalline anhydrous form of the Compound of Formula (I) once a day for ten days. In some embodiments, the loading dose is about 10 mg to about 50 mg of the crystalline anhydrous form of the Compound of Formula (I) once a day for ten days. In some embodiments, the loading dose is about 10 mg to about 40 mg of the crystalline anhydrous form of the Compound of Formula (I) once a day for ten days. In some embodiments, the loading dose is about 10 mg to about 30 mg of the crystalline anhydrous form of the Compound of Formula (I) once a day for ten days. In some embodiments, the loading dose is about 10 mg to about 20 mg of the crystalline anhydrous form of the Compound of Formula (I) once a day for ten days. In some embodiments, the loading dose is about 2 mg of the crystalline anhydrous form of the Compound of Formula (I) once a day for ten days. In some embodiments, the loading dose is about 3 mg of the crystalline anhydrous form of the Compound of Formula (I) once a day for ten days. In some embodiments, the loading dose is about 4 mg of the crystalline anhydrous form of the Compound of Formula (I) once a day for ten days. In some embodiments, the loading dose is about 5 mg of the crystalline anhydrous form of the Compound of Formula (I) once a day for ten days. In some embodiments, the loading dose is about 10 mg of the crystalline anhydrous form of the Compound of Formula (I) once a day for ten days. In some embodiments, the loading dose is about 11 mg of the crystalline anhydrous form of the Compound of Formula (I) once a day for ten days. In some embodiments, the loading dose is about 12 mg of the crystalline anhydrous form of the Compound of Formula (I) once a day for ten days. In some embodiments, the loading dose is about 13 mg of the crystalline anhydrous form of the Compound of Formula (I) once a day for ten days. In some embodiments, the loading dose is about 14 mg of the crystalline anhydrous form of the Compound of Formula (I) once a day for ten days. In some embodiments, the loading dose is about 15 mg of the crystalline anhydrous form of the Compound of Formula (I) once a day for ten days. In some embodiments, the loading dose is about 16 mg of the crystalline anhydrous form of the Compound of Formula (I) once a day for ten days. In some embodiments, the loading dose is about 17 mg of the crystalline anhydrous form of the Compound of Formula (I) once a day for ten days. In some embodiments, the loading dose is about 18 mg of the crystalline anhydrous form of the Compound of Formula (I) once a day for ten days. In some embodiments, the loading dose is about 19 mg of the crystalline anhydrous form of the Compound of Formula (I) once a day for ten days. In some embodiments, the loading dose is about 20 mg of the crystalline anhydrous form of the Compound of Formula (I) once a day for ten days. In some embodiments, the loading dose is about 22 mg of the crystalline anhydrous form of the Compound of Formula (I) once a day for ten days. In some embodiments, the loading dose is about 24 mg of the crystalline anhydrous form of the Compound of Formula (I) once a day for ten days. In some embodiments, the loading dose is about 26 mg of the crystalline anhydrous form of the Compound of Formula (I) once a day for ten days. In some embodiments, the loading dose is about 28 mg of the crystalline anhydrous form of the Compound of Formula (I) once a day for ten days. In some embodiments, the loading dose is about 30 mg of the crystalline anhydrous form of the Compound of Formula (I) once a day for ten days. In some embodiments, the loading dose is about 32 mg of the crystalline anhydrous form of the Compound of Formula (I) once a day for ten days. In some embodiments, the loading dose is about 34 mg of the crystalline anhydrous form of the Compound of Formula (I) once a day for ten days. In some embodiments, the loading dose is about 36 mg of the crystalline anhydrous form of the Compound of Formula (I) once a day for ten days. In some embodiments, the loading dose is about 38 mg of the crystalline anhydrous form of the Compound of Formula (I) once a day for ten days. In some embodiments, the loading dose is about 40 mg of the crystalline anhydrous form of the Compound of Formula (I) once a day for ten days. In some embodiments, the loading dose is about 42 mg of the crystalline anhydrous form of the Compound of Formula (I) once a day for ten days. In some embodiments, the loading dose is about 44 mg of the crystalline anhydrous form of the Compound of Formula (I) once a day for ten days. In some embodiments, the loading dose is about 46 mg of the crystalline anhydrous form of the Compound of Formula (I) once a day for ten days. In some embodiments, the loading dose is about 48 mg of the crystalline anhydrous form of the Compound of Formula (I) once a day for ten days. In some embodiments, the loading dose is about 50 mg of the crystalline anhydrous form of the Compound of Formula (I) once a day for ten days.

In some embodiments, the loading dose is about 2 mg to about 100 mg of the crystalline anhydrous form of the Compound of Formula (I) once a week. In some embodiments, the loading dose is about 5 mg to about 90 mg of the crystalline anhydrous form of the Compound of Formula (I) once a week. In some embodiments, the loading dose is about 10 mg to about 80 mg of the crystalline anhydrous form of the Compound of Formula (I) once a week. In some embodiments, the loading dose is about 10 mg to about 70 mg of the crystalline anhydrous form of the Compound of Formula (I) once a week. In some embodiments, the loading dose is about 10 mg to about 60 mg of the crystalline anhydrous form of the Compound of Formula (I) once a week. In some embodiments, the loading dose is about 10 mg to about 50 mg of the crystalline anhydrous form of the Compound of Formula (I) once a week. In some embodiments, the loading dose is about 10 mg to about 40 mg of the crystalline anhydrous form of the Compound of Formula (I) once a week. In some embodiments, the loading dose is about 10 mg to about 30 mg of the crystalline anhydrous form of the Compound of Formula (I) once a week. In some embodiments, the loading dose is about 10 mg to about 20 mg of the crystalline anhydrous form of the Compound of Formula (I) once a week. In some embodiments, the loading dose is about 2 mg of the crystalline anhydrous form of the Compound of Formula (I) once a week. In some embodiments, the loading dose is about 3 mg of the crystalline anhydrous form of the Compound of Formula (I) once a week. In some embodiments, the loading dose is about 4 mg of the crystalline anhydrous form of the Compound of Formula (I) once a week. In some embodiments, the loading dose is about 5 mg of the crystalline anhydrous form of the Compound of Formula (I) once a week. In some embodiments, the loading dose is about 10 mg of the crystalline anhydrous form of the Compound of Formula (I) once a week. In some embodiments, the loading dose is about 11 mg of the crystalline anhydrous form of the Compound of Formula (I) once a week. In some embodiments, the loading dose is about 12 mg of the crystalline anhydrous form of the Compound of Formula (I) once a week. In some embodiments, the loading dose is about 13 mg of the crystalline anhydrous form of the Compound of Formula (I) once a week. In some embodiments, the loading dose is about 14 mg of the crystalline anhydrous form of the Compound of Formula (I) once a week. In some embodiments, the loading dose is about 15 mg of the crystalline anhydrous form of the Compound of Formula (I) once a week. In some embodiments, the loading dose is about 16 mg of the crystalline anhydrous form of the Compound of Formula (I) once a week. In some embodiments, the loading dose is about 17 mg of the crystalline anhydrous form of the Compound of Formula (I) once a week. In some embodiments, the loading dose is about 18 mg of the crystalline anhydrous form of the Compound of Formula (I) once a week. In some embodiments, the loading dose is about 19 mg of the crystalline anhydrous form of the Compound of Formula (I) once a week. In some embodiments, the loading dose is about 20 mg of the crystalline anhydrous form of the Compound of Formula (I) once a week. In some embodiments, the loading dose is about 22 mg of the crystalline anhydrous form of the Compound of Formula (I) once a week. In some embodiments, the loading dose is about 24 mg of the crystalline anhydrous form of the Compound of Formula (I) once a week. In some embodiments, the loading dose is about 26 mg of the crystalline anhydrous form of the Compound of Formula (I) once a week. In some embodiments, the loading dose is about 28 mg of the crystalline anhydrous form of the Compound of Formula (I) once a week. In some embodiments, the loading dose is about 30 mg of the crystalline anhydrous form of the Compound of Formula (I) once a week. In some embodiments, the loading dose is about 32 mg of the crystalline anhydrous form of the Compound of Formula (I) once a week. In some embodiments, the loading dose is about 34 mg of the crystalline anhydrous form of the Compound of Formula (I) once a week. In some embodiments, the loading dose is about 36 mg of the crystalline anhydrous form of the Compound of Formula (I) once a week. In some embodiments, the loading dose is about 38 mg of the crystalline anhydrous form of the Compound of Formula (I) once a week. In some embodiments, the loading dose is about 40 mg of the crystalline anhydrous form of the Compound of Formula (I) once a week. In some embodiments, the loading dose is about 42 mg of the crystalline anhydrous form of the Compound of Formula (I) once a week. In some embodiments, the loading dose is about 44 mg of the crystalline anhydrous form of the Compound of Formula (I) once a week. In some embodiments, the loading dose is about 46 mg of the crystalline anhydrous form of the Compound of Formula (I) once a week. In some embodiments, the loading dose is about 48 mg of the crystalline anhydrous form of the Compound of Formula (I) once a week. In some embodiments, the loading dose is about 50 mg of the crystalline anhydrous form of the Compound of Formula (I) once a week.

In some embodiments, the loading dose is about 2 mg to about 100 mg of the crystalline anhydrous form of the Compound of Formula (I) twice a week. In some embodiments, the loading dose is about 5 mg to about 90 mg of the crystalline anhydrous form of the Compound of Formula (I) twice a week. In some embodiments, the loading dose is about 10 mg to about 80 mg of the crystalline anhydrous form of the Compound of Formula (I) twice a week. In some embodiments, the loading dose is about 10 mg to about 70 mg of the crystalline anhydrous form of the Compound of Formula (I) twice a week. In some embodiments, the loading dose is about 10 mg to about 60 mg of the crystalline anhydrous form of the Compound of Formula (I) twice a week. In some embodiments, the loading dose is about 10 mg to about 50 mg of the crystalline anhydrous form of the Compound of Formula (I) twice a week. In some embodiments, the loading dose is about 10 mg to about 40 mg of the crystalline anhydrous form of the Compound of Formula (I) twice a week. In some embodiments, the loading dose is about 10 mg to about 30 mg of the crystalline anhydrous form of the Compound of Formula (I) twice a week. In some embodiments, the loading dose is about 10 mg to about 20 mg of the crystalline anhydrous form of the Compound of Formula (I) twice a week. In some embodiments, the loading dose is about 2 mg of the crystalline anhydrous form of the Compound of Formula (I) twice a week. In some embodiments, the loading dose is about 3 mg of the crystalline anhydrous form of the Compound of Formula (I) twice a week. In some embodiments, the loading dose is about 4 mg of the crystalline anhydrous form of the Compound of Formula (I) twice a week. In some embodiments, the loading dose is about 5 mg of the crystalline anhydrous form of the Compound of Formula (I) twice a week. In some embodiments, the loading dose is about 10 mg of the crystalline anhydrous form of the Compound of Formula (I) twice a week. In some embodiments, the loading dose is about 11 mg of the crystalline anhydrous form of the Compound of Formula (I) twice a week. In some embodiments, the loading dose is about 12 mg of the crystalline anhydrous form of the Compound of Formula (I) twice a week. In some embodiments, the loading dose is about 13 mg of the crystalline anhydrous form of the Compound of Formula (I) twice a week. In some embodiments, the loading dose is about 14 mg of the crystalline anhydrous form of the Compound of Formula (I) twice a week. In some embodiments, the loading dose is about 15 mg of the crystalline anhydrous form of the Compound of Formula (I) twice a week. In some embodiments, the loading dose is about 16 mg of the crystalline anhydrous form of the Compound of Formula (I) twice a week. In some embodiments, the loading dose is about 17 mg of the crystalline anhydrous form of the Compound of Formula (I) twice a week. In some embodiments, the loading dose is about 18 mg of the crystalline anhydrous form of the Compound of Formula (I) twice a week. In some embodiments, the loading dose is about 19 mg of the crystalline anhydrous form of the Compound of Formula (I) twice a week. In some embodiments, the loading dose is about 20 mg of the crystalline anhydrous form of the Compound of Formula (I) twice a week. In some embodiments, the loading dose is about 22 mg of the crystalline anhydrous form of the Compound of Formula (I) twice a week. In some embodiments, the loading dose is about 24 mg of the crystalline anhydrous form of the Compound of Formula (I) twice a week. In some embodiments, the loading dose is about 26 mg of the crystalline anhydrous form of the Compound of Formula (I) twice a week. In some embodiments, the loading dose is about 28 mg of the crystalline anhydrous form of the Compound of Formula (I) twice a week. In some embodiments, the loading dose is about 30 mg of the crystalline anhydrous form of the Compound of Formula (I) twice a week. In some embodiments, the loading dose is about 32 mg of the crystalline anhydrous form of the Compound of Formula (I) twice a week. In some embodiments, the loading dose is about 34 mg of the crystalline anhydrous form of the Compound of Formula (I) twice a week. In some embodiments, the loading dose is about 36 mg of the crystalline anhydrous form of the Compound of Formula (I) twice a week. In some embodiments, the loading dose is about 38 mg of the crystalline anhydrous form of the Compound of Formula (I) twice a week. In some embodiments, the loading dose is about 40 mg of the crystalline anhydrous form of the Compound of Formula (I) twice a week. In some embodiments, the loading dose is about 42 mg of the crystalline anhydrous form of the Compound of Formula (I) twice a week. In some embodiments, the loading dose is about 44 mg of the crystalline anhydrous form of the Compound of Formula (I) twice a week. In some embodiments, the loading dose is about 46 mg of the crystalline anhydrous form of the Compound of Formula (I) twice a week. In some embodiments, the loading dose is about 48 mg of the crystalline anhydrous form of the Compound of Formula (I) twice a week. In some embodiments, the loading dose is about 50 mg of the crystalline anhydrous form of the Compound of Formula (I) twice a week.

In some embodiments, the loading dose is about 2 mg to about 100 mg of the crystalline anhydrous form of the Compound of Formula (I) three times a week. In some embodiments, the loading dose is about 5 mg to about 90 mg of the crystalline anhydrous form of the Compound of Formula (I) three times a week. In some embodiments, the loading dose is about 10 mg to about 80 mg of the crystalline anhydrous form of the Compound of Formula (I) three times a week. In some embodiments, the loading dose is about 10 mg to about 70 mg of the crystalline anhydrous form of the Compound of Formula (I) three times a week. In some embodiments, the loading dose is about 10 mg to about 60 mg of the crystalline anhydrous form of the Compound of Formula (I) three times a week. In some embodiments, the loading dose is about 10 mg to about 50 mg of the crystalline anhydrous form of the Compound of Formula (I) three times a week. In some embodiments, the loading dose is about 10 mg to about 40 mg of the crystalline anhydrous form of the Compound of Formula (I) three times a week. In some embodiments, the loading dose is about 10 mg to about 30 mg of the crystalline anhydrous form of the Compound of Formula (I) three times a week. In some embodiments, the loading dose is about 10 mg to about 20 mg of the crystalline anhydrous form of the Compound of Formula (I) three times a week. In some embodiments, the loading dose is about 2 mg of the crystalline anhydrous form of the Compound of Formula (I) three times a week. In some embodiments, the loading dose is about 3 mg of the crystalline anhydrous form of the Compound of Formula (I) three times a week. In some embodiments, the loading dose is about 4 mg of the crystalline anhydrous form of the Compound of Formula (I) three times a week. In some embodiments, the loading dose is about 5 mg of the crystalline anhydrous form of the Compound of Formula (I) three times a week. In some embodiments, the loading dose is about 10 mg of the crystalline anhydrous form of the Compound of Formula (I) three times a week. In some embodiments, the loading dose is about 11 mg of the crystalline anhydrous form of the Compound of Formula (I) three times a week. In some embodiments, the loading dose is about 12 mg of the crystalline anhydrous form of the Compound of Formula (I) three times a week. In some embodiments, the loading dose is about 13 mg of the crystalline anhydrous form of the Compound of Formula (I) three times a week. In some embodiments, the loading dose is about 14 mg of the crystalline anhydrous form of the Compound of Formula (I) three times a week. In some embodiments, the loading dose is about 15 mg of the crystalline anhydrous form of the Compound of Formula (I) three times a week. In some embodiments, the loading dose is about 16 mg of the crystalline anhydrous form of the Compound of Formula (I) three times a week. In some embodiments, the loading dose is about 17 mg of the crystalline anhydrous form of the Compound of Formula (I) three times a week. In some embodiments, the loading dose is about 18 mg of the crystalline anhydrous form of the Compound of Formula (I) three times a week. In some embodiments, the loading dose is about 19 mg of the crystalline anhydrous form of the Compound of Formula (I) three times a week. In some embodiments, the loading dose is about 20 mg of the crystalline anhydrous form of the Compound of Formula (I) three times a week. In some embodiments, the loading dose is about 22 mg of the crystalline anhydrous form of the Compound of Formula (I) three times a week. In some embodiments, the loading dose is about 24 mg of the crystalline anhydrous form of the Compound of Formula (I) three times a week. In some embodiments, the loading dose is about 26 mg of the crystalline anhydrous form of the Compound of Formula (I) three times a week. In some embodiments, the loading dose is about 28 mg of the crystalline anhydrous form of the Compound of Formula (I) three times a week. In some embodiments, the loading dose is about 30 mg of the crystalline anhydrous form of the Compound of Formula (I) three times a week. In some embodiments, the loading dose is about 32 mg of the crystalline anhydrous form of the Compound of Formula (I) three times a week. In some embodiments, the loading dose is about 34 mg of the crystalline anhydrous form of the Compound of Formula (I) three times a week. In some embodiments, the loading dose is about 36 mg of the crystalline anhydrous form of the Compound of Formula (I) three times a week. In some embodiments, the loading dose is about 38 mg of the crystalline anhydrous form of the Compound of Formula (I) three times a week. In some embodiments, the loading dose is about 40 mg of the crystalline anhydrous form of the Compound of Formula (I) three times a week. In some embodiments, the loading dose is about 42 mg of the crystalline anhydrous form of the Compound of Formula (I) three times a week. In some embodiments, the loading dose is about 44 mg of the crystalline anhydrous form of the Compound of Formula (I) three times a week. In some embodiments, the loading dose is about 46 mg of the crystalline anhydrous form of the Compound of Formula (I) three times a week. In some embodiments, the loading dose is about 48 mg of the crystalline anhydrous form of the Compound of Formula (I) three times a week. In some embodiments, the loading dose is about 50 mg of the crystalline anhydrous form of the Compound of Formula (I) three times a week.

In some embodiments, administering a maintenance dose may include administering about 2 mg to about 150 mg of the crystalline anhydrous form of the compound of Formula (I) daily to a patient in need thereof. In some embodiments, the maintenance dose is about 2 mg to about 100 mg of the crystalline anhydrous form of the Compound of Formula (I) daily. In some embodiments, the maintenance dose is about 5 mg to about 90 mg of the crystalline anhydrous form of the Compound of Formula (I) daily. In some embodiments, the maintenance dose is about 10 mg to about 80 mg of the crystalline anhydrous form of the Compound of Formula (I) daily. In some embodiments, the maintenance dose is about 10 mg to about 70 mg of the crystalline anhydrous form of the Compound of Formula (I) daily. In some embodiments, the maintenance dose is about 10 mg to about 60 mg of the crystalline anhydrous form of the Compound of Formula (I) daily. In some embodiments, the maintenance dose is about 10 mg to about 50 mg of the crystalline anhydrous form of the Compound of Formula (I) daily. In some embodiments, the maintenance dose is about 10 mg to about 40 mg of the crystalline anhydrous form of the Compound of Formula (I) daily. In some embodiments, the maintenance dose is about 10 mg to about 30 mg of the crystalline anhydrous form of the Compound of Formula (I) daily. In some embodiments, the maintenance dose is about 10 mg to about 20 mg of the crystalline anhydrous form of the Compound of Formula (I) daily. In some embodiments, the maintenance dose is about 2 mg of the crystalline anhydrous form of the Compound of Formula (I) daily. In some embodiments, the maintenance dose is about 3 mg of the crystalline anhydrous form of the Compound of Formula (I) daily. In some embodiments, the maintenance dose is about 4 mg of the crystalline anhydrous form of the Compound of Formula (I) daily. In some embodiments, the maintenance dose is about 5 mg of the crystalline anhydrous form of the Compound of Formula (I) daily. In some embodiments, the maintenance dose is about 6 mg of the crystalline anhydrous form of the Compound of Formula (I) daily. In some embodiments, the maintenance dose is about 7 mg of the crystalline anhydrous form of the Compound of Formula (I) daily. In some embodiments, the maintenance dose is about 8 mg of the crystalline anhydrous form of the Compound of Formula (I) daily. In some embodiments, the maintenance dose is about 9 mg of the crystalline anhydrous form of the Compound of Formula (I) daily. In some embodiments, the maintenance dose is about 10 mg of the crystalline anhydrous form of the Compound of Formula (I) daily. In some embodiments, the maintenance dose is about 11 mg of the crystalline anhydrous form of the Compound of Formula (I) daily. In some embodiments, the maintenance dose is about 12 mg of the crystalline anhydrous form of the Compound of Formula (I) daily. In some embodiments, the maintenance dose is about 13 mg of the crystalline anhydrous form of the Compound of Formula (I) daily. In some embodiments, the maintenance dose is about 14 mg of the crystalline anhydrous form of the Compound of Formula (I) daily. In some embodiments, the maintenance dose is about 15 mg of the crystalline anhydrous form of the Compound of Formula (I) daily. In some embodiments, the maintenance dose is about 16 mg of the crystalline anhydrous form of the Compound of Formula (I) daily. In some embodiments, the maintenance dose is about 17 mg of the crystalline anhydrous form of the Compound of Formula (I) daily. In some embodiments, the maintenance dose is about 18 mg of the crystalline anhydrous form of the Compound of Formula (I) daily. In some embodiments, the maintenance dose is about 19 mg of the crystalline anhydrous form of the Compound of Formula (I) daily. In some embodiments, the maintenance dose is about 20 mg of the crystalline anhydrous form of the Compound of Formula (I) daily. In some embodiments, the maintenance dose is about 22 mg of the crystalline anhydrous form of the Compound of Formula (I) daily. In some embodiments, the maintenance dose is about 24 mg of the crystalline anhydrous form of the Compound of Formula (I) daily. In some embodiments, the maintenance dose is about 26 mg of the crystalline anhydrous form of the Compound of Formula (I) daily. In some embodiments, the maintenance dose is about 28 mg of the crystalline anhydrous form of the Compound of Formula (I) daily. In some embodiments, the maintenance dose is about 30 mg of the crystalline anhydrous form of the Compound of Formula (I) daily. In some embodiments, the maintenance dose is about 32 mg of the crystalline anhydrous form of the Compound of Formula (I) daily. In some embodiments, the maintenance dose is about 34 mg of the crystalline anhydrous form of the Compound of Formula (I) daily. In some embodiments, the maintenance dose is about 36 mg of the crystalline anhydrous form of the Compound of Formula (I) daily. In some embodiments, the maintenance dose is about 38 mg of the crystalline anhydrous form of the Compound of Formula (I) daily. In some embodiments, the maintenance dose is about 40 mg of the crystalline anhydrous form of the Compound of Formula (I) daily. In some embodiments, the maintenance dose is about 42 mg of the crystalline anhydrous form of the Compound of Formula (I) daily. In some embodiments, the maintenance dose is about 44 mg of the crystalline anhydrous form of the Compound of Formula (I) daily. In some embodiments, the maintenance dose is about 46 mg of the crystalline anhydrous form of the Compound of Formula (I) daily. In some embodiments, the maintenance dose is about 48 mg of the crystalline anhydrous form of the Compound of Formula (I) daily. In some embodiments, the maintenance dose is about 50 mg of the crystalline anhydrous form of the Compound of Formula (I) daily.

In some embodiments, administering a maintenance dose may include administering about 2 mg to about 150 mg of the crystalline anhydrous form of the compound of Formula (I) once a week to a patient in need thereof. In some embodiments, the maintenance dose is about 2 mg to about 100 mg of the crystalline anhydrous form of the Compound of Formula (I) once a week. In some embodiments, the maintenance dose is about 5 mg to about 90 mg of the crystalline anhydrous form of the Compound of Formula (I) once a week. In some embodiments, the maintenance dose is about 10 mg to about 80 mg of the crystalline anhydrous form of the Compound of Formula (I) once a week. In some embodiments, the maintenance dose is about 10 mg to about 70 mg of the crystalline anhydrous form of the Compound of Formula (I) once a week. In some embodiments, the maintenance dose is about 10 mg to about 60 mg of the crystalline anhydrous form of the Compound of Formula (I) once a week. In some embodiments, the maintenance dose is about 10 mg to about 50 mg of the crystalline anhydrous form of the Compound of Formula (I) once a week. In some embodiments, the maintenance dose is about 10 mg to about 40 mg of the crystalline anhydrous form of the Compound of Formula (I) once a week. In some embodiments, the maintenance dose is about 10 mg to about 30 mg of the crystalline anhydrous form of the Compound of Formula (I) once a week. In some embodiments, the maintenance dose is about 10 mg to about 20 mg of the crystalline anhydrous form of the Compound of Formula (I) once a week. In some embodiments, the maintenance dose is about 2 mg of the crystalline anhydrous form of the Compound of Formula (I) once a week. In some embodiments, the maintenance dose is about 3 mg of the crystalline anhydrous form of the Compound of Formula (I) once a week. In some embodiments, the maintenance dose is about 4 mg of the crystalline anhydrous form of the Compound of Formula (I) once a week. In some embodiments, the maintenance dose is about 5 mg of the crystalline anhydrous form of the Compound of Formula (I) once a week. In some embodiments, the maintenance dose is about 6 mg of the crystalline anhydrous form of the Compound of Formula (I) once a week. In some embodiments, the maintenance dose is about 7 mg of the crystalline anhydrous form of the Compound of Formula (I) once a week. In some embodiments, the maintenance dose is about 8 mg of the crystalline anhydrous form of the Compound of Formula (I) once a week. In some embodiments, the maintenance dose is about 9 mg of the crystalline anhydrous form of the Compound of Formula (I) once a week. In some embodiments, the maintenance dose is about 10 mg of the crystalline anhydrous form of the Compound of Formula (I) once a week. In some embodiments, the maintenance dose is about 11 mg of the crystalline anhydrous form of the Compound of Formula (I) once a week. In some embodiments, the maintenance dose is about 12 mg of the crystalline anhydrous form of the Compound of Formula (I) once a week. In some embodiments, the maintenance dose is about 13 mg of the crystalline anhydrous form of the Compound of Formula (I) once a week. In some embodiments, the maintenance dose is about 14 mg of the crystalline anhydrous form of the Compound of Formula (I) once a week. In some embodiments, the maintenance dose is about 15 mg of the crystalline anhydrous form of the Compound of Formula (I) once a week. In some embodiments, the maintenance dose is about 16 mg of the crystalline anhydrous form of the Compound of Formula (I) once a week. In some embodiments, the maintenance dose is about 17 mg of the crystalline anhydrous form of the Compound of Formula (I) once a week. In some embodiments, the maintenance dose is about 18 mg of the crystalline anhydrous form of the Compound of Formula (I) once a week. In some embodiments, the maintenance dose is about 19 mg of the crystalline anhydrous form of the Compound of Formula (I) once a week. In some embodiments, the maintenance dose is about 20 mg of the crystalline anhydrous form of the Compound of Formula (I) once a week. In some embodiments, the maintenance dose is about 22 mg of the crystalline anhydrous form of the Compound of Formula (I) once a week. In some embodiments, the maintenance dose is about 24 mg of the crystalline anhydrous form of the Compound of Formula (I) once a week. In some embodiments, the maintenance dose is about 26 mg of the crystalline anhydrous form of the Compound of Formula (I) once a week. In some embodiments, the maintenance dose is about 28 mg of the crystalline anhydrous form of the Compound of Formula (I) once a week. In some embodiments, the maintenance dose is about 30 mg of the crystalline anhydrous form of the Compound of Formula (I) once a week. In some embodiments, the maintenance dose is about 32 mg of the crystalline anhydrous form of the Compound of Formula (I) once a week. In some embodiments, the maintenance dose is about 34 mg of the crystalline anhydrous form of the Compound of Formula (I) once a week. In some embodiments, the maintenance dose is about 36 mg of the crystalline anhydrous form of the Compound of Formula (I) once a week. In some embodiments, the maintenance dose is about 38 mg of the crystalline anhydrous form of the Compound of Formula (I) once a week. In some embodiments, the maintenance dose is about 40 mg of the crystalline anhydrous form of the Compound of Formula (I) once a week. In some embodiments, the maintenance dose is about 42 mg of the crystalline anhydrous form of the Compound of Formula (I) once a week. In some embodiments, the maintenance dose is about 44 mg of the crystalline anhydrous form of the Compound of Formula (I) once a week. In some embodiments, the maintenance dose is about 46 mg of the crystalline anhydrous form of the Compound of Formula (I) once a week. In some embodiments, the maintenance dose is about 48 mg of the crystalline anhydrous form of the Compound of Formula (I) once a week. In some embodiments, the maintenance dose is about 50 mg of the crystalline anhydrous form of the Compound of Formula (I) once a week.

In some embodiments, administering a maintenance dose may include administering about 2 mg to about 150 mg of the crystalline anhydrous form of the compound of Formula (I) twice a week to a patient in need thereof. In some embodiments, the maintenance dose is about 2 mg to about 100 mg of the crystalline anhydrous form of the Compound of Formula (I) twice a week. In some embodiments, the maintenance dose is about 5 mg to about 90 mg of the crystalline anhydrous form of the Compound of Formula (I) twice a week. In some embodiments, the maintenance dose is about 10 mg to about 80 mg of the crystalline anhydrous form of the Compound of Formula (I) twice a week. In some embodiments, the maintenance dose is about 10 mg to about 70 mg of the crystalline anhydrous form of the Compound of Formula (I) twice a week. In some embodiments, the maintenance dose is about 10 mg to about 60 mg of the crystalline anhydrous form of the Compound of Formula (I) twice a week. In some embodiments, the maintenance dose is about 10 mg to about 50 mg of the crystalline anhydrous form of the Compound of Formula (I) twice a week. In some embodiments, the maintenance dose is about 10 mg to about 40 mg of the crystalline anhydrous form of the Compound of Formula (I) twice a week. In some embodiments, the maintenance dose is about 10 mg to about 30 mg of the crystalline anhydrous form of the Compound of Formula (I) twice a week. In some embodiments, the maintenance dose is about 10 mg to about 20 mg of the crystalline anhydrous form of the Compound of Formula (I) twice a week. In some embodiments, the maintenance dose is about 2 mg of the crystalline anhydrous form of the Compound of Formula (I) twice a week. In some embodiments, the maintenance dose is about 3 mg of the crystalline anhydrous form of the Compound of Formula (I) twice a week. In some embodiments, the maintenance dose is about 4 mg of the crystalline anhydrous form of the Compound of Formula (I) twice a week. In some embodiments, the maintenance dose is about 5 mg of the crystalline anhydrous form of the Compound of Formula (I) twice a week. In some embodiments, the maintenance dose is about 6 mg of the crystalline anhydrous form of the Compound of Formula (I) twice a week. In some embodiments, the maintenance dose is about 7 mg of the crystalline anhydrous form of the Compound of Formula (I) twice a week. In some embodiments, the maintenance dose is about 8 mg of the crystalline anhydrous form of the Compound of Formula (I) twice a week. In some embodiments, the maintenance dose is about 9 mg of the crystalline anhydrous form of the Compound of Formula (I) twice a week. In some embodiments, the maintenance dose is about 10 mg of the crystalline anhydrous form of the Compound of Formula (I) twice a week. In some embodiments, the maintenance dose is about 11 mg of the crystalline anhydrous form of the Compound of Formula (I) twice a week. In some embodiments, the maintenance dose is about 12 mg of the crystalline anhydrous form of the Compound of Formula (I) twice a week. In some embodiments, the maintenance dose is about 13 mg of the crystalline anhydrous form of the Compound of Formula (I) twice a week. In some embodiments, the maintenance dose is about 14 mg of the crystalline anhydrous form of the Compound of Formula (I) twice a week. In some embodiments, the maintenance dose is about 15 mg of the crystalline anhydrous form of the Compound of Formula (I) twice a week. In some embodiments, the maintenance dose is about 16 mg of the crystalline anhydrous form of the Compound of Formula (I) twice a week. In some embodiments, the maintenance dose is about 17 mg of the crystalline anhydrous form of the Compound of Formula (I) twice a week. In some embodiments, the maintenance dose is about 18 mg of the crystalline anhydrous form of the Compound of Formula (I) twice a week. In some embodiments, the maintenance dose is about 19 mg of the crystalline anhydrous form of the Compound of Formula (I) twice a week. In some embodiments, the maintenance dose is about 20 mg of the crystalline anhydrous form of the Compound of Formula (I) twice a week. In some embodiments, the maintenance dose is about 22 mg of the crystalline anhydrous form of the Compound of Formula (I) twice a week. In some embodiments, the maintenance dose is about 24 mg of the crystalline anhydrous form of the Compound of Formula (I) twice a week. In some embodiments, the maintenance dose is about 26 mg of the crystalline anhydrous form of the Compound of Formula (I) twice a week. In some embodiments, the maintenance dose is about 28 mg of the crystalline anhydrous form of the Compound of Formula (I) twice a week. In some embodiments, the maintenance dose is about 30 mg of the crystalline anhydrous form of the Compound of Formula (I) twice a week. In some embodiments, the maintenance dose is about 32 mg of the crystalline anhydrous form of the Compound of Formula (I) twice a week. In some embodiments, the maintenance dose is about 34 mg of the crystalline anhydrous form of the Compound of Formula (I) twice a week. In some embodiments, the maintenance dose is about 36 mg of the crystalline anhydrous form of the Compound of Formula (I) twice a week. In some embodiments, the maintenance dose is about 38 mg of the crystalline anhydrous form of the Compound of Formula (I) twice a week. In some embodiments, the maintenance dose is about 40 mg of the crystalline anhydrous form of the Compound of Formula (I) twice a week. In some embodiments, the maintenance dose is about 42 mg of the crystalline anhydrous form of the Compound of Formula (I) twice a week. In some embodiments, the maintenance dose is about 44 mg of the crystalline anhydrous form of the Compound of Formula (I) twice a week. In some embodiments, the maintenance dose is about 46 mg of the crystalline anhydrous form of the Compound of Formula (I) twice a week. In some embodiments, the maintenance dose is about 48 mg of the crystalline anhydrous form of the Compound of Formula (I) twice a week. In some embodiments, the maintenance dose is about 50 mg of the crystalline anhydrous form of the Compound of Formula (I) twice a week.

In some embodiments, administering a maintenance dose may include administering about 2 mg to about 150 mg of the crystalline anhydrous form of the compound of Formula (I) three times a week to a patient in need thereof. In some embodiments, the maintenance dose is about 2 mg to about 100 mg of the crystalline anhydrous form of the Compound of Formula (I) three times a week. In some embodiments, the maintenance dose is about 5 mg to about 90 mg of the crystalline anhydrous form of the Compound of Formula (I) three times a week. In some embodiments, the maintenance dose is about 10 mg to about 80 mg of the crystalline anhydrous form of the Compound of Formula (I) three times a week. In some embodiments, the maintenance dose is about 10 mg to about 70 mg of the crystalline anhydrous form of the Compound of Formula (I) three times a week.

In some embodiments, the maintenance dose is about 10 mg to about 60 mg of the crystalline anhydrous form of the Compound of Formula (I) three times a week. In some embodiments, the maintenance dose is about 10 mg to about 50 mg of the crystalline anhydrous form of the Compound of Formula (I) three times a week. In some embodiments, the maintenance dose is about 10 mg to about 40 mg of the crystalline anhydrous form of the Compound of Formula (I) three times a week. In some embodiments, the maintenance dose is about 10 mg to about 30 mg of the crystalline anhydrous form of the Compound of Formula (I) three times a week. In some embodiments, the maintenance dose is about 10 mg to about 20 mg of the crystalline anhydrous form of the Compound of Formula (I) three times a week. In some embodiments, the maintenance dose is about 2 mg of the crystalline anhydrous form of the Compound of Formula (I) three times a week. In some embodiments, the maintenance dose is about 3 mg of the crystalline anhydrous form of the Compound of Formula (I) three times a week. In some embodiments, the maintenance dose is about 4 mg of the crystalline anhydrous form of the Compound of Formula (I) three times a week. In some embodiments, the maintenance dose is about 5 mg of the crystalline anhydrous form of the Compound of Formula (I) three times a week. In some embodiments, the maintenance dose is about 6 mg of the crystalline anhydrous form of the Compound of Formula (I) three times a week. In some embodiments, the maintenance dose is about 7 mg of the crystalline anhydrous form of the Compound of Formula (I) three times a week. In some embodiments, the maintenance dose is about 8 mg of the crystalline anhydrous form of the Compound of Formula (I) three times a week. In some embodiments, the maintenance dose is about 9 mg of the crystalline anhydrous form of the Compound of Formula (I) three times a week. In some embodiments, the maintenance dose is about 10 mg of the crystalline anhydrous form of the Compound of Formula (I) three times a week. In some embodiments, the maintenance dose is about 11 mg of the crystalline anhydrous form of the Compound of Formula (I) three times a week. In some embodiments, the maintenance dose is about 12 mg of the crystalline anhydrous form of the Compound of Formula (I) three times a week. In some embodiments, the maintenance dose is about 13 mg of the crystalline anhydrous form of the Compound of Formula (I) three times a week. In some embodiments, the maintenance dose is about 14 mg of the crystalline anhydrous form of the Compound of Formula (I) three times a week. In some embodiments, the maintenance dose is about 15 mg of the crystalline anhydrous form of the Compound of Formula (I) three times a week. In some embodiments, the maintenance dose is about 16 mg of the crystalline anhydrous form of the Compound of Formula (I) three times a week. In some embodiments, the maintenance dose is about 17 mg of the crystalline anhydrous form of the Compound of Formula (I) three times a week. In some embodiments, the maintenance dose is about 18 mg of the crystalline anhydrous form of the Compound of Formula (I) three times a week. In some embodiments, the maintenance dose is about 19 mg of the crystalline anhydrous form of the Compound of Formula (I) three times a week. In some embodiments, the maintenance dose is about 20 mg of the crystalline anhydrous form of the Compound of Formula (I) three times a week. In some embodiments, the maintenance dose is about 22 mg of the crystalline anhydrous form of the Compound of Formula (I) three times a week. In some embodiments, the maintenance dose is about 24 mg of the crystalline anhydrous form of the Compound of Formula (I) three times a week. In some embodiments, the maintenance dose is about 26 mg of the crystalline anhydrous form of the Compound of Formula (I) three times a week. In some embodiments, the maintenance dose is about 28 mg of the crystalline anhydrous form of the Compound of Formula (I) three times a week. In some embodiments, the maintenance dose is about 30 mg of the crystalline anhydrous form of the Compound of Formula (I) three times a week. In some embodiments, the maintenance dose is about 32 mg of the crystalline anhydrous form of the Compound of Formula (I) three times a week. In some embodiments, the maintenance dose is about 34 mg of the crystalline anhydrous form of the Compound of Formula (I) three times a week. In some embodiments, the maintenance dose is about 36 mg of the crystalline anhydrous form of the Compound of Formula (I) three times a week. In some embodiments, the maintenance dose is about 38 mg of the crystalline anhydrous form of the Compound of Formula (I) three times a week. In some embodiments, the maintenance dose is about 40 mg of the crystalline anhydrous form of the Compound of Formula (I) three times a week. In some embodiments, the maintenance dose is about 42 mg of the crystalline anhydrous form of the Compound of Formula (I) three times a week. In some embodiments, the maintenance dose is about 44 mg of the crystalline anhydrous form of the Compound of Formula (I) three times a week. In some embodiments, the maintenance dose is about 46 mg of the crystalline anhydrous form of the Compound of Formula (I) three times a week. In some embodiments, the maintenance dose is about 48 mg of the crystalline anhydrous form of the Compound of Formula (I) three times a week. In some embodiments, the maintenance dose is about 50 mg of the crystalline anhydrous form of the Compound of Formula (I) three times a week.

In some embodiments, such a disclosed method may include, administering a loading dose of 30 mg daily for 5 days, followed by a maintenance dose of 30 mg twice a week, of the crystalline anhydrous form of the Compound of Formula (I) to a patient in need thereof.

In some embodiments, such a disclosed method may include, administering a loading dose of 30 mg daily for 3 days, followed by a maintenance dose of 10 mg daily, of the crystalline anhydrous form of the Compound of Formula (I) to a patient in need thereof.

In some embodiments, such a disclosed method may include, administering a loading dose of 20 mg daily for 3 days, followed by a maintenance dose of 6 mg daily, of the crystalline anhydrous form of the Compound of Formula (I) to a patient in need thereof.

In some embodiments, such a disclosed method may include, administering a dose of 30 mg twice a week, of the crystalline anhydrous form of the Compound of Formula (I) to a patient in need thereof.

In some embodiments, administration of the crystalline anhydrous form of the compound of Formula (I), may be effected by any appropriate route including, but not limited to, oral routes, intravenous routes, intramuscular routes, subcutaneous, intratumoral injection, intraarticular injection, and direct absorption through mucous membrane tissues. In some embodiments, administration of the crystalline anhydrous form of the compound of Formula (I), may be effected by oral routes. In some embodiments, administration of the crystalline anhydrous form of the compound of Formula (I), may be effected by intraarticular injection. In some embodiments, administration of the crystalline anhydrous form of the compound of Formula (I), may be effected by intratumoral injection.

In some embodiments, the most suitable administration in any given case will depend on the nature and severity of the condition being treated. The dosages can be conveniently presented in unit dosage form and prepared by any of the methods well-known in the pharmaceutical arts.

In some embodiments, provided herein is a method of treating graft versus host disease (GVHD), comprising administering to the patient a therapeutically effective amount of the crystalline anhydrous form of the compound represented by Formula (I), or a therapeutically effective amount of the pharmaceutical composition comprising the crystalline anhydrous form of the compound represented by Formula (I). In some embodiments, the graft versus host disease (GVHD) is chronic graft versus host disease (cGVHD). In some embodiments, the graft versus host disease (GVHD) is acute graft versus host disease (aGVHD).

In some embodiments, provided herein is a method of treating a neurodegenerative disease, comprising administering to the patient a therapeutically effective amount of the crystalline anhydrous form of the compound represented by Formula (I), or a therapeutically effective amount of the pharmaceutical composition comprising the crystalline anhydrous form of the compound represented by Formula (I). In some embodiments, the neurodegenerative disease is selected from the group consisting of Parkinson's disease (PD), Alzheimer's Disease (AD), frontotemporal dementia (FTD), amyotrophic lateral sclerosis (ALS), mild cognitive impairment, and Huntington's Disease (HD).

In some embodiments, provided herein is a method of treating a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma, comprising administering to the patient a therapeutically effective amount of the crystalline anhydrous form of the compound represented by Formula (I), or a therapeutically effective amount of the pharmaceutical composition comprising the crystalline anhydrous form of the compound represented by Formula (I). In some embodiments, the solid tumor is selected from the group consisting of ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumor.

In some embodiments, provided herein is a method of treating tumors known to have expression of colony-stimulating factor 1 receptor (CSF-1R) or its ligands, colony stimulating factor-1 (CSF-1), or interleukin (IL)-34 (IL-34), comprising administering to the patient a therapeutically effective amount of the crystalline anhydrous form of the compound represented by Formula (I), or a therapeutically effective amount of the pharmaceutical composition comprising the crystalline anhydrous form of the compound represented by Formula (I).

In some embodiments, provided herein is a method of treating a disease or condition selected from the group consisting of metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis, comprising administering to the patient a therapeutically effective amount of the crystalline anhydrous form of the compound represented by Formula (I), or a therapeutically effective amount of the pharmaceutical composition comprising the crystalline anhydrous form of the compound represented by Formula (I).

The disclosure contemplates administration of the crystalline anhydrous form of the compound represented by Formula (I), to a patient in need thereof prior (neo-adjuvant) or after (adjuvant) surgery (e.g., surgical treatment of TGCT). In some embodiments, the crystalline anhydrous form of the compound represented by Formula (I), is administered as an adjuvant. In some embodiments, the crystalline anhydrous form of the compound represented by Formula (I), is administered as a neo-adjuvant. In some embodiments, the crystalline anhydrous form of the compound represented by Formula (I), is administered as a neo-adjuvant and an adjuvant. In some embodiments, the crystalline anhydrous form of the compound represented by Formula (I), is administered to a patient in need thereof as a neo-adjuvant for a period of 1 month to 6 months, followed by administration of the crystalline anhydrous form of the compound represented by Formula (I), as an adjuvant for a period from 1 day to 100 years. In some embodiments, administration of the crystalline anhydrous form of the compound represented by Formula (I), is administered to a patient in need thereof as a neo-adjuvant for a period of 1 month to 6 months, followed by administration of the crystalline anhydrous form of the compound represented by Formula (I), as an adjuvant for a period from 1 day to 5 years. In some embodiments, administration of the crystalline anhydrous form of the compound represented by Formula (I), is administered to a patient in need thereof as a neo-adjuvant for a period of 3 months to 6 months, followed by administration of the crystalline anhydrous form of the compound represented by Formula (I), as an adjuvant for a period from 1 day to 5 years. In some embodiments, no administration of the crystalline anhydrous form of the compound represented by Formula (I), occurs prior to surgery. In some embodiments, the crystalline anhydrous form of the compound represented by Formula (I), is administered as an adjuvant for a period from 1 day to 100 years. In some embodiments, the crystalline anhydrous form of the compound represented by Formula (I), is administered as an adjuvant for a period from 1 day to 5 years.

In some embodiments, provided herein is a method of treating a disease or condition of any other aspects of the disclosure, further comprising administering to the patient a therapeutically effective amount of one or more additional therapeutic agents. In some embodiments, the disease or condition is graft versus host disease (GVHD). In some embodiments, the disease or condition is chronic graft versus host disease (cGVHD). In some embodiments, the disease or condition is acute graft versus host disease (aGVHD). In some embodiments, the one or more additional therapeutic agents is selected from the group consisting of methoxsalen, abatacept, everolimus, alemtuzumab, antithymocyte globulin, autologous serum eye drops, azathioprine, belumosudil, bortezomib, mycophenolate mofetil, cyclophosphamide, cyclosporine, extracorporeal photopheresis, etanercept, imatinib mesylate, ibrutinib, interleukin-2, infliximab, ruxolitinib, methotrexate, muromab-CD3, pentostatin, denileukin diftitox, prednisone, prednisolone, tacrolimus, psoralen with ultraviolet A light, sirolimus, rituximab, methylprednisolone, budesonide, thalidomide, halofuginone, and hydroxychloroquine. In some embodiments, the one or more additional therapeutic agents is belumosudil.

In some embodiments, provided herein is a method of treating a disease or condition of any other aspects of the disclosure, further comprising administering to the patient a therapeutically effective amount of one or more additional therapeutic agents. In some embodiments, the disease or condition is a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma. In some embodiments, the one or more additional therapeutic agents is an immunomodulatory therapeutic. In some embodiments, the one or more additional therapeutic agents is a chemotherapeutic agent. In some embodiments, the one or more additional therapeutic agents is an immunomodulatory therapeutic and a chemotherapeutic agent.

The crystalline anhydrous form of the compound represented by Formula (I), can be administered in combination with one or more additional therapeutic agents to treat a disorder described herein, such as cancer. For example, provided in the present disclosure is a pharmaceutical composition comprising the crystalline anhydrous form of the compound represented by Formula (I), one or more additional therapeutic agents, and a pharmaceutically acceptable excipient. In some embodiments, the crystalline anhydrous form of the compound represented by Formula (I), and one additional therapeutic agent is administered. In some embodiments, the crystalline anhydrous form of the compound represented by Formula (I), and two additional therapeutic agents are administered. In some embodiments, the crystalline anhydrous form of the compound represented by Formula (I), and three additional therapeutic agents are administered. Combination therapy can be achieved by administering two or more therapeutic agents, each of which is formulated and administered separately. For example, the crystalline anhydrous form of the compound represented by Formula (I), and an additional therapeutic agent can be formulated and administered separately. Combination therapy can also be achieved by administering two or more therapeutic agents in a single formulation, for example a pharmaceutical composition comprising the crystalline anhydrous form of the compound represented by Formula (I), as one therapeutic agent and one or more additional therapeutic agents. For example, crystalline anhydrous form of the compound represented by Formula (I), and an additional therapeutic agent can be administered in a single formulation. Other combinations are also encompassed by combination therapy. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases, even longer intervals are possible. While in many cases it is desirable that the two or more agents used in a combination therapy be present in within the patient's body at the same time, this need not be so.

"Combination therapy" (or "co-therapy") includes the administration of the crystalline anhydrous form of the compound represented by Formula (I) and at least a second agent, e.g., an anti-PD1 or anti-PD-L1 therapeutic, an anti-PD1 or anti-PD-L1 antibody, an immune-check point inhibitor, or a chemotherapeutic agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination can be carried out over a defined time period (usually minutes, hours, days or weeks depending upon the combination selected) or until disease progression. Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single tablet or capsule having a fixed ratio of each therapeutic agent or in multiple, single unit doses for each of the therapeutic agents. Sequential or substantially simultaneous administration of each therapeutic agent can be effected by any appropriate route including, but not limited to, oral routes, intravenous routes, intramuscular routes, subcutaneous, intratumoral injection, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally, or all therapeutic agents may be administered by intravenous injection. The sequence in which the therapeutic agents are administered is not narrowly critical.

Combination therapy also can embrace the administration of the therapeutic agents as described above in further combination with other biologically active ingredients and non-drug therapies, including, but not limited to radiation therapy. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination may be administered to a patient simultaneously, sequentially or in combination. It will be appreciated that when using a composition or method the components may be in the same pharmaceutically acceptable excipient and therefore administered simultaneously. They may be in separate pharmaceutical excipients such as conventional oral dosage forms which are taken simultaneously. The term “combination” further refers to the case where the compounds are provided in separate dosage forms and are administered sequentially.

Although not wishing to be bound by theory, it is thought that the administration of CSF-1R inhibitors in accordance with the methods described herein, in combination with one or more anti-PD1 or anti-PD-L1 therapeutics may provide additive effects in significantly inhibiting primary tumor growth and modulating the immune system into an antitumoral state, which can be beneficial in the treatment of disorders associated with the proliferation, survival, or biological action of macrophages, including the treatment of TGCT. Examples of anti-PD1 or anti-PD-L1 therapeutics that may be administered in combination with CSF-1R inhibitors described herein include, but are not limited to, nivolumab, pidilizumab, cemiplimab, tislelizumab, AMP-224, AMP-514, and pembrolizumab.

The crystalline anhydrous form of the compound represented by Formula (I), can be used in combination with other immunomodulatory agents including but not limited to anti-PD-L1 therapeutics including atezolizumab, durvalumab, BMS-936559, and avelumab, anti-TIM3 therapeutics including TSR-022 and MBG453, anti-LAG3 therapeutics including relatlimab, LAG525, and TSR-033, CD40 agonist therapeutics including SGN-40, CP-870,893 and RO7009789, anti-CD47 therapeutics including Hu5F9-G4, anti-CD20 therapeutics, anti-CD38 therapeutics, or other immunomodulatory therapeutics including thalidomide, lenalidomide, pomalidomide, mezigdomide, prednisone, and dexamethasone.

Sarcomas comprise a diverse group of malignancies including more than fifty subtypes of bone and soft tissue origin. In some embodiments, a method of treating a cancer comprises administering to a patient with locally advanced and metastatic high-grade sarcoma the crystalline anhydrous form of the compound represented by Formula (I), in combination with avelumab. In some embodiments, a method of treating a cancer comprises administering to a patient with locally advanced sarcoma the crystalline anhydrous form of the compound represented by Formula (I), in combination with avelumab. In some embodiments, a method of treating a cancer comprises administering to a patient with metastatic high-grade sarcoma the crystalline anhydrous form of the compound represented by Formula (I), in combination with avelumab. In some embodiments, a method of treating a cancer comprises administering to a patient with advanced metastatic sarcoma the crystalline anhydrous form of the compound represented by Formula (I), in combination with avelumab. In some embodiments, a method of treating a cancer comprises administering to a patient with undifferentiated pleomorphic sarcoma (UPS) the crystalline anhydrous form of the compound represented by Formula (I), in combination with avelumab. In some embodiments, a method of treating a cancer comprises administering to a patient with myxofibrosarcoma (MFS) the crystalline anhydrous form of the compound represented by Formula (I), in combination with avelumab. In some embodiments, a method of treating a cancer comprises administering to a patient with leiomyosarcoma (LMS) the crystalline anhydrous form of the compound represented by Formula (I), in combination with avelumab. In some embodiments, a method of treating a cancer comprises administering to a patient with dedifferentiated liposarcoma (DDLPS) the crystalline anhydrous form of the compound represented by Formula (I), in combination with avelumab.

The crystalline anhydrous form of the compound represented by Formula (I), can also be used in combination with one or more chemotherapeutic agents including but not limited to anti-tubulin agents (e.g., paclitaxel, paclitaxel protein-bound particles for injectable suspension, eribulin, abraxane, docetaxel, ixabepilone, vincristine or vinorelbine), LHRH antagonists including but not limited to leuprolide, goserelin, triptorelin, or histrelin, anti-androgen agents including but not limited to abiraterone, flutamide, bicalutamide, nilutamide, cyproterone acetate, enzalutamide, and apalutamide, anti-estrogen agents including but not limited to tamoxifen, fulvestrant, anastrozole, letrozole, and exemestane, DNA-alkylating agents (including cisplatin, carboplatin, oxaliplatin, cyclophosphamide, ifosfamide, and temozolomide), DNA intercalating agents (including doxorubicin, pegylated liposomal doxorubicin, daunorubicin, idarubicin, and epirubicin), 5-fluorouracil, capecitabine, cytarabine, decitabine, 5-aza cytidine, gemcitabine methotrexate, bortezomib, and carfilzomib.

The crystalline anhydrous form of the compound represented by Formula (I), can also be used in combination with targeted therapeutics including kinase inhibitors erlotinib, gefitinib, lapatanib, everolimus, temsirolimus, abemaciclib, LEE011, palbociclib, ribociclib, crizotinib, cabozantinib, sunitinib, pazopanib, sorafenib, regorafenib, axitinib, dasatinib, imatinib, nilotinib, vemurafenib, dabrafenib, trametinib, cobimetinib, binimetinib, idelalisib, quizartinib, avapritinib, BLU-667, BLU-263, Loxo 292, larotrectinib, and quizartinib, anti-estrogen agents including but not limited to tamoxifen, fulvestrant, anastrozole, letrozole, and exemestane, anti-androgen agents including but not limited to abiraterone acetate, enzalutamide, nilutamide, bicalutamide, flutamide, cyproterone acetate, steroid agents including but not limited to prednisone and dexamethasone, PARP inhibitors including but not limited to neraparib, olaparib, and rucaparib, topoisomerase I inhibitors including but not limited to irinotecan, camptothecin, and topotecan, topoisomerase II inhibitors including but not limited to etoposide, etoposide phosphate, and mitoxantrone, Histone Deacetylase (HDAC) inhibitors including but not limited to vorinostat, romidepsin, panobinostat, valproic acid, and belinostat, DNA methylation inhibitors including but not limited to DZNeP and 5-aza-2'-deoxycytidine, proteasome inhibitors including but not limited to bortezomib and carfilzomib, thalidomide, lenalidomide, pomalidomide, biological agents including but not limited to trastuzumab, ado-trastuzumab, pertuzumab, cetuximab, panitumumab, ipilimumab, tremelimumab, vaccines including but not limited to sipuleucel-T, and radiotherapy.

The crystalline anhydrous form of the compound represented by Formula (I), can also be used in combination with anti-angiogenic agents including AMG386, bevacizumab and aflibercept, and antibody-drug-conjugates (ADCs) including but not limited to gemtuzumab ozogamicin, brentuximab vedotin, trastuzumab emtansine, inotuzumab ozogamicin, polatuzumab vedotin, enfortumab vedotin, trastuzumab deruxtecan, sacituzumab govitecan, belantamab mafodotin, moxetumomab pasudotox, loncastuximab tesirine, wherein the payload contained in the ADCs includes but is not limited to a derivative of camptothecin, a pyrrolobenzodiazepine dimer (PBD), an indolinobenzodiazepine dimer (IGN), DM1, DM4, MMAE, or MMAF.

In some embodiments, the additional therapeutic agent is selected from a luteinizing hormone-releasing hormone (LHRH) analog, including goserelin and leuprolide.

In some embodiments, the additional therapeutic agent is selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, AZD2171, batabulin, of atumtunab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, $IPdR_1$ KRX-0402, lucanthone, LY 317615, neuradiab, vitespan, RTA 744, SDX 102, talampanel, atrasentan, XR 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib, PD0325901, AZD-6244, capecitabine, L-Glutamic acid, N-[4-[2-(2-amino-4,7-dihydro-4-oxo-1H-pyrrolo[2,3-d]pyrimidin-5-yl)-ethyl] benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258), 3-[5-(methylsulfonylpiperadinemethyl)-indolyl]-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutanide, nilutamide, megestrol acetate, CP-724714, TAK-165, HKI-272, erlotinib, lapatanib, canertinib, ABX-EGF antibody, erbitux, EKB-569, PKI-166, GW-572016, Ionafarnib, BMS-214662, tipifarnib, amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa, ipilumumab, vemurafenib, and mixtures thereof.

In some embodiments of any other aspects of the disclosure, the therapeutically effective amount of the crystalline anhydrous form of the compound represented by Formula (I), or the therapeutically effective amount of the pharmaceutical composition comprising the crystalline anhydrous form of the compound represented by Formula (I), is administered orally.

In some embodiments, provided herein is a method of treating a tenosynovial giant cell tumor, comprising orally administering to the patient a therapeutically effective amount of the crystalline anhydrous form of the compound represented by Formula (I), or a therapeutically effective amount of the pharmaceutical composition comprising the crystalline anhydrous form of the compound represented by Formula (I). In some embodiments, the tenosynovial giant cell tumor is a diffuse-type tenosynovial giant cell tumor. In some embodiments, the tenosynovial giant cell tumor is a localized tenosynovial giant cell tumor.

In some embodiments, provided herein is a method of treating graft versus host disease (GVHD), comprising orally administering to the patient a therapeutically effective amount of the crystalline anhydrous form of the compound represented by Formula (I), or a therapeutically effective amount of the pharmaceutical composition comprising the crystalline anhydrous form of the compound represented by Formula (I). In some embodiments, the graft versus host disease (GVHD) is chronic graft versus host disease (cGVHD). In some embodiments, the graft versus host disease (GVHD) is acute graft versus host disease (aGVHD).

In some embodiments, provided herein is a method of treating a neurodegenerative disease, comprising orally administering to the patient a therapeutically effective amount of the crystalline anhydrous form of the compound represented by Formula (I), or a therapeutically effective amount of the pharmaceutical composition comprising the crystalline anhydrous form of the compound represented by Formula (I). In some embodiments, the neurodegenerative disease is selected from the group consisting of Parkinson's disease (PD), Alzheimer's Disease (AD), frontotemporal dementia (FTD), amyotrophic lateral sclerosis (ALS), mild cognitive impairment, and Huntington's Disease (HD).

In some embodiments, provided herein is a method of treating a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma, comprising orally administering to the patient a therapeutically effective amount of the crystalline anhydrous form of the compound represented by Formula (I), or a therapeutically effective amount of the pharmaceutical composition comprising the crystalline anhydrous form of the compound represented by Formula (I). In some embodiments, the solid tumor is selected from the group consisting of ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumor.

In some embodiments, provided herein is a method of treating tumors known to have expression of colony-stimulating factor 1 receptor (CSF-1R) or its ligands, colony stimulating factor-1 (CSF-1), or interleukin (IL)-34 (IL-34), comprising orally administering to the patient a therapeutically effective amount of the crystalline anhydrous form of the compound represented by Formula (I), or a therapeutically effective amount of the pharmaceutical composition comprising the crystalline anhydrous form of the compound represented by Formula (I).

In some embodiments, provided herein is a method of treating a disease or condition selected from the group consisting of metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis, comprising orally administering to the patient a therapeutically effective amount of the crystalline anhydrous form of the compound represented by Formula (I), or a therapeutically effective amount of the pharmaceutical composition comprising the crystalline anhydrous form of the compound represented by Formula (I).

In some embodiments, provided herein is a method of treating a disease or condition of any other aspects of the disclosure, further comprising administering to the patient a therapeutically effective amount of one or more additional therapeutic agents. In some embodiments, the disease or condition is graft versus host disease (GVHD). In some embodiments, the disease or condition is chronic graft versus host disease (cGVHD). In some embodiments, the disease or condition is acute graft versus host disease (aGVHD). In some embodiments, the one or more additional therapeutic agents is selected from the group consisting of methoxsalen, abatacept, everolimus, alemtuzumab, antithymocyte globulin, autologous serum eye drops, azathioprine, belumosudil, bortezomib, mycophenolate mofetil, cyclophosphamide, cyclosporine, extracorporeal photopheresis, etanercept, imatinib mesylate, ibrutinib, interleukin-2, infliximab, ruxolitinib, methotrexate, muromab-CD3, pentostatin, denileukin diftitox, prednisone, prednisolone, tacrolimus, psoralen with ultraviolet A light, sirolimus, rituximab, methylprednisolone, budesonide, thalidomide, halofuginone, and hydroxychloroquine. In some embodiments, the one or more additional therapeutic agents is belumosudil.

In some embodiments, provided herein is a method of treating a disease or condition of any other aspects of the disclosure, further comprising administering to the patient a therapeutically effective amount of one or more additional therapeutic agents. In some embodiments, the disease or condition is a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma. In some embodiments, the one or more additional therapeutic agents is an immunomodulatory therapeutic. In some embodiments, the one or more additional therapeutic agents is a chemotherapeutic agent. In some embodiments, the one or more additional therapeutic agents is an immunomodulatory therapeutic and a chemotherapeutic agent.

In some embodiments, provided herein is a use of the crystalline anhydrous form of the compound represented by Formula (I), in the manufacture of a medicament for the treatment of a tenosynovial giant cell tumor. In some embodiments, the tenosynovial giant cell tumor is a diffuse-type tenosynovial giant cell tumor. In some embodiments, the tenosynovial giant cell tumor is a localized tenosynovial giant cell tumor.

In some embodiments, provided herein is a use of the crystalline anhydrous form of the compound represented by Formula (I), in the manufacture of a medicament for the treatment of graft versus host disease (GVHD. In some embodiments, the graft versus host disease (GVHD) is chronic graft versus host disease (cGVHD). In some embodiments, the graft versus host disease (GVHD) is acute graft versus host disease (aGVHD).

In some embodiments, provided herein is a use of the crystalline anhydrous form of the compound represented by Formula (I), in the manufacture of a medicament for the treatment of a neurodegenerative disease. In some embodiments, the neurodegenerative disease is selected from the group consisting of Parkinson's disease (PD), Alzheimer's Disease (AD), frontotemporal dementia (FTD), amyotrophic lateral sclerosis (ALS), mild cognitive impairment, and Huntington's Disease (HD).

In some embodiments, provided herein is a use of the crystalline anhydrous form of the compound represented by Formula (I), in the manufacture of a medicament for the treatment of a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma. In some embodiments, the solid tumor is selected from the group consisting of ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumor.

In some embodiments, provided herein is a use of the crystalline anhydrous form of the compound represented by Formula (I), in the manufacture of a medicament for the treatment of tumors known to have expression of colony-stimulating factor 1 receptor (CSF-1R) or its ligands, colony stimulating factor-1 (CSF-1), or interleukin (IL)-34 (IL-34.

In some embodiments, provided herein is a use of the crystalline anhydrous form of the compound represented by Formula (I), in the manufacture of a medicament for the treatment of a disease or condition selected from the group consisting of metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis.

In some aspects of the disclosure, in the use of the crystalline anhydrous form of the compound represented by Formula (I), in the manufacture of a medicament for the treatment of a disease or condition, the amount of the crystalline anhydrous form is about 1 mg to about 150 mg. In some embodiments, the amount of the crystalline anhydrous form is about 2 mg to about 35 mg. In some embodiments, the amount of the crystalline anhydrous form is about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, or about 3.0 mg. In some embodiments, the amount of the crystalline anhydrous form is about 2.0 mg. In some embodiments, the amount of the crystalline anhydrous form is about 10.0 mg, about 10.1 mg, about 10.2 mg, about 10.3 mg, about 10.4 mg, about 10.5 mg, about 10.6 mg, about 10.7 mg, about 10.8 mg, about 10.9 mg, or about 11.0 mg. In some embodiments, the amount of the crystalline anhydrous form is about 10.0 mg. In some embodiments, the amount of the crystalline anhydrous form is about 14.0 mg, about 14.1 mg, about 14.2 mg, about 14.3 mg, about 14.4 mg, about 14.5 mg, about 14.6 mg, about 14.7 mg, about 14.8 mg, about 14.9 mg, or about 15.0 mg. In some embodiments, the amount of the crystalline anhydrous form is about 14.0 mg. In some embodiments, the amount of the crystalline anhydrous form is about 21.1 mg, about 21.2 mg, about 21.3 mg, about 21.4 mg, about 21.5 mg, about 21.6 mg, about 21.7 mg, about 21.8 mg, about 21.9 mg, or about 22.0 mg. In some embodiments, the amount of the crystalline anhydrous form is about 21.7 mg. In some embodiments, the amount of the crystalline anhydrous form is about 30.0 mg, about 30.1 mg, about 30.2 mg, about 30.3 mg, about 30.4 mg, about 30.5 mg, about 30.6 mg, about 30.7 mg, about 30.8 mg, about 30.9 mg, or about 31.0 mg. In some embodiments, the amount of the crystalline anhydrous form is about 30.0 mg.

Dose Interruption and Modification

Dose modifications may be made in the methods of administering the compound represented by Formula (I) described herein as a result of adverse events experienced by the patient. In some embodiments, the dose modification is a dose interruption. In some embodiments, the dose modification is a permanent discontinuation in dosing. In some embodiments, the dose modification is a dose reduction. In some embodiments, the dose of the compound represented by Formula (I) administered to the patient is reduced from 30 mg twice a week, e.g., one capsule comprising 30 mg of the anhydrous form of the compound represented by Formula (I) or, e.g., one capsule comprising 32.5 mg of the crystalline dihydrate form of the compound represented by Formula (I), to 20 mg twice a week, e.g., one capsule comprising 20 mg of the anhydrous form of the compound represented by Formula (I) or, e.g., one capsule comprising 21.7 mg of the crystalline dihydrate form of the compound represented by Formula (I). In some embodiments, the dose of the compound represented by Formula (I) administered to the patient is reduced from 30 mg twice a week, e.g., one capsule comprising 30 mg of the anhydrous form of the compound represented by Formula (I)) or, e.g., one capsule comprising 32.5 mg of the crystalline dihydrate form of the compound represented by Formula (I), to 14 mg twice a week, e.g., one capsule comprising 14 mg of the anhydrous form of the compound represented by Formula (I) or, e.g., one capsule comprising 15.2 mg of the crystalline dihydrate form of the compound represented by Formula (I). In some embodiments, the dose of the compound represented by Formula (I) administered to the patient is reduced from 20 mg twice a week, e.g., one capsule comprising 20 mg of the anhydrous form of the compound represented by Formula (I)) or, e.g., one capsule comprising 21.7 mg of the crystalline dihydrate form of the compound represented by Formula (I), to 14 mg twice a week, e.g., one capsule comprising 14 mg of the anhydrous form of the compound represented by Formula (I) or, e.g., one capsule comprising 15.2 mg of the crystalline dihydrate form of the compound represented by Formula (I). In some embodiments, the adverse reaction is selected from the group consisting of a hepatobiliary elevation and a treatment-related skin or subcutaneous disorder. In some embodiments, the treatment-related skin or subcutaneous disorder is selected from the group consisting of maculopapular rash, pruritus, urticaria, eczema, and dry skin.

A patient can also be administered an additional treatment prior to, or during administration of the compound represented by Formula (I) in accordance with the methods described herein to prevent or ameliorate an adverse event. In some embodiments, the patient is administered a topical composition (e.g., an emollient) before and/or during the compound represented by Formula (I) administration to prevent or ameliorate the onset of an adverse dermatologic reaction.

Solid-State Polymorphism

The occurrence of different polymorphs is possible for some compounds. A single compound may give rise to a variety of solids having distinct physical properties, such as X-ray diffraction patterns, infrared absorption spectra, and NMR spectra. This variation in solid forms may be significant and may result in differences with respect to bioavailability, stability, and other differences for formulated pharmaceutical products. Because polymorphic forms can vary in their physical properties, regulatory authorities require that efforts shall be made to identify all polymorphic forms, e.g., crystalline, amorphous, solvated, etc., of new drug substances.

The existence and possible numbers of polymorphic forms for a given compound cannot be predicted, and there are no "standard" procedures that can be used to prepare polymorphic forms of a substance. However, new forms of a pharmaceutically useful compound may provide an opportunity to improve the performance characteristics of pharmaceutical products. Further, discovery of additional polymorphic forms, including solvate polymorphs, may help in the identification of the polymorphic content of a batch of an active pharmaceutical ingredient. For example, in some cases, different forms of the same drug can exhibit very different solubility and different dissolution rates.

Crystalline forms are characterized by scattering techniques, e.g., x-ray diffraction powder pattern, by spectroscopic methods, e.g., infra-red, $^{13}C$ nuclear magnetic resonance spectroscopy, and by thermal techniques, e.g., differential scanning calorimetry or differential thermal analysis. The compound of this disclosure is best characterized by the X-ray powder diffraction pattern determined in accordance with procedures that are known in the art. For a discussion of these techniques, see J. Haleblian, J. Pharm. Sci. 1975 64:1269-1288, and J. Haleblian and W. McCrone, J. Pharm. Sci. 1969 58:91 1-929. It may be noted that one skilled in the art may easily recognize the presence or absence of the certain peaks located in an X-ray powder diffraction pattern and which are characteristic of other crystalline forms.

Generally, a diffraction angle (20) in powder X-ray diffractometry may have an error in the range of ±0.2°. Therefore, the aforementioned diffraction angle values should be understood as including values in the range of about ±0.2°. Accordingly, the present disclosure includes not only crystals whose peak diffraction angles in powder X-ray diffractometry completely coincide with each other, but also crystals whose peak diffraction angles coincide with each other with an error of about ±0.0.2°. Therefore, in the present specification, the phrase "having a diffraction peak at a diffraction angle (2θ+0.2°) of 7.9°" means "having a diffraction peak at a diffraction angle (2θ) of 7.7° to 8.1°." Although the intensities of peaks in the x-ray powder diffraction patterns of different batches of a compound may vary slightly, the peaks and the peak locations are characteristic for a specific polymorphic form. Alternatively, the term "about" means within an acceptable standard error of the mean, when considered by one of ordinary skill in the art. The relative intensities of the XRPD peaks can vary depending on the sample preparation technique, crystal size distribution, various filters used, the sample mounting procedure, and the particular instrument employed. Moreover, instrument variation and other factors can affect the 2-theta values. Therefore, the term "substantially" in the context of XRPD is meant to encompass that peak assignments can vary by plus or minus about 0.2. degree. Moreover, new peaks may be observed, or existing peaks may disappear, depending on the type of the machine or the settings (for example, whether a Ni filter is used or not).

Pharmaceutical Formulations

Pharmaceutical formulations of the present disclosure contain any one or a combination of the crystalline solid-state forms of the compound represented by Formula (I) of the present disclosure, for example, the crystalline dihydrate or crystalline anhydrous forms of the compound represented by Formula (I). In addition to the active ingredient, the pharmaceutical formulations of the present disclosure can contain one or more excipients. Excipients are added to the formulation for a variety of purposes.

Diluents increase the bulk of a solid pharmaceutical composition and can make a pharmaceutical dosage form containing the composition easier for the patient and caregiver to handle. Diluents for solid compositions include, for example, microcrystalline cellulose (e.g., Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g., Carbopol), carboxymethylcellulose sodium, dextrin, ethyl cellulose, gelatin, guar gum, hydrogenated vegetable oil, hydroxyethyl cellulose, hydroxypropyl cellulose (e.g., Klucel®), hydroxypropyl methyl cellulose (e.g., Methocel®), liquid glucose, magnesium aluminum silicate, maltodextrin, methylcellulose, polymethacrylates, povidone (e.g., Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g., Ac-Di-Sol®, Primellose®), colloidal silicon dioxide, croscarmellose sodium, crospovidone (e.g., Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g., Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients tend to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present disclosure, the active ingredient and any other solid excipients may be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present disclosure include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present disclosure can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present disclosure is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, such as a powdered or granulated solid composition of the disclosure, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can comprise any of the aforementioned blends and granulates that were described with reference to tableting, but they are not subjected to a final tableting step.

In further embodiments, a pharmaceutical formulation of crystalline solid-state forms of the compound represented by Formula (I) is formulated for administration to a mammal, such as a human. Crystalline solid-state forms of the compound represented by Formula (I) can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringe ability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al, Pharmaceutical Dosage Forms and Drug Delivery Systems, 7th ed.

The present disclosure encompasses a process to prepare said formulations of crystalline solid-state forms of the compound represented by Formula (I) by combining the crystalline solid-state forms prepared according to the present disclosure and at least one pharmaceutically acceptable excipient.

Process of Making

Crystalline solid-state forms of the compound represented by Formula (I) can be prepared and isolated by controlling the conditions under which the compound represented by Formula (I) solid-state forms are obtained. Provided herein, in part, are processes for the preparation of crystalline solid-state forms of the compound represented by Formula (I) designated as the crystalline dihydrate form and the crystalline anhydrous form, mixtures of these forms, and pharmaceutical compositions comprising these solid-state forms and mixtures thereof.

Crystalline Dihydrate Form

In some embodiments, provided herein is a process for the preparation of the crystalline dihydrate form of the compound represented by Formula (I), said process comprising precipitating said crystalline dihydrate form from a mixture comprising the compound represented by Formula (I) and a solvent and water, isolating the precipitate, and drying the precipitate. In some embodiments, the solvent is selected from the group consisting of alcohol, ketone, ether, ester, halogenated alkane, amide, sulfone, acid, nitro compound, methanol, ethanol, n-propanol, iso-propanol, butanol, acetone, methyl ethyl ketone (MEK), methyl isobutyl ketone (MIBK), methyl acetate, ethyl acetate, propyl acetate, diethyl ether, tetrahydrofuran (THF), 2-methyl THF, 2,5-dimethyl THF, 2,2,5,5-tetramethyl THF, acetonitrile, methylene chloride, toluene, 1,1,1-trichloroethane, dimethyl acetamide (DMAC), nitromethane, acetic acid, and dimethyl sulfoxide (DMSO). In some embodiments, the solvent is DMAC or DMSO. In some embodiments, provided herein is the crystalline dihydrate form of the compound represented by Formula (I), which is produced by the process comprising precipitating said crystalline dihydrate form from a mixture comprising the compound represented by Formula (I) and a solvent and water, isolating the precipitate, and drying the precipitate.

In some embodiments, provided herein is a process for the preparation of the crystalline dihydrate form of the compound represented by Formula (I), comprising: (i) providing a mixture of the compound represented by Formula (I), a solvent and water; (ii) heating the mixture to obtain a clear solution; (iii) cooling the clear solution; (iv) charging milled seed material of the crystalline dihydrate form of the compound represented by Formula (I) and water to the solution; (v) cooling the resulting mixture; (vi) isolating the precipitate by filtering the resulting mixture; and (vii) drying the isolated precipitate to afford crystalline dihydrate form of the compound represented by Formula (I).

In some embodiments, provided herein is a process for the preparation of the crystalline dihydrate form of the compound represented by Formula (I), comprising: (i) providing a mixture of the compound represented by Formula (I) in dimethylacetamide (DMAC) and water; (ii) heating the mixture to between about 40° C. and about 80° C. to obtain a clear solution; (iii) cooling the clear solution to a temperature between about 55° C. and about 65° C.; (iv) charging milled seed material of the crystalline dihydrate form of the compound represented by Formula (I) and water to the solution; (v) cooling the resulting mixture to about 25° C.; (vi) isolating the precipitate by filtering the resulting mixture; and (vii) drying the isolated precipitate to afford crystalline dihydrate form of the compound represented by Formula (I).

In some embodiments, provided herein is a process for the preparation of the crystalline dihydrate form of the compound represented by Formula (I), comprising: (i) providing a mixture of the compound represented by Formula (I) in dimethylacetamide (DMAC) and water; (ii) heating the mixture to about 80° C. to obtain a clear solution; (iii) cooling the clear solution to about 65° C.; (iv) charging milled seed material of the crystalline dihydrate form of the compound represented by Formula (I) and water to the solution; (v) cooling the resulting mixture to about 25° C.; (vi) isolating the precipitate by filtering the resulting mixture; and (vii) drying the isolated precipitate to afford crystalline dihydrate form of the compound represented by Formula (I).

In some embodiments, provided herein is a crystalline solid-state form, which is the crystalline dihydrate form of the compound represented by Formula (I), prepared by the process comprising: (i) providing a mixture of the compound represented by Formula (I), a solvent and water; (ii) heating the mixture to obtain a clear solution; (iii) cooling the clear solution; (iv) charging milled seed material of the crystalline dihydrate form of the compound represented by Formula (I) and water to the solution; (v) cooling the resulting mixture; (vi) isolating the precipitate by filtering the resulting mixture; and (vii) drying the isolated precipitate to afford crystalline dihydrate form of the compound represented by Formula (I).

In some embodiments, provided herein is a crystalline solid-state form, which is the crystalline dihydrate form of the compound represented by Formula (I), prepared by the process comprising: (i) providing a mixture of the compound represented by Formula (I) in dimethylacetamide (DMAC) and water; (ii) heating the mixture to between about 40° C. and about 80° C. to obtain a clear solution; (iii) cooling the clear solution to a temperature between about 55° C. and about 65° C.; (iv) charging milled seed material of the crystalline dihydrate form of the compound represented by Formula (I) and water to the solution; (v) cooling the resulting mixture to about 25° C.; (vi) isolating the precipitate by filtering the resulting mixture; and (vii) drying the isolated precipitate to afford crystalline dihydrate form of the compound represented by Formula (I).

In some embodiments, provided herein is the crystalline dihydrate form of the compound represented by Formula (I) prepared by the process comprising: (i) providing a mixture of the compound represented by Formula (I) in dimethylacetamide (DMAC) and water; (ii) heating the mixture to about 80° C. to obtain a clear solution; (iii) cooling the clear solution to about 65° C.; (iv) charging milled seed material of the crystalline dihydrate form of the compound represented by Formula (I) and water to the solution; (v) cooling the resulting mixture to about 25° C.; (vi) isolating the precipitate by filtering the resulting mixture; and (vii) drying the isolated precipitate to afford crystalline dihydrate form of the compound represented by Formula (I)

In some embodiments, provided herein is a process for the preparation of the crystalline dihydrate form of the compound represented by Formula (I), comprising heating the mixture of the compound represented by Formula (I) and solvent to a temperature between about 40° C. and about 80° C. degrees. In some embodiments, provided herein is a process for the preparation of the crystalline dihydrate form of the compound represented by Formula (I), comprising heating the mixture of the compound represented by Formula (I) and solvent to a temperature between about 50° C. and about 80° C. degrees. In some embodiments, provided herein is a process for the preparation of the crystalline dihydrate form of the compound represented by Formula (I), comprising heating the mixture of the compound represented by Formula (I) and solvent to a temperature between about 60° C. and about 80° C. degrees.

In some embodiments, provided herein is a process for the preparation the crystalline dihydrate form of the compound represented by Formula (I), comprising cooling a solution of the compound represented by Formula (I) and solvent to a temperature between about 50° C. and about 70° C. degrees and charging milled seed material of the crystalline dihydrate form of the compound represented by Formula (I). In some embodiments, provided herein is a process for the preparation of the crystalline dihydrate form of the compound represented by Formula (I), comprising cooling a solution of the compound represented by Formula (I) and solvent to a temperature between about 55° C. and about 65° C. degrees and charging milled seed material of the crystalline dihydrate form of the compound represented by Formula (I). In some embodiments, provided herein is a process for the preparation of the crystalline dihydrate form of the compound represented by Formula (I), comprising cooling a solution of the compound represented by Formula (I) and solvent to a temperature of about 65° C. degrees and charging milled seed material of the crystalline dihydrate form of the compound represented by Formula (I).

In some embodiments, provided herein is a process for the preparation of the crystalline dihydrate form of the compound represented by Formula (I), of the compound represented by Formula (I) comprising combining the compound represented by Formula (I) and a solvent selected from alcohol, ketone, ether, ester, halogenated alkane, amide, sulfone, acid, nitro compound, methanol, ethanol, n-propanol, iso-propanol, butanol, acetone, methyl ethyl ketone (MEK), methyl isobutyl ketone (MIBK), methyl acetate, ethyl acetate, propyl acetate, diethyl ether, tetrahydrofuran (THF), 2-methyl THF, 2,5-dimethyl THF, 2,2,5,5-tetramethyl THF, acetonitrile, methylene chloride, toluene, 1,1,1-trichloroethane, dimethyl acetamide (DMAC), nitromethane, acetic acid, and dimethyl sulfoxide (DMSO).

In some embodiments, provided herein is a process for the preparation of the crystalline dihydrate form of the compound represented by Formula (I) comprising combining the compound represented by Formula (I) and a solvent selected from acetone, dimethyl acetamide (DMAC), and dimethyl sulfoxide (DMSO). In some embodiments, provided herein is a process for the preparation of the crystalline dihydrate form of the compound represented by Formula (I), comprising combining the compound represented by Formula (I) and a solvent selected from dimethyl acetamide (DMAC) and dimethyl sulfoxide (DMSO). In some embodiments, provided herein is a process for the preparation of the crystalline dihydrate form of the compound represented by Formula (I), comprising combining the compound represented by Formula (I) and dimethyl acetamide (DMAC).

In some embodiments, provided herein is a process of preparation of the crystalline dihydrate form of the compound represented by Formula (I), comprising combining the compound represented by Formula (I), a solvent and water, wherein the solvent to water ratio is about 1:1 to about 30:1. In some embodiments, provided herein is a process of preparation of the crystalline dihydrate form of the compound represented by Formula (I), comprising combining the compound represented by Formula (I), a solvent and water, wherein the solvent to water ratio is about 1:1 to about 20:1. In some embodiments, provided herein is a process of preparation of the crystalline dihydrate form of the compound represented by Formula (I), of the compound represented by Formula (I) comprising combining the compound represented by Formula (I), a solvent and water, wherein the solvent to water ratio is about 5:1 to about 20:1.

In some embodiments, provided herein is a process of preparation of the crystalline dihydrate form of the compound represented by Formula (I), comprising combining the compound represented by Formula (I), a solvent and water, and drying the resultant isolated solid at a temperature no greater than about 50° C. In some embodiments, provided herein is a process of preparation of the crystalline dihydrate form of the compound represented by Formula (I), comprising combining the compound represented by Formula (I), a solvent and water, and drying the resultant isolated solid at a temperature no greater than about 45° C. In some embodiments, provided herein is a process of preparation of the crystalline dihydrate form of the compound represented by Formula (I), comprising combining the compound represented by Formula (I), a solvent and water, and drying the resultant isolated solid at a temperature no greater than about 40° C.

In some embodiments, provided herein is a process of preparation of the crystalline dihydrate form of the compound represented by Formula (I), comprising:

(i) providing a mixture of a compound represented by Formula (I) and a solvent;

(ii) charging the mixture with milled seed material of a dihydrate form of the compound represented by Formula (I);

(iii) further charging the mixture in (ii) with a solvent to obtain a charged suspension system;

(iv) cooling the charged suspension system to result in a solid precipitate; and (v) isolating the resulting solid precipitate to obtain the crystalline dihydrate form, having a uniform particle sized distribution which is a multiple of the seed material particle size distribution.

In some embodiments, the solvent in step (i) is selected from the group consisting of water, alcohol, ketone, ether, ester, halogenated alkane, amide, sulfone, acid, nitro compound, methanol, ethanol, n-propanol, iso-propanol, butanol, acetone, methyl ethyl ketone (MEK), methyl isobutyl ketone (MIBK), methyl acetate, ethyl acetate, propyl acetate, diethyl ether, tetrahydrofuran (THF), 2-methyl THF, 2,5-dimethyl THF, 2,2,5,5-tetramethyl THF, acetonitrile, methylene chloride, toluene, 1,1,1-trichloroethane, dimethyl acetamide (DMAC), nitromethane, acetic acid, and dimethyl sulfoxide (DMSO), and a combination thereof. For example, the solvent is water, acetone, DMAC, or DMSO, or a combination thereof.

In some embodiments, the solvent in step (iii) is water.

In some embodiments, in step (iii), the charging is at a temperature above 25° C. For example, the charging is at a temperature of about 50° C., about 55° C., about 60° C., about 65° C., about 70° C., about 75° C., or about 80° C.

In some embodiments, in step (iv), the cooling is to about 15° C., about 20° C., about 25° C., about 30° C., or about 35° C. In some embodiments, in step (iv), the cooling is at about 0.01-10° C./min, such as, at about 0.1° C./min, 0.5° C./min, 1.0° C./min or about 2° C./min.

Crystalline Anhydrous Form

In some embodiments, provided herein is a process for the preparation of the crystalline anhydrous form of the compound represented by Formula (I), said process comprising precipitating said crystalline anhydrous form from a mixture comprising the compound represented by Formula (I) and a solvent, isolating the precipitate, and drying the precipitate. In some embodiments, the solvent is selected from the group consisting of alcohol, ketone, ether, ester, halogenated alkane, amide, sulfone, acid, nitro compound, methanol, ethanol, n-propanol, iso-propanol, butanol, acetone, methyl ethyl ketone (MEK), methyl isobutyl ketone (MIBK), methyl acetate, ethyl acetate, propyl acetate, diethyl ether, tetrahydrofuran (THF), 2-methyl THF, 2,5-dimethyl THF, 2,2,5,5-tetramethyl THF, acetonitrile, methylene chloride, toluene, 1,1,1-trichloroethane, dimethyl acetamide (DMAC), nitromethane, acetic acid, and dimethyl sulfoxide (DMSO). In some embodiments, the solvent is acetone, DMAC, or DMSO. In some embodiments, provided herein is the crystalline anhydrous form of the compound represented by Formula (I), which is produced by the process comprising precipitating said crystalline dihydrate form from a mixture comprising the compound represented by Formula (I) and a solvent, isolating the precipitate, and drying the precipitate.

In some embodiments, provided herein is a process for the preparation of the crystalline anhydrous form of the compound represented by Formula (I), said process comprising drying the crystalline dihydrate form of the compound represented by Formula (I) in a vacuum oven. In some embodiments, provided herein is the crystalline anhydrous form of the compound represented by Formula (I), which is produced by the process comprising drying the crystalline dihydrate form of the compound represented by Formula (I) in a vacuum oven.

In some embodiments, provided herein is a process for the preparation of the crystalline anhydrous form of the compound represented by Formula (I), said process comprising precipitating said crystalline anhydrous form from a solution comprising the compound represented by Formula (I) and solvent and drying the resultant isolated solid. In some embodiments, milled seed material of the crystalline anhydrous form of the compound represented by Formula (I) is charged to the solution.

In some embodiments, provided herein is a process of preparing the crystalline anhydrous form of the compound represented by Formula (I), comprising: i) providing a mixture of the compound represented by Formula (I) or the crystalline dihydrate form of the compound represented by Formula (I) and solvent; ii) heating the mixture to obtain a clear solution; iii) cooling the resulting solution; iv) charging milled seed material of the crystalline anhydrous form of the compound represented by Formula (I) and solvent (alternatively, charging the solvent and then charging milled seed material of the crystalline anhydrous form of the compound represented by Formula (I)); v) cooling the resulting mixture; vi) filtering the resulting mixture and vii) drying the isolated precipitate to obtain the crystalline anhydrous form of the compound represented by Formula (I).

In some embodiments, provided herein is a process for the preparation of the crystalline anhydrous form of the compound represented by Formula (I), comprising: i) providing a mixture of the crystalline dihydrate form of the compound represented by Formula (I) in dimethyl sulfoxide (DMSO); ii) heating the mixture to between about 65° C. and about 70° C. to obtain a clear solution; iii) cooling the resulting solution to between about 60° C. and about 65° C.; iv) charging milled seed material of the crystalline anhydrous form of the compound represented by Formula (I), then charging isopropanol (alternatively, (iv) charging isopropanol, then charging milled seed material of the crystalline anhydrous form of the compound of Formula (I)); v) cooling the resulting mixture to between about 5° C. and about 10° C.; vi) isolating the precipitate by filtering the resulting mixture; and vii) drying the isolated precipitate to afford the crystalline anhydrous form of the compound represented by Formula (I).

In some embodiments, provided herein is a process for the preparation of the crystalline anhydrous form of the compound represented by Formula (I), comprising: i) providing a mixture of the crystalline dihydrate form of the compound represented by Formula (I) in dimethyl sulfoxide (DMSO); ii) heating the mixture to about 70° C. to obtain a clear solution; iii) cooling the solution to about 65° C.; iv) charging milled seed material of the crystalline anhydrous form of the compound represented by Formula (I), then charging isopropanol (alternatively, (iv) charging isopropanol, then charging milled seed material of the crystalline anhydrous form of the compound of Formula (I)); v) cooling the resulting mixture to about 5° C.; vi) isolating the precipitate by filtering the resulting mixture; and vii) drying the isolated precipitate to afford the crystalline anhydrous form of the compound represented by Formula (I).

In some embodiments, provided herein is the crystalline anhydrous form of the compound represented by Formula (I), prepared by the process comprising: i) providing a mixture of the crystalline dihydrate form of the compound represented by Formula (I) in dimethyl sulfoxide (DMSO); ii) heating the mixture to between about 65° C. and about 70° C. to obtain a clear solution; iii) cooling the resulting solution to between about 60° C. and about 65° C.; iv) charging milled seed material of the crystalline anhydrous form of the compound represented by Formula (I), then charging isopropanol (alternatively, (iv) charging isopropanol, then charging milled seed material of the crystalline anhydrous form of the compound of Formula (I)); v) cooling the resulting mixture to between about 5° C. and about 10° C.; vi) isolating the precipitate by filtering the resulting mixture; and vii) drying the isolated precipitate to afford the crystalline anhydrous form of the compound represented by Formula (I).

In some embodiments, provided herein is the crystalline anhydrous form of the compound represented by Formula (I), prepared by the process comprising: i) providing a mixture of the crystalline dihydrate form of the compound represented by Formula (I) in dimethyl sulfoxide (DMSO); ii) heating the mixture to about 70° C. to obtain a clear solution; iii) cooling the solution to about 65° C.; iv) charging milled seed material of the crystalline anhydrous form of the compound represented by Formula (I), then charging isopropanol (alternatively, (iv) charging isopropanol, then charging milled seed material of the crystalline anhydrous form of the compound of Formula (I)); v) cooling the resulting mixture to about 5° C.; vi) isolating the precipitate by filtering the resulting mixture; and vii) drying the isolated precipitate to afford the crystalline anhydrous form of the compound represented by Formula (I).

In some embodiments, provided herein is a process for the preparation of the crystalline anhydrous form of the compound represented by Formula (I), comprising heating the mixture of the compound represented by Formula (I) or the crystalline dihydrate form of the compound represented by Formula (I) and solvent or water to a temperature between about 40° C. and about 80° C. degrees. In some embodiments, provided herein is a process for the preparation of the crystalline anhydrous form of the compound represented by Formula (I), comprising heating the mixture of the compound represented by Formula (I) or the crystalline dihydrate form of the compound represented by Formula (I) and solvent or water to a temperature between about 50° C. and about 80° C. degrees. In some embodiments, provided herein is a process for the preparation of the crystalline anhydrous form of the compound represented by Formula (I), comprising heating the mixture of the compound represented by Formula (I) or the crystalline dihydrate form of the compound represented by Formula (I) and solvent or water to a temperature between about 60° C. and about 80° C. degrees.

In some embodiments, provided herein is a process for the preparation of the crystalline anhydrous form of the compound represented by Formula (I), comprising combining the compound represented by Formula (I) or the crystalline dihydrate form and a solvent selected from alcohol, ketone, ether, ester, halogenated alkane, amide, sulfone, acid, nitro compound, methanol, ethanol, n-propanol, iso-propanol, butanol, acetone, methyl ethyl ketone (MEK), methyl isobutyl ketone (MIBK), methyl acetate, ethyl acetate, propyl acetate, diethyl ether, tetrahydrofuran (THF), 2-methyl THF, 2,5-dimethyl THF, 2,2,5,5-tetramethyl THF, acetonitrile, methylene chloride, toluene, 1,1,1-trichloroethane, dimethyl acetamide (DMAC), nitromethane, acetic acid, and dimethyl sulfoxide (DMSO).

In some embodiments, provided herein is a process for the preparation of the crystalline anhydrous form of the compound represented by Formula (I), comprising combining the compound represented by Formula (I) or the crystalline dihydrate form and a solvent selected from acetone, dimethyl acetamide (DMAC), and dimethyl sulfoxide (DMSO).

In some embodiments, provided herein is a process for the preparation of the crystalline anhydrous form of the compound represented by Formula (I), comprising combining the compound represented by Formula (I) or the crystalline dihydrate form and a solvent selected from dimethyl acetamide (DMAC) or dimethyl sulfoxide (DMSO).

In some embodiments, provided herein is a process for the preparation of the crystalline anhydrous form of the compound represented by Formula (I), comprising combining the compound represented by Formula (I) or the crystalline dihydrate form and a solvent, and drying the resultant isolated solid at a temperature no greater than about 160° C. In some embodiments, provided herein is a process for the preparation of the crystalline anhydrous form of the compound represented by Formula (I) comprising combining the compound represented by Formula (I) or the crystalline dihydrate form and a solvent, and drying the resultant isolated solid at a temperature no greater than about 155° C. In some embodiments, provided herein is a process for the preparation of the crystalline anhydrous form of the compound represented by Formula (I) comprising combining the compound represented by Formula (I) or the crystalline dihydrate form and a solvent, and drying the resultant isolated solid at a temperature no greater than about 150° C.

Stability of Crystalline Solid-State Forms

Crystalline solid-state forms of the compound represented by Formula (I) are highly stable. The term "stable form" when used herein refers to solid-state forms of the compound of Formula (I) following storage comprises at least 75% (w/v or w/w), 80% (w/v or w/w), 85% (w/v or w/w), 90% (w/v or w/w), 95% (w/v or w/w), 96% (w/v or w/w), 97% (w/v or w/w), 98% (w/v or w/w), or 99% (w/v or w/w) of said particular solid-state forms after static storage (e.g., after static storage for at least 4 weeks at about 25° C. to about 40° C. at about 0-97% relative humidity). In some embodiments, storage conditions for stability testing are about 25° C. at about 60% relative humidity, such as about 25° C. at about 60% relative humidity of at least 1 year, 2 years, 3 years, 4 years, or 5 years. In some embodiments, the storage conditions for stability testing are about 25° C. and about 0-97% relative humidity for at least 4 weeks, such as about 25° C. and about 0% relative humidity for at least 4 weeks or about 25° C. and about 97% relative humidity for at least 4 weeks. In some embodiments, storage conditions for stability testing are about 40° C. and about 0-75% relative humidity for at least 4 weeks, such as about 40° C. and about 0% relative humidity for at least 4 weeks or about 40° C. and about 75% relative humidity for at least 4 weeks.

In some embodiments, the stability of the particular solid-state form of compound of Formula (I) requires at least 75% (w/v or w/w), 80% (w/v or w/w), 85% (w/v or w/w), 90% (w/v or w/w), 95% (w/v or w/w), 96% (w/v or w/w), 97% (w/v or w/w), 98% (w/v or w/w), or 99% (w/v or w/w) of said form remaining as said form at the end of the storage period, e.g., without converting to another form of the compound of Formula (I).

In some embodiments, the crystalline dihydrate form of the compound of Formula (I) is stable upon static storage at about 25° C. at about 60% relative humidity for at least 1 year. In some embodiments, the crystalline dihydrate form of the compound of Formula (I) is stable upon static storage at about 25° C. at about 60% relative humidity for at least 2 years. In some embodiments, the crystalline dihydrate form of the compound of Formula (I) is stable upon static storage at about 25° C. at about 60% relative humidity for at least 3 years. In some embodiments, the crystalline dihydrate form of the compound of Formula (I) is stable upon static storage at about 25° C. at about 60% relative humidity for at least 4 years. In some embodiments, the crystalline dihydrate form of the compound of Formula (I) is stable upon static storage at about 25° C. at about 60% relative humidity for at least 5 years.

In some embodiments, the crystalline dihydrate form of the compound of Formula (I) is stable upon static storage at about 25° C. at about 97% relative humidity for at least 1 week. In some embodiments, the crystalline dihydrate form of the compound of Formula (I) is stable upon static storage at about 25° C. at about 97% relative humidity for at least 2 weeks. In some embodiments, the crystalline dihydrate form of the compound of Formula (I) is stable upon static storage at about 25° C. at about 97% relative humidity for at least 3 weeks. In some embodiments, the crystalline dihydrate form of the compound of Formula (I) is stable upon static storage at about 25° C. at about 97% relative humidity for at least 4 weeks. In some embodiments, the crystalline dihydrate form of the compound of Formula (I) is stable upon static storage at about 25° C. at about 97% relative humidity for at least 1 month. In some embodiments, the crystalline dihydrate form of the compound of Formula (I) is stable upon static storage at about 25° C. at about 97% relative humidity for at least 2 months. In some embodiments, the crystalline dihydrate form of the compound of Formula (I) is stable upon static storage at about 25° C. at about 97% relative humidity for at least 3 months. In some embodiments, the crystalline dihydrate form of the compound of Formula (I) is stable upon static storage at about 25° C. at about 97% relative humidity for at least 4 months. In some embodiments, the crystalline dihydrate form of the compound of Formula (I) is stable upon static storage at about 25° C. at about 97% relative humidity for at least 5 months. In some embodiments, the crystalline dihydrate form of the compound of Formula (I) is stable upon static storage at about 25° C. at about 97% relative humidity for at least 6 months. In some embodiments, the crystalline dihydrate form of the compound of Formula (I) is stable upon static storage at about 25° C. at about 97% relative humidity for at least 12 months. In some embodiments, the crystalline dihydrate form of the compound of Formula (I) is stable upon static storage at about 25° C. at about 97% relative humidity for at least 24 months.

In some embodiments, the crystalline dihydrate form of the compound of Formula (I) is stable upon static storage at about 40° C. at about 75% relative humidity for at least 1 week. In some embodiments, the crystalline dihydrate form of the compound of Formula (I) is stable upon static storage at about 40° C. at about 75% relative humidity for at least 2 weeks. In some embodiments, the crystalline dihydrate form of the compound of Formula (I) is stable upon static storage at about 40° C. at about 75% relative humidity for at least 3 weeks. In some embodiments, the crystalline dihydrate form of the compound of Formula (I) is stable upon static storage at about 40° C. at about 75% relative humidity for at least 4 weeks. In some embodiments, the crystalline dihydrate form of the compound of Formula (I) is stable upon static storage at about 40° C. at about 75% relative humidity for at least 1 month. In some embodiments, the crystalline dihydrate form of the compound of Formula (I) is stable upon static storage at about 40° C. at about 75% relative humidity for at least 2 months. In some embodiments, the crystalline dihydrate form of the compound of Formula (I) is stable upon static storage at about 40° C. at about 75% relative humidity for at least 3 months. In some embodiments, the crystalline dihydrate form of the compound of Formula (I) is stable upon static storage at about 40° C. at about 75% relative humidity for at least 4 months. In some embodiments, the crystalline dihydrate form of the compound of Formula (I) is stable upon static storage at about 40° C. at about 75% relative humidity for at least 5 months. In some embodiments, the crystalline dihydrate form of the compound of Formula (I) is stable upon static storage at about 40° C. at about 75% relative humidity for at least 6 months. In some embodiments, the crystalline dihydrate form of the compound of Formula (I) is stable upon static storage at about 40° C. at about 75% relative humidity for at least 12 months. In some embodiments, the crystalline dihydrate form of the compound of Formula (I) is stable upon static storage at about 40° C. at about 75% relative humidity for at least 24 months.

In some embodiments, the crystalline anhydrous form of the compound of Formula (I) is stable upon static storage at about 25° C. at about 97% relative humidity for at least 1 week. In some embodiments, the crystalline anhydrous form of the compound of Formula (I) is stable upon static storage at about 25° C. at about 97% relative humidity for at least 2 weeks. In some embodiments, the crystalline anhydrous form of the compound of Formula (I) is stable upon static storage at about 25° C. at about 97% relative humidity for at least 3 weeks. In some embodiments, the crystalline anhydrous form of the compound of Formula (I) is stable upon static storage at about 25° C. at about 97% relative humidity for at least 4 weeks. In some embodiments, the crystalline anhydrous form of the compound of Formula (I) is stable upon static storage at about 25° C. at about 97% relative humidity for at least 1 month. In some embodiments, the crystalline anhydrous form of the compound of Formula (I) is stable upon static storage at about 25° C. at about 97% relative humidity for at least 2 months. In some embodiments, the crystalline anhydrous form of the compound of Formula (I) is stable upon static storage at about 25° C. at about 97% relative humidity for at least 3 months. In some embodiments, the crystalline anhydrous form of the compound of Formula (I) is stable upon static storage at about 25° C. at about 97% relative humidity for at least 4 months. In some embodiments, the crystalline anhydrous form of the compound of Formula (I) is stable upon static storage at about 25° C. at about 97% relative humidity for at least 5 months. In some embodiments, the crystalline anhydrous form of the compound of Formula (I) is stable upon static storage at about 25° C. at about 97% relative humidity for at least 6 months. In some embodiments, the crystalline anhydrous form of the compound of Formula (I) is stable upon static storage at about 25° C. at about 97% relative humidity for at least 12 months. In some embodiments, the crystalline anhydrous form of the compound of Formula (I) is stable upon static storage at about 25° C. at about 97% relative humidity for at least 24 months.

In some embodiments, the crystalline anhydrous form of the compound of Formula (I) is stable upon static storage at about 40° C. at about 75% relative humidity for at least 1 week. In some embodiments, the crystalline anhydrous form of the compound of Formula (I) is stable upon static storage at about 40° C. at about 75% relative humidity for at least 2 weeks. In some embodiments, the crystalline anhydrous form of the compound of Formula (I) is stable upon static storage at about 40° C. at about 75% relative humidity for at least 3 weeks. In some embodiments, the crystalline anhydrous form of the compound of Formula (I) is stable upon static storage at about 40° C. at about 75% relative humidity for at least 4 weeks. In some embodiments, the crystalline anhydrous form of the compound of Formula (I) is stable upon static storage at about 40° C. at about 75% relative humidity for at least 1 month. In some embodiments, the crystalline anhydrous form of the compound of Formula (I) is stable upon static storage at about 40° C. at about 75% relative humidity for at least 2 months. In some embodiments, the crystalline anhydrous form of the compound of Formula (I) is stable upon static storage at about 40° C. at about 75% relative humidity for at least 3 months. In some embodiments, the crystalline anhydrous form of the compound of Formula (I) is stable upon static storage at about 40° C. at about 75% relative humidity for at least 4 months. In some embodiments, the crystalline anhydrous form of the compound of Formula (I) is stable upon static storage at about 40° C. at about 75% relative humidity for at least 5 months. In some embodiments, the crystalline anhydrous form of the compound of Formula (I) is stable upon static storage at about 40° C. at about 75% relative humidity for at least 6 months. In some embodiments, the crystalline anhydrous form of the compound of Formula (I) is stable upon static storage at about 40° C. at about 75% relative humidity for at least 12 months. In some embodiments, the crystalline anhydrous form of the compound of Formula (I) is stable upon static storage at about 40° C. at about 75% relative humidity for at least 24 months.

In some embodiments, provided herein is a stable crystalline dihydrate form of the compound of Formula (I).

In another embodiment, provided herein is a stable crystalline anhydrous form of the compound of Formula (I).

In another embodiment, provided herein is a composition comprising the stable crystalline dihydrate form of the compound of Formula (I).

In another embodiment, provided herein is a pharmaceutical composition consisting essentially of the stable crystalline dihydrate form of the compound of formula (I) and a pharmaceutically acceptable excipient.

In another embodiment, provided herein is a composition comprising the crystalline anhydrous form of compound of formula (I).

In another embodiment, provided herein is a pharmaceutical composition consisting essentially of the stable anhydrous form of compound of formula (I) and a pharmaceutically acceptable excipient.

EXAMPLES

The present disclosure is not to be limited in scope by the specific embodiments disclosed in the examples which are intended as illustrations of a few aspects of the disclosure and any embodiments that are functionally equivalent are within the scope of this disclosure. Indeed, various modifications in addition to those shown and described herein will become apparent to those skilled in the art and are intended to fall within the scope of the appended claims Example 1. Exemplary Preparation of the Crystalline Dihydrate Form of the Compound of Formula (I)

An exemplary crystallization procedure for the crystalline dihydrate form of the compound of Formula (I) is as follows. Dimethylacetamide was added to a clean reactor. Then, the dry solid compound cake was added into the reactor, followed by deionized water. The reactor contents were heated to a temperature of about 80° C. for at least 3 hours. Then, the reactor contents were cooled to a temperature of about 65° C. for at least 1 hour. Next, the reactor contents were stirred for at least 20 minutes at a temperature of about 65° C. Then, the reactor was charged with micronized seeds of the compound of Formula (I), and the reactor contents were stirred for at least 15 minutes (but less than 1 hour) at a temperature of about 65° C. Deionized water was added to the reactor while a temperature of about 65° C. was maintained for at least 4 hours. Then, the reactor contents were cooled to a temperature of about 25° C. for at least 6.5 hours (a cooling ramp of about 0.1° C./min is recommended). Next, the reactor contents were stirred for at least 5 hours at a temperature of about 25° C. Afterwards, the reactor contents were filtered, and the filter cake washed twice with deionized water. Then, the filter cake was dried under vacuum with nitrogen flow at a jacket temperature of about 40° C.

For example, the crystalline dihydrate form of the compound of Formula (I) was prepared according to Example 1A:

Example 1A: Preparation of the Crystalline Dihydrate Form of the Compound of Formula (I)

The compound represented by Formula (I) was dispensed into a vessel with impeller and thermocouple. DMAC (dimethylacetamide) and water were charged to the vessel to give 5 volumes of DMAC:$H_2O$ (4.25 volumes DMAC and 0.75 volumes $H_2O$) ratio. The system was stirred to give complete suspension of material and heated to about 80° C. to access clear solution. The system was then cooled to about 65° C. and held for about 15 minutes. Milled seed material of the crystalline dihydrate form of the Compound of Formula (I) (prepared by, for example, by Example 1B) (about 5 wt. % of the weight of the compound of Formula (I)) was charged to the vessel. The system was held for 15-60 minutes. Water (2 volumes) was charged to the vessel at 65° C. over about 4 hours (0.5 volumes/hour). The system was allowed to cool to about 25° C. at about 0.1° C./min over about 6.5 hours before the mixture was stirred at room temperature for about 5 hours. The solid precipitate was isolated via vacuum filtration, washed with water (about 10 volumes) and dried under vacuum and nitrogen flow at a temperature no higher than 40° C. until moisture content by Karl Fischer analysis (KF) was no more than about 8% and no less than about 6%.

Example 1B describes another exemplary method of preparing the crystalline dihydrate form of the compound of Formula (I):

Example 1B: Preparation of the Crystalline Dihydrate Form of the Compound of Formula (I)

To a solution of the compound of Formula (I) in DCM (dichloromethane)-methanol (about 2 liters) at a temperature not higher than 45° C. was added acetone (about 5 liters). The resulting mixture was concentrated under reduced pressure to a volume of about 2 liters at a temperature not higher than 45° C. Acetone (about 5 liters) was added and the resulting mixture was concentrated under reduced pressure to a volume of about 2 liters at a temperature not higher than 45° C. To the resulting mixture, was added acetone (about 10 liters, 11.6 volumes) and water (about 0.5 liters, 0.61 volumes). The mixture was heated at about 50° C. for at least 8 h and then cooled to ambient temperature. The solid was filtered, washed with a mixture of acetone (about 3 liters) and water (about 0.2 liters), and dried under reduced pressure at no higher than 40° C. until moisture content determined by Karl Fischer analysis (KF) was no more than about 8% and no less than about 6%.

Example 2: Preparation of the Crystalline Anhydrous Form of the Compound of Formula (I)

The crystalline dihydrate form was combined with DMSO (5 volumes) and heated to about 70° C. to obtain a clear solution. The solution was cooled to about 65° C. and isopropanol (1.5 volumes) was charged to the vessel, followed by seeds of the crystalline anhydrous form (5 wt. % of the initial crystalline dihydrate form). The resulting suspension was stirred at about 65° C. for about 1 hour and then isopropanol (3.5 volumes) was added via a syringe pump over about 2 hours. The suspension was cooled to about 5° C. at about 0.1° C./min and stirred overnight. Alternatively, the clear solution (DMSO, 5 volumes, 70° C.) was cooled to about 60° C. and seeds of the crystalline anhydrous form (5 wt. % of the initial crystalline dihydrate form) were added. The resulting suspension was stirred at about 60° C. for about 1 h and then isopropanol (5.0 volumes) was added over about 2 hours. The suspension was cooled to about 5° C. at about 0.1° C./min and stirred overnight. In each case, the resulting solid was isolated by filtration, washed with isopropanol and dried under reduced pressure to afford the crystalline anhydrous form.

Example 3: Controlled Particle Size Seeding

Surprisingly, it was found that during the DMAC-water crystallization using controlled particle sized milled crystalline dihydrate form of the compound represented by Formula (I) as seeds enabled controlling the particle size distribution (PSD) of the resulting crystalline dihydrate form of the compound represented by Formula (I). In some embodiments, the PSD of the crystalline dihydrate form of the Compound of Formula (I) is controlled by the PSD of the seeds used in the crystallization. In some embodiments, the PSD of the crystalline dihydrate form of the Compound of Formula (I) is controlled by the PSD of the seeds used in the crystallization, without the need of a particle size adjustment step.

The solid of the compound of Formula (I) was dissolved in DMAC-water and the crystallization procedure was developed at a seeding temperature of about 65° C. using about 3% seeds (by weight of the solid of the compound of Formula (I). The crystalline dihydrate form of the compound represented by Formula (I) was crystallized at laboratory and production scale using milled seeds with the particle size of about 3 μm ($d_{10}$) μm, about 6 μm ($d_{50}$), and about 12 μm ($d_{90}$) (Table 1), to afford the crystalline dihydrate form of the compound of Formula (I) with a consistent particle size of about 6-8 μm ($d_{10}$), about 16-22 μm ($d_{50}$), and about 33-40 μm ($d_{90}$) (Table 2). Further crystallization development using seeds of a smaller size (about 1 μm ($d_{10}$), about 3 μm ($d_{50}$), and about 5 μm ($d_{90}$)), resulted in the crystallization outputs with PSD of about 4 μm ($d_{10}$), about 8 μm ($d_{50}$), and about 16 μm ($d_{90}$) (Table 3). Whether using seeds with larger or smaller PSD, the respective outputs were that the $d_{90}$ of the crystalline dihydrate form of the Compound of Formula (I) was about 3 times the doo of the seeds, the $d_{50}$ of the crystalline dihydrate form of the Compound of Formula (I) was about 3 times the $d_{50}$ of the seeds, and the $d_{10}$ of the crystalline dihydrate form of the Compound of Formula (I) was about 2 times to about 3 times the $d_{10}$ of the seeds. At least the crystallization procedures of Example 1, Example 1A, and Example 3 demonstrate the means for controlling particle sizes and particle size distribution $d_{90}$, $d_{50}$, and $d_{10}$ values.

TABLE 1

PSD of milled seeds of crystalline dihydrate form of the compound represented by Formula (I) used as seeds in DMAC-water crystallization

| | Particle Size (microns) | | |
|---|---|---|---|
| Lot No | $d_{10}$ | $d_{50}$ | $d_{90}$ |
| 1 | 2 | 5 | 13 |
| 2 | 2 | 6 | 11 |
| 3 | 3 | 6 | 12 |

TABLE 2

PSD of batches of the crystalline dihydrate form of the compound represented by Formula (I) batches crystallized using seeds

| | | Particle Size (microns) | | |
|---|---|---|---|---|
| Batch No | Seed Lot | $d_{10}$ | $d_{50}$ | $d_{90}$ |
| 1 | 1 | 6.2 | 16.0 | 34.3 |
| 2 | 1 | 5.8 | 16.1 | 38.1 |
| 3 | 1 | 5.9 | 17.2 | 39.1 |
| 4 | 2 | 6.5 | 18.4 | 37.4 |
| 5 | 3 | 6.8 | 19.2 | 40.4 |
| 6 | 3 | 7.9 | 20.0 | 39.0 |
| 7 | 2 | 6.2 | 17.9 | 36.7 |
| 8 | 3 | 6.1 | 16.8 | 32.9 |
| 9 | 3 | 6.9 | 18.6 | 35.8 |
| 10 | 3 | 5.0 | 17.0 | 37.0 |

TABLE 3

PSD of batches of the crystalline dihydrate form of the compound represented by Formula (I) produced using seeds

| | | Particle Size (microns) | | |
|---|---|---|---|---|
| Batch No | Process details | $d_{10}$ | $d_{50}$ | $d_{90}$ |
| Seed batch | obtained by jet milling | 1.4 | 2.7 | 5.0 |
| Crystalline dihydrate form of the compound represented by Formula (I) (crystallization 1) | Crystallization at 60° C. with 7% seeds | 3.6 | 8.4 | 16.2 |
| Crystalline dihydrate form of the compound represented by Formula (I) (crystallization 2) | Crystallization at 64° C. with 5% seeds | 3.9 | 8.5 | 16.0 |

A larger particle size batch was prepared by crystallization from DMAC-water using a non-milled batch of crystalline dihydrate form of the compound represented by Formula (I) with a particle size distribution of about 5 μm ($d_{10}$), about 15 μm ($d_{50}$), and about 36 μm ($d_{90}$), as seeds. The resulting material displayed a particle size distribution of about 13.6 μm ($d_{10}$), about 42.2 μm ($d_{50}$), and about 95.1 μm ($d_{90}$), revealing a similar trend as observed earlier wherein the $d_{10}$, $d_{50}$, and $d_{90}$ of the output were about 3-fold that of the respective $d_{10}$, $d_{50}$, and $d_{90}$ of the seeds.

Analytical Methods:

X-Ray Powder Diffraction Method

The XRPD data was collected on a Bruker AXS D8 Advance using Cu Ka radiation (40 kV, 40 mA) in reflection geometry and a θ-2θ goniometer fitted with a Ge monochromator. The incident beam passes through a 2.0 mm divergence slit followed by a 0.2 mm antiscatter slit and knife edge. The diffracted beam passes through an 8.0 mm receiving slit with 2.5° Soller slits followed by the Lynxeye Detector. The software used for data collection was Diffrac Plus XRD Commander and data analysis was HighScore Plus.

Samples were run under ambient conditions as flat plate specimens using powder as received. The sample was prepared on a polished, zero-background (510) silicon wafer by gently pressing onto the flat surface or packed into a cut cavity. The sample was rotated in its own plane.

The details of the standard data collection method:

Angular range: 2 to 42° 2θ

Step size: 0.05° 2θ

Collection time: 0.5 s/step (total collection time: 6.40 min)

TABLE 4

XRPD parameters for 4 min method

| Parameters | Reflection Mode |
|---|---|
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence slit | Automatic |
| Scan mode | Continuous |
| Scan range (°2TH) | 3°-40° |
| Step size (°2TH) | 0.0131 |
| Scan speed (°/s) | 0.16 |
| Experiment time | ~4 min |

DSC Method:

DSC data was collected on a TA Instruments Q2000 equipped with a 50-position auto-sampler. Typically, 0.5-3 mg of each sample, in a pin-holed aluminum pan unless otherwise specified, was heated at either 10° C./min or 2° C./min from 25° C. to 300° C. A purge of dry nitrogen at 50 mL/min was maintained over the sample.

The instrument control software was Advantage for Q Series and Thermal Advantage, and the data were analyzed using Universal Analysis or TRIOS.

TGA Method:

TGA data were collected on a TA Instruments Q500 TGA, equipped with a 16-position auto-sampler. Typically, 5-10 mg of each sample was loaded onto a pre-tared aluminum DSC pan and heated at 10° C./min maintained over the sample.

The instrument control software was Advantage for Q Series and Thermal Advantage, and the data were analyzed using Universal Analysis or TRIOS.

TABLE 5

| TGA and DSC parameters | | |
|---|---|---|
| Parameters | TGA | DSC |
| Method | Ramp | Ramp |
| Sample pan | Aluminum, open | Aluminum, crimped |
| Heating rate | 10° C./min | 10° C./min |
| Procedure | RT-300° C. | 25° C.-desired temperature |
| Purge gas | $N_2$ | $N_2$ |

$^{13}C$ Solid-State Nuclear Magnetic Resonance ("ssNMR" or $^{13}C$ Solid-State NMR) Method Solid-state NMR spectra Solid-state NMR (ssNMR) experiments were acquired on a Bruker Avance Neo console using a wide bore Bruker 4 mm BB/1H WVT MAS prone and TopSpin 4.0 software at a static magnetic field strength of 14.1 T (V° ($^1$H)=600 MHz). For $^{13}C$, the probe was tuned to 150.94 MHz and spectra referenced to the aniline $CH_3$ signal at 20.5 ppm. Powdered samples were packed into zirconia MAS rotors with Kel-F caps, with before and after weightings providing the sample mass. The rotors were spun using room-temperature purified compressed air.

All spectra were recorded using cross polarization (CP), in which magnetism is transferred from $^1$H to $^{13}C$ nuclei via dipolar coupling (i.e., through space rather than through bond-interaction). This method enhances the observed signal, and significantly reduces the time taken to record a spectrum; however, a CP spectrum is not fully quantitative, as the peak intensity is partially dependent on the magnitude of the $^1$H-($^{13}C$/$^{15}N$) interaction. A contact time of 1.6 ms was used for the $^{13}C$ experiments. High power (100 W) SPINAL-64 decoupling was applied to the $^1$H channel during acquisition.

Polymorphic Forms

Solid-state forms of the compound represented by Formula (I) were characterized by X-ray powder diffraction ("XRPD") patterns, differential scanning calorimetry ("DSC") curves, thermogravimetric analysis ("TGA") curves, and solid-state NMR ("ssNMR") spectra.

Crystalline Dihydrate Form

The crystalline dihydrate form of the compound represented by Formula (I) is represented by the XRPD pattern of FIG. 1, the DSC thermogram of FIG. 2, the TGA thermogram of FIG. 3, and the ssNMR analysis as shown in FIG. 4. The TGA thermogram (FIG. 3) of the crystalline dihydrate form of the compound represented by Formula (I) exhibits weight loss of ca. 7.5-8% between room temperature and ca. 150-220° C., corresponding to the loss of ca. 2 moles of water. The DSC thermogram (FIG. 2) for the crystalline dihydrate form of the compound represented by Formula (I) in an open pan exhibits the following transitions: 1. a broad endothermic event with onset varying between ca. 75-95° C., corresponding to volatilization of water (dehydration); 2. an exothermic event with onset varying between ca. 123-150° C., corresponding to recrystallization (of the anhydrous form of the compound represented by Formula (I)); and 3. a sharp endotherm with onset at ca. 214° C., corresponding to the melt of the anhydrous form of the compound represented by Formula (I). The DSC thermogram comprises a sharp endothermic peak at about 215° C. The ssNMR analysis is as shown in FIG. 4, asterisks indicating spinning side bands. These analyses indicate a crystalline dihydrate form.

The crystalline dihydrate form of the compound represented by Formula (I) has an X-ray powder diffraction pattern comprising peaks in terms of 2-theta, as shown in Table 6, below.

TABLE 6

XRPD pattern comprising peaks in terms of 2-theta below for crystalline solid-state dihydrate form of the compound represented by Formula (I)

| No. | Pos. [°2θ] | FWHM Left [°2θ] | d-spacing [Å] | Rel. Int. [%] |
|---|---|---|---|---|
| 1 | 5.917 | 0.1476 | 14.93661 | 17.3 |
| 2 | 8.284 | 0.1476 | 10.67348 | 8.7 |
| 3 | 10.872 | 0.1476 | 8.13828 | 23.3 |
| 4 | 11.861 | 0.1476 | 7.4617 | 29.4 |
| 5 | 12.214 | 0.1476 | 7.24674 | 30.5 |
| 6 | 13.101 | 0.1476 | 6.75799 | 72.5 |
| 7 | 13.666 | 0.1476 | 6.47981 | 14.5 |
| 8 | 15.461 | 0.0984 | 5.73114 | 8.8 |
| 9 | 15.813 | 0.1476 | 5.60445 | 17.8 |
| 10 | 16.815 | 0.1476 | 5.27265 | 8.2 |
| 11 | 17.833 | 0.1476 | 4.97383 | 25.7 |
| 12 | 18.323 | 0.246 | 4.84209 | 10.6 |
| 13 | 18.996 | 0.1476 | 4.67207 | 22.6 |
| 14 | 20.806 | 0.1476 | 4.2695 | 100 |
| 15 | 21.787 | 0.1476 | 4.0794 | 44 |
| 16 | 22.143 | 0.0984 | 4.01461 | 7.4 |
| 17 | 22.623 | 0.1476 | 3.93042 | 56.2 |
| 18 | 24.151 | 0.0984 | 3.6851 | 7.4 |
| 19 | 24.599 | 0.2952 | 3.61901 | 19.9 |
| 20 | 25.275 | 0.1968 | 3.5237 | 50.9 |
| 21 | 25.809 | 0.1968 | 3.4521 | 24.7 |
| 22 | 26.212 | 0.09 | 3.39709 | 11.7 |
| 23 | 26.412 | 0.1476 | 3.3746 | 31.2 |
| 24 | 27.106 | 0.1968 | 3.28973 | 71.9 |
| 25 | 28.303 | 0.1968 | 3.15327 | 13.9 |
| 26 | 28.666 | 0.1476 | 3.11423 | 9.9 |
| 27 | 29.67 | 0.1476 | 3.01104 | 14.8 |
| 28 | 30.026 | 0.1476 | 2.9762 | 15.9 |
| 29 | 30.827 | 0.1476 | 2.90061 | 6.3 |
| 30 | 31.209 | 0.1476 | 2.86601 | 5.6 |

Crystalline Anhydrous Form

The crystalline anhydrous form of the compound represented by Formula (I) is represented by the XRPD pattern of FIG. 5, the DSC thermogram of FIG. 6, the TGA thermogram of FIG. 7, and the ssNMR analysis as shown in FIG. 8. The TGA and DSC analyses (FIGS. 6 and 7, respectively) for the crystalline anhydrous form of the compound represented by Formula (I) showed no weight loss with a sharp endotherm at 215° C. (onset) rising to about 330° C. before decomposition. The ssNMR analysis is as shown in FIG. 8). The crystalline anhydrous form of the compound represented by Formula (I) has a DSC thermogram comprising an endothermic peak between about 215° C. and substantially as shown in FIG. 6, corresponding to the melt of the crystalline anhydrous form of the compound represented by Formula (I). The TGA thermogram (FIG. 6) does not show weight loss until ca. 330° C., the onset of decomposition. These analyses indicate a crystalline anhydrous form.

The anhydrous form of the compound represented by Formula (I) has an XRPD pattern comprising peaks in terms of 2-theta, as shown in Table 7, below.

TABLE 7

XRPD pattern comprising peaks in terms of 2-theta below for crystalline solid-state anhydrous form of the compound represented by Formula (I)

| No. | Pos. [°2θ] | FWHM Left [°2θ] | d-spacing [Å] | Rel. Int. [%] |
|---|---|---|---|---|
| 1 | 10.462 | 0.1476 | 8.45576 | 5.7 |
| 2 | 11.364 | 0.1476 | 7.7867 | 18.8 |
| 3 | 12.181 | 0.1476 | 7.26609 | 11.4 |
| 4 | 13.063 | 0.1476 | 6.77756 | 62.7 |

TABLE 7-continued

| XRPD pattern comprising peaks in terms of 2-theta below for crystalline solid-state anhydrous form of the compound represented by Formula (I) | | | | |
|---|---|---|---|---|
| No. | Pos. [°2θ] | FWHM Left [°2θ] | d-spacing [Å] | Rel. Int. [%] |
| 5 | 14.664 | 0.0984 | 6.041 | 8.2 |
| 6 | 14.964 | 0.1476 | 5.92048 | 12.9 |
| 7 | 15.5 | 0.1968 | 5.71708 | 100 |
| 8 | 15.849 | 0.0984 | 5.59199 | 18.2 |
| 9 | 17.12 | 0.1476 | 5.17954 | 8.4 |
| 10 | 17.603 | 0.1968 | 5.03849 | 46.3 |
| 11 | 19.107 | 0.1968 | 4.64508 | 10.1 |
| 12 | 19.772 | 0.1476 | 4.49027 | 39.6 |
| 13 | 20.099 | 0.0984 | 4.4179 | 14.4 |
| 14 | 20.75 | 0.1968 | 4.28083 | 12.4 |
| 15 | 21.316 | 0.1476 | 4.16836 | 8.2 |
| 16 | 21.802 | 0.1476 | 4.07659 | 6.9 |
| 17 | 22.294 | 0.1968 | 3.98776 | 66 |
| 18 | 22.665 | 0.1476 | 3.92338 | 15 |
| 19 | 22.837 | 0.0984 | 3.89407 | 11.9 |
| 20 | 23.328 | 0.1476 | 3.81326 | 91.2 |
| 21 | 24.477 | 0.1476 | 3.63688 | 12.6 |
| 22 | 25.198 | 0.1968 | 3.53434 | 18 |
| 23 | 25.714 | 0.1476 | 3.46455 | 32.2 |
| 24 | 26.008 | 0.09 | 3.42331 | 29.4 |
| 25 | 26.294 | 0.09 | 3.38672 | 11.2 |
| 26 | 26.653 | 0.1968 | 3.34463 | 32.3 |
| 27 | 29.103 | 0.1968 | 3.06843 | 9.4 |
| 28 | 29.547 | 0.1476 | 3.02331 | 13 |

Example 4: Stability Testing of Crystalline Dihydrate and Anhydrous Forms of the Compound Represented by Formula (I)

The stability of crystalline dihydrate and anhydrous forms of the compound represented by Formula (I) at varying relative humidity (RH) and temperature was investigated.

For example, the stability of crystalline dihydrate and anhydrous forms of the compound represented by Formula (I), as prepared according to Example 1 and Example 2, respectively, was studied under other conditions by placing aliquots of each form in static storage at conditions of 40° C./75% RH, 25° C./97% RH, 40° C./0% RH and 25° C./0% RH and analyzing the aliquots once weekly for four weeks using XRPD, DSC, and KF.

The crystalline dihydrate form (having average crystal sizes of about 1 mm) partially converted to the crystalline anhydrous form after 4 weeks of storage at 40° C./0% RH. In addition, the crystalline dihydrate form partially converted to the crystalline anhydrous form after 4 weeks of storage at 25° C./0% RH. The corresponding KF analysis indicated a water content of 5.8% for the crystalline dihydrate form stored at 25° C./0% RH for 4 weeks, which was higher than that of the crystalline dihydrate form stored at 40° C./0% RH for 4 weeks (0.2% as determined by KF), indicating a lower degree of conversion to the crystalline anhydrous form at the lower temperature. The crystalline dihydrate form remained stable and unchanged as evidenced by XRPD under the other storage conditions for the full 4 week timeframe (40° C./75% RH and 25° C./97% RH). The crystalline anhydrous form remained stable under all storage conditions after 4 weeks.

Figure 9:
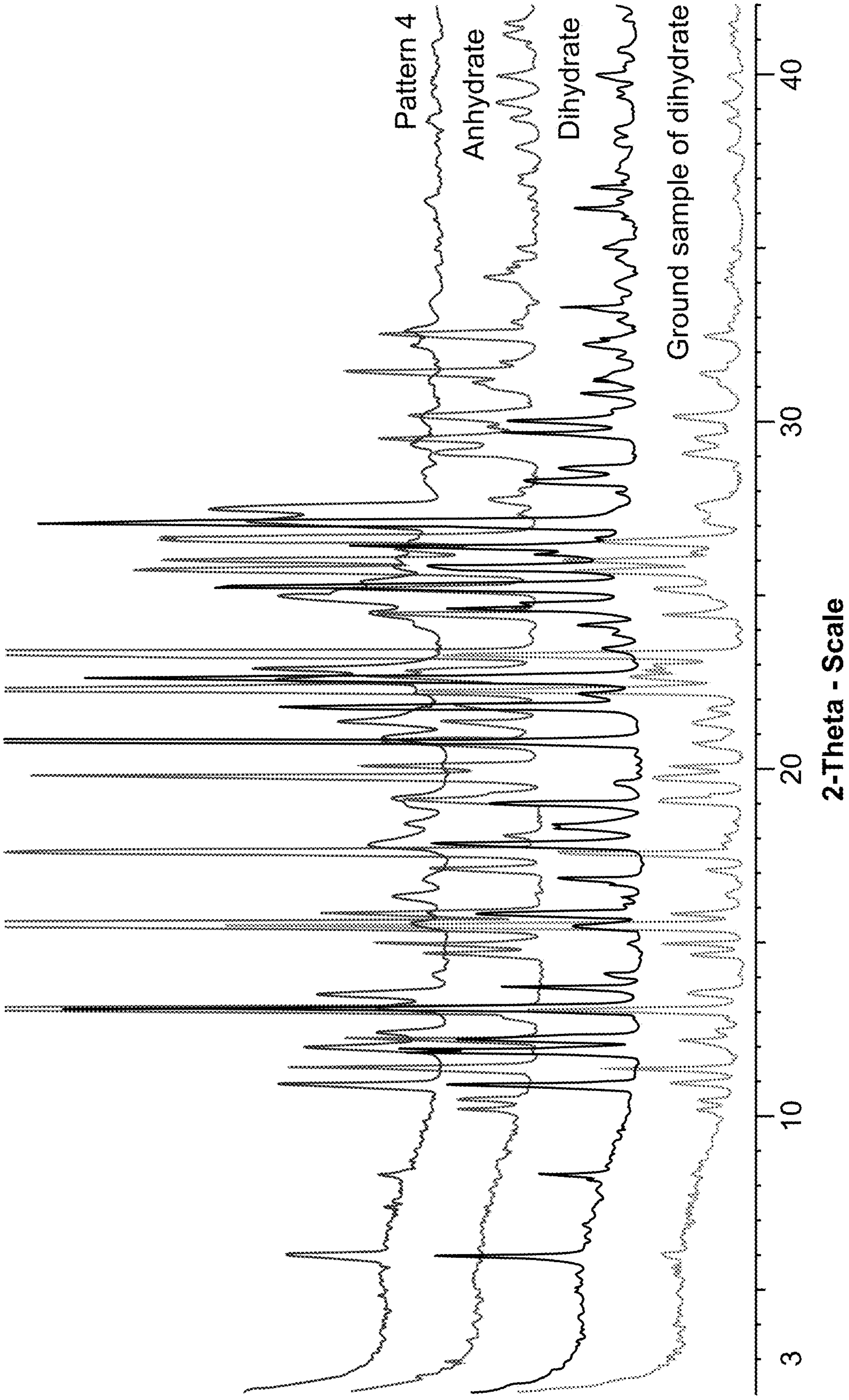
FIG. 9 shows an XRPD pattern of the ground crystalline dihydrate form subjected to static storage at 40° C./0% RH for one week.

When crystalline dihydrate form (having crystal sizes in the range of about 10-50 μm estimated by polarized light microscopy) was stored at 40° C./0% RH, Pattern 4 (a hemi-hydrate form of the compound represented by Formula (I)) was observed at weeks 1-2. By weeks 3-4 at 40° C./0% RH, Pattern 4 and peaks at 9.9° and 10.6°, corresponding to Pattern 5 peaks, were observed. When the crystalline dihydrate form (having average crystal sizes of about 1 mm) was ground in a mortar and pestle (thus having crystal sizes about 10 μm to about 100 μm) and stored at 40° C./0% RH for 1 week, Pattern 4 and the crystalline anhydrous form were observed (FIG. 9). When Pattern 4 was subsequently stored at higher humidities (e.g., 40° C./75% RH) for one week, it was converted to the crystalline dihydrate form. Tables 8-9 summarize the stability of crystalline dihydrate and anhydrous forms of the compound represented by Formula (I).

TABLE 8

| Stability of the crystalline dihydrate and anhydrous forms of the compound represented by Formula (I) | | | | | | |
|---|---|---|---|---|---|---|
| Dihydrate form of the compound represented by Formula (I) (having average crystal sizes of about 1 mm) | | | | | | |
| | Week 1 | | | Week 2 | | |
| Storage Condition | XRPD | DSC | KF (%) | XRPD | DSC | KF (%) |
| 40° C./ 75% RH | Dihydrate form | Broad endotherm onset 99.2° C. (96 J/g) Exotherm onset 136.4° C. (5 J/g) Multi-endotherm onset 159.2° C. (87 J/g) Sharp endotherm split into two, onset 214.7° C. (25 J/g and 28 J/g) | 7.7 | Dihydrate form | Broad endotherm onset 94.8° C. (67 J/g) Broad multi-endotherm onset 151.6° C. (104 J/g) Sharp endotherm onset 215.0° C. (33 J/g) | 7.6 |
| 25° C./ 97% RH | Dihydrate form | Broad endotherm onset 93.3° C. (69 J/g) Multi-endotherm onset 151.9° C. (96 J/g) Sharp endotherm onset 214.4° C. (39 J/g | 7.7 | Dihydrate form | Broad endotherm onset 99.1° C. (97 J/g) Multi-endotherm onset 151.8° C. (75 J/g) Sharp endotherm onset 214.8° C. (46 J/g | 7.7 |

TABLE 8-continued

| Stability of the crystalline dihydrate and anhydrous forms of the compound represented by Formula (I) | | | | | | |
|---|---|---|---|---|---|---|
| 40° C./ 0% RH | Dihydrate and Anhydrous forms | Multi-endotherm onset 144.9° C. (2 J/g) Double endotherm onset 156.7° C. (4 J/g) Sharp endotherm onset 214.4° C. (122 J/g) | 0.8 | Dihydrate and Anhydrous forms | Sharp endotherm onset 214.3° C. (123 J/g) | 0.3 |
| 25° C./ 0% RH | Dihydrate form | Broad endotherm onset 95.6° C. (43 J/g) Multi-endotherm onset 157.4° C. (104. J/g) Sharp endotherm onset 214.7° C. (70 J/g) | 7.7 | Dihydrate form | Broad multi-endotherm onset 155.3° C. (215 J/g) Sharp endotherm split into two, onset 214.7° C. (57 J/g and 34 J/g) | 7.6 |

| | Week 3 | | | Week 4 | | |
|---|---|---|---|---|---|---|
| Storage Condition | XRPD | DSC | KF (%) | XRPD | DSC | KF (%) |
| 40° C./ 75% RH | Dihydrate form | Broad endotherm onset 96.8° C. (99 J/g) Multi-endotherm onset 154.2 (80 J/g) Sharp endotherm onset 214.0° C. (65 J/g) | 7.7 | Dihydrate form | Broad endotherm onset 90.9° C. (113 J/g) Multi-endotherm onset 156.9° C. (70 J/g) Endotherm onset 158.4° C. (0 J/g) Sharp endotherm onset 214.5° C. (18 J/g) | 7.7 |
| 25° C./ 97% RH | Dihydrate form | Broad endotherm onset 91.3° C. (72 J/g) Multi-endotherm onset 153.2° C. (93 J/g) Sharp endotherm onset 214.0° C. (69 J/g) | 7.4 | Dihydrate form | Broad endotherm onset 93.4° C. (68 J/g) Multi-endotherm onset 152.9° C. (124 J/g) Small endotherms onset (160.3° C. (1 J/g), 161.5° C. (0 J/g), 162.0° C. (0 J/g), 164.2° C. (0 J/g) Small endotherm onset 173.8° C. (0 J/g) Sharp endotherm onset 214.4° C. (82 J/g) | 7.7 |
| 40° C./ 0% RH | Anhydrous form* | Sharp endotherm onset 214.4° C. (121 J/g) | 0.1 | Dihydrate and Anhydrous forms | Sharp endotherm onset 213.8° C. (116 J/g) | 0.2 |
| 25° C./ 0% RH | Dihydrate form | Broad endotherm onset 96.0° C. (28 J/g) Multi-endotherm onset 148.3° (50 J/g) Two small endotherms onset 162.2° C. (0 J/g) and 166.6° C. (0 J/g) Sharp endotherm onset 215.0° (18 J/g) | 7.2 | Dihydrate and Anhydrous forms | Broad endotherm onset 95.4° C. (25 J/g) Multi-endotherm onset 155.1° C. (66 J/g) Two small endotherms onset 162.7° C. (0 J/g) and 171.8° C. (0 J/g) Sharp endotherm onset 214.3° C. (98 J/g) | 5.8 |

| Anhydrous form of the compound represented by Formula (I) | | | | | | |
|---|---|---|---|---|---|---|
| | Week 1 | | | Week 2 | | |
| Storage Condition | XRPD | DSC | KF (%) | XRPD | DSC | KF (%) |
| 40° C./ 75% RH | Anhydrous form | Sharp endotherm onset 214.5° C. (119 J/g) | 0.3 | Anhydrous form | Sharp endotherm onset 214.5° C. (180 J/g) | 0.2 |
| 25° C./ 97% RH | Anhydrous form | Sharp endotherm onset 214.3° C. (121 J/g) | 0.3 | Anhydrous form | Sharp endotherm onset 213.0° C. (1 J/g) immediately followed by sharp endotherm onset 214.9° C. (120 J/g | 0.3 |
| 40° C./ 0% RH | Anhydrous form | Sharp endotherm split into two, onset 214.7° C. (98 J/g and 22 J/g) | 0.1 | Anhydrous form | Multi-endotherm onset 214.9° C. (124 J/g) | 0.0 |
| 25° C./ 0% RH | Anhydrous form | Sharp endotherm onset 214.4° C. (119 J/g) | 0.1 | Anhydrous form | Multi-endotherm onset 214.2° C. (124 J/g) | 0.1 |

TABLE 8-continued

| Stability of the crystalline dihydrate and anhydrous forms of the compound represented by Formula (I) | | | | | | |
|---|---|---|---|---|---|---|
| | Week 3 | | | Week 4 | | |
| Storage Condition | XRPD | DSC | KF (%) | XRPD | DSC | KF (%) |
| 40° C./ 75% RH | Anhydrous form | Sharp endotherm onset 214.1° C. (124 J/g) | 0.1 | Anhydrous form | Sharp endotherm onset 214.1° C. (125 J/g) | 0.3 |
| 25° C./ 97% RH | Anhydrous form | Sharp endotherm onset 214.3° C. (126 J/g) | 0.2 | Anhydrous form | Sharp endotherm onset 214.6° C. (123 J/g) | 0.4 |
| 40° C./ 0% RH | Anhydrous form | Sharp endotherm onset 214.7° C. (121 J/g) | 0.0 | Anhydrous form | Sharp endotherm onset 214.9° C. (118 J/g) | 0.2 |
| 25° C./ 0% RH | Anhydrous form | Sharp endotherm onset 214.5° C. (123 J/g) | 0.0 | Anhydrous form | Sharp endotherm onset 214.4° C. (119 J/g) | 0.2 |

*due to sample homogeneity

TABLE 9

| Stability of the crystalline dihydrate form of the compound represented by Formula (I) Dihydrate form of the compound represented by Formula (I) (having crystal sizes in the range of about 10-50 μm) | | | | | | |
|---|---|---|---|---|---|---|
| | Week 1 | | | Week 2 | | |
| Storage Condition | XRPD | DSC | KF (%) | XRPD | DSC | KF (%) |
| 40° C./ 75% RH | Dihydrate form | Endotherm onset 95.6° C. (158 J/g) Exotherm onset 131.0° C. (42 J/g) Sharp endotherm split into two onset 213.7° C. (9 J/g and 63 J/g) | 7.5 | Dihydrate form | Endotherm onset 95.0° C. (169 J/g) Exotherm onset 136.2° C. (76 J/g) Sharp endotherm onset 213.8° C. (108 J/g) | 7.9 |
| 25° C./ 97% RH | Dihydrate form | Endotherm onset 93.6° C. (252 J/g) Exotherm onset 129.5° C. (78 J/g) Sharp endotherm split into two onset 213.7° C. (70 J/g and 42 J/g) | 7.6 | Dihydrate form | Endotherm onset 95.5° C. (171 J/g) Exotherm onset 132.0° C. (74 J/g) Sharp endotherm onset 213.7° C. (110 J/g) | 7.5 |
| 40° C./ 0% RH | Pattern 4 | Endotherm onset 99.1° C. (35 J/g) Exotherm onset 128.8° C. (84 J/g) Sharp endotherm split into two onset 213.7° C. (83 J/g and 32 J/g) | 7.5 | Pattern 4 | Endotherm onset 102.1° C. (33.4 J/g) Exotherm onset 130.6° C. (84 J/g) Sharp endotherm onset 213.7° C. (116 J/g) | 7.4 |
| 25° C./ 0% RH | Dihydrate form | Endotherm onset 96.6° C. (266 J/g) Exotherm onset 132.2° C. (68 J/g) Sharp endotherm split into two onset 213.7° C. (86 J/g and 20 J/g) | 7.5 | Dihydrate form | Endotherm onset 95.3° C. (170 J/g) Exotherm onset 131.9° C. (73 J/g) Sharp endotherm onset 213.6° C. (105 J/g) | 7.7 |
| | Week 3 | | | Week 4 | | |
| Storage Condition | XRPD | DSC | KF (%) | XRPD | DSC | KF (%) |
| 40° C./ 75% RH | Dihydrate form | Broad endotherm onset 95.2° C. (231 J/g) Exotherm onset 138.3° C. (79 J/g) Sharp endotherm onset 213.7° C. (109 J/g) | 8.0 | Dihydrate form | Broad endotherm onset 95.6° C. (172 J/g) Exotherm onset 132.2° C. (72 J/g) Endotherm onset 213.6° C. (114 J/g) | 7.9 |
| 25° C./ 97% RH | Dihydrate form | Broad endotherm onset 94.9° C. (235 J/g) Exotherm onset 145.5° C. (91 J/g) Sharp endotherm onset 213.8° C. (112 J/g) | 7.9 | Dihydrate form | Broad endotherm onset 103.1° C. (163 J/g) Exotherm onset 133.0° C. (76 J/g) Endotherm onset 213.7° C. (112 J/g) | 7.9 |
| 40° C./ 0% RH | Pattern 4 with additional peaks at 2θ = 9.9° and 10.6° | Broad endotherm onset 99.4° C. (34 J/g) Exotherm onset 129.5° C. (87 J/g) Sharp endotherm onset 213.8° C. (125 J/g) | 7.0 | Pattern 4 with additional peaks at 2θ = 9.9° and 10.6° | Broad endotherm onset 97.8° C. (131 J/g) Exotherm onset 129.6° C. (88 J/g) Small endotherm onset 196.2° C. (0 J/g) Sharp endotherm onset 213.5° C. (121 J/g) | 3.4 |

TABLE 9-continued

| Stability of the crystalline dihydrate form of the compound represented by Formula (I) Dihydrate form of the compound represented by Formula (I) (having crystal sizes in the range of about 10-50 μm) | | | | | | |
|---|---|---|---|---|---|---|
| 25° C./ 0% RH | Dihydrate form | Broad endotherm onset 95.6° C. (155 J/g) Exotherm onset 130.4° C. (65 J/g) | 8.1 | Dihydrate form | Broad endotherm onset 95.0° C. (193 J/g) Exotherm onset 134.4° C. (89 J/g) Small endotherm onset 147.8° C. (0 J/g) Sharp endotherm onset 213.6° C. (114 J/g) | 7.9 |

Example 5: Solvent Screening for the Compound Represented by Formula (I)

The effect of solvent systems and crystallization conditions on the compound represented by Formula (I) was studied using an amorphous sample of the compound represented by Formula (I). Table 10 summarizes the crystalline form produced under certain solvent conditions and techniques.

For the temperature cycling, the amorphous compound represented by Formula (I) in each solvent was heated to 40° C. for about 20 minutes. Where dissolution occurred, additional amorphous material was added to obtain a slurry. The resultant slurries were subjected to successive 4-hour heat-cool cycles between 40° C. and room temperature for 72 hours. The solid materials were isolated from the slurries by filtration then analyzed by XRPD. The filtrate was used for evaporation, crash cooling, and anti-solvent addition experiments. For the evaporation experiment, the solution of the compound of Formula (I) was left uncapped in a vial to evaporate the solvent at ambient conditions. For the crash cooling experiments at 2° C. and −20° C., the solutions of the compound of Formula (I) were left to cool to 2° C. and −20° C. in the fridge and freezer, respectively. For the anti-solvent experiment, an anti-solvent was added to the saturated solution of the compound of Formula (I). The anti-solvent for samples 1-5, 7-9, 14-18, 20-21, and 23-24 was MTBE; the anti-solvent for samples 10-13 and 22 was DIPE; and the anti-solvent for sample 19 was acetone.

TABLE 10

Summary of the solvent screening for the compound represented by Formula (I)

| | | Technique | | | | |
|---|---|---|---|---|---|---|
| Sample | Solvent | Temperature cycling | Evaporation | Crash Cooling (2° C.) | Crash Cooling (−20° C.) | Anti-solvent Addition |
| 1 | Acetone | Anhydrous | Anhydrous | NS | NS | NS |
| 2 | Acetone/water 75:25 | Dihydrate | Dihydrate | NS | NS | Amorphous |
| 3 | Acetonitrile | Anhydrous | Anhydrous | Anhydrous | NS | NS |
| 4 | Anisole | Anhydrous | Dihydrate | NS | Dihydrate | NS |
| 5 | 1-Butanol | Anhydrous | Anhydrous | NS | NS | NS |
| 6 | Chloroform | Anhydrous | Dihydrate | NS | NS | NS |
| 7 | Cyclohexane | Anhydrous | Anhydrous | NS | NS | NS |
| 8 | Dichloromethane | Anhydrous | Anhydrous | Anhydrous | Anhydrous | Anhydrous |
| 9 | Diisopropyl ether | Anhydrous | Anhydrous | NS | NS | NS |
| 10 | 1,4-Dioxane | Anhydrous | Anhydrous | NS | NS | Anhydrous |
| 11 | Ethanol | Anhydrous | Anhydrous | NS | NS | NS |
| 12 | Ethanol/water 97:3 | Dihydrate | Dihydrate | Dihydrate | Dihydrate | Dihydrate |
| 13 | Ethanol/water 75:25 | Dihydrate | Dihydrate | Dihydrate | Dihydrate | Dihydrate |
| 14 | Ethyl acetate | Anhydrous | Anhydrous | NS | NS | NS |
| 15 | Heptane | Anhydrous | Anhydrous | NS | NS | NS |
| 16 | Methanol | Anhydrous | Anhydrous | Anhydrous | Anhydrous | NS |
| 17 | Methanol/water 90:10 | Dihydrate | Dihydrate | NS | Dihydrate | NS |
| 18 | Methanol/water 60:40 | Dihydrate | Dihydrate | NS | NS | NS |
| 19 | 2-Methoxyethanol | Anhydrous | Anhydrous | NS | NS | NS |
| 20 | Methyl acetate | Anhydrous | Anhydrous | Anhydrous | Anhydrous | Anhydrous |
| 21 | Methylethyl ketone | Anhydrous | Anhydrous | NS | Anhydrous | Anhydrous |
| 22 | Methylisobutyl ketone | Dihydrate | Anhydrous | NS | NS | NS |
| 23 | Tetrahydrofuran | Anhydrous | Anhydrous | NS | NS | Anhydrous |
| 24 | Acetonitrile/water 75:25 | Dihydrate | Dihydrate | Dihydrate | Dihydrate | NS |

NS in Table 10 refers to no solid formed for XRPD analysis.

In a hydration experiment, a slurry of the crystalline anhydrous form of the compound represented by Formula (I) and deionized water was subjected to successive 4-hour heat-cool cycles between 40° C. and room temperature for 72 hours. The isolated solid was identified as the crystalline dihydrate form of the compound represented by Formula (I) by XRPD.

In a competitive slurry experiment, a 1:1 mixture of the crystalline anhydrous form and the crystalline dihydrate form was slurried for 48 hours at room temperature or 60° C. Table 11 summarizes the experiment conditions and the isolated crystalline forms, as determined by XRPD.

TABLE 11

Summary of the competitive slurry experiments

| Solvent | Approximate water activity | Temperature | Observed form |
|---|---|---|---|
| Acetone/water (99:1) | 0.1 | Ambient | Dihydrate |
| Acetone/water (70:30) | 0.9 | Ambient | Dihydrate |
| 1,4-Dioxane/water (90:10) | 0.1 | Ambient | Dihydrate |
| 1,4-Dioxane/water (35:65) | 0.9 | Ambient | Dihydrate |
| Acetone/water (99:1) | 0.1 | 60° C. | Anhydrous |
| Acetone/water (70:30) | 0.9 | 60° C. | Dihydrate |
| 1,4-Dioxane/water (90:10) | 0.1 | 60° C. | Dihydrate |
| 1,4-Dioxane/water (35:65) | 0.9 | 60° C. | Dihydrate |

The hydration of the crystalline anhydrous form was studied using aqueous solvent systems with low water activity of 0.1. Slurries of the crystalline anhydrous form in the respective solvent were agitated for 6 days at room temperature. Aliquots of isolated materials were analyzed after 24, 48, and 144 hours of agitation. Table 12 summarizes the experiment conditions and isolated crystalline forms, as determined by XRPD.

TABLE 12

Summary of hydration experiment in low water activity solvents

| Solvent | Temperature | Observed Forms 24 h | 48 h | 144 h |
|---|---|---|---|---|
| Acetone/water (99:1) | Ambient | Anhydrous | Mixture of Anhydrous and Dihydrate | Anhydrous |
| MEK/water (99:1) | Ambient | Anhydrous | Mixture of Anhydrous and Dihydrate | Dihydrate |

Example 6. Dose Interruption and Modification of Vimseltinib

This is dose interruption and modification protocol in a Phase 3, randomized, placebo-controlled, double-blind study of vimseltinib to assess the efficacy and safety in Patients with tenosynovial giant cell tumor. Administration of vimseltinib may be interrupted and/or modified at the discretion of the Investigator at any time due to adverse events (AEs). Vimseltinib may also be interrupted for other reasons in consultation with the Sponsor Medical Monitor. Any vimseltinib interruption unrelated to an AE will be limited to 28 days. Upon resumption of vimseltinib following a dose interruption, the Investigator must continue with the participant's original visit schedule calculated from Cycle 1 Day 1. Clinic visits and assessments should continue during dose interruptions.

Severity Assessment

The Investigator must determine and record the severity of all serious and nonserious AEs. The NCI-CTCAE, v5.0, must be used for grading the severity of AEs (NCI-CTCAE, 2020). When there is a change in severity of an existing adverse event including improvement or worsening of an event, a new AE should be reported.

The severity of an AE that does not appear in the CTCAE scale must be determined according to Table 13.

TABLE 13

Severity Grading Scale

| Classification | Definition |
|---|---|
| Grade 1 (Mild) | Asymptomatic or mild symptoms; clinical or diagnostic observations only; intervention not indicated. |
| Grade 2 (Moderate) | Minimal, local, or noninvasive intervention indicated; limiting age-appropriate instrumental Activities of Daily Living. |
| Grade 3 (Severe) | Severe or medically significant but not immediately life-threatening; hospitalization or prolongation of hospitalization indicated; disabling; limiting self-care Activities of Daily Living. |
| Grade 4 (Life threatening) | Life-threatening consequences; urgent intervention indicated. |
| Grade 5 (Death) | Death related to AE. |

Abbreviation: AE = adverse event

Dose Interruption and Modification

Vimseltinib must be interrupted for treatment-related Grade 3 AEs of any duration with the following exceptions: Asymptomatic/nonclinically significant Grade ≥3 elevation of CPK not accompanied by myalgias, worsening renal function, signs of rhabdomyolysis or cardiac muscle damage (e.g., myoglobinuria, CPK isozyme profile, troponin), and not requiring additional evaluation/testing; treatment-related Grade 3 nausea, vomiting, and diarrhea resolved to Grade 1 or baseline within 2 days with optimal treatment; treatment-related transient Grade 3 fatigue (lasting less than 3 days); treatment-related transient (lasting less than 3 days) Grade >3 laboratory abnormalities that resolve with optimal supplementation or support For the treatment-related Grade 3 AEs resulting in dose interruptions, vimseltinib may be resumed at the same dose, or dose reduced per Investigator discretion, when the toxicity has recovered to Grade 1 or baseline, unless otherwise specified in management tables.

For all other treatment-related AEs resulting in dose interruptions, vimseltinib may be resumed at the same dose, unless otherwise specified in management tables.

Vimseltinib will be permanently discontinued for participants with treatment-related Grade 4 AEs except transient laboratory abnormalities as described above and Grade 4 neutropenia lasting for 7 days or fewer. If, in the opinion of the Investigator and the Sponsor, it is in the participant's best interest to continue treatment with vimseltinib, then the dose of vimseltinib will be reduced by at least 1 dose level when treatment resumes, after recovery of the toxicity or toxicities in question to Grade 1 or to baseline values.

Dose Reduction Steps

If dose reduction is required, dose reduction steps are as described in Table 14.

TABLE 14

| Dose Reduction Steps for Vimseltinib and Vimseltinib Dihydrate | | | |
|---|---|---|---|
| Dose of Vimseltinib at the Time of Dose Modification | Equivalent Amount of Vimseltinib Dihydrate at the Time of Dose Modification | Reduced Vimseltinib Dose | Reduced Vimseltinib Dihydrate Equivalent Amount |
| 30 mg | 32.5 mg | 20 mg | 21.7 mg |
| 20 mg | 21.7 mg | 14 mg | 15.2 mg |

If a dose reduction of vimseltinib is required, re-escalation of dose may be permitted based on agreement between the Investigator and Sponsor.

A participant will be allowed to have 2 dose level reductions. If more than 2 dose level reductions are required, the vimseltinib will be discontinued.

Dose Interruption and Management of Toxicities

Guidelines for Hepatobiliary Lab Elevations

Recommended dose interruption and management of treatment-related hepatobiliary lab elevations are shown in Table 15.

TABLE 15

| Dose Interruption and Management of Treatment-related Hepatobiliary Laboratory Elevations | |
|---|---|
| Toxicity Grade CTCAE v5.0 | Dose Interruption and Management |
| Grade 2 ALT and/or AST increase (>3-5 × ULN) and total bilirubin ≤ULN | Continue treatment with vimseltinib<br>Check for changes to medications and symptoms<br>Perform confirmation liver enzyme (AST, ALT and ALP) and bilirubin tests within 48-72 hours<br>Repeat liver enzyme tests weekly for 8 weeks to ensure stability |
| Grade 2 ALT and/or AST increase (>3-5 × ULN) and total bilirubin increase up to 2 × ULN<br>OR<br>Total bilirubin increase up to 2 × ULN | Hold treatment with vimseltinib<br>Check for changes to medications and symptoms<br>Perform confirmation liver enzyme (AST, ALT, and ALP) and bilirubin tests within 48-72 hours<br>Repeat liver enzyme tests weekly<br>Vimseltinib may be resumed at 1 dose level reduction once Hy's law has been definitively ruled out, labs resolve to Grade 1 or baseline, after discussion with Sponsor<br>If ALT/AST/bilirubin continue to increase, or the increased level persists more than 28 days:<br>Discontinue vimseltinib<br>Refer for gastroenterology/hepatology consultation<br>Consider liver ultrasound |
| Grade 2 ALT and/or AST increase (>3-5 × ULN) and total bilirubin increase >2 × ULN or INR >1.5 and ALP <2 × ULN<br>OR<br>Total bilirubin increase >2 × ULN | Hold treatment with vimseltinib<br>Check for changes to medications and symptoms<br>Perform confirmation liver enzyme (AST, ALT and ALP), bilirubin, and INR tests within 48-72 hours<br>Refer for gastroenterology/hepatology consultation<br>Consider liver ultrasound<br>Repeat liver enzyme, bilirubin, and INR tests weekly until resolution to Grade 1 or baseline<br>Vimseltinib may be resumed at 1 dose level reduction once Hy's law has been definitively ruled out, labs resolve to Grade 1 or baseline, after discussion with Sponsor<br>If ALT/AST/bilirubin/INR continue to increase, or the increased level persists more than 28 days:<br>Discontinue vimseltinib |
| Grade 3 ALT and/or AST increase (>5-8 × ULN) and total bilirubin ≤ULN and without clinical symptoms | Hold treatment with vimseltinib<br>Check for changes to medications and symptoms<br>Perform confirmation liver enzyme (AST, ALT and ALP) and bilirubin tests within 48-72 hours<br>Repeat liver enzyme tests weekly until resolution to Grade 1 or baseline<br>Vimseltinib may be resumed at 1 dose level reduction once labs resolve to Grade 1 or baseline, after discussion with Sponsor<br>If ALT/AST/bilirubin continue to increase, or the increased level persists more than 28 days:<br>Discontinue vimseltinib<br>Refer for gastroenterology/hepatology consultation<br>Perform liver ultrasound |
| Grade 3 ALT and/or AST increase (>5-8 × ULN) and total bilirubin increase >ULN or INR >1.5 or ALP >2 × ULN | Discontinue treatment with vimseltinib<br>Check for changes to medications and symptoms<br>Perform confirmation liver enzyme (AST, ALT, and ALP), bilirubin, and INR tests within 48-72 hours<br>Consider gastroenterology/hepatology consultation<br>Perform liver ultrasound<br>Repeat liver enzyme, bilirubin, and INR tests at least twice weekly until resolution to Grade 1 or baseline |

TABLE 15-continued

| Dose Interruption and Management of Treatment-related Hepatobiliary Laboratory Elevations | |
|---|---|
| Toxicity Grade CTCAE v5.0 | Dose Interruption and Management |
| Grade ≥3 ALT and/or AST increase (>8 × ULN) | Discontinue treatment with vimseltinib<br>Check for changes to medications and symptoms<br>Repeat liver enzymes and bilirubin tests at least twice weekly until resolution to Grade ≤2<br>Refer for gastroenterology/hepatology consultation<br>Perform liver ultrasound |

Abbreviations:
ALP = alkaline phosphatase;
ALT = alanine aminotransferase;
AST = aspartate aminotransferase;
CTCAE = Common Terminology Criteria for Adverse Events;
INR = international normalized ratio;
ULN = upper limit of normal.
Note:
Cases of Hy's law must be reported as a serious adverse event and vimseltinib must be discontinued immediately.

Guidelines for Prolonged QTcF Interval

Recommended dose interruption and management of treatment-related prolonged QTcF interval is provided in Table 16.

TABLE 16

| Recommended Dose Interruption and Management of Treatment-related Prolonged QTcF Interval | |
|---|---|
| Toxicity Grade CTCAE v5.0 (ECG QTc interval prolonged) | Dose Interruption and Management |
| Grade 2 (QTc 481-500 ms) | Continue vimseltinib<br>Continue ECG monitoring per protocol |
| Grade 3 (QTc ≥501 ms; >60 ms change from baseline) | Hold treatment with vimseltinib<br>Continue close ECG monitoring and consult cardiologist<br>Upon resolution to Grade 1 or baseline in ≤14 days, may resume study treatment at same dose. If >14 days for resolution to Grade 1 or baseline, may resume study treatment at reduced dose. |
| Grade 4 | Discontinue vimseltinib<br>Continue close ECG monitoring and consult cardiologist |

Abbreviations:
CTCAE = Common Terminology Criteria for Adverse Events;
ECG = electrocardiogram;
QTc = QT interval corrected;
QTcF = QT interval corrected by Fridericia's formula.

Guidelines for Dermatologic Adverse Events

Recommended dose interruption and management of treatment-related skin and subcutaneous disorder and recommendations for management of dry skin are presented in Table 17.

General guidelines for treatment-related dermatologic adverse events: Symptoms and signs of hypersensitivity reaction should be monitored at each clinic visit; use "Rule of 9s" (refer to Appendix 2) to calculate body surface area (BSA) for CTCAE grading; participant should be advised to use fragrance-free detergents and soaps, wear sunscreen with sun protection factor ≥30, and moisturize the skin at least once daily, preferably twice daily; standardized photos for any Grade ≥2 dermatologic AEs should be submitted to the Sponsor; skin biopsy sample (ie, punch biopsy) may be collected locally if a participant experiences a treatment-related dermatologic AE. If collected, the sample will be shipped to a central laboratory and may be analyzed for histopathology and potentially for molecular markers. Specific instructions on collection and shipping of samples will be provided in a separate laboratory manual.

TABLE 17

| Recommended Dose Interruption and Management of Treatment-related Adverse Events | | |
|---|---|---|
| Toxicity Grade (CTCAE v5.0) | Maculopapular Rash | Pruritus/Urticaria |
| Grade 1 | Continue treatment with vimseltinib<br>Treat with mid- to high-potency topical corticosteroid bid | Continue treatment with vimseltinib<br>Treat with cooling lotions containing menthol and/or camphor<br>Treat with mid- to high-potency topical corticosteroid bid |
| Grade 2 | Continue treatment with vimseltinib<br>Treat with high-potency topical corticosteroid 1-2 times per day<br>Treat with anti-H1 therapy (if rash is associated with symptoms such as pruritus and/or urticaria) or GABA agonists<br>Standardized photographs[a]<br>Dermatologic consultation recommended | Continue treatment with vimseltinib<br>Treat with high-potency topical corticosteroid bid<br>Initiate anti-H1 therapy or GABA agonists<br>Standardized photographs[a]<br>Dermatologic consultation recommended |

TABLE 17-continued

| Recommended Dose Interruption and Management of Treatment-related Adverse Events | | |
|---|---|---|
| Toxicity Grade (CTCAE v5.0) | Maculopapular Rash | Pruritus/Urticaria |
| Grade 3 | Hold treatment with vimseltinib<br>Check CBC/differential-evaluate for eosinophilia<br>Standardized photographs[a]<br>Refer for dermatologic consultation and obtain skin biopsy<br>Treat with oral corticosteroids following dermatologic evaluation (prednisone 0.5 mg/kg/day) for 10-14 days<br>Once AE resolves to Grade ≤1, may resume vimseltinib at 1 dose level reduction | Hold treatment with vimseltinib<br>Standardized photographs[a]<br>Refer for dermatologic consultation and obtain skin biopsy<br>Consider anti-IgE antibody following dermatologic evaluation<br>Once AE resolves to Grade ≤1, restart vimseltinib at 1 dose level reduction |

Abbreviations:
AE = adverse event;
bid = twice daily;
CBC = complete blood count;
CTCAE = Common Terminology Criteria for Adverse Events;
GABA = gamma-aminobutyric acid;
H1 = histamine-1;
IgE = immunoglobulin E.
[a]Guidance for standardized photographs will be provided separately

EQUIVALENTS

Those skilled in the art will recognize or be able to ascertain using no more than routine experimentation, numerous equivalents to the specific embodiments described specifically in this disclosure. Such equivalents are intended to be encompassed in the scope of the following claims.

The invention claimed is:

1. A crystalline dihydrate form of the compound represented by Formula (I):

Formula (I)

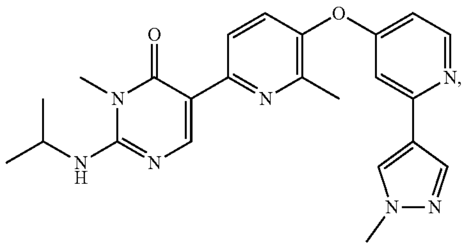

having an X-ray powder diffraction (XRPD) pattern comprising peaks, in terms of 2-theta, at about 5.9°, about 10.9°, about 11.9°, about 13.7°, about 16.8°, and about 27.1° as measured by CuKα radiation, wherein the crystalline dihydrate form has a $d_{10}$ particle size distribution of about 2 microns to about 10 microns, a $d_{50}$ particle size distribution of about 12 microns to about 24 microns, and a $d_{90}$ particle size distribution of about 32 microns to about 40 microns.

2. The crystalline dihydrate form of claim 1, having an XRPD pattern comprising peaks, in terms of 2-theta, at about 5.9°, about 10.9°, about 11.9°, about 13.7°, about 16.8°, about 27.1°, about 28.3° and about 28.7° as measured by CuKα radiation.

3. The crystalline dihydrate form of claim 2, having an XRPD pattern substantially as shown in FIG. 1.

4. The crystalline dihydrate form of claim 2, having a differential scanning calorimetry (DSC) thermogram comprising an endothermic event with onset between about 75° C. and about 95° C., an exothermic event with onset between about 123° C. to about 150° C., and an endothermic peak at about 215° C.

5. The crystalline dihydrate form of claim 2, having a differential scanning calorimetry (DSC) thermogram substantially as shown in FIG. 2.

6. The crystalline dihydrate form of claim 2, having a thermogravimetric analysis (TGA) thermogram substantially as shown in FIG. 3.

7. The crystalline dihydrate form of claim 1, having not more than about 10 mol %, not more than about 3 mol %, or not more than about 1 mol % of other solid-state forms of the compound represented by Formula (I).

8. The crystalline dihydrate form of claim 3, having not more than about 1 mol % of other solid-state forms of the compound represented by Formula (I).

9. The crystalline dihydrate form of claim 1, which is stable after four weeks of storage at 40° C./75% RH or 25° C./97% RH.

10. A pharmaceutical composition comprising the crystalline dihydrate form of claim 1, and a pharmaceutically acceptable excipient.

11. A pharmaceutical composition comprising the crystalline dihydrate form of claim 3, and a pharmaceutically acceptable excipient.

12. The pharmaceutical composition of claim 11, wherein the crystalline dihydrate form is present in the composition in an amount of at least about 90% by weight, based on the total weight of the compound represented by Formula (I).

13. A pharmaceutically acceptable composition comprising:

a crystalline dihydrate form of the compound represented by Formula (I):

Formula (I)

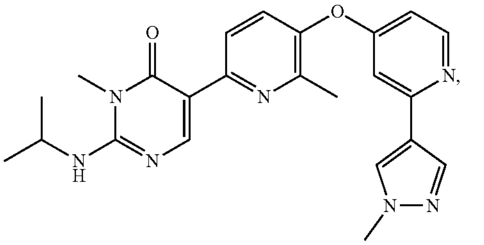

having an X-ray powder diffraction (XRPD) pattern comprising peaks, in terms of 2-theta, at about 5.9°, about 10.9°, about 11.9°, about 13.7°, about 16.8°, and about 27.1° as measured by CuKα radiation;

wherein the crystalline dihydrate form is present in the composition with a $d_{10}$ particle size distribution of about 2 microns to about 10 microns; a $d_{50}$ particle size distribution of about 12 microns to about 24 microns, and a $d_{90}$ particle size distribution of about 32 microns to about 40 microns; and a pharmaceutically acceptable excipient.

14. The pharmaceutically acceptable composition of claim 13, wherein the composition is in the form of a capsule and the capsule contains about 15.2 mg of the crystalline dihydrate form.

15. The pharmaceutically acceptable composition of claim 13, wherein the composition is in the form of a capsule and the capsule contains about 21.7 mg of the crystalline dihydrate form.

16. The pharmaceutically acceptable composition of claim 13, wherein the composition is in the form of a capsule and the capsule contains about 32.5 mg of the crystalline dihydrate form.

17. A pharmaceutically acceptable composition comprising:

a crystalline dihydrate form of the compound represented by Formula (I):

Formula (I)

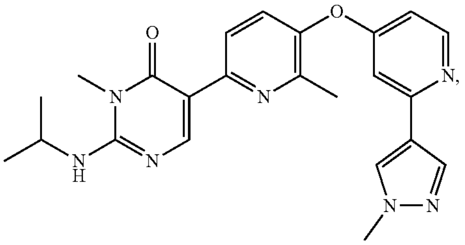

having an X-ray powder diffraction (XRPD) pattern comprising peaks, in terms of 2-theta, at about 5.9°, about 10.9°, about 11.9°, about 13.7°, about 16.8°, and about 27.1° as measured by CuKα radiation;

wherein the crystalline dihydrate form is present in the composition with a $d_{10}$ particle size distribution of about 4 microns; a $d_{50}$ particle size distribution of about 8 microns, and a $d_{90}$ particle size distribution of about 16 microns; and a pharmaceutically acceptable excipient.

18. The pharmaceutically acceptable composition of claim 17, wherein the composition is in the form of a capsule and the capsule contains about 15.2 mg of the crystalline dihydrate form.

19. The pharmaceutically acceptable composition of claim 17, wherein the composition is in the form of a capsule and the capsule contains about 21.7 mg of the crystalline dihydrate form.

20. The pharmaceutically acceptable composition of claim 17, wherein the composition is in the form of a capsule and the capsule contains about 32.5 mg of the crystalline dihydrate form.

* * * * *